United States Patent
LaVoie et al.

(10) Patent No.: US 11,180,459 B2
(45) Date of Patent: Nov. 23, 2021

(54) BACTERIAL EFFLUX PUMP INHIBITORS

(71) Applicant: RUTGERS, THE STATE UNIVERSITY OF NEW JERSEY, New Brunswick, NJ (US)

(72) Inventors: Edmond J. LaVoie, New Brunswick, NJ (US); Ajit Parhi, New Brunswick, NJ (US); Yongzheng Zhang, Monmouth Junction, NJ (US); Yi Yuan, Monmouth Junction, NJ (US); Yangsheng Sun, Monmouth Junction, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/492,907

(22) PCT Filed: Mar. 9, 2018

(86) PCT No.: PCT/US2018/021849
§ 371 (c)(1),
(2) Date: Sep. 10, 2019

(87) PCT Pub. No.: WO2018/165612
PCT Pub. Date: Sep. 13, 2018

(65) Prior Publication Data
US 2020/0140393 A1    May 7, 2020

Related U.S. Application Data

(60) Provisional application No. 62/470,009, filed on Mar. 10, 2017.

(51) Int. Cl.
| | | |
|---|---|---|
| C07D 403/12 | (2006.01) | |
| A61P 31/04 | (2006.01) | |
| C07D 235/14 | (2006.01) | |
| A61K 45/06 | (2006.01) | |

(52) U.S. Cl.
CPC ............ C07D 235/14 (2013.01); A61P 31/04 (2018.01); C07D 403/12 (2013.01); A61K 45/06 (2013.01)

(58) Field of Classification Search
CPC ................. C07D 403/12; A61P 31/04
See application file for complete search history.

(56) References Cited

U.S. PATENT DOCUMENTS

| | | | |
|---|---|---|---|
| 3,978,224 A | 8/1976 | Steinman et al. | |
| 4,938,949 A | 7/1990 | Borch et al. | |
| 5,663,152 A | 9/1997 | Hayano et al. | |
| 6,204,279 B1 | 3/2001 | Leger et al. | |
| 6,326,391 B1 | 12/2001 | Markham et al. | |
| 6,555,569 B2 | 4/2003 | Sutcliffe et al. | |
| 6,730,684 B1 | 5/2004 | Miller et al. | |
| 7,414,046 B2* | 8/2008 | Grillot ................. | C07D 401/12 514/215 |
| 7,855,228 B2 | 12/2010 | Gitai et al. | |
| 7,893,020 B2 | 2/2011 | Glinka et al. | |
| 8,642,076 B2 | 2/2014 | Manoharan et al. | |
| 9,926,261 B2 | 3/2018 | Lavoie et al. | |
| 9,950,993 B2 | 4/2018 | Lavoie et al. | |
| 2004/0204378 A1 | 10/2004 | Nelson et al. | |
| 2008/0132457 A1 | 6/2008 | Bostian et al. | |
| 2009/0042866 A1 | 2/2009 | Lennox et al. | |
| 2010/0256112 A1 | 10/2010 | Bradbury et al. | |
| 2013/0296228 A1 | 11/2013 | Patel et al. | |
| 2014/0323532 A1 | 10/2014 | Wei et al. | |
| 2015/0175539 A1 | 6/2015 | Jiricek et al. | |
| 2015/0291565 A1 | 10/2015 | Djaballah et al. | |
| 2016/0271081 A1 | 9/2016 | Lavoie et al. | |
| 2016/0271082 A1 | 9/2016 | Lavoie et al. | |
| 2018/0179158 A1 | 6/2018 | Dreier et al. | |
| 2019/0031624 A1 | 1/2019 | Lavoie et al. | |

(Continued)

FOREIGN PATENT DOCUMENTS

| | | |
|---|---|---|
| WO | 1992004017 A1 | 3/1992 |
| WO | 2005113579 A1 | 12/2005 |
| WO | 2009110002 A1 | 9/2009 |

(Continued)

OTHER PUBLICATIONS

PubChem CID 145820, National Center for Biotechnology Information. PubChem Compound Summary for CID 145820, (1H-Benzo[d]imidazol-2-yl)methanamine. https://pubchem.ncbi.nlm.nih.gov/compound/1H-Benzo_d_imidazol-2-yl_methanamine. Accessed Oct. 1, 2020, create date Mar. 26, 2005. (Year: 2005).*

Ozden et al., Journal of Heterocyclic Chemistry (2011), 48(6), pp. 1317-1322 (Year: 2011).*

PubChem CID 53617626, National Center for Biotechnology Information. PubChem Compound Summary for CID 53617626. https://pubchem.ncbi.nlm.nih.gov/compound/53617626. Accessed Feb. 23, 2021, create date Dec. 3, 2011. (Year: 2011).*

(Continued)

*Primary Examiner* — Laura L Stockton
(74) *Attorney, Agent, or Firm* — Viksnins Harris Padys Malen LLP

(57) ABSTRACT

Disclosed herein are compounds of formula I and salts thereof. Also disclosed are compositions comprising compounds of formula I and methods using compounds of formula I.

(I)

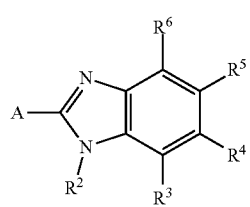

19 Claims, No Drawings

(56) References Cited

U.S. PATENT DOCUMENTS

| | | |
|---|---|---|
| 2019/0055188 A1 | 2/2019 | Lavoie et al. |
| 2019/0084919 A1 | 3/2019 | Lavoie et al. |

FOREIGN PATENT DOCUMENTS

| | | |
|---|---|---|
| WO | 2012084971 A1 | 6/2012 |
| WO | 2014078294 A1 | 5/2014 |
| WO | 2015164482 A1 | 10/2015 |
| WO | 2018165611 A1 | 9/2018 |
| WO | 2018165612 A1 | 9/2018 |
| WO | 2018165614 A1 | 9/2018 |
| WO | 2018218192 A1 | 11/2018 |
| WO | 2019005841 A1 | 1/2019 |

OTHER PUBLICATIONS ubChem CID 69859718, National Center for Biotechnology Information. PubChem Compound Summary for CID 69859718, 2-(Pyrrolidin-2-ylmethyl)-1H-benzimidazole. https://pubchem.ncbi.nlm.nih.gov/compound/2-_Pyrrolidin-2-ylmethyl_-1H-benzimidazole. Accessed Feb. 24, 2021, create date Dec. 1, 2012 (Year: 2012).*

Astolfi, A., et al., "Pharmacophore-Based Repositioning of Approved Drugs as Novel *Staphylococcus aureus* NorA Efflux Pump Inhibitors", J Med Chem 60(4), 1598-1604 (2017).

Awuni, E., et al., "Effect of A22 on the Conformation of Bacterial Actin MreB", International Journal of Molecular Sciences 20, 1304 (2019).

Awuni, Y., et al., "Exploring the A22-Bacterial Actin MreB Interaction through Molecular Dynamics Simulations", J. Phys. Chem, B 120(37), 4867-4874 (2016).

Barker, C., et al., "Degradation of MAC13243 and studies of the interaction of resulting thiourea compounds with the ipoprotein targeting chaperone LoIA", Bioorganic & Medicinal Chemistry Letters 23, 2426-2431 (2013).

Bean, G., et al., "A22 disrupts the bacterial actin cytoskeleton by directly binding and inducing a low-affinity state in MreB", Biochemistry 48 (22), 4852-7 (2009).

Bohnert, J., et al., "Efflux inhibition by selective serotonin reuptake inhibitors in *Escherichia coli*", J Antimicrob Chemother 66, 2057-2060 (2011).

Bonez, P., et al., "Antibacterial, cyto and genotoxic activities of A22 compound ((S-3,4-dichlorobenzyl) Isothiourea hydrochloride)", Microbial Pathogenesis 99, 14-18 (2016).

Bonez, P., et al., "Anti-biofilm activity of A22 ((S-3,4-dichlorobenzyl) isothiourea hydrochloride) against Pseudomonas aeruginosa: Influence on biofilm formation, motility and bioadhesion", Microbial Pathogenesis 111, 6-13 (2017).

Buonerba, F., et al., "Improved Potency of Indole-Based NorA Efflux Pump Inhibitors: From Serendipity toward Rational Design and Development", J. Med. Chem DOI:10.1021/acs.jmedchem.6b01281, 8 pages (Dec. 2, 2016).

Fleeman, R., et al., "Identification of a Novel Polyamine Scaffold With Potent Efflux Pump Inhibition Activity Toward Multi-Drug Resistant Bacterial Pathogens", Frontiers in Microbiology 9, 1301, 16 pages (2018).

Grossman, T., et al., "The Efflux Pump Inhibitor Timcodar Improves the Potency of Antimycobacterial Agents", Antimicrobial Agents and Chemotherapy 59(3),1534-1541 (2015).

Gupta, S., et al., "Acceleration of Tuberculosis Treatment by Adjunctive Therapy with Verapamil as an Efflux Inhibitor", American Journal of respiratory and Critical Care Medicince 188, 600-607 (2013).

Handzlik, J., et al., "Recent Advances in Multi-Drug Resistance (MDR) Efflux Pump Inhibitors of Gram-Positive Bacteria *S. aureus*", Antibiotics 2, 28-45 (2013).

Iwai, N., et al., "Novel S-Benzylisothiourea Compound That Induces Spherical Cells in *Escherichia coli* Probably by Acting on a Rod-shape-determining Protein(s) Other Than Penicillin-binding Protein 2", Biosci Biotechnol Biochem 66 (12), 2658-2662 (2002).

Iwai, N., et al., "Structure-Activity Relationship of S-Benzylisothiourea Derivatives to Induce Spherical Cells in *Escherichia coli*", Biosci Biotechnol Biochem 68(11), 2265-2269 (2004).

Iwai, N., et al., "Structure-Activity Relationship Study of the Bacterial Actin-Like Protein MreB Inhibitors: Effects of Substitution of Benzyl Group in S-Benzylisothiourea", Biosci. Biotechnol. Biochem 71 (1), 246-248 (2007).

Lee, J., et al., "Roles of Indole as an Interspecies and Interkingdom Signaling Molecule", Trends in Microbiology 23 (11), 707-718 (2015).

Noguchi, N., et al., "Anti-infectious Effect of S-Benzylisothiourea Compound A22, Which Inhibits the Actin-Like Protein, MreB, in Shigella flexneri", Biol. Pharm. Bull 31 (7), 1327-1332 (2008).

Patent Cooperation Treaty, International Searching Authority, Search Report and Written Opinion for PCT/US2018/021849, 10 pages, dated Jun. 21, 2018.

Perry, J., et al., "In vitro activity of S-(3,4-dichlorobenzyl)isothiourea hydrochloride and novel structurally related compounds against multidrug-resistant bacteria, including Pseudomonas aeruginosa and Burkholderia cepacian complex", International Journal of Antimicrobial Agents, 39 (1), 27-32 (2012).

Pubchem, "10143777", CID 101437777, 9 pages, Create Date Dec. 18, 2015.

Pubchem, "10954401", CID 10954401, 14 pages, Create Date Oct. 26, 2006.

Pubchem, "67894517", CID 67894517, 10 pages, Create Date Nov. 30, 2012.

Pubchem, "6-Chloro-2,3,4,9-tetrahydro-1H-carbazol-1-amine", Compound Summary for CID 17743497, 15 pages (Create Date Nov. 13, 2007).

Pubchem, "LLVYCKNUAXLGFC-UHFFFAOYSA-N", Compound Summary for CID 67376113, 11 pages (create date Nov. 30, 2012).

Pubchem, "SCHEMBL9670581", Substance Record for SID 235049721, 7 pages, Feb. 13, 2015.

Pubchem Database, "Acetamide, N-cyclohexyl-2-phenyl-", Compound Summary for CID 82500, 16 pages (Create Date: Mar. 26, 2005).

Pubchem Database, "Cyclohexyloxybenzene", CID 137492, 17 pages (Create date: Mar. 27, 2005).

Pubchem Database, "N-Cyclohexyl-3-methylbenzamide", Compound Summary for CID 236099,14 pages (create date: Mar. 26, 2005).

Robertson, Gt, et al., "A Novel Indole Compound That Inhibits Pseudomonas aeruginosa Growth by Targeting MreB is a Substrate for MexAB-OprM", Journal of Bacteriology 189 (19), 6870-6881 (2007).

Samosorn, S., et al., "Synthesis of functionalised 2-aryl-5-nitro-1H-indoles and their activity as bacterial NorA efflux pump inhibitors", Bioorganic & Medicinal Chemistry 14, 857-865 (2006).

Stn Cas Registry No., Registry File No. 1026060-58-1, 1 page (2008).

Stn Cas Registry No., Registry File No. 788126-67-0, 1 page (2004).

Stn Cas Registry No., Registry File No. 860554-34-3, 1 page (2005).

Tambat, R., et al., "Microbe-Derived Indole Metabolite Demonstrates Potent Multidrug Efflux Pump Inhibition in *Staphylococcus aureus*", Frontiers in Microbiology 10, 2153, 13 pages (2019).

Taylor, P., et al., "A Forward Chemical Screen Identifies Antibiotic Adjuvants in *Escherichia coli*", ACS Chem Biol 7, 1547-1555 (2012).

Yamachika, S., et al., "Anti-Pseudomonas aeruginosa Compound, 1,2,3,4-Tetrahydro-1,3,5-triazine Derivative, Exerts Its Action by Primarily Targeting MreB", Biol Pharm Bull 35(10), 1740-1744 (2012).

Yang, X., et al., "A tobramycin vector enhances synergy and efficacy of efflux pump inhibitors against multidrug-resistant Gram-negative bacteria", J. Med. Chem 60, 3913-1932 (2017).

Yaqub, G., et al., "Conventional-Microwave Mediated Synthesis and in Vitro Antimicrobial Activity of Novel Carbazole-Efflux Pump Inhibitor Hybrid Antibacterials", Hindawi J. Chemistry, doi: 10.1155/2017/7243279, Article ID 724329, 5 pages (2017).

(56) References Cited

OTHER PUBLICATIONS

Charles, E , "Inhibition of MreB and ftsZ proteins to minimize *E. coli* biofilms formation", doi: https://doi.org/10.1101/523167, 20 pages (2019).

Shi, H , et al., "Chiral twisting in a bacterial cytoskeletal polymer affects filament size and orientation", Nature Communications 11, 1408, 1-12 (2020).

* cited by examiner

BACTERIAL EFFLUX PUMP INHIBITORS

PRIORITY OF INVENTION

This application claims priority from U.S. Provisional Patent Application No. 62/470,009 that was filed Mar. 10, 2017. The entire content of the application referenced above is hereby incorporated by reference herein.

BACKGROUND OF THE INVENTION

Antibiotics have been effective tools in the treatment of infectious diseases. However, bacteria have developed several different mechanisms to overcome the action of antibiotics. These mechanisms of resistance can be specific such as for a molecule or a family of antibiotics, or the mechanisms can be non-specific. Several mechanisms of resistance can exist in a single bacterial strain, and those mechanisms may act independently or they may act synergistically to overcome the action of an antibiotic or a combination of antibiotics. Specific mechanisms include, for example, degradation of the drug, inactivation of the drug by enzymatic modification, and alteration of the drug target. Additional mechanisms of drug resistance include mechanisms in which access of the antibiotic to the target is prevented or reduced by decreasing the transport of the antibiotic into the cell or by increasing the efflux of the drug from the cell to the outside medium. Both of these mechanisms can lower the concentration of drug at the target site and allow bacterial survival in the presence of one or more antibiotics that would otherwise inhibit or kill the bacterial cells. Some bacteria utilize both mechanisms, combining low permeability of the cell wall (including membranes) with an active efflux of antibiotics. It has been shown that efflux of antibiotics can be mediated by more than one pump in a single organism and that almost all antibiotics are subject to resistance by this mechanism.

These multiple resistance mechanisms have become widespread and threaten the clinical utility of antibacterial therapy. The increase in antibiotic resistant strains has been particularly noted in major hospitals and care centers. The consequences of the increase in resistant strains include, for example higher morbidity and mortality, longer patient hospitalization, and an increase in treatment costs. Accordingly, there is a need for agents and methods for inhibiting one or more of these mechanisms of bacterial resistance.

SUMMARY OF THE INVENTION

Compounds disclose herein, when tested in combination with a known antibiotic, lower the minimum inhibitory concentration of the known antibiotic to inhibit bacterial cell growth. Not to be bound by theory the compounds are believed to exert this effect by the inhibition of a bacterial efflux pump(s).

Accordingly, one embodiment provides a compound of formula I:

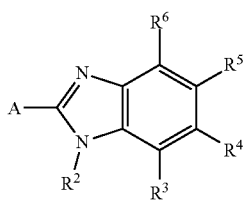

wherein:
A is —C(=O)N($R^{a1}$)—$R^1$, —($C_1$-$C_3$)alkyl-C(=O)N($R^{a1}$)$R^1$, —($C_1$-$C_3$)alkyl-O—$R^1$, —O—$R^1$, —($C_1$-$C_3$)alkyl-N($R^{a1}$)—$R^1$, —N($R^{a1}$)—$R^1$, or $R^1$;

$R^2$ is hydrogen, ($C_1$-$C_6$)alkyl or phenyl($C_1$-$C_6$)alkyl-, wherein the phenyl is optionally substituted with one or more ($C_1$-$C_6$)alkyl, —O($C_1$-$C_6$)alkyl, halo or —$NO_2$;

each $R^1$ is independently:
(a) ($C_1$-$C_{16}$)alkyl substituted with one or more groups selected from the group consisting of —$NR^{b2}R^{c2}$, —$NHNH_2$, —C(=$NR^{a2}$)($NR^{b2}R^{c2}$), —$NR^{a2}$C(=$NR^{a2}$)($R^{d2}$), and —$NR^{a2}$C(=$NR^{a2}$)($NR^{b2}R^{c2}$); or
(b) ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, wherein each ($C_3$-$C_7$)carbocyclyl or ($C_3$-$C_7$)carbocyclyl-($C_1$-$C_4$)alkyl- is independently substituted with one or more groups selected from the group consisting of Z and —($C_1$-$C_6$)alkyl substituted with one or more Z, and wherein each 4-7 membered monocyclic heterocyclyl or 4-7 membered monocyclic heterocyclyl-($C_1$-$C_4$)alkyl- is independently optionally substituted with one or more groups selected from the group consisting of Z and —($C_1$-$C_6$)alkyl substituted with one or more Z, wherein each Z is independently selected from the group consisting of $NR^{b2}R^{c2}$, —$NHNH_2$, —C(=$NR^{a2}$)($NR^{b2}R^{c2}$)—$NR^{a2}$C(=$NR^{a2}$)($R^{d2}$), and —$NR^{a2}$C(=$NR^{a2}$)($NR^{b2}R^{c2}$) and wherein each ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, is independently optionally substituted independently with one or more ($C_1$-$C_4$)alkyl;

$R^3$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of $NR^{a3}R^{b3}$, halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^4$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of $NR^{a3}R^{b3}$, halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^5$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of $NR^{a3}R^{b3}$, halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^6$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of $NR^{a3}R^{b3}$, halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

each $R^{a1}$ is independently hydrogen, ($C_1$-$C_4$)alkyl or ($C_3$-$C_7$)carbocyclyl;

each $R^{a2}$ is independently hydrogen, ($C_1$-$C_4$)alkyl or ($C_3$-$C_7$)carbocyclyl;

each $R^{b2}$ and $R^{c2}$ is independently hydrogen, ($C_1$-$C_4$)alkyl or ($C_3$-$C_7$)carbocyclyl;

$R^{d2}$ is ($C_1$-$C_6$)alkyl or ($C_3$-$C_7$)carbocyclyl; and each $R^{a3}$ and $R^{b3}$ is independently hydrogen $(C_1-C_4)$alkyl or $(C_3-C_7)$carbocyclyl;

or a salt thereof.

One embodiment provides a compound of formula I:

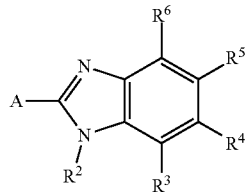

wherein:

A is $-C(=O)N(R^{a1})-R^1$, $-(C_1-C_3)$alkyl-$C(=O)N(R^{a1})R^1$, $-(C_1-C_3)$alkyl-O-R, $-O-R^1$, $-(C_1-C_3)$alkyl-$N(R^{a1})-R^1$, $-N(R^{a1})-R^1$, or $R^1$;

$R^2$ is hydrogen, $(C_1-C_6)$alkyl or phenyl$(C_1-C_6)$alkyl-, wherein the phenyl is optionally substituted with one or more $(C_1-C_6)$alkyl, $-O(C_1-C_6)$alkyl, halogen or $-NO_2$;

each $R^1$ is independently:

(a) $(C_1-C_{16})$alkyl substituted with one or more groups selected from the group consisting of $-NR^{b2}R^{c2}$, $-NHNH_2$, $-C(=NR^{a2})(NR^{b2}R^{c2})$, $-NR^{a2}C(=NR^{a2})(R^{d2})$, and $-NR^{a2}C(=NR^{a2})(NR^{b2}R^{c2})$; or (b) $(C_3-C_7)$carbocyclyl, $(C_3-C_7)$carbocyclyl-$(C_1-C_4)$alkyl-, 4-7 membered monocyclic heterocyclyl, or 4-7 membered monocyclic heterocyclyl-$(C_1-C_4)$alkyl-, wherein each $(C_3-C_7)$carbocyclyl or $(C_3-C_7)$carbocyclyl-$(C_1-C_4)$alkyl- is independently substituted with one or more groups selected from the group consisting of Z and $-(C_1-C_6)$alkyl substituted with one or more Z, and wherein each 4-7 membered monocyclic heterocyclyl or 4-7 membered monocyclic heterocyclyl-$(C_1-C_4)$alkyl- is independently optionally substituted with one or more groups selected from the group consisting of Z and $-(C_1-C_6)$alkyl substituted with one or more Z, wherein each Z is independently selected from the group consisting of $NR^{b2}R^{c2}$, $-NHNH_2$, $-C(=NR^{a2})(NR^{b2}R^{c2})$, $-NR^{a2}C(=NR^{a2})(R^{d2})$, and $-NR^{a2}C(=NR^{a2})(NR^{b2}R^{c2})$ and wherein each $(C_3-C_7)$carbocyclyl, $(C_3-C_7)$carbocyclyl-$(C_1-C_4)$alkyl-, 4-7 membered monocyclic heterocyclyl, or 4-7 membered monocyclic heterocyclyl-$(C_1-C_4)$alkyl-, is independently optionally substituted independently with one or more $(C_1-C_4)$alkyl;

$R^3$ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, $-OH$, $-NO_2$, $-CN$, $(C_1-C_4)$alkyl, $(C_1-C_4)$haloalkyl, $(C_1-C_4)$alkoxy, and $(C_1-C_4)$haloalkoxy;

$R^4$ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, $-OH$, $-NO_2$, $-CN$, $(C_1-C_4)$alkyl, $(C_1-C_4)$haloalkyl, $(C_1-C_4)$alkoxy, and $(C_1-C_4)$haloalkoxy;

$R^5$ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, $-OH$, $-NO_2$, $-CN$, $(C_1-C_4)$alkyl, $(C_1-C_4)$haloalkyl, $(C_1-C_4)$alkoxy, and $(C_1-C_4)$haloalkoxy;

$R^6$ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, $-OH$, $-NO_2$, $-CN$, $(C_1-C_4)$alkyl, $(C_1-C_4)$haloalkyl, $(C_1-C_4)$alkoxy, and $(C_1-C_4)$haloalkoxy;

each $R^{a1}$ is independently hydrogen, $(C_1-C_4)$alkyl or $(C_3-C_7)$carbocyclyl;

each $R^{a2}$ is independently hydrogen, $(C_1-C_4)$alkyl or $(C_3-C_7)$carbocyclyl;

each $R^{b2}$ and $R^{c2}$ is independently hydrogen, $(C_1-C_4)$alkyl or $(C_3-C_7)$carbocyclyl;

$R^{d2}$ is $(C_1-C_6)$alkyl or $(C_3-C_7)$carbocyclyl;

each $R^{a3}$ is independently hydrogen $(C_1-C_4)$alkyl or $(C_3-C_7)$carbocyclyl;

each $R^{b3}$ and $R^{c3}$ is independently hydrogen $(C_1-C_4)$alkyl or $(C_3-C_7)$carbocyclyl; and $R^{d3}$ is $(C_1-C_4)$alkyl or $(C_3-C_7)$carbocyclyl;

or a salt thereof.

One embodiment provides a pharmaceutical composition comprising a compound of formula I or a pharmaceutically acceptable salt thereof as described herein, and a pharmaceutically acceptable vehicle.

One embodiment provides pharmaceutical composition comprising a compound of formula I or a pharmaceutically acceptable salt thereof as described herein, one or more antibacterial agents and a pharmaceutically acceptable vehicle.

One embodiment provides a method of inhibiting a bacterial efflux pump in an animal (e.g., a mammal such as a human) comprising administering to the animal a compound of formula I or a pharmaceutically acceptable salt thereof as described herein.

One embodiment provides a method of inhibiting a bacterial efflux pump in an animal (e.g., a mammal such as a human) comprising administering to the animal in need thereof a compound of formula I or a pharmaceutically acceptable salt thereof as described herein.

One embodiment provides a method of treating or preventing a bacterial infection in an animal (e.g., a mammal such as a human) comprising co-administering to the animal a compound of formula I or a pharmaceutically acceptable salt thereof as described herein and one or more antibacterial agents.

One embodiment provides a method of treating or preventing a bacterial infection in an animal (e.g., a mammal such as a human) comprising co-administering to the animal in need thereof a compound of formula I or a pharmaceutically acceptable salt thereof as described herein and one or more antibacterial agents.

One embodiment provides a method of inhibiting a bacterial efflux pump in an animal (e.g., a mammal such as a human) with a bacterial infection comprising administering to the animal a compound of formula I or a pharmaceutically acceptable salt thereof as described herein.

One embodiment provides a method of treating or preventing a bacterial infection in an animal (e.g., a mammal such as a human) infected with bacteria comprising co-administering to the animal a compound of formula I or a pharmaceutically acceptable salt thereof as described herein and one or more antibacterial agents.

One embodiment provides a compound of formula I or a pharmaceutically acceptable salt thereof as described herein for use in medical treatment.

One embodiment provides a compound of formula I or a pharmaceutically acceptable salt thereof as described herein for the prophylactic or therapeutic inhibition of a bacterial efflux pump for the treatment of a bacterial infection.

One embodiment provides a compound of formula I or a pharmaceutically acceptable salt thereof as described herein which is used in combination with one or more antibacterial agents for the prophylactic or therapeutic treatment of a bacterial infection.

One embodiment provides the use of a compound of formula I or a pharmaceutically acceptable salt thereof as described herein for the preparation of a medicament for inhibiting a bacterial efflux pump.

One embodiment provides the use of a compound of formula I or a pharmaceutically acceptable salt thereof as described herein for the preparation of a medicament for treating a bacterial infection in an animal (e.g., a mammal such as a human).

One embodiment provides the use of a compound of formula I or a pharmaceutically acceptable salt thereof as described herein for the preparation of a medicament which is used in combination with one or more antibacterial agents for treating a bacterial infection in an animal (e.g., a mammal such as a human).

One embodiment provides processes and intermediates disclosed herein that are useful for preparing compounds of formula I or salts thereof.

DETAILED DESCRIPTION

The following definitions are used, unless otherwise described: halo or halogen is fluoro, chloro, bromo, or iodo. Alkyl and alkoxy, etc. denote both straight and branched groups but reference to an individual radical such as propyl embraces only the straight chain radical (a branched chain isomer such as isopropyl being specifically referred to).

As used herein, the term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

The term "aryl" as used herein refers to a single aromatic ring or a multiple condensed ring system wherein the ring atoms are carbon. For example, an aryl group can have 6 to 10 carbon atoms, or 6 to 12 carbon atoms. Aryl includes a phenyl radical. Aryl also includes multiple condensed ring systems (e.g., ring systems comprising 2 rings) having about 9 to 12 carbon atoms or 9 to 10 carbon atoms in which at least one ring is aromatic. Such multiple condensed ring systems may be optionally substituted with one or more (e.g., 1 or 2) oxo groups on any cycloalkyl portion of the multiple condensed ring system. It is to be understood that the point of attachment of a multiple condensed ring system, as defined above, can be at any position of the ring system including an aryl or a cycloalkyl portion of the ring. Typical aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 rings) wherein a heteroaryl group, as defined above, can be condensed with one or more heteroaryls (e.g., naphthyridinyl), heterocycles, (e.g., 1, 2, 3, 4-tetrahydronaphthyridinyl), cycloalkyls (e.g., 5,6,7,8-tetrahydroquinolyl) or aryls (e.g. indazolyl) to form a multiple condensed ring system. Such multiple condensed ring systems may be optionally substituted with one or more (e.g., 1 or 2) oxo groups on the cycloalkyl or heterocycle portions of the condensed ring. In one embodiment a monocyclic or bicyclic heteroaryl has 5 to 10 ring atoms comprising 1 to 9 carbon atoms and 1 to 4 heteroatoms. It is to be understood that the point of attachment of a multiple condensed ring system (as defined above for a heteroaryl) can be at any position of the multiple condensed ring system including a heteroaryl, heterocycle, aryl or cycloalkyl portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl and thianaphthenyl.

The term "heterocyclyl" or "heterocycle" as used herein refers to a single saturated or partially unsaturated ring or a multiple condensed ring system. The term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. It is to be understood that the point of attachment for a heterocycle can be at any suitable atom of the heterocycle. Exemplary heterocycles include, but are not limited to, aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl and tetrahydrothiopyranyl.

The term "haloalkyl" includes an alkyl group as defined herein that is substituted with one or more (e.g., 1, 2, 3, or 4) halo groups. One specific halo alkyl is a "$(C_1-C_6)$haloalkyl".

The term cycloalkyl, carbocycle, or carbocyclyl includes saturated and partially unsaturated carbocyclic ring systems. In one embodiment the cycloalkyl is a monocyclic carbocyclic ring. Such cycloalkyls include "$(C_3-C_7)$carbocyclyl" and "$(C_3-C_5)$cycloalkyl".

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_3-C_8)$cycloalkyl can be cyclopropyl, cyclobutyl, cyclopentyl, or cyclohexyl; $(C_1-C_6)$haloalkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; aryl can be phenyl, indenyl, or naphthyl; and heteroaryl can be furyl, imidazolyl, triazolyl, triazinyl, oxazolyl, isoxazolyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

It is to be understood that the embodiments provided below are for compounds of formula I and all sub-formulas thereof (e.g., formula Ia). It is to be understood the two or more embodiments may be combined.

In one embodiment the compound of formula I is a compound of formula Ia

Ia or a salt thereof.

In one embodiment A is —C(=O)N($R^{a1}$)—$R^1$, —($C_1$-$C_3$)alkyl-C(=O)N($R^{a1}$)$R^1$, or $R^1$.

In one embodiment A is —C(=O)N($R^{a1}$)—$R^1$.

In one embodiment A is —($C_1$-$C_3$)alkyl-C(=O)N($R^{a1}$)$R^1$.

In one embodiment $R^{a1}$ is hydrogen.

In one embodiment A is $R^1$.

In one embodiment $R^2$ is hydrogen, ($C_1$-$C_6$)alkyl or phenyl($C_1$-$C_6$)alkyl-, wherein the phenyl is optionally substituted with one or more ($C_1$-$C_6$)alkyl, —O($C_1$-$C_6$)alkyl, halogen or —$NO_2$;

In one embodiment $R^2$ is hydrogen or ($C_1$-$C_6$)alkyl.

In one embodiment $R^2$ is hydrogen, methyl, or 4-fluorobenzyl.

In one embodiment $R^2$ is hydrogen or methyl.

In one embodiment $R^2$ is hydrogen, methyl, 4-fluorobenzyl, benzyl, or 2-fluoro-5-nitrobenzyl.

In one embodiment $R^3$ is hydrogen, halo, ($C_1$-$C_4$)alkyl, ($C_1$-$C_4$)haloalkyl, or ($C_1$-$C_4$)alkoxy.

In one embodiment $R^3$ is hydrogen, ($C_1$-$C_4$)haloalkyl, or aryl wherein the aryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^3$ is hydrogen, ($C_1$-$C_4$)haloalkyl, or phenyl wherein the phenyl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^3$ is hydrogen, ($C_1$-$C_4$)haloalkyl, or aryl wherein the aryl is optionally substituted with one or more groups independently selected from the group consisting of $NR^{a3}R^{b3}$, halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^3$ is hydrogen, ($C_1$-$C_4$)haloalkyl, or phenyl wherein the phenyl is optionally substituted with one or more groups independently selected from the group consisting of $NR^{a3}R^{b3}$, halo, —OH, —$NO_2$, —CN, ($C_1$-$C_4$) alkyl, ($C_1$-$C_4$)haloalkyl, ($C_1$-$C_4$)alkoxy, and ($C_1$-$C_4$)haloalkoxy.

In one embodiment $R^3$ is hydrogen, trifluoromethyl or 4-fluorophenyl.

In one embodiment $R^4$ is hydrogen, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is hydrogen or aryl wherein the aryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is hydrogen or phenyl wherein the phenyl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is hydrogen, aryl, or heteroaryl wherein the aryl or heteroaryl is optionally substituted with one or more groups independently selected from the group consisting of $NR^{a3}R^{b3}$, halo, —OH, —$NO_2$, —CN, ($C_1$-$C_4$) alkyl, ($C_1$-$C_4$)haloalkyl, ($C_1$-$C_4$)alkoxy, and ($C_1$-$C_4$)haloalkoxy.

In one embodiment $R^4$ is hydrogen or aryl wherein the aryl is optionally substituted with one or more groups independently selected from the group consisting of $NR^{a3}R^{b3}$, halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is hydrogen or phenyl wherein the phenyl is optionally substituted with one or more groups independently selected from the group consisting of $NR^{a3}R^{b3}$, halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is hydrogen or 4-fluorophenyl.

In one embodiment $R^4$ is hydrogen, 4-fluorophenyl, 4-aminophenyl, 4-nitrophenyl, 3,4-difluorophenyl, or 4-methoxyphenyl.

In one embodiment $R^5$ is hydrogen, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^5$ is hydrogen or aryl wherein the aryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^5$ is hydrogen or phenyl wherein the phenyl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^5$ is hydrogen, aryl, or heteroaryl wherein the aryl or heteroaryl is optionally substituted with one or more groups independently selected from the group consisting of $NR^{a3}R^{b3}$, halo, —OH, —$NO_2$, —CN, ($C_1$-$C_4$) alkyl, ($C_1$-$C_4$)haloalkyl, ($C_1$-$C_4$)alkoxy, and ($C_1$-$C_4$)haloalkoxy.

In one embodiment $R^5$ is hydrogen or aryl wherein the aryl is optionally substituted with one or more groups independently selected from the group consisting of $NR^{a3}R^{b3}$, halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^5$ is hydrogen or phenyl wherein the phenyl is optionally substituted with one or more groups independently selected from the group consisting of $NR^{a3}R^{b3}$, halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^5$ is hydrogen or 4-fluorophenyl, 4-trifluormethylphenyl, 4-methoxyphenyl.

In one embodiment $R^5$ is hydrogen, 4-fluorophenyl, 4-trifluormethylphenyl, 4-methoxyphenyl, 3-cyanophenyl, bromo, 4-nitrophenyl, or 3,4-difluorophenyl.

In one embodiment $R^6$ is hydrogen, halo, ($C_1$-$C_4$)alkyl, ($C_1$-$C_4$)haloalkyl, or ($C_1$-$C_4$)alkoxy.

In one embodiment $R^6$ is hydrogen.

In one embodiment $R^4$ is halo, ($C_1$-$C_4$)alkyl, ($C_1$-$C_4$) haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)

alkyl, ($C_1$-$C_4$)haloalkyl, ($C_1$-$C_4$)alkoxy, and ($C_1$-$C_4$)haloalkoxy; and $R^5$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy; and $R^5$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is aryl, wherein the aryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy; and $R^5$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is aryl, wherein the aryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy; and $R^5$ is hydrogen or aryl, wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy; and $R^5$ is halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy; and $R^5$ aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy; and $R^5$ aryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is hydrogen or aryl, wherein the aryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy; and $R^5$ is aryl, wherein the aryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^1$ is:

(a) ($C_2$-$C_{10}$)alkyl substituted with one or more groups selected from the group consisting of —$NR^{b2}R^{c2}$; or (b) 4-7 membered monocyclic heterocyclyl-($C_1$-$C_4$)alkyl-, wherein the 4-7 membered monocyclic heterocyclyl-($C_1$-$C_4$)alkyl- is independently optionally substituted with one or more groups selected from the group consisting of Z and —($C_1$-$C_6$)alkyl substituted with one or more Z, wherein each Z is independently $NR^{b2}R^{c2}$.

In one embodiment $R^1$ is:

(a) ($C_3$-$C_5$)alkyl substituted with one or more groups selected from the group consisting of —$NR^{b2}R^{c2}$; or (b) pyrrolidinyl-($C_1$-$C_4$)alkyl-, wherein the pyrrolidinyl-($C_1$-$C_4$)alkyl- is independently optionally substituted with one or more groups selected from the group consisting of Z and —($C_1$-$C_6$)alkyl substituted with one or more Z, wherein each Z is independently $NR^{b2}R^{c2}$.

In one embodiment $R^1$ is:

(a) ($C_3$-$C_8$)alkyl substituted with one or more groups selected from the group consisting of —$NR^{b2}R^{c2}$; or (b pyrrolidinyl-($CH_2$)—, wherein the pyrrolidinyl-($CH_2$)— is independently optionally substituted with one or more groups selected from the group consisting of Z and —($C_1$-$C_6$)alkyl substituted with one or more Z, wherein each Z is independently $NR^{b2}R^{c2}$.

In one embodiment each $R^{b2}$ and $R^{c2}$ is hydrogen

In one embodiment $R^1$ is:

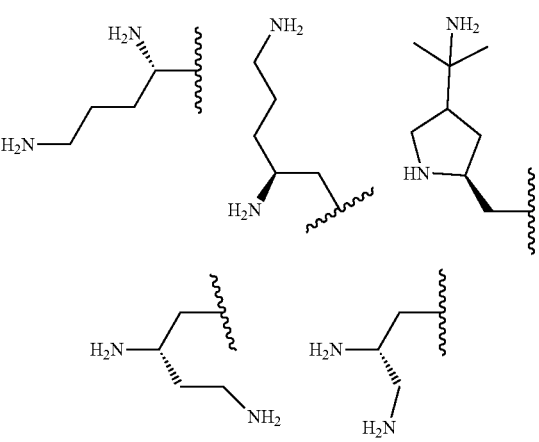

-continued
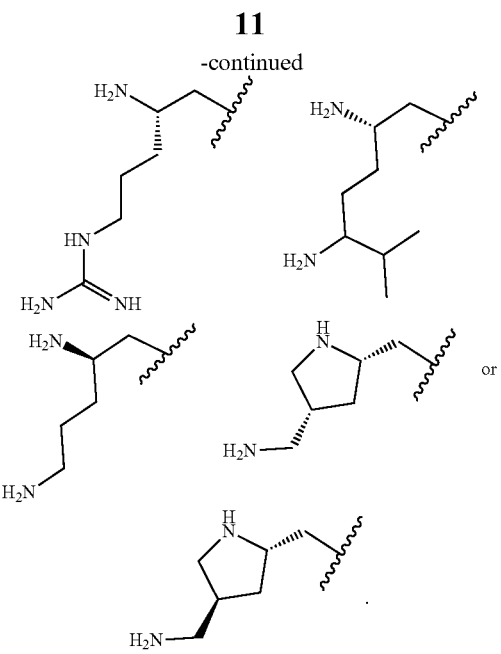
In one embodiment A is:
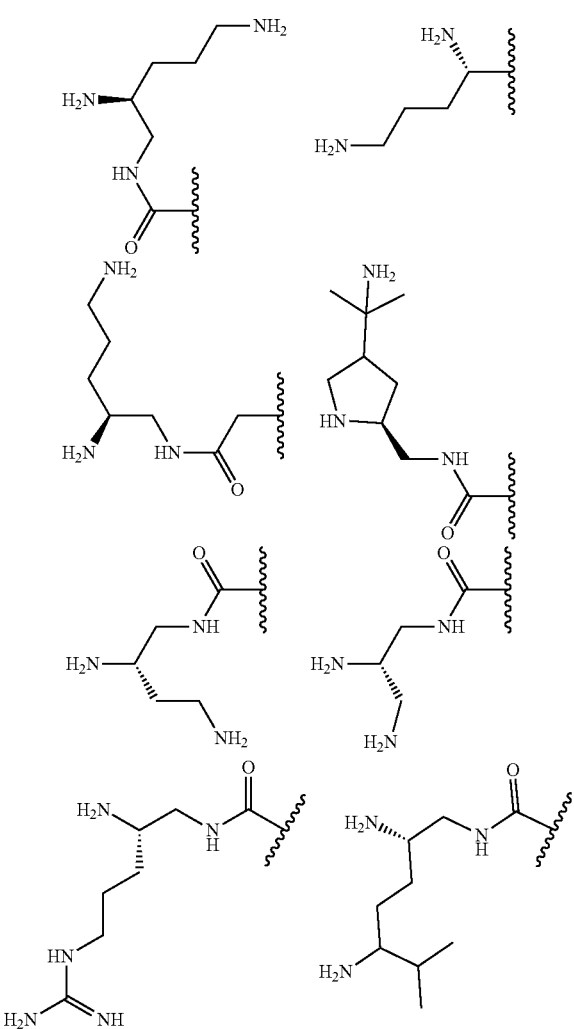
-continued
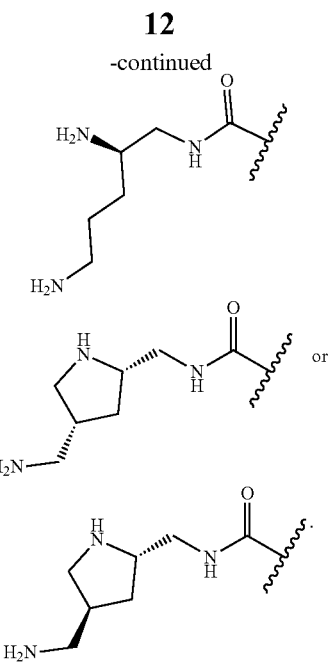
One embodiment provides a compound that is:
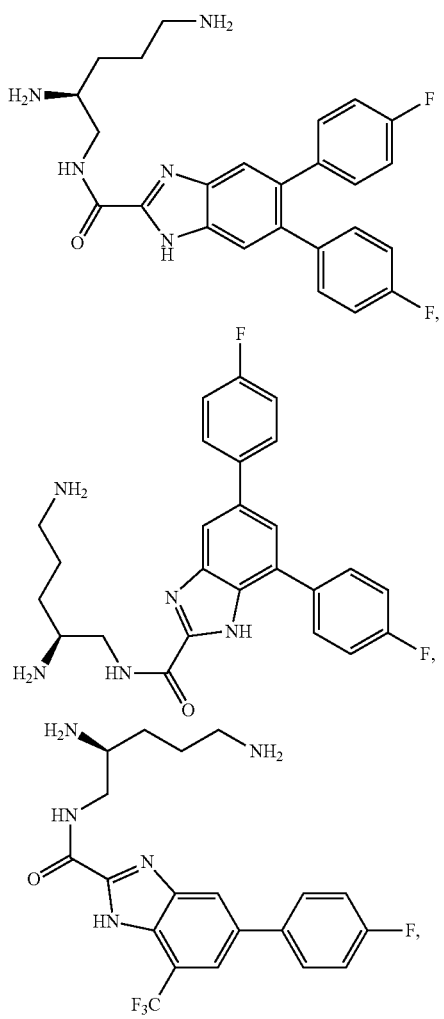

-continued
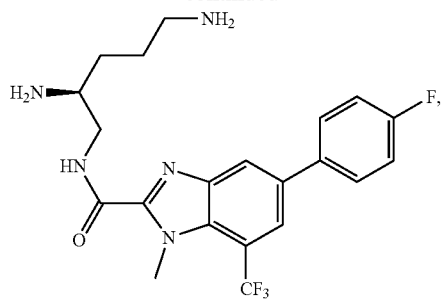
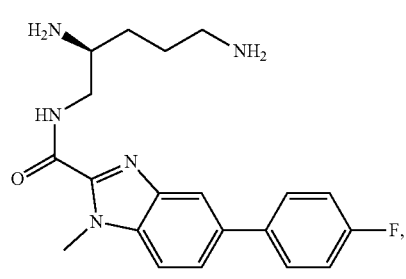
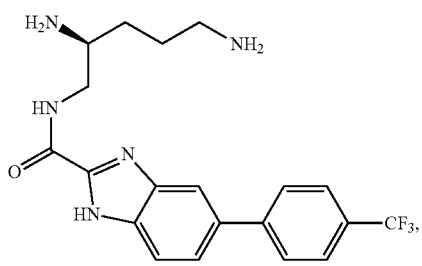
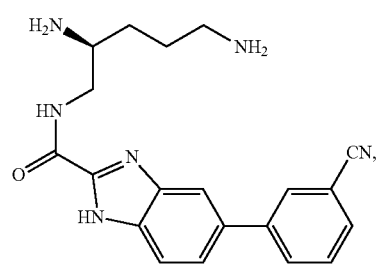
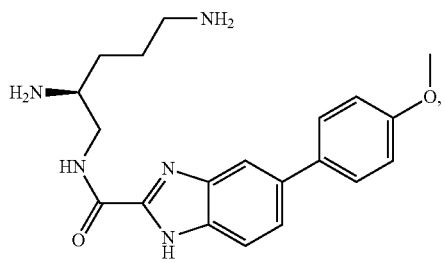
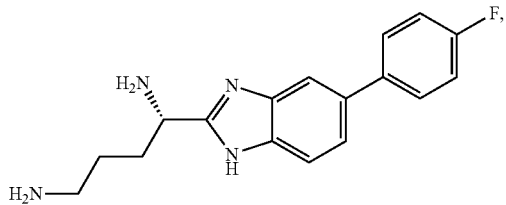
-continued
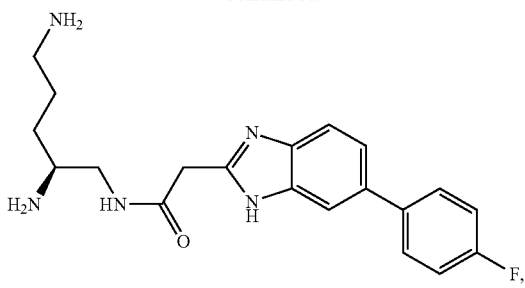
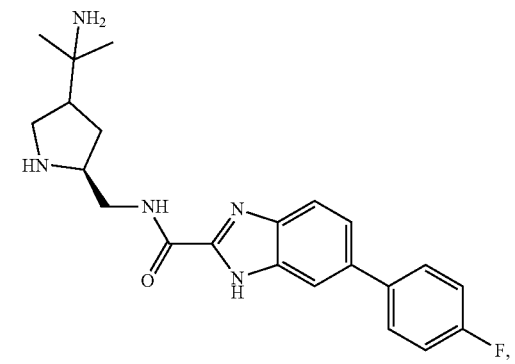
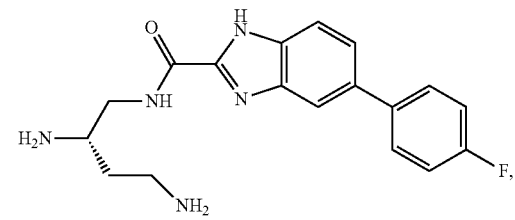
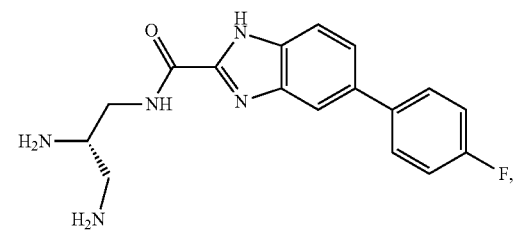
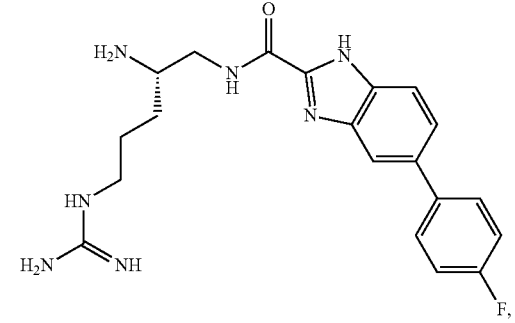
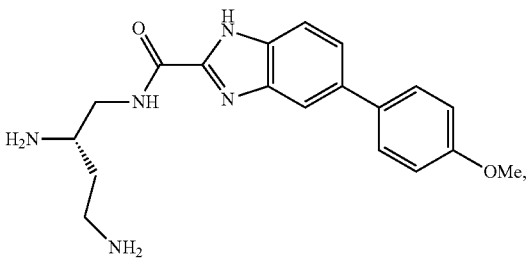

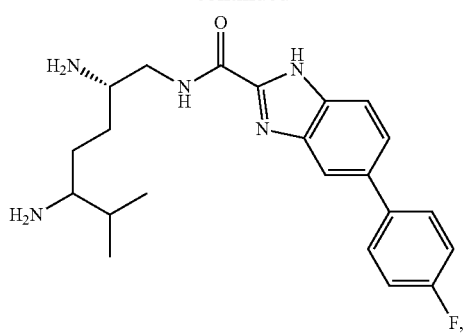
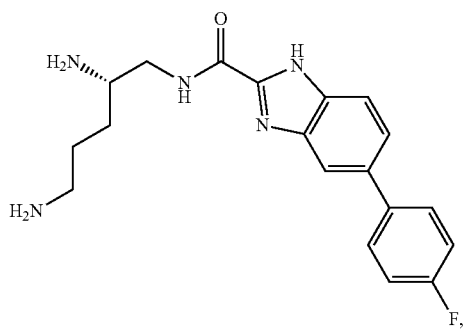
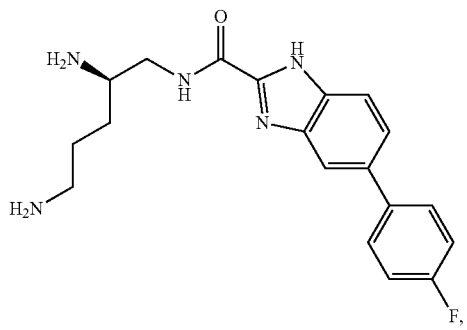
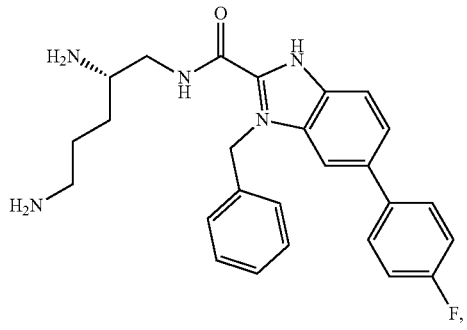
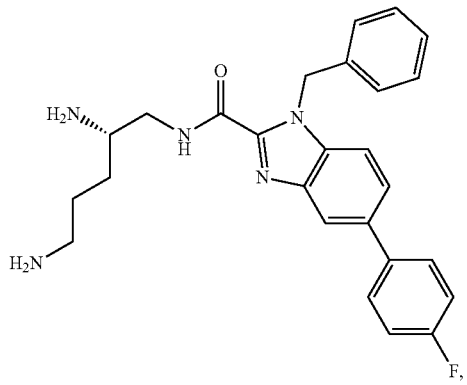
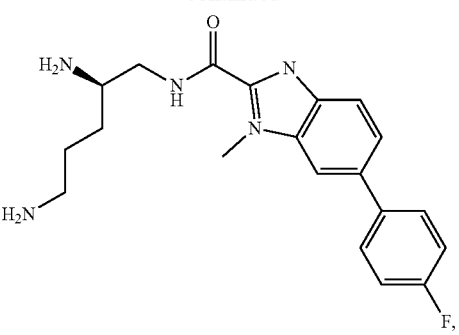
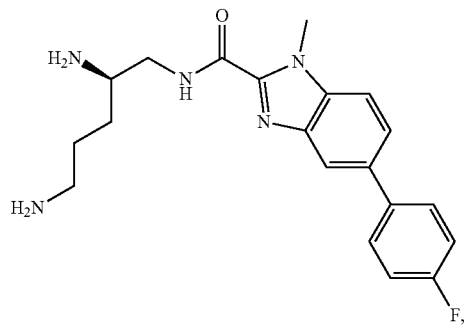
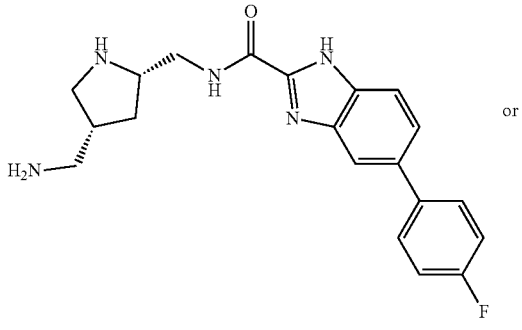
or
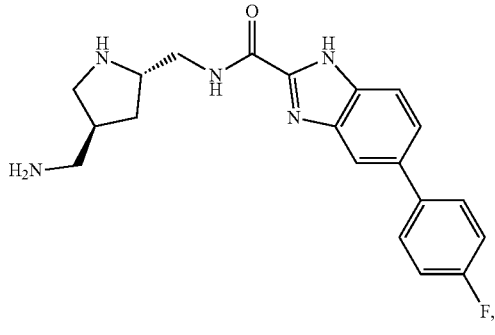
or a salt thereof.
One embodiment provides a compound that is:
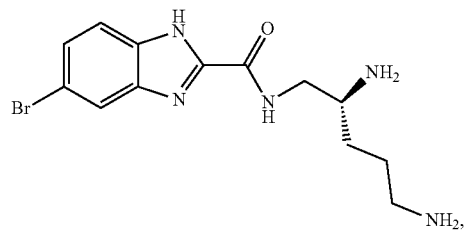

17
-continued
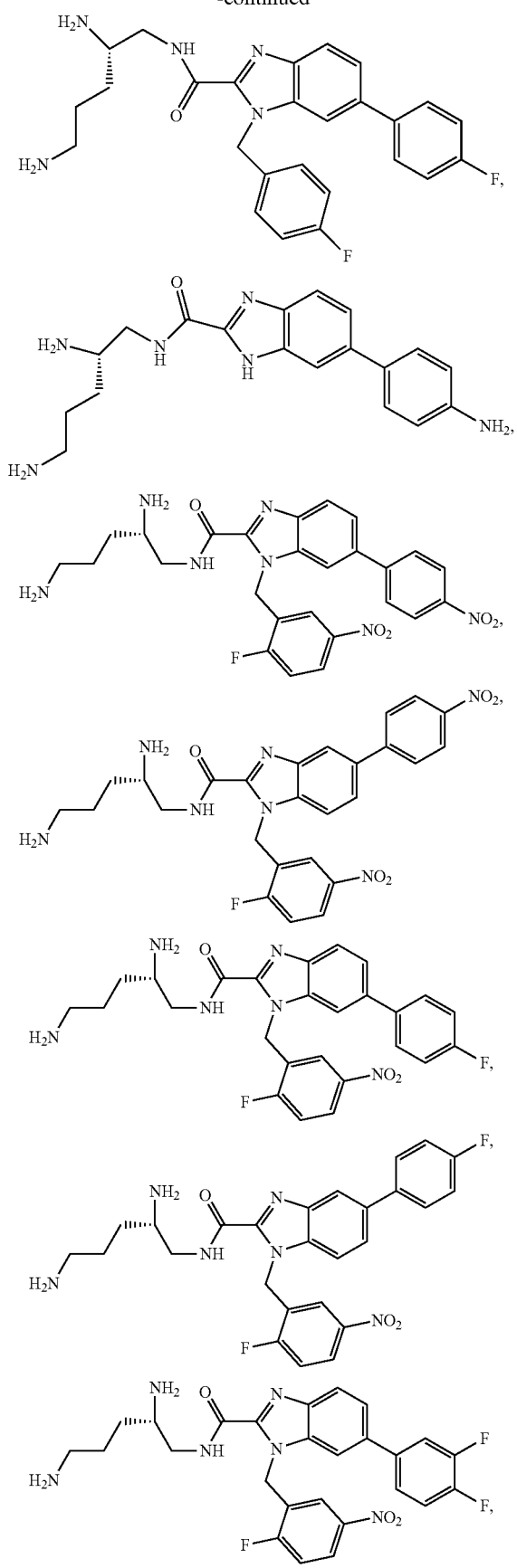
18
-continued
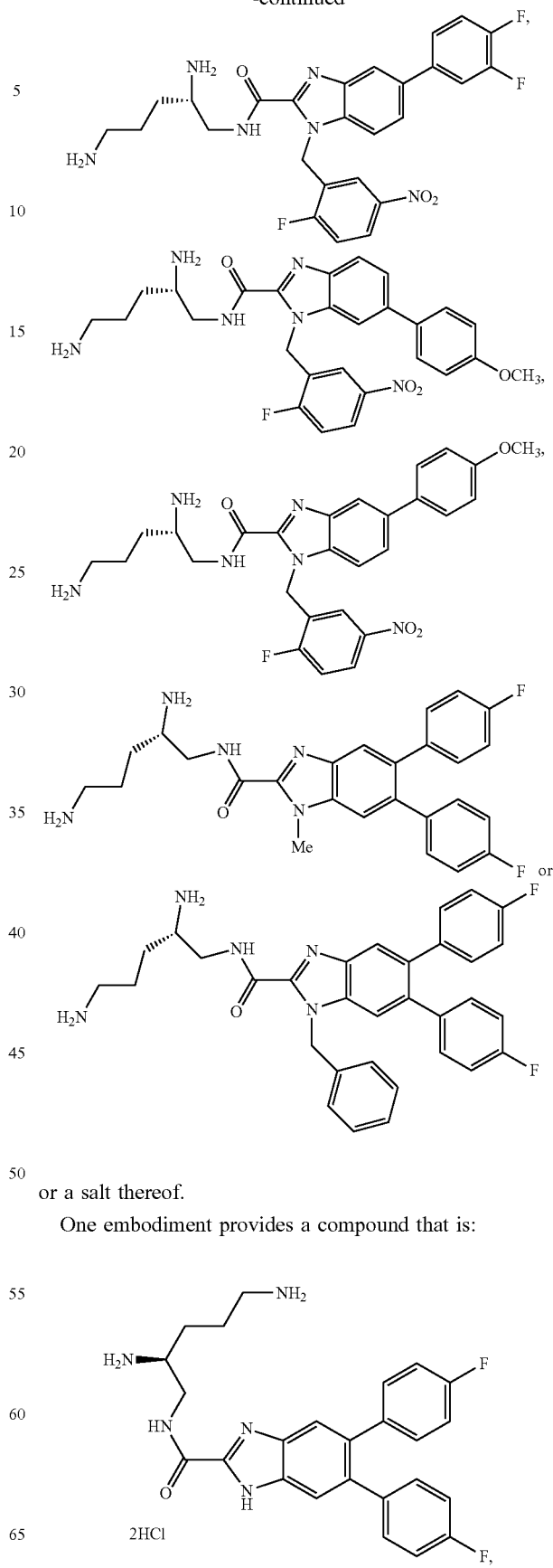
or a salt thereof.
One embodiment provides a compound that is:

-continued
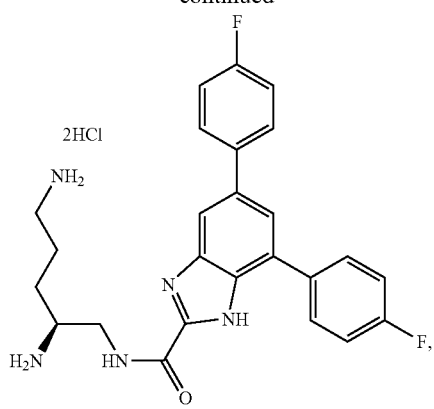
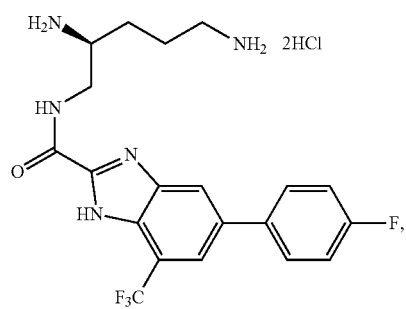
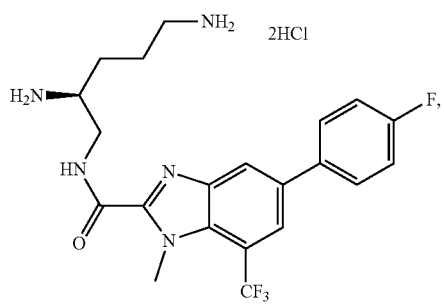
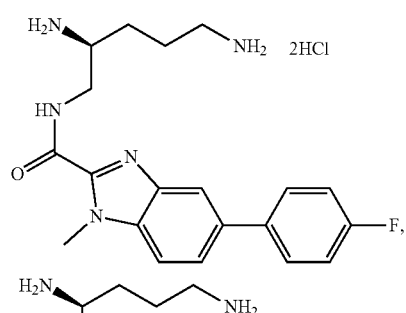
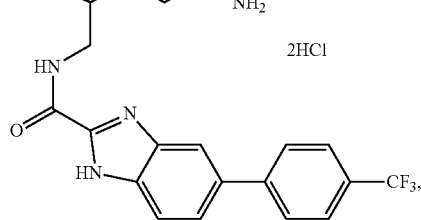
-continued
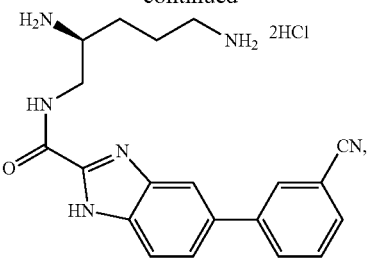
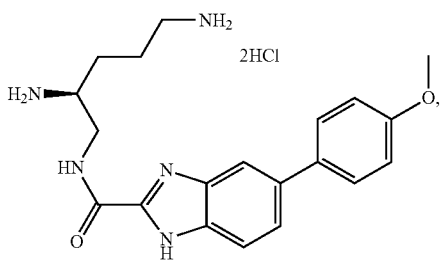
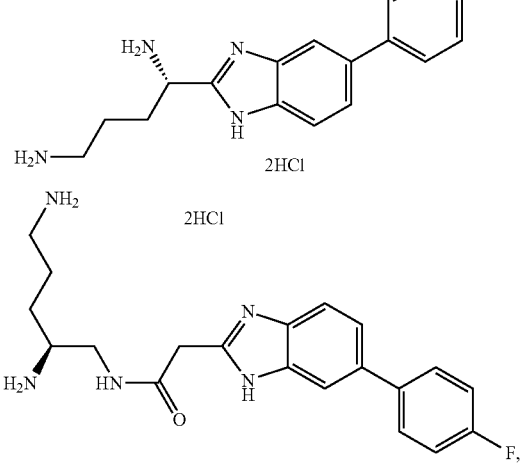
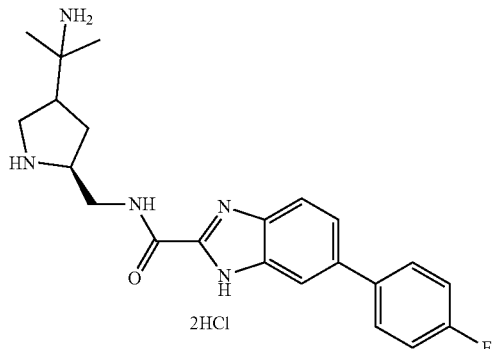
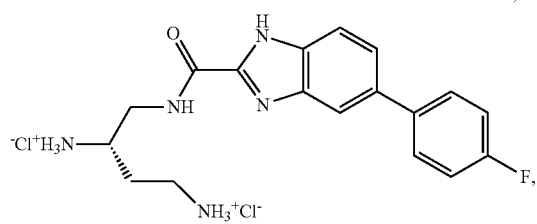

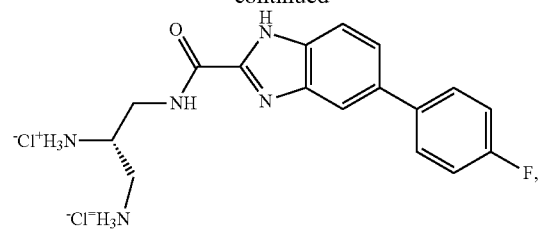
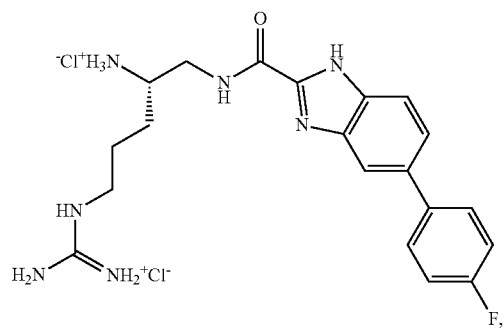
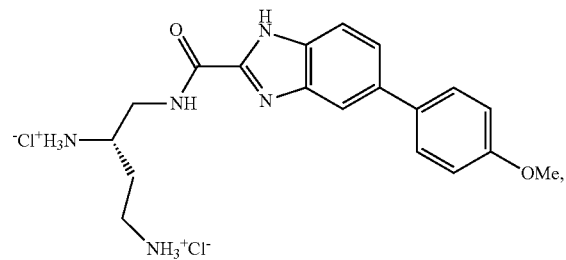
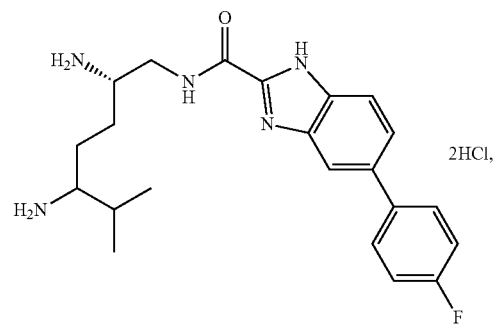
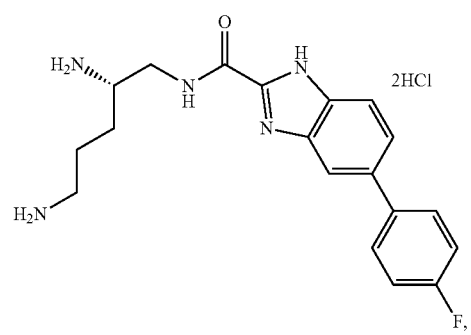
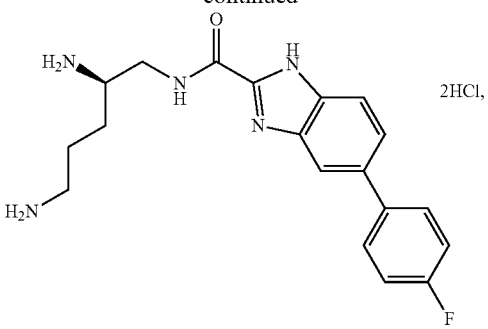
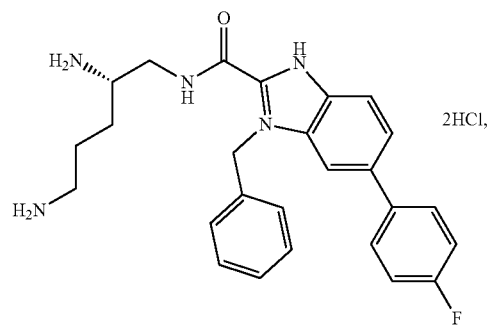
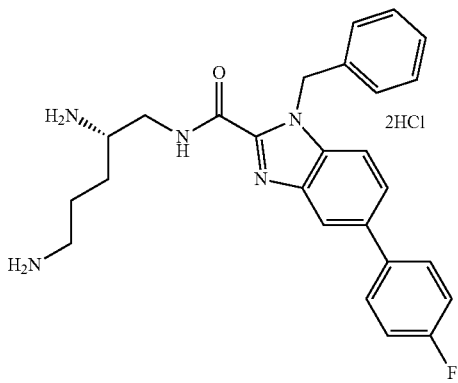
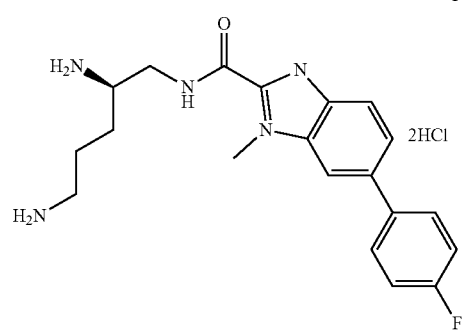
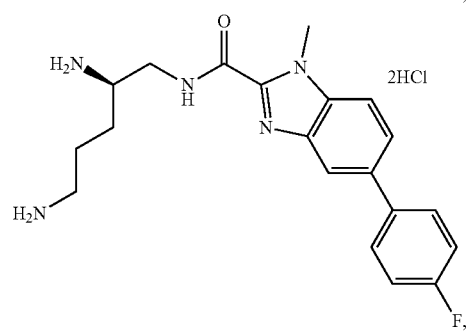

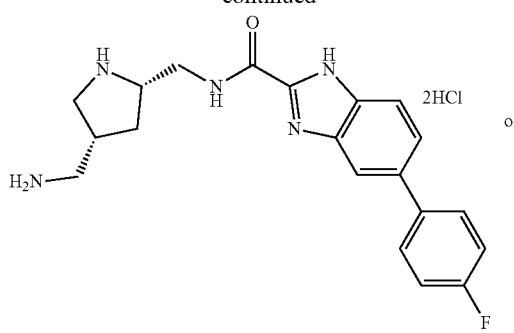
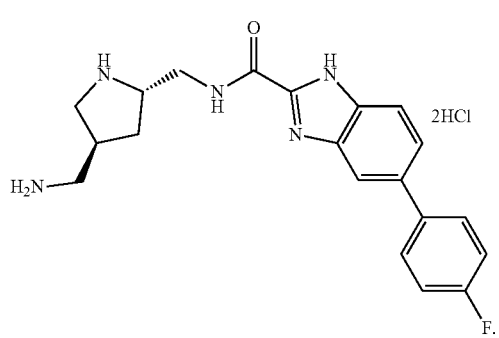
One embodiment provides a compound that is:
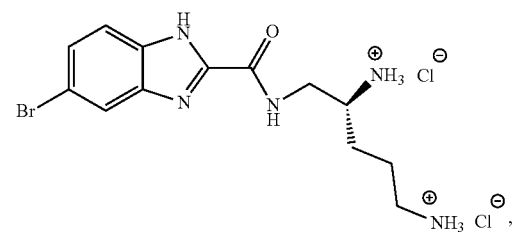
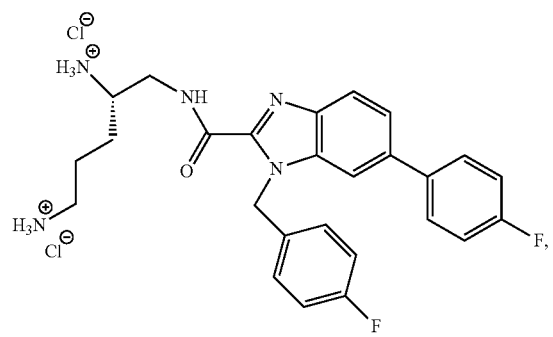
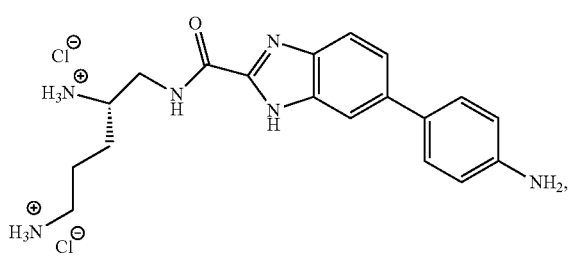
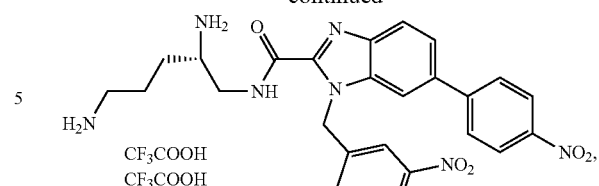
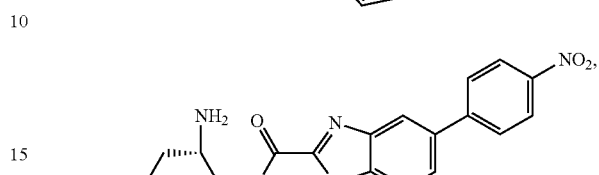
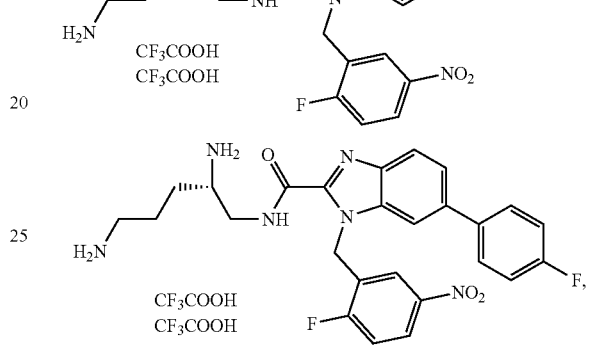
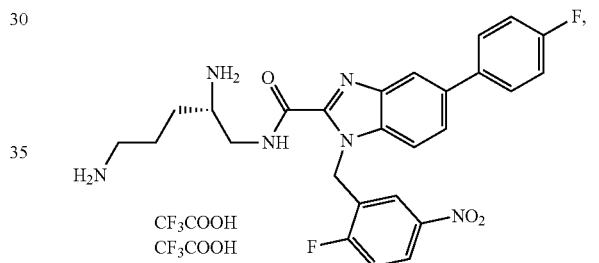
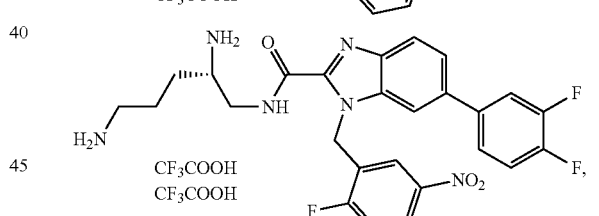
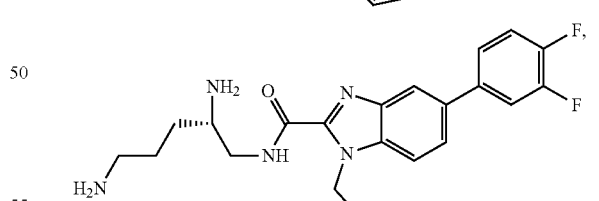
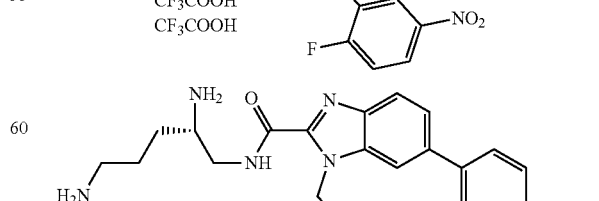
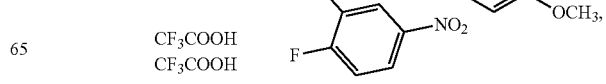

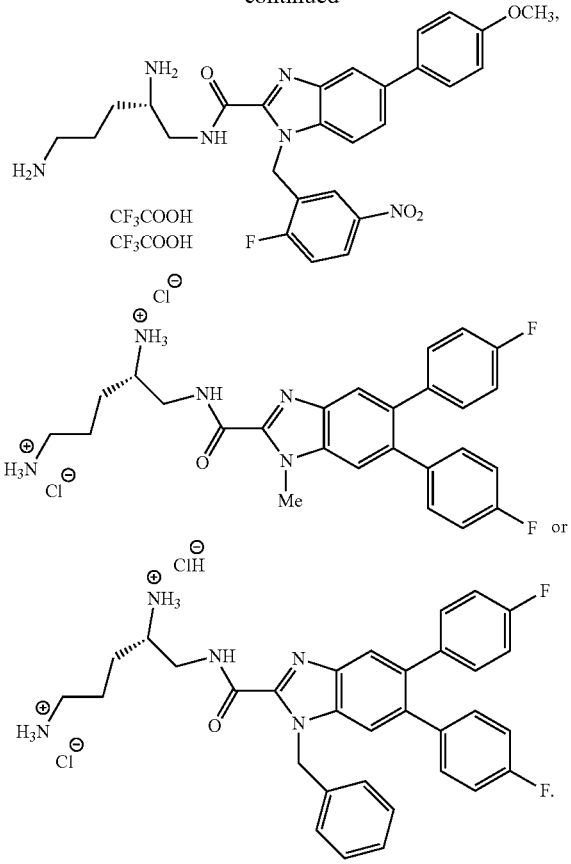

One embodiment provides a compound of formula I:

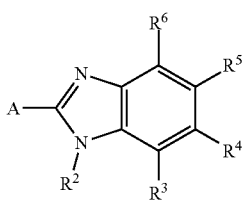

wherein:

A is —C(=O)N($R^{a1}$)—$R^1$, —($C_1$-$C_3$)alkyl-C(=O)N($R^{a1}$)$R^1$, —($C_1$-$C_3$)alkyl-O—$R^1$, —O—$R^1$, —($C_1$-$C_3$)alkyl-N($R^{a1}$)—$R^1$, —N($R^{a1}$)—$R^1$, or $R^1$;

$R^2$ is hydrogen, ($C_1$-$C_6$)alkyl or phenyl($C_1$-$C_6$)alkyl-, wherein the phenyl is optionally substituted with one or more ($C_1$-$C_6$)alkyl, —O($C_1$-$C_6$)alkyl, halogen or —$NO_2$;

each $R^1$ is independently:

(a) ($C_1$-$C_{16}$)alkyl substituted with one or more groups selected from the group consisting of —$NR^{b2}R^{c2}$, —$NHNH_2$, —C(=$NR^{a2}$)($NR^{b2}R^{c2}$), —$NR^{a2}$C(=$NR^{a2}$)($R^{d2}$), and —$NR^{a2}$C(=$NR^{a2}$)($NR^{b2}R^{c2}$); or (b) ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, wherein each ($C_3$-$C_7$)carbocyclyl or ($C_3$-$C_7$)carbocyclyl-($C_1$-$C_4$)alkyl- is independently substituted with one or more groups selected from the group consisting of Z and —($C_1$-$C_6$)alkyl substituted with one or more Z, and wherein each 4-7 membered monocyclic heterocyclyl or 4-7 membered monocyclic heterocyclyl-($C_1$-$C_4$)alkyl- is independently optionally substituted with one or more groups selected from the group consisting of Z and —($C_1$-$C_6$)alkyl substituted with one or more Z, wherein each Z is independently selected from the group consisting of $NR^{b2}R^{c2}$, —$NHNH_2$, —C(=$NR^{a2}$)($NR^{b2}R^{c2}$), —$NR^{a2}$C(=$NR^{a2}$)($R^{d2}$), and —$NR^{a2}$C(=$NR^{a2}$)($NR^{b2}R^{c2}$) and wherein each ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, is independently optionally substituted independently with one or more ($C_1$-$C_4$)alkyl;

$R^3$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^4$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^5$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^6$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

each $R^{a1}$ is independently hydrogen, ($C_1$-$C_4$)alkyl or ($C_3$-$C_7$)carbocyclyl;

each $R^{a2}$ is independently hydrogen, ($C_1$-$C_4$)alkyl or ($C_3$-$C_7$)carbocyclyl;

each $R^{b2}$ and $R^{c2}$ is independently hydrogen, ($C_1$-$C_4$)alkyl or ($C_3$-$C_7$)carbocyclyl; and $R^{d2}$ is ($C_1$-$C_6$)alkyl or ($C_3$-$C_7$)carbocyclyl;

or a salt thereof.

One embodiment provides a method for identifying a test compound capable of inhibiting a bacterial efflux inhibitor, comprising 1) contacting bacteria with a sub-inhibitory concentration of an antibiotic;
2) contacting the bacteria, either sequentially or simultaneously, with a) an inhibitory concentration of the antibiotic; and b) a test compound; and
3) quantifying the minimum inhibitory concentration (MIC) of the antibiotic, wherein a MIC that is lower than the intrinsic MIC of the antibiotic alone indicates the test compound is effective to inhibit a bacterial efflux pump inhibitor.

In certain embodiments, steps 1 and 2 are separated by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, 44, 45, 46, 47 or 48 hours. In certain embodiments, steps 1 and 2 are separated by about 12 hours. In certain embodiments, steps 1 and 2 are separated by about 24 hours.

One embodiment provides a method for identifying a test compound capable of inhibiting a bacterial efflux inhibitor, comprising 1) contacting bacteria with a sub-inhibitory concentration of an antibiotic;
2) contacting a first subset of the bacteria with an inhibitory concentration of the antibiotic;
3) contacting a second subset of the bacteria, either sequentially or simultaneously, with a) an inhibitory concentration of the antibiotic; and b) a test compound; and
4) quantifying the minimum inhibitory concentration (MIC) of the antibiotic for the first subset of bacteria and the second subset of bacteria, wherein a lower MIC in the second subset indicates the test compound is effective to inhibit a bacterial efflux pump inhibitor.

In certain embodiments, steps 1 and 2 and/or 1 and 3 are separated by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, 44, 45, 46, 47 or 48 hours. In certain embodiments, steps 1 and 2 are separated by about 12 hours. In certain embodiments, steps 1 and 2 are separated by about 24 hours. In certain embodiments, steps 1 and 3 are separated by about 12 hours. In certain embodiments, steps 1 and 3 are separated by about 24 hours. In certain embodiments, steps 2 and 3 are performed at substantially the same time (e.g., at about less than 10, 30, 60, 90 or 120 seconds apart, or about 3, 4 or 5 minutes apart).

One embodiment provides a method for identifying a test compound capable of lowering the minimum inhibitory concentration (MIC) of an antibiotic, comprising
1) contacting bacteria with a sub-inhibitory concentration of the antibiotic;
2) contacting the bacteria, either sequentially or simultaneously, with a) an inhibitory concentration of the antibiotic; and b) the test compound; and
3) quantifying the minimum inhibitory concentration (MIC) of the antibiotic, wherein a MIC that is lower than the intrinsic MIC of the antibiotic indicates the test compound is effective to lower the MIC of the antibiotic.

In certain embodiments, steps 1 and 2 are separated by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, 44, 45, 46, 47 or 48 hours. In certain embodiments, steps 1 and 2 are separated by about 12 hours. In certain embodiments, steps 1 and 2 are separated by about 24 hours.

One embodiment provides a method for identifying a test compound capable of lowering the minimum inhibitory concentration (MIC) of an antibiotic, comprising
1) contacting bacteria with a sub-inhibitory concentration of an antibiotic;
2) contacting a first subset of the bacteria with an inhibitory concentration of the antibiotic;
3) contacting a second subset of the bacteria, either sequentially or simultaneously, with a) an inhibitory concentration of the antibiotic; and b) a test compound; and
4) quantifying the minimum inhibitory concentration (MIC) of the antibiotic for the first subset of bacteria and the second subset of bacteria, wherein a lower MIC in the second subset indicates the test compound is effective to lower the MIC of the antibiotic.

In certain embodiments, steps 1 and 2 and/or 1 and 3 are separated by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, 44, 45, 46, 47 or 48 hours. In certain embodiments, steps 1 and 2 are separated by about 12 hours. In certain embodiments, steps 1 and 2 are separated by about 24 hours. In certain embodiments, steps 1 and 3 are separated by about 12 hours. In certain embodiments, steps 1 and 3 are separated by about 24 hours. In certain embodiments, steps 2 and 3 are performed at substantially the same time (e.g., at about less than 10, 30, 60, 90 or 120 seconds apart, or about 3, 4 or 5 minutes apart).

Such methods may also be used to determine synergy between a test compound and an antibiotic.

As used herein, the term "minimum inhibitory concentration (MIC)" refers to the lowest concentration of a compound (e.g., an antibiotic) that prevents visible growth of a bacterium (most commonly by 90%). Assays for measuring the MIC of a compound are known in the art, for example, as described herein. As used herein, the term "intrinsic MIC" refers the MIC of a compound (e.g., an antibiotic) for the particular bacterial species that has not been pre-exposed to the compound.

As used herein, the term "sub-inhibitory concentration" refers to a concentration of the antibiotic that does not reduce the visible growth of the bacteria. In certain embodiments, the sub-inhibitory concentration is ½×MIC of the antibiotic. In certain embodiments, the sub-inhibitory concentration of the antibiotic is a concentration that is capable of inducing the expression of one or more efflux pumps in the bacteria.

As used herein, the term "inhibitory concentration" refers to a concentration of the antibiotic that reduces the visible growth of the bacteria. In certain embodiments, this concentration is the intrinsic MIC of the antibiotic.

In certain embodiments, the bacteria are a species of bacteria described herein. In certain embodiments, the bacteria are *P. aeruginosa*.

In certain embodiments, the antibiotic is an antibiotic described herein. In certain embodiments, the antibiotic is cefepime, clarithromycin, or levofloxacin.

In certain embodiments, the test compound is a compound described herein, such as a compound of formula I, an efflux pump inhibitor (EPI), etc.

One embodiment provides a method of identifying a combination of a test compound and an antibiotic that is capable of treating septicemia in an animal comprising:
1) administering the test compound to the animal intravenously;
2) administering the antibiotic to the animal either orally or intravenously;
3) administering the test compound to the animal subcutaneously;
4) administering the antibiotic to the animal either orally or intravenously; and
5) evaluating the animal for symptoms of septicemia, wherein a reduction in symptoms indicates the combination is effective to treat septicemia.

In certain embodiments, each administration is independently separated by approximately about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or 60 min. In certain embodiments, each administration is separated by about 5 minutes.

In certain embodiments, the method further comprises repeating steps 1-4. For example, in certain embodiments, steps 1-4 are repeated 24 hours after the antibiotic has been administered for the second time.

In certain embodiments, the combination of the test compound and antibiotic is a synergistic combination.

In certain embodiments, the animal is a non-human animal. For example, in certain embodiments, the animal is a mouse.

In certain embodiments, the antibiotic is an antibiotic described herein. In certain embodiments, the antibiotic is cefepime, clarithromycin, or levofloxacin.

In certain embodiments, the antibiotic is a cephalosporin.

In certain embodiments, the test compound is a compound described herein, such as a compound of formula I, an efflux pump inhibitor (EPI), etc.

One embodiment provides a method described herein for identifying a compound capable of inhibiting a bacterial efflux pump inhibitor (e.g., using an assay described in the Examples).

Generally, compounds of formula I as well as synthetic intermediates that can be used for preparing compounds of formula I can be prepared as illustrated in the following General Methods and Schemes. It is understood that variable groups shown below (e.g., $R^1$, $R^2$, $R^3$, $R^4$, $R^5$, $R^6$) can represent the final corresponding groups present in a compound of formula I or that these groups can represent groups that can be converted to the final corresponding groups present in a compound of formula I at a convenient point in a synthetic sequence. For example, the variable groups can contain one or more protecting groups that can be removed at a convenient point in a synthetic sequence to provide the final corresponding groups in the compound of formula I.

Generally, compounds of formula I as well as synthetic intermediates that can be used for preparing compounds of formula I can be prepared as illustrated in the following general scheme. It is understood that variable groups shown below (e.g., $R^2$, $R^3$, $R^4$, $R^5$, $R^6$) can represent the final corresponding groups present in a compound of formula I or that these groups can represent groups that can be converted to the final corresponding groups present in a compound of formula I at a convenient point in a synthetic sequence. For example, the variable groups can contain one or more protecting groups that can be removed at a convenient point in a synthetic sequence to provide the final corresponding groups in the compound of formula I.

Schemes 1 and 2 illustrate some general methods for the preparation of certain compounds of formula I.

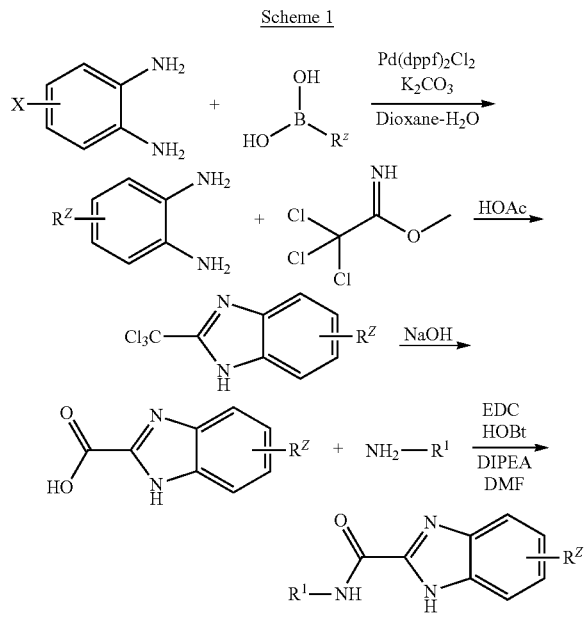

(X is an appropriate group (e.g., halogen) for coupling with the boronic acid and $R^z$ corresponds to any of $R^3$, $R^4$, $R^5$ or $R^6$)

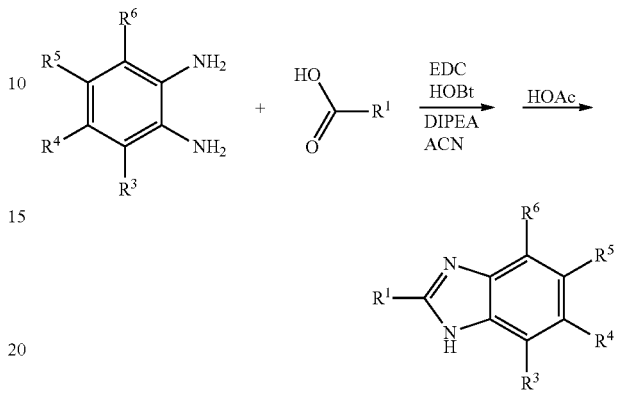

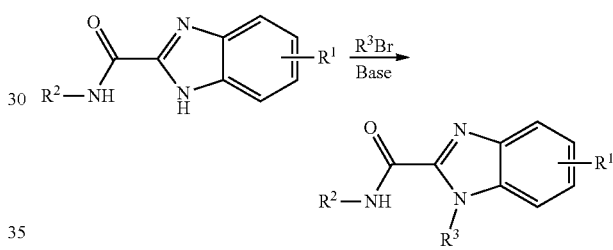

The compounds disclosed herein are bacterial efflux pump inhibitors. An efflux pump inhibitor is a compound that interferes with the ability of an efflux pump to export a substrate.

The inhibitor may have intrinsic antibacterial properties of its own. The compounds disclosed herein may be useful for treating bacterial infections (e.g., gram negative and gram positive) when administered with an antibacterial agent.

In one embodiment the bacterial infection being treated is a Gram-negative bacterial strain infection. In one embodiment the Gram-negative bacterial strain is selected from the group consisting of *Acinetobacter baumannii, Acinetobacter calcoaceticus, Acinetobacter haemolyticus, Acinetobacter lwoffi, Actinobacillus actinomycetemcomitans, Aeromonas hydrophilia, Aggregatibacter actinomycetemcomitans, Agrobacterium tumefaciens, Bacteroides distasonis, Bacteroides eggerthii, Bacteroides forsythus, Bacteroides fagilis, Bacteroides ovalus, Bacteroides splanchnicus, Bacteroides thetaiotaomicron, Bacteroides uniformis, Bacteroides vulgatus, Bordetella bronchiseptica, Bordetella parapertussis, Bordetella pertussis, Borrelia burgdorferi, Branhamella catarrhalis, Burkholderia cepacia, Campylobacter coli, Campylobacter fetus, Campylobacter jejuni, Caulobacter crescentus, Chlamydia trachomatis, Citrobacter diversus, Citrobacter feundii, Enterobacter aerogenes, Enterobacter asburiae, Enterobacter cloacae, Enterobacter sakazakii, Escherchia coli, Francisella tularensis, Fusobacterium nucleatum, Gardnerella vaginalis, Haemophilus ducreyi, Haemophilus haemolyticus, Haemophilus influenzae,* Hae-

*mophilus parahaemolyticus, Haemophilus parainfluenzae, Helicobacter pylori, Kingella denitrificans, Kingella indologenes, Kingella kingae, Kingella oralis, Klebsiella oxytoca, Klebsiella pneumoniae, Klebsiella rhinoscleromatis, Legionella pneumophila, Listeria monocytogenes, Moraxella bovis, Moraxella catarrhalis, Moraxella lacunata, Morganella morganii, Neisseria gonorrhoeae, Neisseria meningitidis, Pantoea agglomerans, Pasteurella canis, Pasteurella haemolytica, Pasteurella multocida, Pasteurella tularensis, Porphyromonas gingivalis, Proteus mirabilis, Proteus vulgaris, Providencia alcalifaciens, Providencia rettgeri, Providencia stuartii, Pseudomonas acidovorans, Pseudomonas aeruginosa, Pseudomonas alcaligenes, Pseudomonas fluorescens, Pseudomonas putida, Salmonella enteriditis, Salmonella paratyphi, Salmonella typhi, Salmonella typhimurium, Serratia marcescens, Shigella dysenteriae, Shigella jlexneri, Shigella sonnei, Stenotrophomonas maltophilla, Veillonella parvula, Vibrio cholerae, Vibrio parahaemolyticus, Yersinia enterocolitica, Yersinia intermedia, Yersinia pestis* and *Yersinia pseudotuberculosis.*

In one embodiment the bacterial infection being treated is a Gram-positive bacterial strain infection. In one embodiment the Gram-positive bacterial strain is selected from the group consisting of *Actinomyces naeslundii, Actinomyces viscosus, Bacillus anthracis, Bacillus cereus, Bacillus subtilis, Clostridium difficile, Corynebacterium diphtheriae, Corynebacterium ulcerans, Enterococcus faecalis, Enterococcus faecium, Micrococcus luteus, Mycobacterium avium, Mycobacterium intracellulare, Mycobacterium leprae, Mycobacterium tuberculosis, Propionibacterium acnes, Staphylococcus aureus, Staphylococcus epidermidis, Staphylococcus haemolyticus, Staphylococcus hominis, Staphylococcus hyicus, Staphylococcus intermedius, Staphylococcus saccharolyticus, Staphylococcus saprophyticus, Streptococcus agalactiae, Streptococcus mutans, Streptococcus pneumoniae, Streptococcus pyogenes, Streptococcus salivarius* and *Streptococcus sanguis.*

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, an antimicrobial (for example, an aminoglycoside, an antifungal, an antiparasitic, an antiviral, a carbapenem, a cephalosporin (e.g., cefepime), a fluoroquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropoietin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

In one embodiment the antibacterial agent is selected from quinolones, tetracyclines, glycopeptides, aminoglycosides, β-lactams, cephalosporins, rifamycins, macrolides, ketolides, oxazolidinones, coumermycins, and chloramphenicol.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

It will also be appreciated by those skilled in the art that certain compounds of the invention can exist in more than one tautomeric form. For example, a substituent of formula —NH—C(=O)H in a compound of formula (I) could exist in tautomeric form as —N=C(OH)H. The present invention encompasses all tautomeric forms of a compound of formula I as well as mixtures thereof that can exist in equilibrium with non-charged and charged entities depending upon pH, which possess the useful properties described herein In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, fumarate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to, those described above (e.g. physiologically acceptable anions) including $Cl^-$, $Br^-$, $I^-$, $CH_3SO_3^-$, $H_2PO_4^-$, $CF_3SO_3^-$, $p\text{-}CH_3C_6H_4SO_3^-$, citrate, tartrate, phosphate, malate, fumarate, formate, or acetate.

It will be appreciated by those skilled in the art that a compound of the invention comprising a counterion can be converted to a compound of the invention comprising a different counterion. Such a conversion can be accomplished using a variety of well-known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. For oral administration the compounds can be formulated as a solid dosage form with or without an enteric coating.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 to about 500 mg/kg, e.g., from about 5 to about 400 mg/kg of body weight per day, such as 1 to about 250 mg per kilogram body weight of the recipient per day.

The compound is conveniently formulated in unit dosage form; for example, containing 5 to 500 mg, 10 to 400 mg, or 5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Co-administration of a compound disclosed herein with one or more other active therapeutic agents (e.g., antibacterial agents) generally refers to simultaneous or sequential administration of a compound disclosed herein and one or more other active therapeutic agents, such that therapeutically effective amounts of disclosed herein and one or more other active therapeutic agents are both present in the body of the patient.

The ability of a compound disclosed herein to inhibit a bacterial efflux pump can be determined using a method like Test A or Test B as described for Example 3 (see Example 33. Standard EPI Assays) and as shown in Table 1.

TABLE 1

| Example | Structure | Enhanced Activity in *E. coli** | Enhanced Activity in *P. aeruginosa*** |
|---|---|---|---|
| 1 | 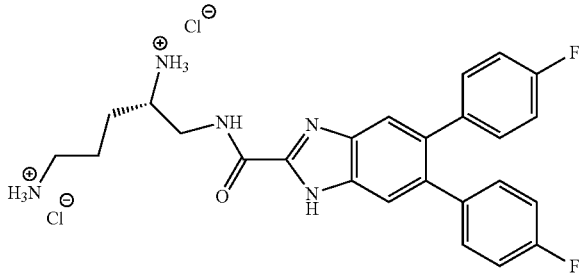 Chemical Formula: C$_{25}$H$_{27}$Cl$_2$F$_2$N$_5$O  Molecular Weight: 522.4218 | 512×/6.25 | 1×/3.13 |
| 2 | 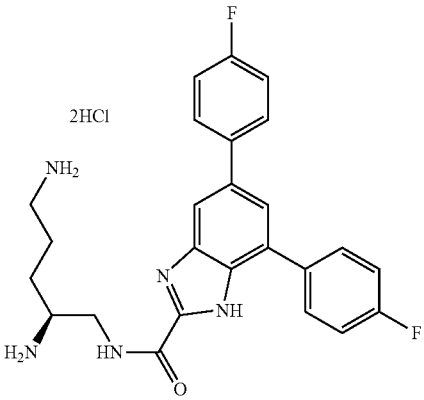 [SMILES: NCCC[C@H](N)CNC(=O)c1nc2cc(-c3ccc(F)cc3)cc(-c3ccc(F)cc3)c2[nH]1] | 8×/12.5 | 1×/12.5 |
| 3 | 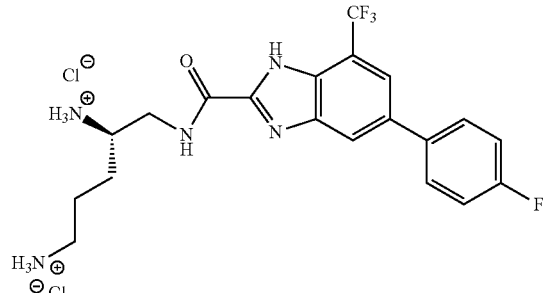 Chemical Formula: C$_{20}$H$_{23}$Cl$_2$F$_4$N$_5$O  Molecular Weight: 496.33 | 8×/6.25 | 64×/12.5 |

TABLE 1-continued
| Example | Structure | Enhanced Activity in E. coli* | Enhanced Activity in P. aeruginosa** |
|---|---|---|---|
| 4 | 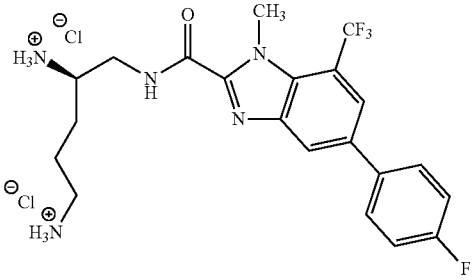<br>Exact Mass: 439.20<br>Molecular Weight: 439.46 | 512x/50 | 8x/12.5 |
| 5 | 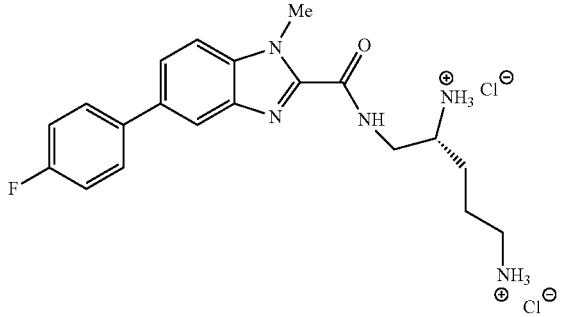<br>Chemical Formula: $C_{20}H_{26}Cl_2FN_5O$<br>Molecular Weight: 442.3604 | 64x/50 | 128x/50 |
| 6 | 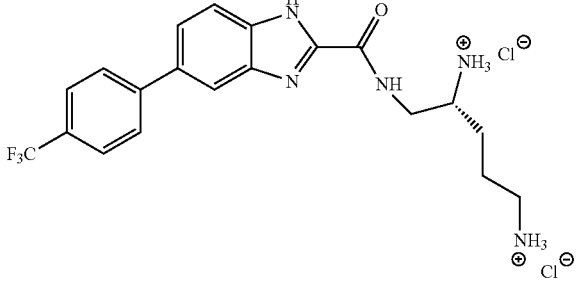<br>Chemical Formula: $C_{51}H_{67}Cl_2F_4N_{15}O_3{}^{4+}$<br>Molecular Weight: 1085.0904 | 64x/12.5 | 1x/3.13 |
| 7 | 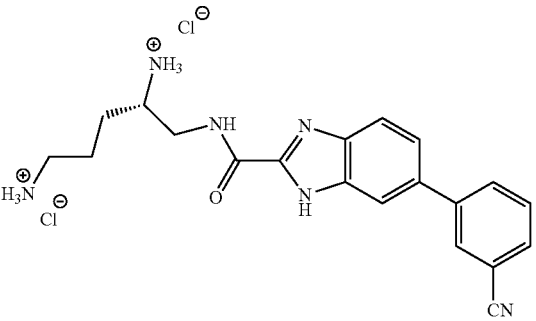<br>Chemical Formula: $C_{20}H_{24}Cl_2N_6O$<br>Molecular Weight: 435.3530 | 2x/12.5 | 4x/12.5 |

TABLE 1-continued
| Example | Structure | Enhanced Activity in E. coli* | Enhanced Activity in P. aeruginosa** |
|---|---|---|---|
| 8 | 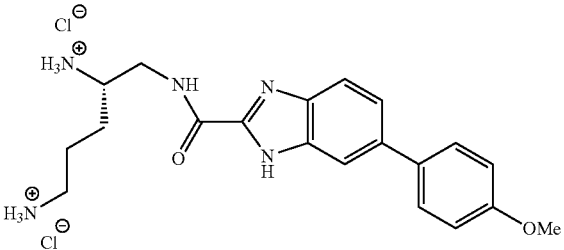<br>Chemical Formula: C$_{20}$H$_{27}$Cl$_2$N$_5$O$_2$<br>Molecular Weight: 440.3690 | 2×/50 | 2×/12.5 |
| 9 | 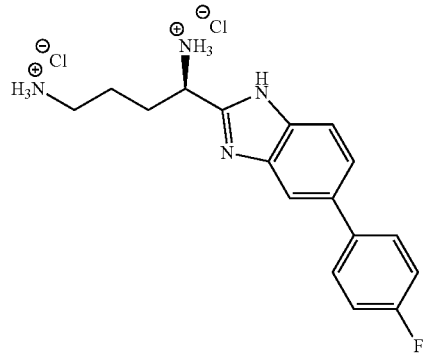<br>Exact Mass: 300.17<br>Molecular Weight: 300.38 | 256×/50 | 1×/25 |
| 10 | 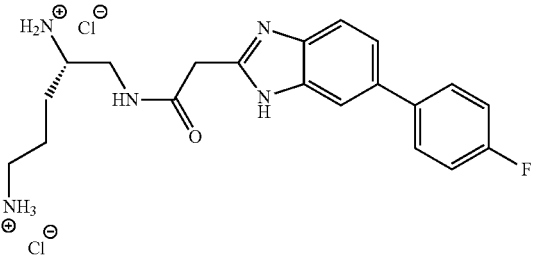<br>Chemical Formula: Cl$^-$<br>Molecular Weight: 35.4505 | 1×/50 | 1×/50 |
| 11 | 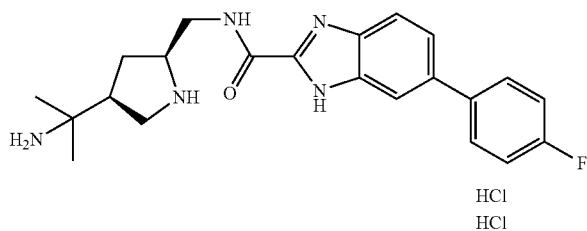<br>HCl<br>HCl<br>Chemical Formula: C$_{22}$H$_{28}$Cl$_2$FN$_5$O<br>Molecular Weight: 468.3984 | 2×/12.5 | 2×/12.5 |

TABLE 1-continued

| Example | Structure | Enhanced Activity in *E. coli** | Enhanced Activity in *P. aeruginosa*** |
|---|---|---|---|
| 12 | 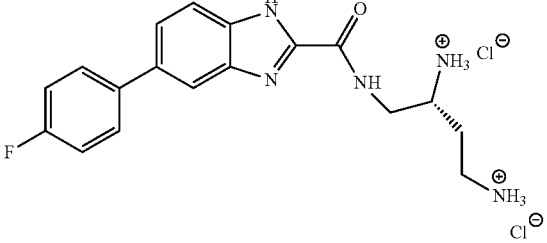<br>Chemical Formula: C$_{18}$H$_{22}$Cl$_2$FN$_5$O<br>Molecular Weight: 414.3064 | 8×/50 | 4×/12.5 |
| 13 | 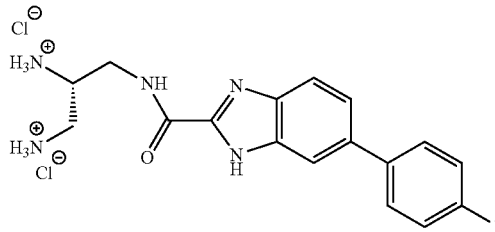<br>Chemical Formula: C$_{17}$H$_{20}$Cl$_2$FN$_5$O<br>Molecular Weight: 400.2794 | 32×/24 | 4×/25 |
| 14 | 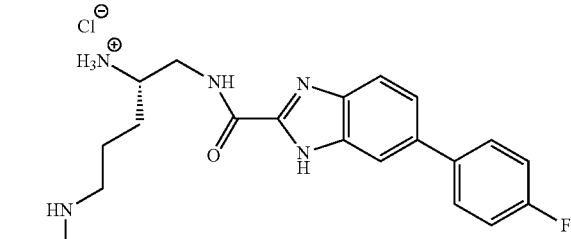<br>Chemical Formula: C$_{20}$H$_{24}$Cl$_2$FN$_7$O$^{2+}$<br>Molecular Weight: 468.3573 | 2×/50 | 4×/12.5 |
| 15 | 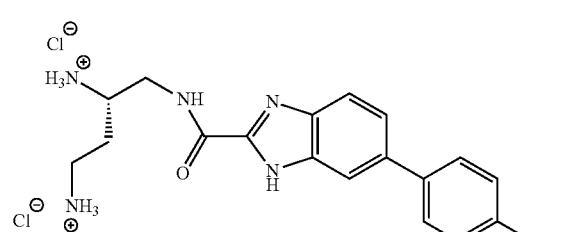<br>Chemical Formula: C$_{19}$H$_{25}$Cl$_2$N$_5$O$_2$<br>Molecular Weight: 426.3420 | 2×/50 | 2×/12.5 |

TABLE 1-continued
| Example | Structure | Enhanced Activity in *E. coli** | Enhanced Activity in *P. aeruginosa*** |
|---|---|---|---|
| 16 | 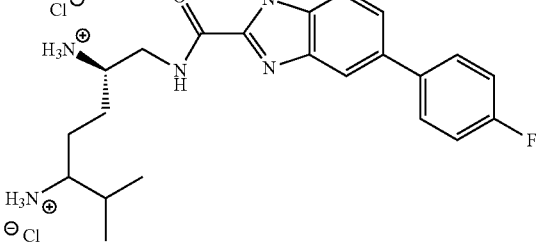 Chemical Formula: C$_{22}$H$_{30}$Cl$_2$FN$_5$O<br>Molecular Weight: 470.41 | 4×/6.25 | 2×/6.25 |
| 17 | 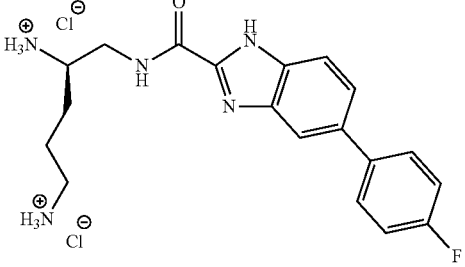 Exact Mass: 357.20<br>Molecular Weight: 357.42 | 256×/50 | 4×/50 |
| 18 | 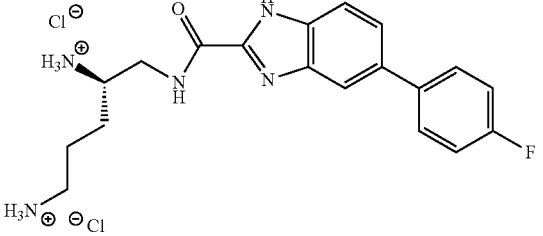 Chemical Formula: C$_{19}$H$_{24}$Cl$_2$FN$_5$O<br>Molecular Weight: 428.33 | 2×/6.25 | 2×/6.25 |
| 19 | 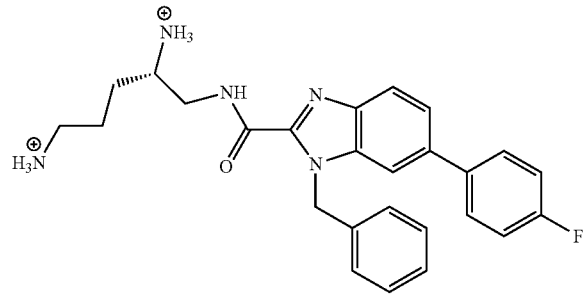 Chemical Formula: C$_{26}$H$_{30}$FN$_5$O$^{2+}$<br>Molecular Weight: 447.5573 | 128×/6.25 | 64×/12.5 |

TABLE 1-continued

| Example | Structure | Enhanced Activity in *E. coli** | Enhanced Activity in *P. aeruginosa*** |
|---------|-----------|-------------------------------|--------------------------------------|
| 20 | Chemical Formula: $C_{60}H_{77}Cl_2F_3N_{14}O_3^{4+}$<br>Molecular Weight: 1170.2640 | 64×/50 | 128×/50 |
| 21 | Exact Mass: 439.13<br>Molecular Weight: 440.34 | 256×/50 | 8×/25 |
| 22 | Chemical Formula: $C_{20}H_{24}Cl_2FN_5O$<br>Molecular Weight: 440.3444 | 2×/6.25 | 32×/12.5 |
| 23 | Chemical Formula: $C_{13}H_{20}BrCl_2N_5O$<br>Molecular Weight: 413.14 | 2×/50 μg | — |

TABLE 1-continued
| Example | Structure | Enhanced Activity in *E. coli** | Enhanced Activity in *P. aeruginosa*** |
|---------|-----------|-------------------------------|---------------------------------------|
| 24 | 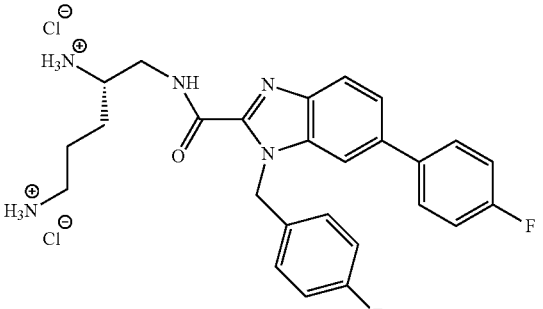<br>Chemical Formula: $C_{26}H_{29}Cl_2F_2N_5O$<br>Molecular Weight: 536.4488 | 32×/6.25 μg | 2×/12.5 μg |
| 25 | Chemical Formula: $C_{19}H_{26}Cl_2N_6O$<br>Molecular Weight: 425.3580 | 2×/50 μg | — |
| 26 | 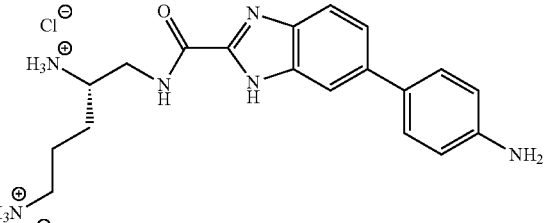<br>Chemical Formula: $C_{30}H_{28}F_7N_7O_9$<br>Molecular Weight: 763.5828 | 32×/6.25 μg | — |

TABLE 1-continued

| Example | Structure | | Enhanced Activity in *E. coli** | Enhanced Activity in *P. aeruginosa*** |
|---|---|---|---|---|
| 27 | (structure) | CF$_3$COOH<br>CF$_3$COOH<br>+ | 32×/6.25 µg | 128×/12.5 µg |
| | Chemical Formula: C$_{30}$H$_{28}$F$_8$N$_6$O$_7$<br>Molecular Weight: 736.58 | | | |
| 28 | (structure) | CF$_3$COOH<br>CF$_3$COOH<br>+ | 64×/6.25 µg | 32×/25 µg |
| | Chemical Formula: C$_{30}$H$_{27}$F$_9$N$_6$O$_7$<br>Molecular Weight: 754.57 | | | |
| 29 | (structure) | CF$_3$COOH<br>CF$_3$COOH<br>+ | 64×/6.25 µg | 32×/25 µg |

TABLE 1-continued

| Example | Structure | Enhanced Activity in *E. coli*\* | Enhanced Activity in *P. aeruginosa*\*\* |
|---|---|---|---|
| | 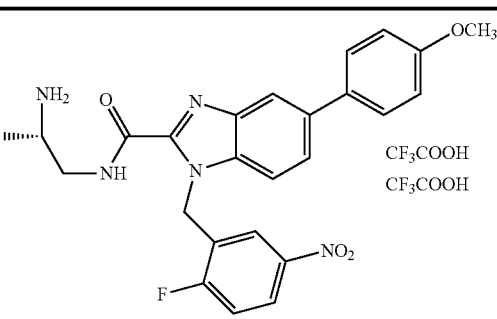  Chemical Formula: $C_{31}H_{31}F_7N_6O_8$  Molecular Weight: 748.61 | | |
| 30 | 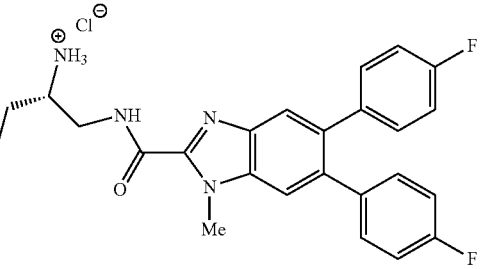  Chemical Formula: $C_{46}H_{54}Cl_2F_3N_9O_2{}^{2+}$  Molecular Weight: 892.8931 | 512×/6.25 μg | — |
| 31 | 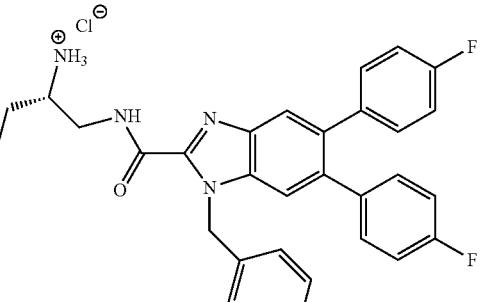  Chemical Formula: $C_{32}H_{33}Cl_2F_2N_5O$  Molecular Weight: 612.5468 | 8×/6.25 μg | — |

\*These data were generated using clarithromycin as the antibiotic and the various EPIs against *Escherichia coli* ATCC 25922.
\*\*These data were generated using levofloxacin as the antibiotic and the various EPIs against *Pseudomonas aeruginosa* ATCC 27853.

The invention will now be illustrated by the following non-limiting examples.

Preparation of Intermediates

Table 2 shows intermediates that were used or could be used to prepare compounds of described herein.

TABLE 2

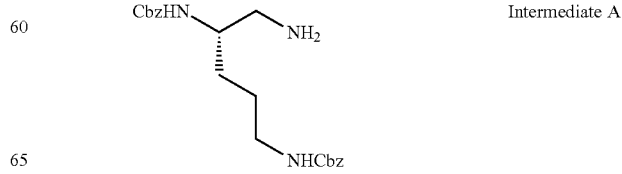

Intermediate A

TABLE 2-continued

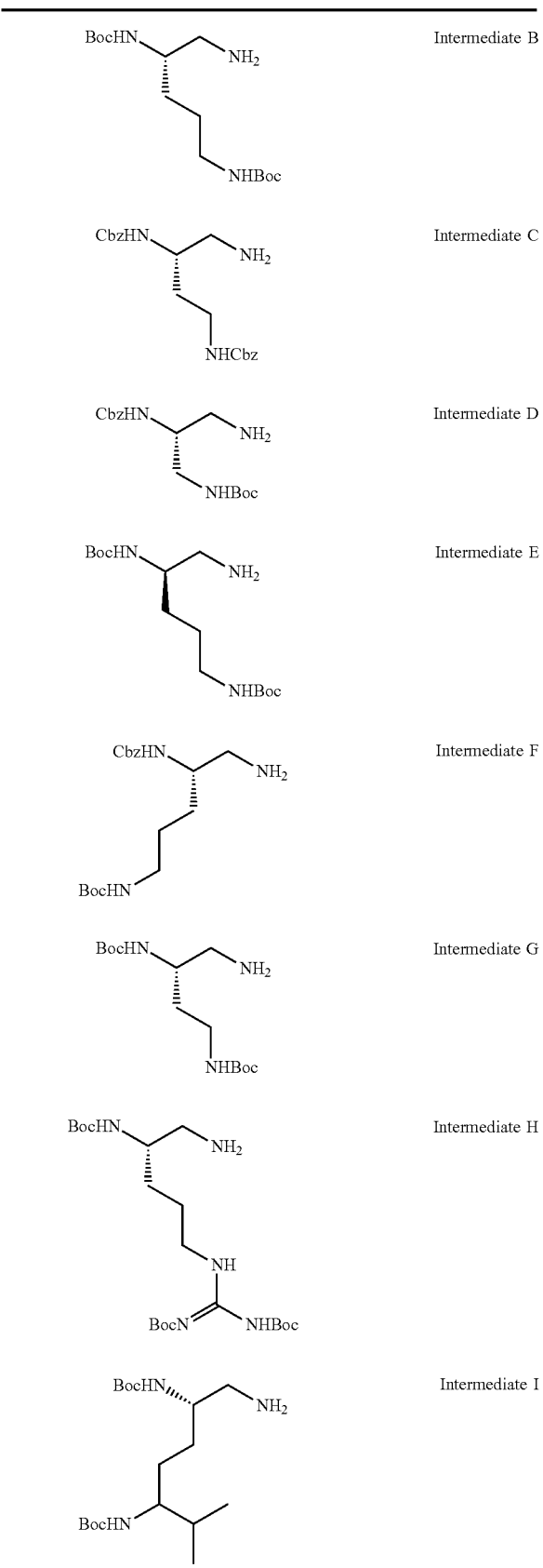

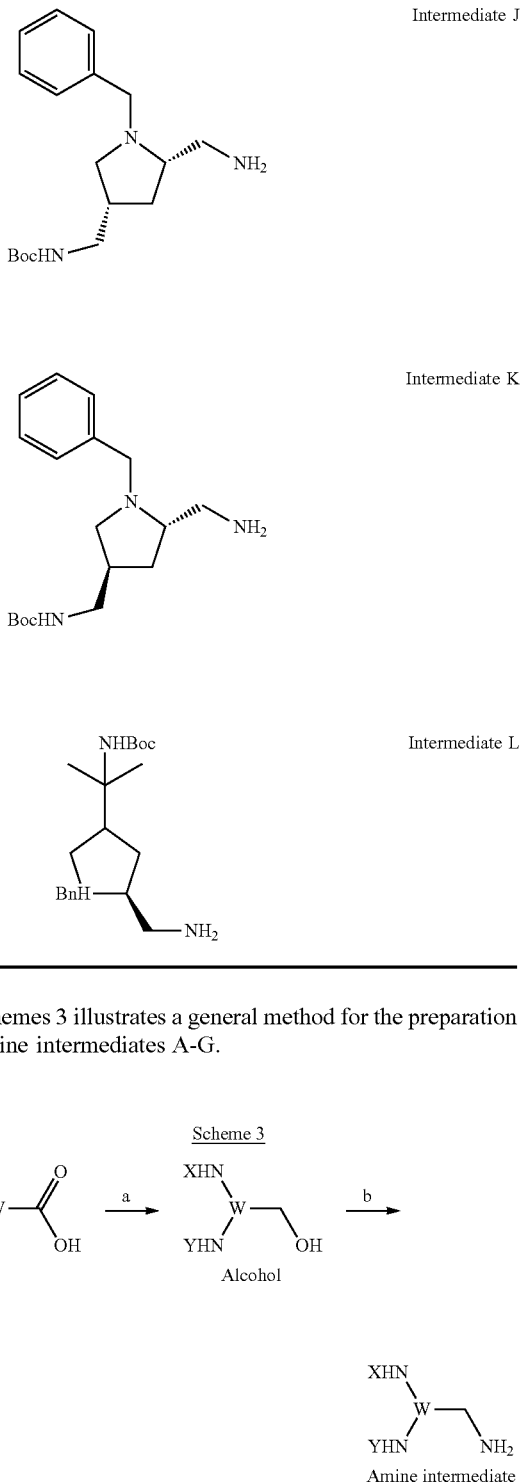

Schemes 3 illustrates a general method for the preparation of amine intermediates A-G.

Reagents and Conditions:
a (i) N-methylmorpholine, isobutylchloroformate, DME; (ii) NaBH4, DME/H$_2$O);
b (i) phthalimide, DIAD, PPh3, THF; (ii) hydrazine, Methanol
The variables X and Y represent protecting groups as needed. The variable W represents a (C$_2$-C$_{13}$) alkyl corresponding to the R$^1$ variable for compounds of formula I. It is to be understood that the two nitrogen atoms attache to W are attached on different carbon atoms of W.

Preparation of Amine Intermediate A ((dibenzyl (5-aminopentane-1,4-diyl)(S)-dicarbamate)

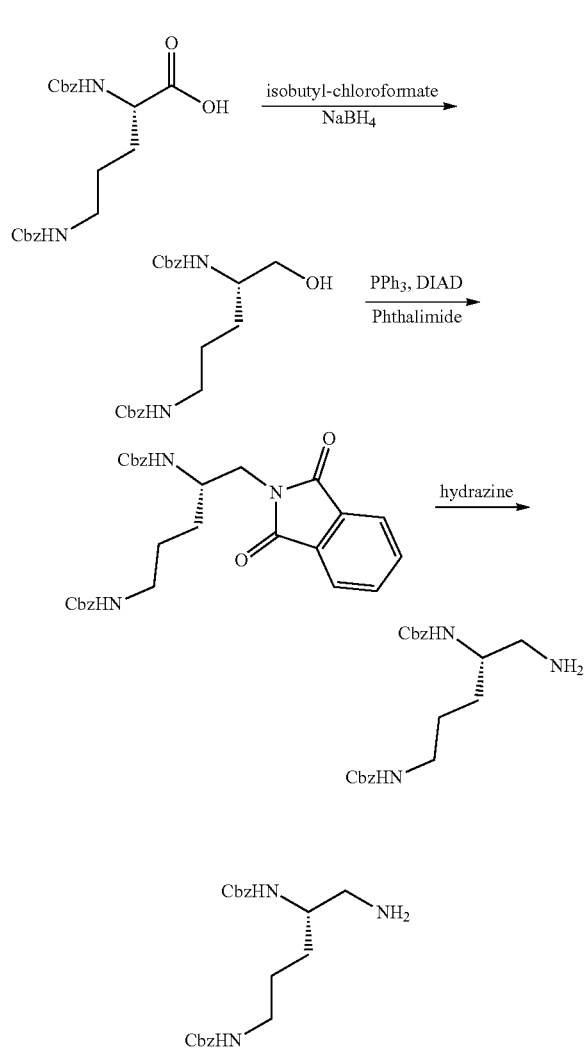

Dibenzyl (5-aminopentane-1,4-diyl)(S)-dicarbamate

Dibenzyl (5-(1,3-dioxoisoindolin-2-yl)pentane-1,4-diyl) (S)-dicarbamate (400 mg, 0.78 mmol) formed was dissolved in methanol (20 mL) and hydrazine monohydrate (80 μL, 1.55 mmol) was added. The reaction mixture was then refluxed for 2 hours and cooled to room temperature. The precipitate formed was filtered and methanol used to wash the filtrate. The filtrate was concentrated under reduced pressure and the remaining solid purified on an ISCO chromatograph using silica gel (0-10% methanol/methylene chloride with 1% $NH_3$—$H_2O$) to give product as a white powder. (206 mg, 68% yield); $^1$H NMR (CDCl$_3$) (400 MHz) δ 7.36 (m, 10H), 5.18 (m, 6H), 3.60 (m, 1H), 3.19 (m, 2H), 2.70 (m, 2H), 1.70 (s, 2H), 1.46 (m, 4H); $^{13}$C NMR (400 MHz, CDCl$_3$) δ 156.6, 136.6, 136.5, 128.53, 128.51, 128.1, 128.0, 66.6, 66.5, 53.0, 45.6, 40.7, 29.7. 26.5.

The requisite intermediates were prepared as described in the following steps:

Step 1

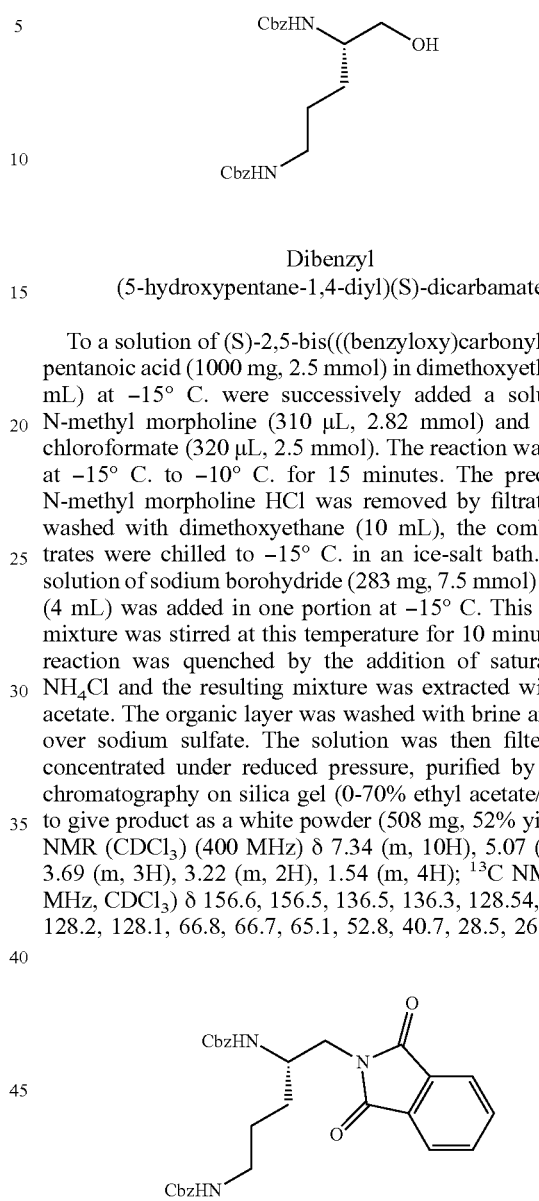

Dibenzyl (5-hydroxypentane-1,4-diyl)(S)-dicarbamate

To a solution of (S)-2,5-bis(((benzyloxy)carbonyl)amino) pentanoic acid (1000 mg, 2.5 mmol) in dimethoxyethane (20 mL) at −15° C. were successively added a solution of N-methyl morpholine (310 μL, 2.82 mmol) and isobutyl chloroformate (320 μL, 2.5 mmol). The reaction was stirred at −15° C. to −10° C. for 15 minutes. The precipitated N-methyl morpholine HCl was removed by filtration and washed with dimethoxyethane (10 mL), the combine filtrates were chilled to −15° C. in an ice-salt bath. Then a solution of sodium borohydride (283 mg, 7.5 mmol) in water (4 mL) was added in one portion at −15° C. This reaction mixture was stirred at this temperature for 10 minutes. The reaction was quenched by the addition of saturated aq. $NH_4Cl$ and the resulting mixture was extracted with ethyl acetate. The organic layer was washed with brine and dried over sodium sulfate. The solution was then filtered and concentrated under reduced pressure, purified by column chromatography on silica gel (0-70% ethyl acetate/hexane) to give product as a white powder (508 mg, 52% yield); $^1$H NMR (CDCl$_3$) (400 MHz) δ 7.34 (m, 10H), 5.07 (m, 6H), 3.69 (m, 3H), 3.22 (m, 2H), 1.54 (m, 4H); $^{13}$C NMR (100 MHz, CDCl$_3$) δ 156.6, 156.5, 136.5, 136.3, 128.54, 128.52, 128.2, 128.1, 66.8, 66.7, 65.1, 52.8, 40.7, 28.5, 26.5.

Dibenzyl (5-(1,3-dioxoisoindolin-2-yl)pentane-1,4-diyl)(S)-dicarbamate

Triphenylphosphine (325 mg, 1.24 mmol) and phthalimide (182 mg, 1.24 mmol) were added to a flask containing dry THF (5 mL). Dibenzyl (5-hydroxypentane-1,4-diyl)(S)-dicarbamate (400 mg, 1.03 mmol) was added and the flask was cooled to 0° C. DIAD (250 mg, 1.24 mmol) was added dropwise and reaction allowed to stir for 30 minutes at 0° C. and overnight at room temperature. The mixture was concentrated under reduced pressure and residue was purified on an ISCO chromatograph using silica gel (0-70% ethyl acetate/hexane) to give product as a white solid. (491 mg, 92% yield); $^1$H NMR (CDCl$_3$) (400 MHz) δ 7.83 (m, 2H), 7.72 (m, 2H), 7.32 (m, 10H), 5.10 (m, 3H), 4.97 (m, 3H), 4.03 (m, 1H) 3.76 (m, 2H), 3.24 (m, 2H), 1.57 (m, 4H); $^{13}$C NMR (100 MHz, CDCl$_3$) δ 168.5, 156.4, 156.2, 136.6, 136.5, 134.0, 132.1, 123.0, 131.9, 131.8, 128.6, 128.5, 128.4, 128.3, 128.0, 127.9, 127.8, 123.4, 66.6, 66.5, 50.7, 41.7, 40.6, 30.0, 26.3.

Preparation of Amine Intermediate B ((di-tert-butyl (5-aminopentane-1,4-diyl)(S)-dicarbamate)

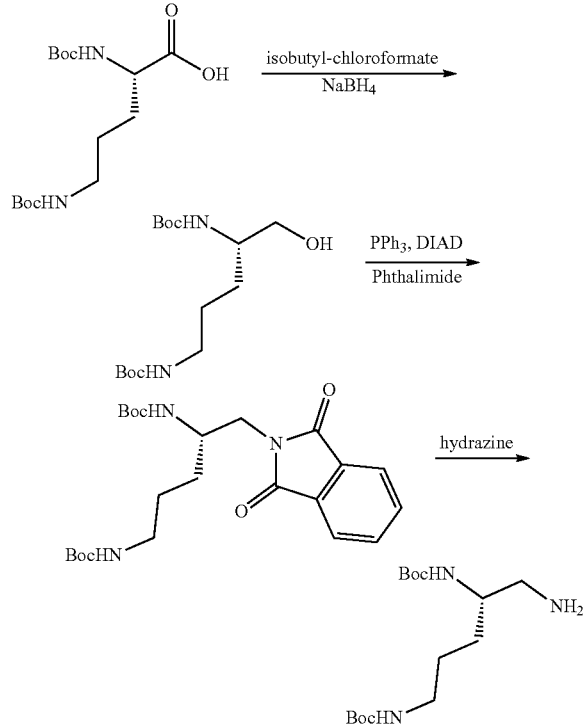

di-tert-butyl (5-aminopentane-1,4-diyl)(S)-dicarbamate

Di-tert-butyl (5-(1,3-dioxoisoindolin-2-yl)pentane-1,4-diyl)(S)-dicarbamate (760 mg, 1.70 mmol) formed was dissolved in methanol (30 mL) and hydrazine monohydrate (177 μL, 3.40 mmol) was added. The reaction mixture was then refluxed for 2 hours and cooled to room temperature. The precipitate formed was filtered and methanol used to wash the filtrate. The filtrate was concentrated under reduced pressure and the remaining oil purified on an ISCO chromatograph using silica gel (0-10% methanol/methylene chloride with 1% NH$_3$—H$_2$O) to give product as a yellow oil. (450 mg, 83% yield); $^1$H NMR (CDCl$_3$) (300 MHz) δ 4.63 (m, 2H), 3.52-3.49 (m, 1H), 3.14-3.12 (m, 2H), 2.79-2.60 (m, 2H), 1.54-1.57 (m, 4H), 1.53-1.26 (m, 18H).

The requisite intermediates were prepared as described in the following paragraphs.

Step 1

Di-tert-butyl (5-hydroxypentane-1,4-diyl)(S)-dicarbamate

To a solution of (S)-2,5-bis((tert-butoxycarbonyl)amino)pentanoic acid (1000 mg, 3.01 mmol) in THF 30 mL at −15° C. were successively added a solution of N-methyl morpholine (305 μL, 3.32 mmol) and isobutyl chloroformate (411 μL, 3.01 mmol). The reaction was stirred at −15° C. to −10° C. for 15 minutes. The precipitated N-methyl morpholine HCl was removed by filtration and washed with THF (10 mL), the combine filtrates were chilled to −15° C. in an ice-salt bath. Then a solution of sodium borohydride (342 mg, 9.03 mmol) in water (4 mL) was added in one portion at −15° C. This reaction mixture was stirred at this temperature for 10 minutes. The reaction was quenched by the addition of saturated aq. NH$_4$Cl and the resulting mixture was extracted with ethyl acetate. The organic layer was washed with brine and dried over sodium sulfate. The solution was then filtered and concentrated under reduced pressure, purified on a silica gel column (0-100% ethyl acetate/hexane) to give product as a white powder (750 mg, 78% yield); $^1$H NMR (CDCl$_3$) (300 MHz) δ 4.74-4.64 (m, 2H), 3.63-3.55 (m, 3H), 3.14-3.13 (m, 2H), 2.45 (m, 1H), 1.68-1.58 (m, 4H), 1.56-1.44 (m, 18H).

Di-tert-butyl (5-(1,3-dioxoisoindolin-2-yl)pentane-1,4-diyl)(S)-dicarbamate

Triphenylphosphine (742 mg, 2.83 mmol) and phthalimide (417 mg, 2.83 mmol) were added to a flask containing dry THF (15 mL). Di-tert-butyl (5-hydroxypentane-1,4-diyl)(S)-dicarbamate (750 mg, 2.36 mmol) was added and the flask was cooled to 0° C. DIAD (573 mg, 2.83 mmol) was added dropwise and reaction allowed to stir for 30 minutes at 0° C. and overnight at room temperature. The mixture was concentrated under reduced pressure and residue was purified using ISCO chromatography with silica gel (0-100% ethyl acetate/hexane) to give product as a white solid. (760 mg, 72% yield); $^1$H NMR (CDCl$_3$) (300 MHz) δ 7.86-7.83 (m, 2H), 7.72-7.69 (m, 2H), 4.64-4.61 (m, 2H), 3.97-3.94 (m, 1H) 3.70-3.67 (m, 2H), 3.15-3.13 (m, 2H), 1.67-1.54 (m, 4H), 1.52-1.37 (m, 9H), 1.37-1.22 (m, 9H).

Preparation of Amine Intermediate C (dibenzyl (4-aminobutane-1,3-diyl)(S)-dicarbamate)

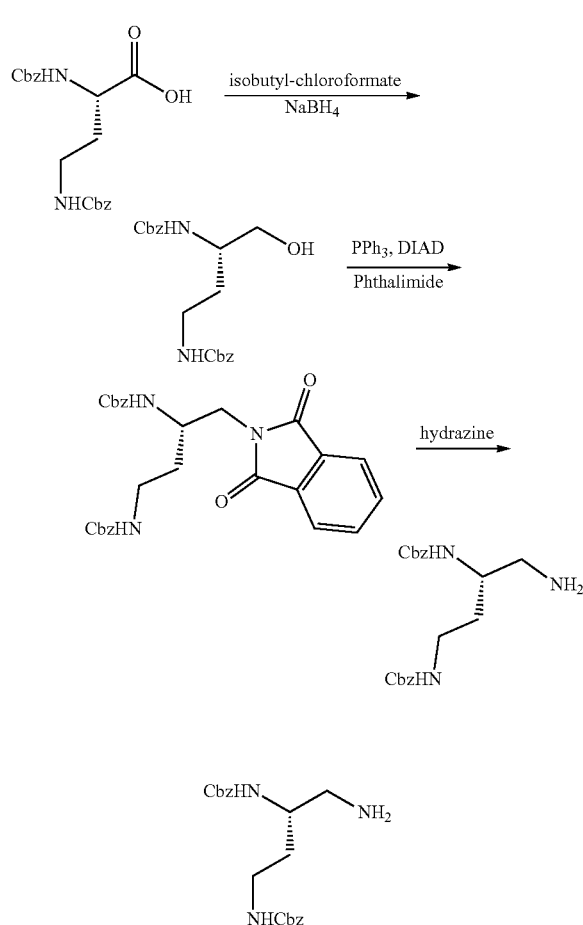

Dibenzyl (4-aminobutane-1,3-diyl)(S)-dicarbamate

Dibenzyl (4-(1,3-dioxoisoindolin-2-yl)butane-1,3-diyl)(S)-dicarbamate (170 mg, 0.34 mmol) was dissolved in methanol (5 mL) and hydrazine monohydrate (0.03 mL, 0.68 mmol) was added. The reaction mixture was then refluxed for 2 hours and cooled to room temperature. The precipitate formed was filtered and methanol used to wash the filtrate. The filtrate was concentrated under reduced pressure and the remaining solid was purified on an ISCO chromatography with silica gel (0-10% methanol/methylene chloride with 1% $NH_3$—$H_2O$) to give product as a white powder. (77 mg, 61% yield); $^1$H NMR (CDCl$_3$) (400 MHz) δ 7.34 (m, 10H), 5.77 (brs, 1H), 5.56 (d, 1H, J=8 Hz), 5.09 (m, 4H), 3.69 (m, 1H), 3.44 (m, 1H), 3.02 (m, 1H), 2.74 (m, 2H), 2.26 (s, 2H), 1.68 (m, 1H), 1.47 (m, 1H); $^{13}$C NMR (100 MHz, CDCl$_3$) δ 157.0, 156.5, 136.7, 136.4, 128.5, 128.4, 128.1, 128.0, 66.8, 66.5, 50.5, 45.5, 37.6, 33.0.

The requisite intermediates were prepared as described in the following paragraphs.

Step 1

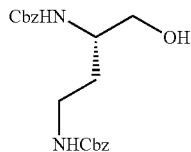

Dibenzyl (4-hydroxybutane-1,3-diyl)(S)-dicarbamate

To a solution of (S)-2,4-bis(((benzyloxy)carbonyl)amino)butanoic acid (1000 mg, 2.77 mmol) in dimethoxymethane (10 mL) at −15° C. were successively added N-methyl morpholine (340 μL, 3.13 mmol) and isobutyl chloroformate (360 μL, 2.77 mmol). The reaction was stirred at −15° C. to −10° C. for 15 minutes. The precipitated N-methyl morpholine HCl was removed by filtration and washed with dimethoxyethane (10 mL) and the combine filtrates were chilled to −15° C. in an ice-salt bath. Then a solution of sodium borohydride (378 mg, 8.31 mmol) in water (5 mL) was added in one portion at −15° C. This reaction mixture was stirred at this temperature for 10 minutes. The reaction was quenched by the addition of saturated aq. NH$_4$Cl and the resulting mixture was extracted with ethyl acetate. The organic layer was washed with brine and dried over sodium sulfate. The solution was then filtered and concentrated under reduced pressure, purified by column chromatography using silica gel (0-70% ethyl acetate/hexane) to give product as a white powder (491 mg, 48% yield); $^1$H NMR (CDCl$_3$) (400 MHz) 7.33 (m, 10H), 5.72 (s, 1H), 5.63 (d, 1H, J=8 Hz), 5.08 (s, 4H), 3.48 (m, 5H), 3.02 (m, 1H), 1.71 (m, 1H), 1.57 (m, 1H); $^{13}$C NMR (100 MHz, CDCl$_3$) δ 157.0, 156.7, 136.5, 136.3, 128.55, 128.50, 128.1, 128.07, 128.02, 66.8, 66.6, 64.6, 50.4, 37.7, 31.7.

Step 2

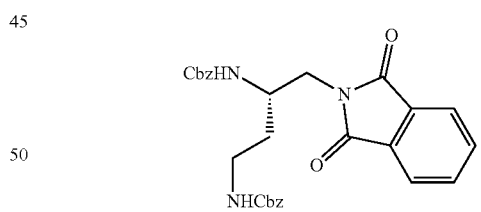

Dibenzyl (4-(1,3-dioxoisoindolin-2-yl)butane-1,3-diyl)(S)-dicarbamate

Triphenylphosphine (365 mg, 1.39 mmol) and phthalimide (204 mg, 1.39 mmol) were added to a flask containing dry THF (6 mL). Dibenzyl (4-hydroxybutane-1,3-diyl)(S)-dicarbamate (432 mg, 1.39 mmol) was added and the flask was cooled to 0° C. DIAD (281 mg, 1.39 mmol) was added dropwise and reaction allowed to stir for 30 minutes at 0° C. and overnight at room temperature. The mixture was concentrated under reduced pressure and residue was purified on an ISCO chromatograph with silica gel (0-70% ethyl acetate/hexane) to give product as a white solid. (237 mg, 41% yield); ¹H NMR (CDCl₃) (400 MHz) δ 7.83 (m, 2H), 7.70 (m, 2H), 7.36 (m, 10H), 5.61 (brs, 1H), 5.46 (d, 1H, J=8 Hz), 5.10 (m, 4H), 4.12 (m, 1H), 3.78 (m, 2H), 3.51 (m, 1H), 3.08 (m, 1H), 1.83 (m, 1H), 1.54 (m, 1H); ¹³C NMR (100 MHz, CDCl₃) δ 168.5, 156.7, 156.5, 136.7, 136.4, 134.1, 131.7, 128.5, 128.4, 128.0, 127.9, 127.7, 123.4, 66.6, 66.5, 53.4, 48.8, 41.8, 37.4, 33.2.

Preparation of Amine Intermediate D (benzyl t-butyl (3-aminopropane-1,2-diyl)(R)-dicarbamate)

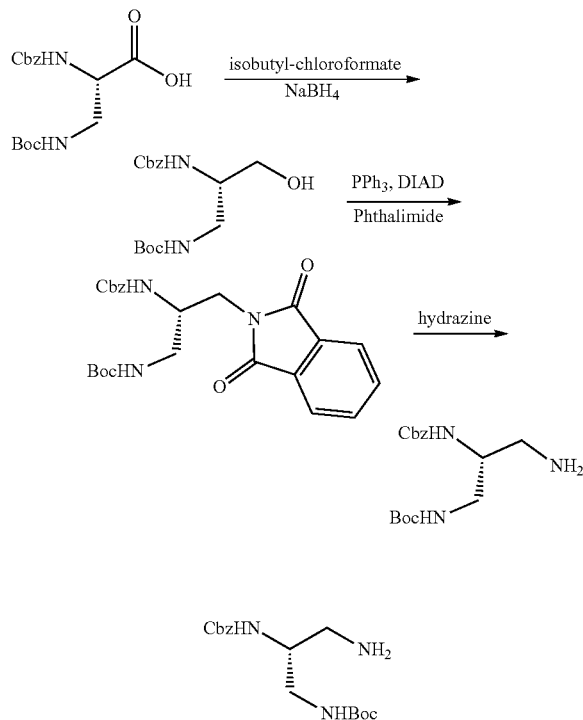

Benzyl t-butyl (3-aminopropane-1,2-diyl)(R)-dicarbamate

Benzyl t-butyl (3-(1,3-dioxoisoindolin-2-yl)propane-1,2-diyl)(S)-dicarbamate (450 mg, 0.99 mmol) was dissolved in methanol (10 mL) and hydrazine monohydrate (0.1 mL, 1.98 mmol) was added. The reaction mixture was then refluxed for 2 hours and cooled to room temperature. The precipitate formed was filtered and methanol used to wash the filtrate. The filtrate was concentrated under reduced pressure and the remaining solid purified on an ISCO column chromatograph using silica gel (0-10% methanol/methylene chloridemethylene chloride with 1% NH₃—H₂O) to give product as a colorless oil. (140 mg, 44% yield); ¹H NMR (CDCl₃, 400 MHz) δ 7.27 (m, 5H), 6.37 (s, 1H), 5.87 (s, 1H), 5.02 (s, 2H), 3.94 (s, 4H), 3.60 (m, 1H), 3.12 (m, 2H), 2.70 (m, 2H), 1.36 (s, 9H).

The requisite intermediates were prepared as described in the following steps:

Step 1) Benzyl t-butyl (3-hydroxypropane-1,2-diyl)(S)-dicarbamate

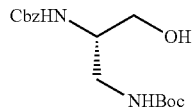 [SMILES: CC(C)(C)OC(=O)NC[C@@H](CO)NC(=O)OCc1ccccc1]

Benzyl t-butyl (3-hydroxypropane-1,2-diyl)(S)-dicarbamate

To a solution of (S)-2-(((benzyloxy)carbonyl)amino)-3-((t-butoxycarbonyl)amino)propanoic acid (900 mg, 2.66 mmol) in DME (10 mL) at −15° C. were successively added a solution of N-methyl morpholine (0.33 mL, 3 mmol) and isobutyl chloroformate (0.35 mL, 2.66 mmol). The reaction was stirred at −15 to −10° C. for 15 minutes. The precipitated N-methyl morpholine HCl was removed by filtration and washed with DME (10 mL), the combine filtrates were chilled to −15° C. in an ice-salt bath. Then a solution of sodium borohydride (301 mg, 7.98 mmol) in water (5 mL) was added in one portion at −15° C. This reaction mixture was stirred at this temperature for 10 minutes. The reaction was quenched by the addition of saturated aqueous NH₄Cl and the resulting mixture was extracted with ethyl acetate. The organic layer was washed with brine and dried over sodium sulfate. The solution was then filtered and concentrated under reduced pressure, purified by column chromatography on silica gel (0-70% ethyl acetate/hexane) to give product as a white powder (675 mg, 78% yield); ¹H NMR (400 MHz) (CD₃OD) δ 7.34 (m, 5H), 5.09 (s, 2H), 3.73 (m, 1H), 3.24 (m, 4H), 1.44 (s, 9H); ¹³C NMR (100 MHz, CD₃OD) δ 158.6, 138.3, 129.5, 129.0, 128.9, 80.3, 67.5, 63.0, 54.6, 42.1, 28.8.

Step 2) Benzyl t-butyl (3-(1,3-dioxoisoindolin-2-yl) propane-1,2-diyl)(S)-dicarbamate

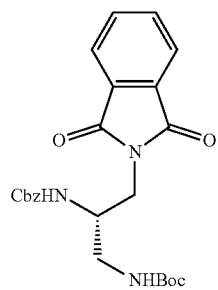 [SMILES: CC(C)(C)OC(=O)NC[C@@H](CN1C(=O)c2ccccc2C1=O)NC(=O)OCc1ccccc1]

Benzyl t-butyl (3-(1,3-dioxoisoindolin-2-yl)propane-1,2-diyl)(S)-dicarbamate

Triphenylphosphine (709 mg, 2.71 mmol) and phthalimide (398 mg, 2.71 mmol) were added to a flask containing dry THF (6 mL). Benzyl t-butyl (3-hydroxypropane-1,2-diyl)(S)-dicarbamate (730 mg, 2.26 mmol) was added and the flask was cooled to 0° C. DIAD (548 mg, 2.71 mmol) was added dropwise and reaction allowed to stir for 30 minutes at 0° C. and overnight at room temperature. The mixture was concentrated under reduced pressure and residue purified on an ISCO chromatograph using silica gel (0-70% ethyl acetate/hexane) to give the product as a white solid. (556 mg, 55% yield); NMR (CDCl₃) (400 MHz) δ 7.83 (m, 2H), 7.71 (m, 2H), 7.28 (m, 5H), 5.70 (m, 1H), 5.26 (m, 1H), 5.02 (s, 2H), 4.06 (m, 1H), 3.84 (m, 2H), 3.31 (m, 2H), 1.44 (s, 9H), $^{13}$C NMR (100 MHz, CDCl₃) δ 168.5, 156.6, 156.3, 136.4, 134.1, 131.8, 128.3, 127.9, 123.4, 79.7, 66.6, 51.6, 41.9, 39.2, 28.3, 21.9.

Preparation of Amine Intermediate E ((di-terttert-butyl (5-aminopentane-1,4-diyl)(R)-dicarbamate)

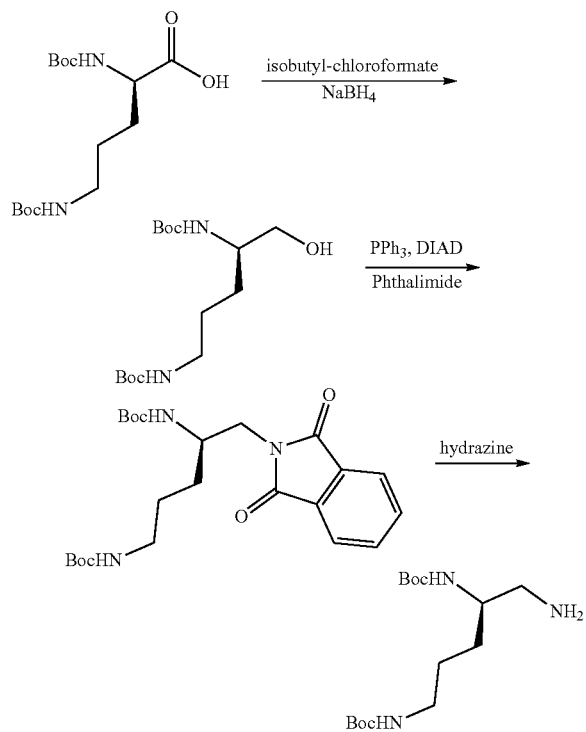

Di-tert-butyl (5-aminopentane-1,4-diyl)(R)-dicarbamate

Di-tert-butyl (5-(1,3-dioxoisoindolin-2-yl)pentane-1,4-diyl)(R)-dicarbamate (1.71 g, 2.24 mmol) formed was dissolved in methanol (20 mL) and hydrazine monohydrate (220 μL, 4.47 mmol) was added. The reaction mixture was then refluxed for 2 hours and cooled to room temperature. The precipitate formed was filtered and methanol used to wash the filtrate. The filtrate was concentrated under reduced pressure and the remaining oil purified on an ISCO chromatograph using silica gel (0-10% methanol/methylene chloride+1% NH₄OH) to give product as a yellow oil. (560 mg, 79%); ¹H NMR (CDCl₃) (300 MHz) δ 4.62 (m, 2H), 3.52 (m, 1H), 3.14-3.09 (m, 2H), 2.79-2.60 (m, 2H), 1.64-1.57 (m, 4H), 1.48-1.23 (m, 18H)

The requisite intermediates were prepared as described in the following paragraphs.

Step 1

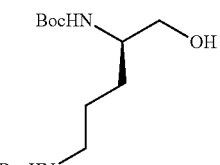

Di-tert-butyl (5-hydroxypentane-1,4-diyl)(R)-dicarbamate

To a solution of (R)-2,5-bis((tert-butoxycarbonyl)amino)pentanoic acid (1.70 g, 5.11 mmol) in THF 30 mL at −15° C. were successively added a solution of N-methyl morpholine (620 μL, 5.70 mmol) and isobutyl chloroformate (668 μL, 5.11 mmol). The reaction was stirred at −15° C. to −10° C. for 15 minutes. The precipitated N-methyl morpholine HCl was removed by filtration and washed with THF (10 mL), the combine filtrates were chilled to −15° C. in an ice-salt bath. Then a solution of sodium borohydride (580 mg, 15.33 mmol) in water (4 mL) was added in one portion at −15° C. This reaction mixture was stirred at this temperature for 10 minutes. The reaction was quenched by the addition of saturated aq. NH₄Cl and the resulting mixture was extracted with ethyl acetate. The organic layer was washed with brine and dried over sodium sulfate. The solution was then filtered and concentrated under reduced pressure. The crude product was used directly for next step without further purification.

Step 2

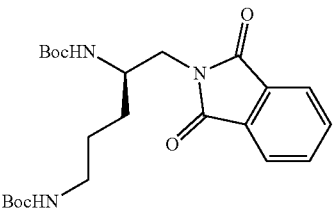 [SMILES: CC(C)(C)OC(=O)NCCC[C@H](CN1C(=O)c2ccccc2C1=O)NC(=O)OC(C)(C)C]

Di-tert-butyl (5-(1,3-dioxoisoindolin-2-yl)pentane-1,4-diyl)(R)-dicarbamate

Triphenylphosphine (1.61 g, 6.13 mmol) and phthalimide (902 mg, 6.13 mmol) were added to a flask containing dry THF (40 mL). Di-tert-butyl (5-hydroxypentane-1,4-diyl)(R)-dicarbamate (1.63 g, 5.11 mmol) was added and the flask was cooled to 0° C. DIAD (1.24 g, 6.13 mmol) was added dropwise and reaction allowed to stir for 30 minutes at 0° C. and overnight at room temperature. The mixture was concentrated under reduced pressure and the residue purified using an ISCO chromatograph using silica gel (0-100% ethyl acetate/hexane) to give product as a white solid. (1.71 g, 74%); ¹H NMR (CDCl₃) (300 MHz) δ 7.89-7.82 (m, 2H), 7.76-7.69 (m, 2H), 4.64-4.62 (m, 2H), 3.97-3.94 (m, 1H) 3.74-3.67 (m, 2H), 3.15-3.13 (m, 2H), 1.66-1.52 (m, 4H), 1.52-1.43 (m, 9H), 1.27-1.23 (m, 9H).

Preparation of Amine Intermediate F (Benzyl t-butyl (5-aminopentane-1,4-diyl)(S)-dicarbamate).

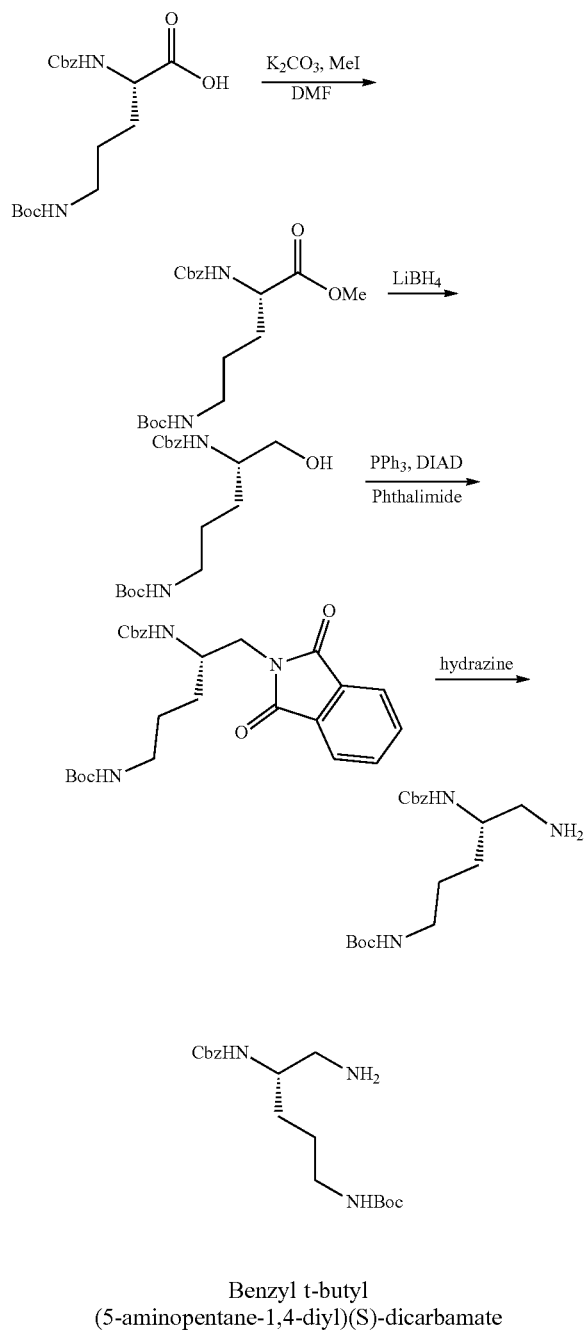

Benzyl t-butyl (5-aminopentane-1,4-diyl)(S)-dicarbamate

The phthalimide (340 mg, 0.71 mmol) formed was dissolved in methanol (20 mL) and hydrazine monohydrate (0.07 mL, 1.41 mmol) was added. The reaction mixture was then refluxed for 2 hours and cooled to room temperature. The precipitate formed was filtered and methanol was used to wash the filtrate. The filtrate was concentrated under reduced pressure and the remaining solid was purified by an ISCO column chromatography on silica gel using (0-10% Methanol/methylene chloride with 1% NH₃—H₂O) to give product as a white powder. (164 mg, 66% yield); ¹H NMR (CDCl₃) (400 MHz) δ 7.25 (m, 5H), 5.41 (d, 1H, J=8 Hz), 5.00 (s, 1H), 4.84 (brs, 1H); 3.50 (m, 1H), 3.01 (m, 2H), 2.61 (m, 2H), 1.40 (m, 4H), 1.36 (s, 9H); ¹³C NMR (100 MHz, CDCl₃) δ 156.6, 156.0, 136.6, 128.4, 128.1, 128.0, 78.9, 66.6, 53.2, 45.7, 40.2, 29.7, 28.4, 26.6, 25.0, 24.9.

The requisite intermediates were prepared as described in the following paragraphs.

Step 1

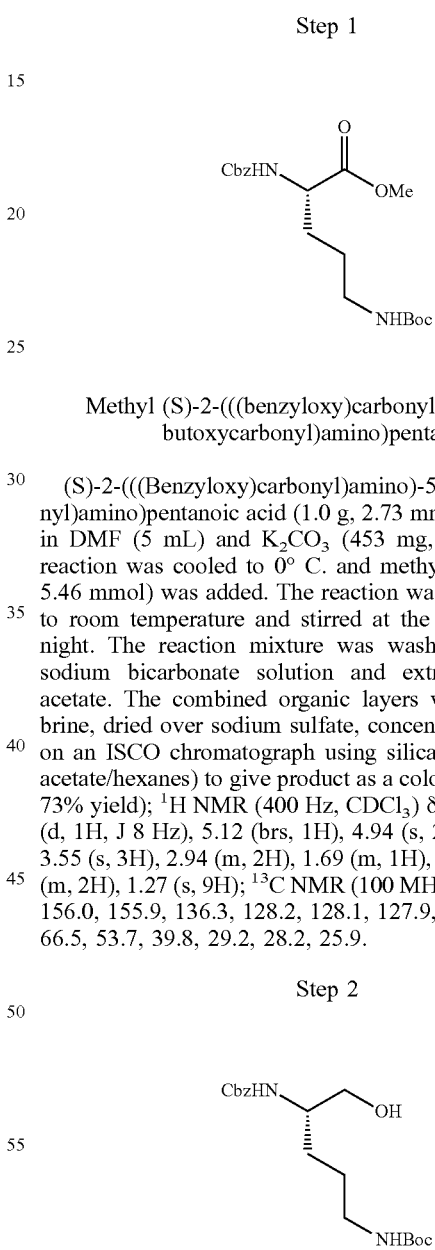

Methyl (S)-2-(((benzyloxy)carbonyl)amino)-5-((t-butoxycarbonyl)amino)pentanoate (S)-2-(((Benzyloxy)carbonyl)amino)-5-((t-butoxycarbonyl)amino)pentanoic acid (1.0 g, 2.73 mmol) was dissolved in DMF (5 mL) and K₂CO₃ (453 mg, 3.26 mmol). The reaction was cooled to 0° C. and methyl iodide (775 mg, 5.46 mmol) was added. The reaction was allowed to warm to room temperature and stirred at the temperature overnight. The reaction mixture was washed with saturated sodium bicarbonate solution and extracted with ethyl acetate. The combined organic layers were washed with brine, dried over sodium sulfate, concentrated and purified on an ISCO chromatograph using silica gel (0-60% ethyl acetate/hexanes) to give product as a colorless oil. (761 mg, 73% yield); ¹H NMR (400 Hz, CDCl₃) δ 7.19 (s, 5H), 6.06 (d, 1H, J 8 Hz), 5.12 (brs, 1H), 4.94 (s, 2H), 4.17 (m, 1H), 3.55 (s, 3H), 2.94 (m, 2H), 1.69 (m, 1H), 1.55 (m, 1H), 1.40 (m, 2H), 1.27 (s, 9H); ¹³C NMR (100 MHz, CDCl₃) δ 172.7, 156.0, 155.9, 136.3, 128.2, 128.1, 127.9, 127.8, 78.6, 67.2, 66.5, 53.7, 39.8, 29.2, 28.2, 25.9.

Step 2

To a solution of methyl (S)-2-(((benzyloxy)carbonyl)amino)-5-((t-butoxycarbonyl)amino)pentanoate (431 mg, 1.13 mmol) in THF (5 mL)/ethanol (1 mL) was added LiBH₄ (32 mg, 1.47 mmol) at 0° C. The mixture was stirred at that temperature for 30 minutes and warmed to room temperature and stirred for overnight. The reaction mixture was poured into water and extracted with ethyl acetate. The combine organic layers were washed with brine and dried over sodium sulfate and concentrated under reduced pressure. It was purified with an ISCO chromatograph using silica gel (0-70% ethyl acetate/hexane to give product as a colorless oil. (385 mg, 97% yield); $^1$H NMR (CDCl$_3$) (400 MHz) δ 7.28 (m, 5H), 5.02 (s, 3H), 3.60 (m, 4H), 3.04 (m, 2H), 1.47 (m, 4H), 1.36 (m, 9H); $^{13}$C NMR (100 MHz, CDCl$_3$) δ 156.6, 156.1, 136.4, 128.5, 128.1, 128.0, 79.3, 66.8, 65.0, 62.7, 52.9, 52.4, 40.3, 29.8, 28.4, 26.7, 26.0.

Step 3

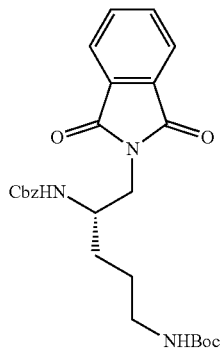 [SMILES: CC(C)(C)OC(=O)NCCC[C@@H](CN1C(=O)c2ccccc2C1=O)NC(=O)OCc1ccccc1]

Benzyl t-butyl (5-(1,3-dioxoisoindolin-2-yl)pentane-1,4-diyl)(S)-dicarbamate

Triphenylphosphine (325 mg, 1.24 mmol) and phthalimide (182 mg, 1.24 mmol) were added to a flask containing dry THF (5 mL). Dibenzyl (5-hydroxypentane-1,4-diyl)(S)-dicarbamate (400 mg, 1.03 mmol) was added and the flask was cooled to 0° C. DIAD (250 mg, 1.24 mmol) was added dropwise and reaction allowed to stir for 30 minutes at 0° C. and overnight at room temperature. The mixture was concentrated under reduced pressure and residue purified on an ISCO chromatograph using silica gel (0-70% ethyl acetate/ hexane) to give product as a white solid. (340 mg, 69% yield); $^1$H NMR (CDCl$_3$) (400 MHz) δ 7.82 (m, 2H), 7.71 (m, 2H), 7.27 (m, 5H), 5.18 (brs, 1H), 4.96 (m, 2H), 4.67 (brs, 1H), 4.02 (m, 1H) 3.75 (m, 2H), 3.14 (m, 2H), 1.55 (m, 4H), 1.44 (s, 9H); $^{13}$C NMR (100 MHz, CDCl$_3$) δ 168.4, 156.3, 156.0, 136.6, 133.9, 131.8, 128.4, 128.3, 127.8, 127.7, 123.3, 78.9, 66.3, 60.3, 50.7, 41.9, 40.2, 29.9, 28.4, 26.4.

Preparation of Amine Intermediate G ((di-tert-butyl (4-aminobutane-1,3-diyl)(S)-dicarbamate)

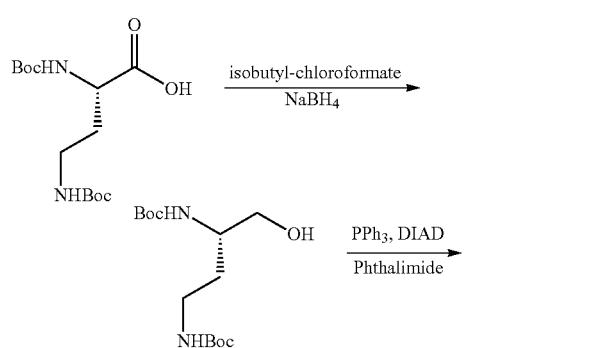

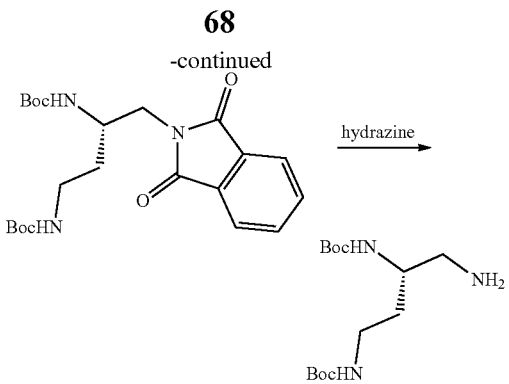

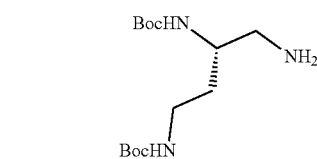 [SMILES: CC(C)(C)OC(=O)NCC[C@@H](CN)NC(=O)OC(C)(C)C]

Di-tert-butyl (4-aminobutane-1,3-diyl)(S)-dicarbamate

Di-tert-butyl (4-(1,3-dioxoisoindolin-2-yl)butane-1,3-diyl)(S)-dicarbamate (900 mg, 2.08 mmol) formed was dissolved in methanol (10 mL) and hydrazine monohydrate (203 µL, 4.16 mmol) was added. The reaction mixture was then refluxed for 2 hours and cooled to room temperature. The precipitate formed was filtered and methanol used to wash the filtrate. The filtrate was concentrated under reduced pressure and the remaining oil purified on an ISCO chromatograph using silica gel (0-10% methanol/methylene chloride with 1% NH$_3$H$_2$O) to give product as a colorless oil. (436 mg, 70% yield); $^1$H NMR (CDCl$_3$) (300 MHz) δ 5.30-5.24 (m, 1H), 4.75 (m, 1H), 3.62-3.60 (m, 1H), 3.40 (m, 1H), 2.95-2.94 (m, 1H), 1.73-1.62 (m, 2H), 1.45-1.37 (m, 18H).

The requisite intermediates were prepared as described in the following paragraphs.

Step 1

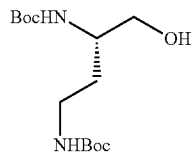

Di-tert-butyl (4-hydroxybutane-1,3-diyl)(S)-dicarbamate

To a solution of (S)-2,4-bis((tert-butoxycarbonyl)amino) butanoic acid (1.17 g, 3.67 mmol) in THF 40 mL) at −15° C. were successively added a solution of N-methyl morpholine (451 µL, 4.10 mmol) and isobutyl chloroformate (481 µL, 3.67 mmol). The reaction was stirred at −15° C. to −10° C. for 15 minutes. The precipitated N-methyl morpholine HCl was removed by filtration and washed with THF (10 mL), the combine filtrates were chilled to −15° C. in an ice-salt bath. A solution of sodium borohydride (417 mg, 11.01 mmol) in water (4 mL) was then added in one portion at −15° C. This reaction mixture was stirred at this temperature for 10 minutes. The reaction was quenched by the addition of saturated aq. NH₄Cl and the resulting mixture was extracted with ethyl acetate. The organic layer was washed with brine and dried over sodium sulfate. The solution was then filtered and concentrated under reduced pressure. The crude product was used directly for next step without further purification.

Step 2

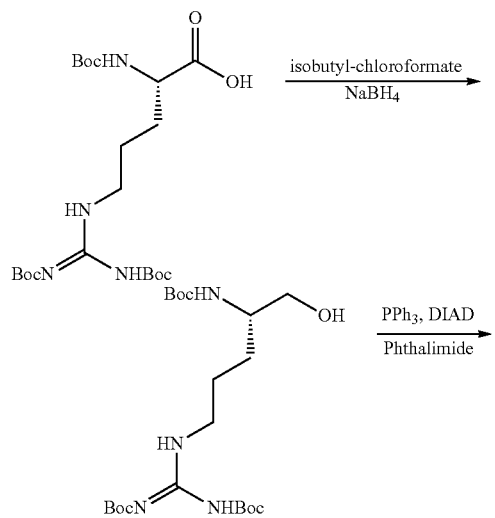

Di-tert-butyl (4-(1,3-dioxoisoindolin-2-yl)butane-1, 3-diyl)(S)-dicarbamate

Triphenylphosphine (1.16 g, 4.41 mmol) and phthalimide (649 mg, 4.41 mmol) were added to a flask containing dry THF (40 mL). Di-tert-butyl (4-hydroxybutane-1,3-diyl)(S)-dicarbamate (1.12 g, 3.67 mmol) was added and the flask was cooled to 0° C. DIAD (892 mg, 4.41 mmol) was added dropwise and reaction allowed to stir for 30 minutes at 0° C. and overnight at room temperature. The mixture was concentrated under reduced pressure and residue purified on an ISCO column chromatography using silica gel (0-100% ethyl acetate/hexane) to give product as a white solid. (901 mg, 57% yield); ¹H NMR (CDCl₃) (300 MHz) δ 7.87-7.83 (m, 2H), 7.75-7.71 (m, 2H), 5.08 (m, 1H), 4.79-4.76 (m, 1H), 4.02 (m, 1H), 3.75-3.73 (m, 2H) 3.42 (m, 1H), 3.02-3.00 (m, 1H), 1.79-1.73 (m, 2H), 1.57-1.45 (m, 9H), 1.27-1.24 (m, 9H).

Preparation of Amine Intermediate H ((S)-1-(4-N-Boc-amino-5-aminopentyl)-1,3-di-Boc-guanidine)

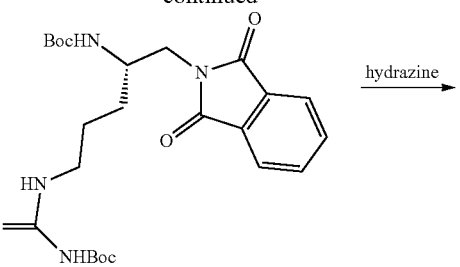

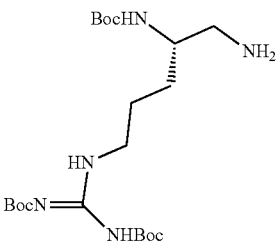

(S)-1-(4-N-Boc-amino-5-aminopentyl)-2,3-di-Boc-guanidine tert-Butyl (S)-(5-2',3'-di-Boc-guanidino-1-(1,3-dioxoisoindolin-2-yl)pentan-2-yl)carbamate (484 mg, 0.83 mmol) formed was dissolved in methanol (10 mL) and hydrazine monohydrate (82 μL, 1.65 mmol) was added. The reaction mixture was then refluxed for 2 hours and cooled to room temperature. The precipitate formed was filtered and methanol used to wash the filtrate. The filtrate was concentrated under reduced pressure and the remaining oil purified on an ISCO column chromatography using silica gel (0-10% methanol/methylene chloride+1% NH₄OH) to give product as a clear oil. (294 mg, 77%); ¹H NMR (CDCl₃) (300 MHz) δ 6.33 (s, 1H), 5.11-4.93 (m, 2H), 3.44 (m, 1H), 3.03-3.01 (m, 2H), 2.70-2.49 (m, 2H), 1.57-1.55 (m, 2H), 1.51-1.44 (m, 4H), 1.36-1.34 (m, 9H), 1.25-1.08 (m, 18H).

The requisite intermediates were prepared as described in the following paragraphs.

Step 1

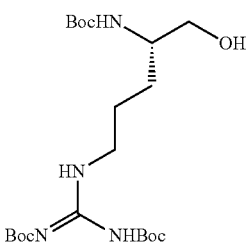

(S)-1-(4-N-Boc-Amino-5-hydroxylpentyl)-2,3-di-Boc-guanidine

To a solution of (Z)—N²,Nʷ,Nʷ'-tris(tert-butoxycarbonyl)-L-arginine (500 mg, 1.06 mmol) in THF (20 mL) at −15° C. were successively added a solution of N-methyl morpholine (129 μL, 1.16 mmol) and isobutyl chloroformate (138 μL, 1.06 mmol). The reaction was stirred at −15° C. to −10° C. for 15 minutes. The precipitated N-methyl morpholine HCl was removed by filtration and washed with THF (10 mL), the combine filtrates were chilled to −15° C. in an ice-salt bath. A solution of sodium borohydride (121 mg, 3.18 mmol) in water (4 mL) was then added in one portion at −15° C. This reaction mixture was stirred at this temperature for 10 minutes. The reaction was quenched by the addition of saturated aq. NH₄Cl and the resulting mixture was extracted with ethyl acetate. The organic layer was washed with brine and dried over sodium sulfate. The solution was then filtered and concentrated under reduced pressure. The crude product was used directly for next step without further purification.

Step 2

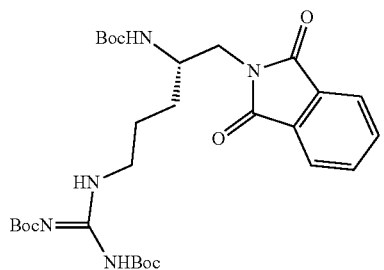

tert-Butyl (S)-(5-2',3'-di-Boc-guanidino-1-(1,3-dioxoisoindolin-2-yl)pentan-2-yl)carbamate Triphenylphosphine (334 mg, 1.28 mmol) and phthalimide 188 mg, 1.28 mmol) were added to a flask containing dry THF (15 mL). (S)-1-(4-N-Boc-amino-5-hydroxylpentyl)-2,3-di-Boc-guanidine (488 mg, 1.06 mmol) was added and the flask was cooled to 0° C. DIAD (259 mg, 1.28 mmol) was added dropwise and reaction allowed to stir for 30 minutes at 0° C. and overnight at room temperature. The mixture was concentrated under reduced pressure and residue purified on an ISCO chromatograph using silica gel (0-100% ethyl acetate/hexane) to give product as a white solid. (484 mg, 78%); ¹H NMR (CDCl₃) (300 MHz) δ 7.76-7.72 (m, 2H), 7.65-7.59 (m, 2H), 5.03-5.00 (m, 1H), 4.02-3.99 (m, 1H) 3.85-3.76 (m, 2H), 3.67-3.60 (m, 2H), 2.89-2.82 (m, 1H), 2.65 (m, 1H), 1.65-1.58 (m, 4H), 1.41-1.25 (m, 9H), 1.24-1.13 (m, 18H).

Preparation of Amine Intermediate I (di-tert-butyl ((2S)-1-amino-6-methylheptane-2,5-diyl)dicarbamate)

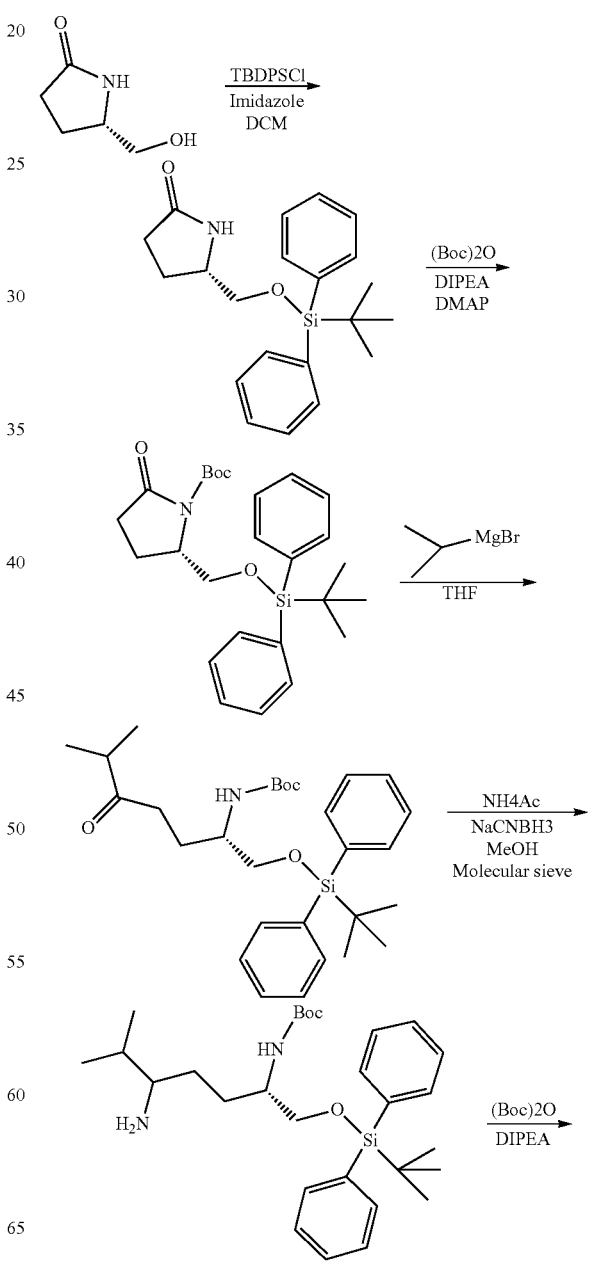

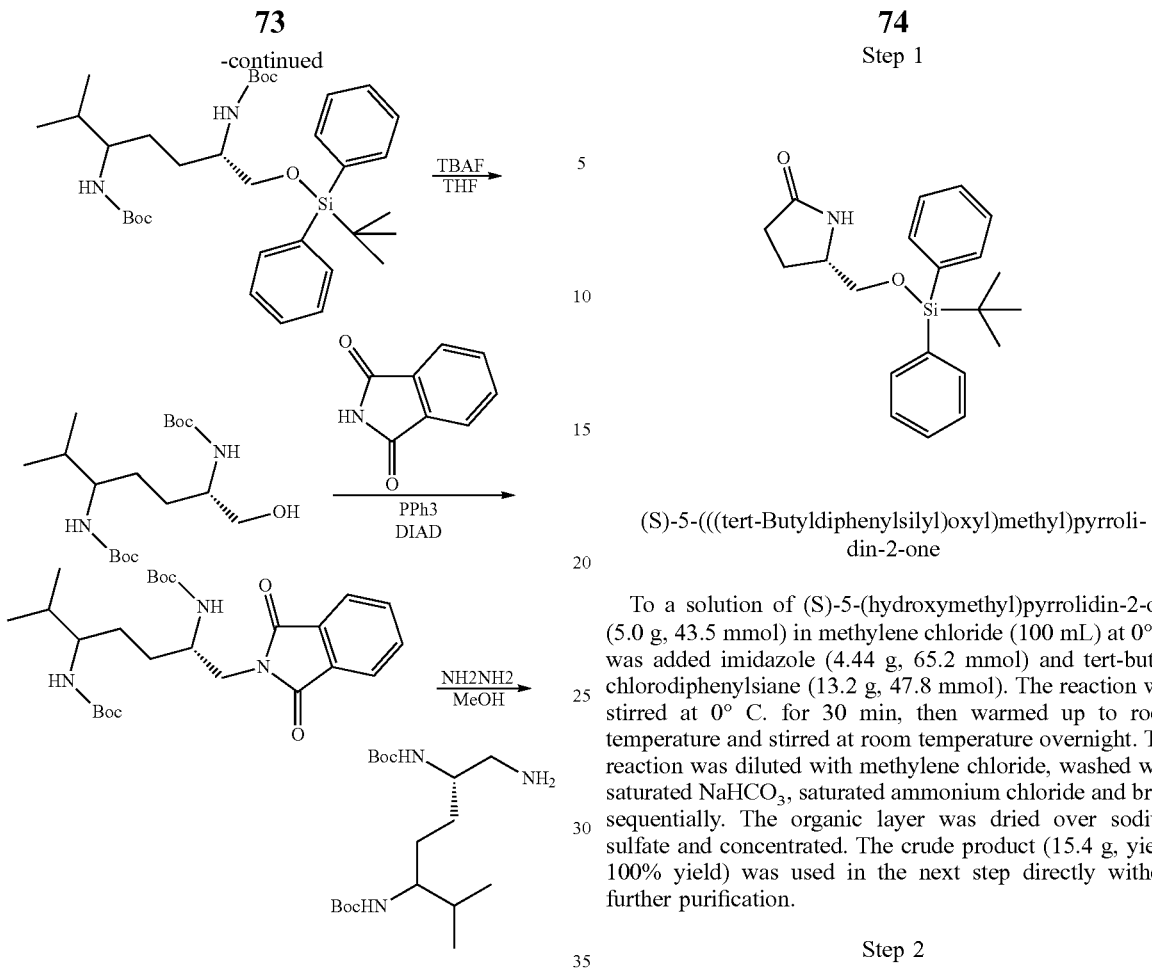

Di-tert-butyl ((2S)-1-amino-6-methylheptane-2,5-diyl)dicarbamate

Di-tert-butyl ((2S)-1-(1,3-dioxoisoindolin-2-yl)-6-methylheptane-2,5-diyl)dicarbamate (3.0 g, 6.13 mmol) was dissolved in methanol (50 mL), and hydrazine monohydrate (1.2 mL, 24.5 mmol) was added to this solution. After the reaction mixture was refluxed for 2 hours, it was cooled to room temperature. The precipitate formed was filtered and methanol was used to wash the filtrate. The filtrate was concentrated under reduced pressure. The reaction mixture was diluted with EtOAc, washed with saturated NaHCO$_3$, saturated ammonium chloride and brine sequentially. The organic layer was dried over sodium sulfate and concentrated. The crude product (2.4 g, 100% yield) was used directly without further purification. $^1$H NMR (CDCl3) (300 MHz) δ 4.99 (m, 1H), 4.60 (m, 1H), 3.50 (m, 1H), 2.70 (m, 1H), 1.67 (m, 4H), 1.31 (s, 9H), 1.27 (s, 9H), 0.85 (m, 6H).

The requisite intermediates were prepared as described in the following paragraphs.

Step 1

(S)-5-(((tert-Butyldiphenylsilyl)oxy)methyl)pyrrolidin-2-one

To a solution of (S)-5-(hydroxymethyl)pyrrolidin-2-one (5.0 g, 43.5 mmol) in methylene chloride (100 mL) at 0° C. was added imidazole (4.44 g, 65.2 mmol) and tert-butylchlorodiphenylsiane (13.2 g, 47.8 mmol). The reaction was stirred at 0° C. for 30 min, then warmed up to room temperature and stirred at room temperature overnight. The reaction was diluted with methylene chloride, washed with saturated NaHCO$_3$, saturated ammonium chloride and brine sequentially. The organic layer was dried over sodium sulfate and concentrated. The crude product (15.4 g, yield: 100% yield) was used in the next step directly without further purification.

Step 2

(S)-tert-Butyl 2-(((tert-butyldiphenylsilyl)oxy)methyl)-5-oxopyrrolidine-1-carboxylate To a solution (S)-5-(((tert-butyldiphenylsilyl)oxy)methyl)pyrrolidin-2-one (15.4 g, 43.5 mmol) in methylene chloride (150 mL) at 0° C. was added DIPEA (15.2 mL, 87 mmol), 4-dimethylaminopyridine (0.532 g, 4.35 mmol) and (Boc)$_2$O (19.0 g, 87 mmol). After the mixture was stirred at 0° C. for 30 minutes, the reaction was warmed up to room temperature and stirred at room temperature overnight. The reaction mixture was diluted with methylene chloridemethylene chloride, washed with saturated NaHCO$_3$ and brine, dried over sodium sulfate and concentrated. The residue was purified on an ISCO chromatograph using silica gel (0-50% ethyl acetate/hexane) to give product as a white solid. (5.5 g, 84% yield); $^1$H NMR (300 MHz, CDCl$_3$) δ 7.55-7.52 (m, 4H), 7.37-7.19 (m, 6H), 4.15 (m, 1H), 3.81 (m, 1H), 3.63 (m, 1H), 2.72 (m, 1H), 2.37 (m, 1H), 2.05 (m, 2H), 1.36 (s, 9H), 0.97 (s, 9H).

Step 3

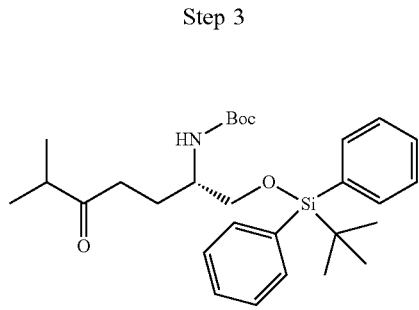

(S)-tert-Butyl (1-(((tert-butyldiphenylsilyl)oxy)-6-methyl-5-oxoheptan-2-yl)carbamate To a solution (S)-tert-butyl 2-(((tert-butyldiphenylsilyl)oxy)methyl)-5-oxopyrrolidine-1-carboxylate (5.0 g, 11.0 mmol) in THF (150 mL) at −78° C. was added 1 M isopropyl magnesium chloride (13.2 mL, 13.2 mmol) dropwise. After the mixture was stirred at −78° C. for 2 hours, the reaction was warmed up to 0° C. and stirred at room temperature for another 2 hours. The reaction mixture was quenched with saturated ammonium chloride solution, and extracted with EtOAc three times, the combined organic layers were washed with brine, dried over sodium sulfate and concentrated under reduced pressure. The residue was purified on an ISCO chromatograph using silica gel (0-40% ethyl acetate/hexanes to give product as a white solid. (4.8 g, 87.7% yield); $^1$H NMR (300 MHz, CDCl$_3$) 7.65 (m, 4H), 7.40 (m, 6H), 4.64 (br, 1H), 3.66-3.60 (m, 2H), 2.60-2.48 (m, 2H), 1.82 (m, 2H), 1.64 (s, 1H), 1.44-0.86 (m, 24H).

Step 4

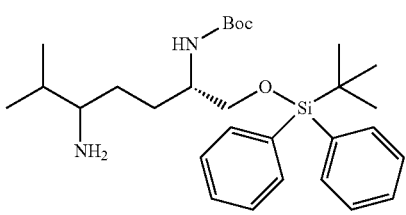 [SMILES: CC(C)C(N)CC[C@@H](CO[Si](c1ccccc1)(c1ccccc1)C(C)(C)C)NC(=O)OC(C)(C)C]

tert-Butyl ((2S)-5-amino-1-((tert-butyldiphenylsilyl)oxy)-6-methylheptan-2yl)carbamate To a solution (S)-tert-butyl (1-((tert-butyldiphenylsilyl)oxy)-6-methyl-5-oxoheptan-2-yl)carbamate (4.5 g, 9.03 mmol) and ammonium acetate (6.97 g, 90.3 mmol) in MeOH (100 mL) was added molecular sieve and sodium cyanoborohydride (5.68 g, 90.3 mmol). The reaction mixture was stirred at room temperature overnight after molecular sieve was filtered off and was washed with EtOAc. The combined organic layers was washed with sodium bicarbonate and brine, dried over sodium sulfate and concentrated. The crude product was used directly in the next step without further purification.

Step 5

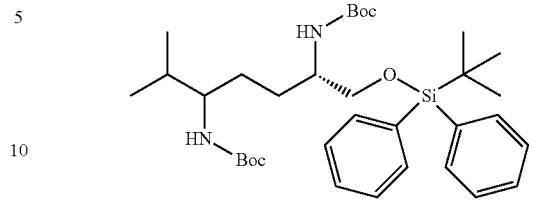

di-tert-Butyl ((2S)-1-((tert-butyldiphenylsilyl)oxy)-6-methylheptane-2,5-diyl)dicarbamate To a solution tert-butyl ((2S)-5-amino-1-((tert-butyldiphenylsilyl)oxy)-6-methylheptan-2-yl)carbamate (4.5 g, 9.03 mmol) in methylene chloridemethylene chloride (100 mL) at room temperature was added DIPEA (1.88 mL, 10.8 mmol) and (Boc)$_2$O (2.37 g, 10.8 mmol). The reaction was stirred at room temperature overnight. The reaction mixture was diluted with methylene chloridemethylene chloride, washed with saturated NaHCO$_3$ and brine, dried over sodium sulfate and concentrated under reduced pressure. The residue was purified by ISCO column chromatography on silica gel (0-30% ethyl acetate/hexane) to give product as a white solid. (4.5 g, 83% yield); $^1$H NMR (300 MHz, CDCl$_3$) δ 7.61 (m, 4H), 7.60-7.34 (m, 6H), 4.68 (m, 1H), 4.25 (m, 1H), 3.66-3.55 (m, 3H), 3.38 (m, 1H), 1.63-1.05 (m, 31H), 0.88 (m, 6H).

Step 6

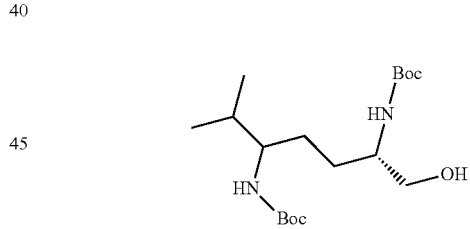

Di-tert-butyl ((2S)-1-hydroxy 6-methylheptan-2,5-diyl)dicarbamate

To a solution di-tert-butyl ((2S)-1-((tert-butyldiphenylsilyl)oxy)-6-methylheptane-2,5-diyl)dicarbamate (4.5 g, 7.51 mmol) in THF (100 mL) at 0° C. was added 1 M TBAF (30.0 mL, 30 mmol). The reaction was stirred at room temperature overnight. The reaction mixture was quenched with saturated ammonium chloride and extracted with EtOAc three times. The combined organic layer was washed with brine, dried over sodium sulfate and concentrated. The residue was purified by ISCO column chromatography on silica gel (0-100% ethyl acetate/hexanes) to give product as a white solid. (2.4 g, 89% yield). $^1$H NMR (300 MHz, CDCl$_3$) δ 4.75 (m, 1H), 4.41-4.29 (m, 1H), 3.62-3.38 (m, 4H), 1.71-1.33 (m, 23H), 0.88 (m, 6H).

Step 7

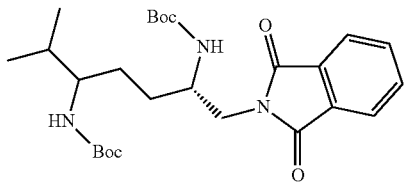 [SMILES: CC(C)C(CC[C@@H](CN1C(=O)c2ccccc2C1=O)NC(=O)OC(C)(C)C)NC(=O)OC(C)(C)C]

Di-tert-butyl ((2S)-1-(1,3-dioxoisoindolin-2-yl)-6-methylheptane-2,5-diyl)dicarbamate Triphenylphosphine (1.57 g, 6.0 mmol) and phthalimide (0.882 g, 6.0 mmol) were added to a flask containing dry THF (50 mL). Di-tert-butyl ((2S)-1-hydroxy-6-methylheptane-2,5-diyl)dicarbamate (1.81 g, 1.03 mmol) was added and the flask was cooled to 0° C. DIAD (1.21 g, 6.0 mmol) was added drop wise and reaction allowed to stir for 30 minutes at 0° C. and overnight at room temperature. The mixture was concentrated under reduced pressure and residue was purified on an ISCO chromatograph using silica gel (0-70% ethyl acetate/hexanes) to give product as a white solid. $^1$H NMR (300 MHz, CDCl$_3$) δ 7.97-7.70 (m, 4H), 6.39 (bs, 2H), 4.97 (m, 2H), 4.34 (m, 1H), 3.94 (m, 1H), 3.69 (m, 1H), 1.67-0.85 (m, 29H).

Preparation of Amine Intermediate J and K (tert-butyl (((3S,5R)-5-(aminomethyl)-1-benzylpyrrolidin-3-yl)methyl)carbamate and tert-butyl (((3R,5S)-5-(aminomethyl)-1-benzylpyrrolidin-3-yl)methyl)carbamate)

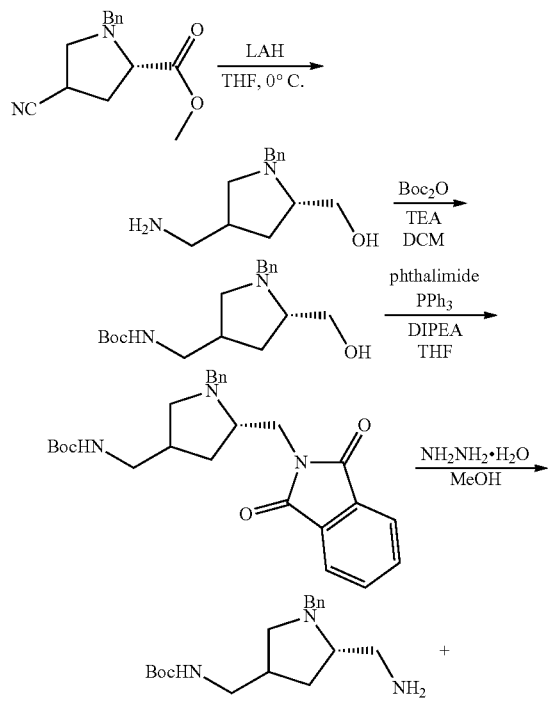

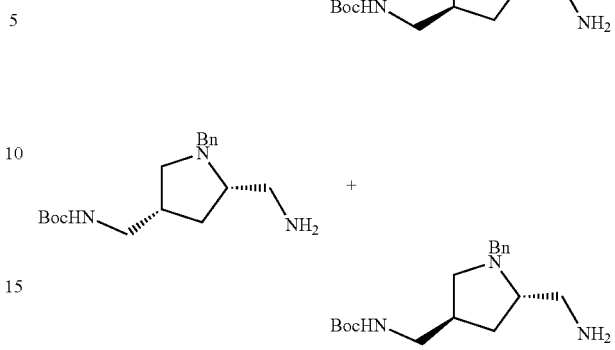

tert-Butyl (((3S,5R)-5-(aminomethyl)-1-benzylpyrrolidin-3-yl)methyl)carbamate and tert-Butyl (((3R,5S)-5-(aminomethyl)-1-benzylpyrrolidin-3-yl)methyl)carbamate To a solution of tert-butyl (((5S)-1-benzyl-5-(hydroxymethyl)pyrrolidin-3-yl)methyl)carbamate (1.58 g, 5.23 mmol), triphenylphosphine (1.51 g, 5.75 mmol) and phthalimide (846 mg, 5.75 mmol) in THF (20 mL) was added DIAD (1.16 mL, 5.75 mmol) at 0° C. It was stirred at 0° C.—room temperature and monitored by TLC. After finishing the reaction it was concentrated and purified on column chromatography with silica gel using 50-90% ethyl acetate in hexanes to give crude product as an off white solid (2.8 g, ~80% purity).

To the solution of the above crude product (2.8 g, ~80% purity, ~5.2 mmol) in MeOH (30 mL) was added hydrazine monohydrate (1.8 mL, 36.0 mmol). The mixture was stirred at 80° C. for 1 h then cooled to room temperature. The solvent was removed and the residue was triturated with CH$_2$Cl$_2$. The white solid was removed by filtration and the filtrate was concentrated and purified by column chromatography on silica gel. Elution with EtOAc then 1% NH$_3$.H$_2$O in 10% MeOH/CH$_2$Cl$_2$ afforded the top spot (386 mg, yellow oil, 25% yield in 2 steps) as tert-butyl (((3S,5R)-5-(aminomethyl)-1-benzylpyrrolidin-3-yl)methyl)carbamate. $^1$H NMR (300 MHz, CDCl$_3$) δ 7.30 (m, 5H), 5.28 (br. S, 1H), 3.99 (d, J=13.5 Hz, 1H), 3.15 (d, J=12.9 Hz, 1H), 3.09 (m, 2H), 2.70-2.90 (m, 3H), 2.51 (m, 1H), 2.04-2.34 (m, 3H), 1.36-1.50 (m, 10H), and the bottom spot (498 mg, white solid, 32% yield in 2 steps) as tert-butyl (((3 S,5R)-5-(aminomethyl)-1-benzylpyrrolidin-3-yl)methyl)carbamate. $^1$H NMR (300 MHz, CDCl$_3$) δ 7.30 (m, 5H), 4.52 (br. S, 1H), 3.57 (d, J=12.9 Hz, 1H), 3.47 (d, J=12.9 Hz, 1H), 2.81-3.02 (m, 5H), 1.80-1.95 (m, 2H), 1.59 (m, 1H), 1.43 (s, 9H), 0.70 (m, 1H)

The requisite intermediates were prepared as described in the following paragraphs.

Step 1

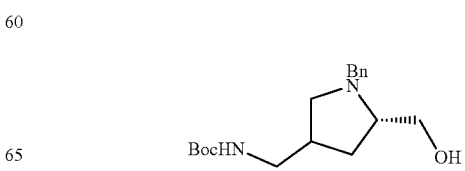

(tert-Butyl (((5S)-1-benzyl-5-(hydroxymethyl)pyrrolidin-3-yl)methyl)carbamate To a solution of commercially available (2S)-methyl 1-benzyl-4-cyanopyrrolidine-2-carboxylate (2.37 g mg, 9.72 mmol) in dry THF (50 mL) at 0° C. under $N_2$ was added LAH (73 mg, 19.4 mmol) in several portions. The reaction mixture was stirred at 0° C. for 30 minutes then room temperature for 1 h. Then the reaction mixture was cooled to 0° C. and slowly added $H_2O$ (0.7 mL), 15% NaOH solution (0.7 mL), EtOAc, and $H_2O$ (2.8 mL). After stirring at room temperature for 30 min $Na_2SO_4$ was added. Continued to stir for 30 minutes then the solid was removed by passing a Celite pad. The filtrate was concentrated to give a crude intermediate ((2S)-4-(aminomethyl)-1-benzylpyrrolidin-2-yl)methanol. The crude intermediate was not further purified and identified. It was directly used in next step. The above intermediate was dissolved in methylene chloride (30 mL) then it was added $Boc_2O$ (2.54 g, 11.7 mmol) and TEA (2.02 mL, 14.6 mmol). The reaction mixture was stirred at room temperature room temperature overnight. The reaction mixture was diluted with methylene chloridemethylene chloride and washed with water, brine then dried over anhydrous sodium sulfate. The solvent was removed and the residue was purified by column chromatography on silica gel using EtOAc. The desired product was collected (1.58 g, 54% yield) as a light yellow oil. $^1$H NMR (300 MHz, CDCl$_3$) δ 7.30 (m, 5H), 4.84 (br. S, 1H), 3.98 (d, J=13.5 Hz, 1H), 3.72 (m, 1H), 3.48 (d, J=11.1 Hz, 1H), 3.26 (d, J=12.9 Hz, 1H), 3.07 (m, 2H), 2.73 (m, 2H), 2.43 (m, 1H), 2.26 (m, 1H), 2.10 (m, 1H), 1.60 (m, 2H), 1.42 (s, 9H).

Preparation of Amine Intermediate L (tert-butyl (2-((3S,5S)-5-(aminomethyl)-1-benzylpyrrolidin-3-yl)propan-2-yl)carbamate)

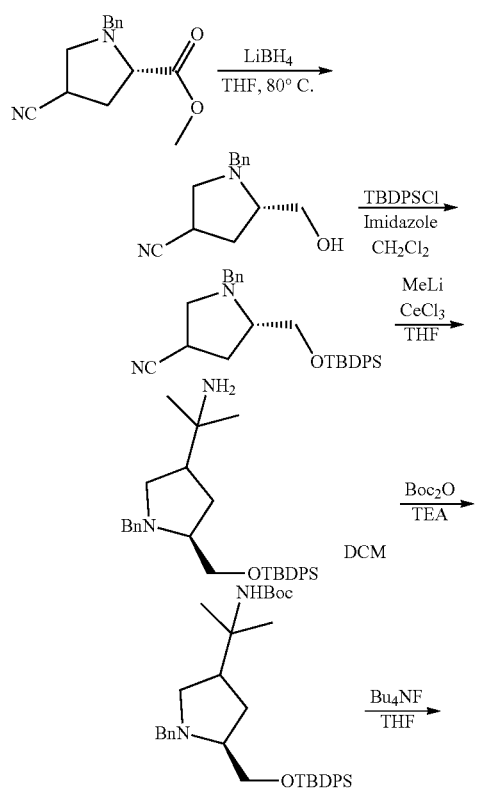

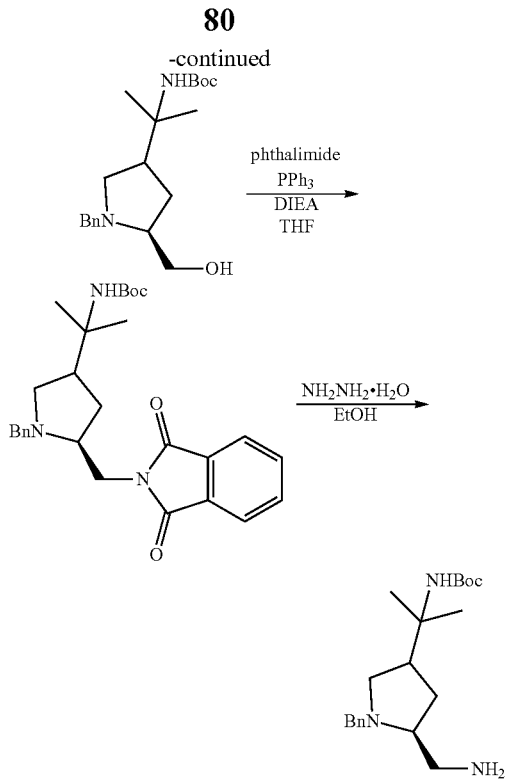

tert-Butyl (2-((5S)-5-(aminomethyl)-1-benzylpyrrolidin-3-yl)propan-2-yl)carbamate To a solution of tert-butyl (2-((5S)-1-benzyl-5-((1,3-dioxoisoindolin-2-yl)methyl)pyrrolidin-3-yl)propan-2-yl)carbamate (55 mg, 0.12 mmol) in EtOH (4 mL) was added hydrazine monohydrate (10 mg, 0.23 mmol). The mixture was stirred at room temperature and the precipitate formed was filtered off and washed with ethanol. The filtrate was concentrated and diluted with EtOAc, washed with saturated NaHCO$_3$ and brine sequentially. The organic layer was dried over anhydrous sodium sulfate and concentrated. The crude product (40 mg, 98% yield) was used directly without further purification. $^1$H NMR (300 MHz, CD$_3$OD) δ 7.24 (m, 5H), 6.03 (br, 1H), 4.56 (d, J=12.9 Hz, 1H), 3.17 (d, J=12.9 Hz, 1H), 2.86 (d, J=10.5 Hz, 1H), 2.77 (m, 1H), 2.43 (m, 1H), 2.23 (m, 1H), 2.12 (m, 1H), 1.95 (m, 1H), 1.62 (m, 2H), 1.37 (s, 9H), 1.21 (s, 3H), 1.14 (s, 3H).

The requisite intermediates were prepared as described in the following paragraphs.

Step 1

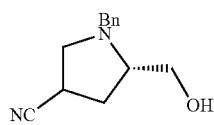 [SMILES: N#CC1C[C@@H](CO)N(Cc2ccccc2)C1]

(5S)-1-Benzyl-5-(hydroxymethyl)pyrrolidine-3-carbonitrile

To a solution of (2S)-methyl 1-benzyl-4-cyanopyrrolidine-2-carboxylate (2.0 g, 8.2 mmol) in dry THF (30 mL) was added LiBH$_4$ (360 mg, 16.4 mmol) in several portions. The reaction mixture was stirred at 80° C. for 1 hour then cooled to 0° C. Acetone (1.0 mL) was added slowly to the reaction mixture to quench the reaction. After stirring at room temperature for 30 minutes, the solvent was removed to give a residue. The residue was dissolved in EtOAc and washed with water, saturated NaHCO$_3$, and brine. The organic layer was dried over anhydrous sodium sulfate and filtered. The filtrate was concentrated and purified on silica gel to give the product (1.33 g, 75% yield) as a colorless oil. $^1$H NMR (300 MHz, CDCl$_3$) δ 7.30 (m, 5H), 4.02 (d, J=13.5 Hz, 1H), 3.77 (m, 1H), 3.50 (m, 1H), 3.40 (d, J=13.5 Hz, 1H), 3.22 (m, 1H), 2.96 (m, 1H), 2.81 (m, 1H), 2.58 (m, 1H), 2.35 (m, 1H), 2.28 (m, 1H).

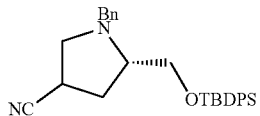

(5S)-1-Benzyl-5-(((tert-butyldiphenylsilyl)oxy)methyl)pyrrolidine-3-carbonitrile To a solution of (5S)-1-benzyl-5-(hydroxymethyl)pyrrolidine-3-carbonitrile (1.0 g, 4.63 mmol) in CH$_2$Cl$_2$ (10 mL) was added imidazole (472 mg, 6.94 mmol), and TBDPSCl (1.33 mL, 5.10 mmol). The above reaction mixture was stirred at room temperature overnight, then diluted with CH$_2$Cl$_2$ and washed with water, saturated NaHCO$_3$, and brine. The organic layer was dried over anhydrous sodium sulfate and filtered. The filtrate was concentrated and purified on silica gel to give the desired product (1.81 g, 86% yield). $^1$H NMR (300 MHz, CDCl$_3$) δ 7.67 (m, 4H), 7.40 (m, 6H), 7.26 (m, 5H), 4.04 (d, J=13.5 Hz, 1H), 3.79 (m, 1H), 3.67 (m, 1H), 3.34 (d, J=13.5 Hz, 1H), 3.15 (m, 1H), 2.92 (m, 1H), 2.80 (m, 1H), 2.50 (m, 1H), 2.37 (m, 1H), 2.10 (m, 1H), 1.16 (s, 9H).

Step 3

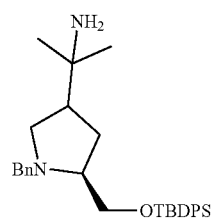

2-((5S)-1-Benzyl-5-(((tert-butyldiphenylsilyl)oxy)methyl)pyrrolidin-3-yl)propan-2-amine To anhydrous CeCl$_3$ (1.63 g, 6.6 mmol) was added THF (12 mL) and it was stirred at room temperature for 2 hour then it was put in a dry ice-acetone bath. MeLi (1.6M in hexane, 3.7 mL, 6 mmol) solution was added dropwise slowly. The color of reaction mixture changed to yellow. It was stirred at −78° C. for 0.5 h then the solution of (5S)-1-benzyl-5-(((tert-butyldiphenylsilyl)oxy)methyl)pyrrolidine-3-carbonitrile (0.91 g, 2 mmol) in THF (3 mL) was added slowly. The reaction mixture was stirred at −78° C. for 3 hour. Crude $^1$H NMR showed the desired product signals. It was quenched with ammonia (1 mL), then extracted with EtOAc, dried over anhydrous Na$_2$SO$_4$ and concentrated to give the product as a colorless oil (0.826 g, 85% yield) which was used for next step reaction without purification. $^1$H NMR (300 MHz, CDCl$_3$) δ 7.88 (m, 4H), 7.43 (m, 6H), 7.27 (m, 5H), 4.14 (d, J=13.5 Hz, 1H), 3.83 (m, 1H), 3.66 (m, 1H), 3.19 (d, J=13.5 Hz, 1H), 2.78 (m, 2H), 2.59 (m, 1H), 2.01 (m, 2H), 1.42 (m, 1H), 1.05 (s, 9H), 1.01 (s, 3H).

Step 4

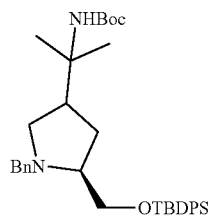

tert-Butyl (2-((5S)-1-benzyl-5-(((tert-butyldiphenylsilyl)oxy)methyl)pyrrolidin-3-yl)propan-2-yl)carbamate To a solution of 2-((5S)-1-benzyl-5-(((tert-butyldiphenylsilyl)oxy)methyl)pyrrolidin-3-yl)propan-2-amine (0.82 g, 1.68 mmol) in methylene chloridemethylene chloride (20 mL) was added Boc$_2$O (0.74 g, 3.4 mmol) and DIPEA (0.6 mL, 3.4 mmol). It was stirred at room temperature overnight and TLC showed no starting material left. It was washed with water, brine and dried over anhydrous sodium sulfate. The crude product was purified by column chromatography on silica gel using 0-10% EtOAc in hexane. A colorless powder was collected (0.95 g, 96% yield). $^1$H NMR (300 MHz, CDCl$_3$) δ 7.68 (m, 4H), 7.40 (m, 6H), 7.33 (m, 5H), 6.09 (br, 1H), 4.25 (d, J=13.5 Hz, 1H), 3.80 (m, 1H), 3.70 (m, 1H), 3.06 (d, J=13.5 Hz, 1H), 2.87 (d, J=9.9 Hz, 1H), 2.58 (m, 1H), 2.03 (m, 2H), 1.69 (m, 2H), 1.42 (s, 9H), 1.25 (s, 3H), 1.16 (s, 3H), 1.06 (s, 9H).

Step 5

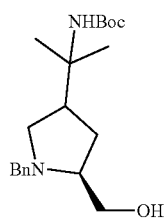

tert-Butyl (2-((5S)-1-benzyl-5-(hydroxymethyl)pyrrolidin-3-yl)propan-2-yl)carbamate To a solution of tert-butyl (2-((5S)-1-benzyl-5-(((tert-butyldiphenylsilyl)oxy)methyl)pyrrolidin-3-yl)propan-2-yl) carbamate (0.93 g, 1.58 mmol) in THF (15 mL) was added TBAF solution in THF (1.0 M, 8 mL, 8 mmol). It was stirred at room temperature until no starting material left. The crude product was purified by column chromatography on silica gel using 30-50% EtOAc in hexane. A colorless oil was collected (0.405 g, 74% yield). $^1$H NMR (300 MHz, CDCl$_3$) δ 7.26 (m, 5H), 6.03 (br, 1H), 3.95 (d, J=12.9 Hz, 1H), 3.68 (dd, J=3.0, 10.5 Hz, 1H), 3.46 (d, J=10.5 Hz, 1H), 3.24 (d, J=12.9 Hz, 1H), 3.17 (d, J=12.9 Hz, 1H), 2.82 (m, 1H), 2.76 (m, 1H), 2.44 (m, 1H), 2.35 (m, 1H), 1.84 (t, J=8.1 Hz, 2H), 1.18 (m, 1H), 0.98 (s, 6H), 0.87 (m, 1H).

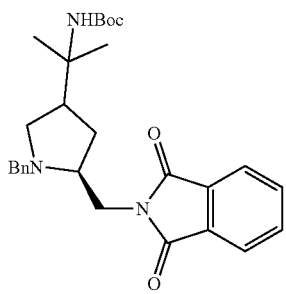 [SMILES: CC(C)(C)OC(=O)NC(C)(C)C1C[C@@H](CN2C(=O)c3ccccc3C2=O)N(Cc2ccccc2)C1]

tert-Butyl (2-((5S)-1-benzyl-5-((1,3-dioxoisoindolin-2-yl)methyl)pyrrolidin-3-yl)propan-2-yl)carbamate To a solution of tert-butyl (2-((5S)-1-benzyl-5-(hydroxymethyl)pyrrolidin-3-yl)propan-2-yl)carbamate (105 mg, 0.3 mmol), triphenylphosphine (94 mg, 0.36 mmol) and phthalimide (53 mg, 0.36 mmol) in THF (5 mL) was added DIAD (73 mg, 0.24 mmol) at 0° C. It was stirred at 0° C.—room temperature and monitored by TLC. After finishing the reaction it was concentrated and purified on column chromatography on silica gel using 50-90% ethyl acetate in hexanes to give product as a white solid (60 mg, 42% yield). $^1$H NMR (300 MHz, CDCl$_3$) δ 7.84 (m, 2H), 7.74 (m, 2H), 7.29 (m, 5H), 5.77 (br, 1H), 4.56 (d, J=13.2 Hz, 1H), 3.86 (m, 2H), 3.17 (d, J=13.2 Hz, 1H), 2.86 (d, J=8.1 Hz, 1H), 2.77 (m, 1H), 2.19 (m, 1H), 2.16 (m, 1H), 2.04 (m, 1H), 1.78 (m, 1H), 1.37 (s, 9H), 1.12 (s, 6H).

Example 1. Preparation of (S)—N-(2,5-diaminopentyl)-5,6-bis(4-fluorophenyl)-1H-benzo[d]imidazole-2-carboxamide Dihydrochloride

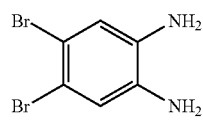

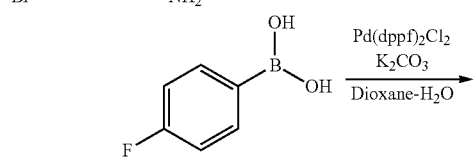

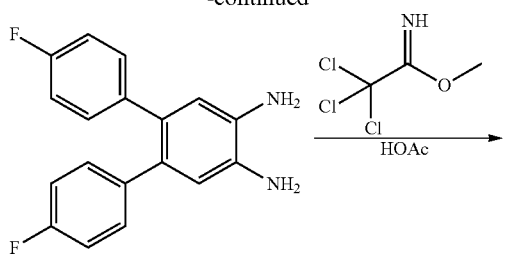

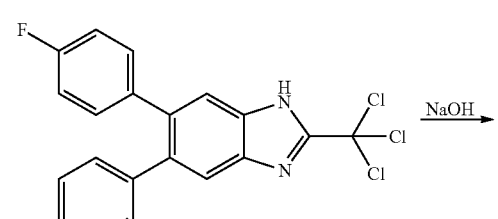

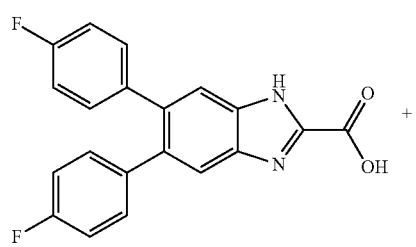

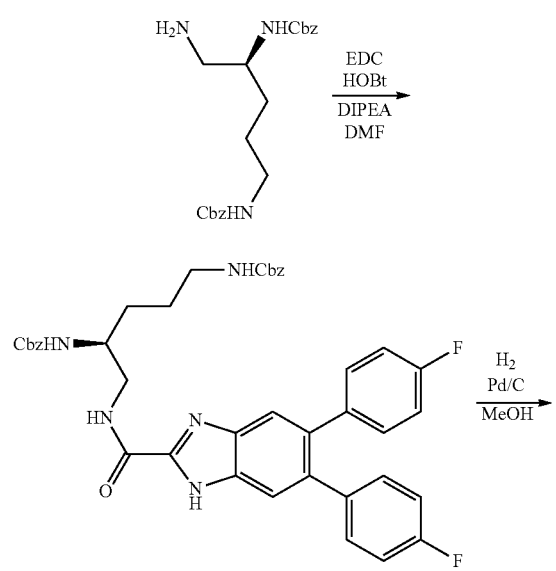

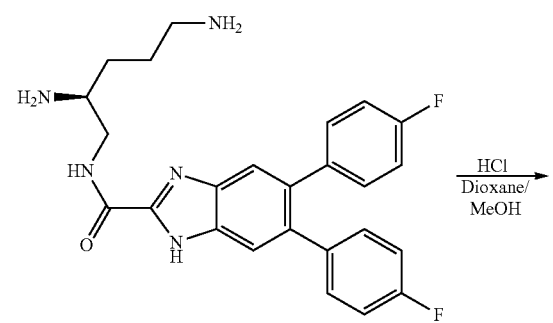

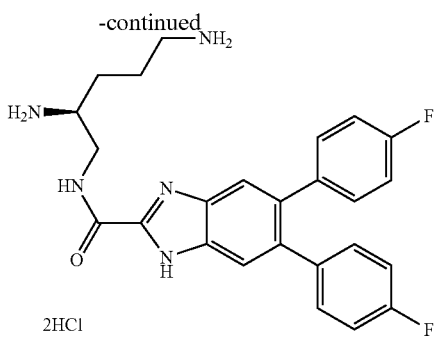

2HCl

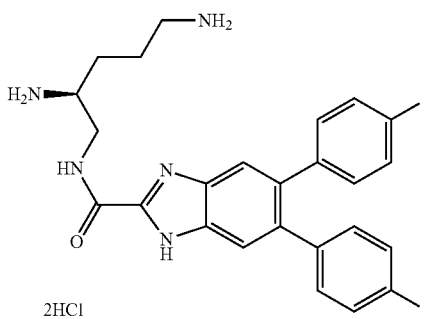

2HCl (S)—N-(2,5-Diaminopentyl)-5,6-bis(4-fluorophenyl)-1H-benzo[d]imidazole-2-carboxamide Dihydrochloride To a solution of dibenzyl (5-(5,6-bis(4-fluorophenyl)-1H-benzo[d]imidazole-2-carboxamido)pentane-1,4-diyl)(S)-dicarbamate (30 mg, 0.036 mmol) in MeOH (5 mL) was added Pd/C (10%, 20 mg). The reaction mixture was hydrogenated under hydrogen gas balloon at room temperature overnight. The solid was filtered off through a Celite pad, washed with methanol and concentrated under reduced pressure. To the solution in MeOH (5 mL) was added HCl solution in dioxane (4 M, 0.02 mL, 0.08 mmol) and it was stirred at room temperature then solvent was removed under reduced pressure. The residue was triturated with EtOAc and the precipitate was collected and dried under reduced pressure to provide the title compound (15 mg, 71% yield in two steps) as an off-white powder. $^1$H NMR (300 MHz, D$_2$O) δ 7.80 (s, 2H), 7.11 (m, 4H), 6.96 (m, 4H), 3.80 (m, 1H), 3.73 (m, 1H), 3.61 (m, 1H), 3.11 (m, 2H), 1.84 (m, 4H).

The requisite intermediates were prepared as described in the following paragraphs.

Step 1

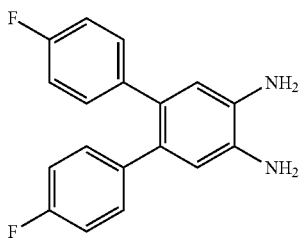 [SMILES: Nc1cc(-c2ccc(F)cc2)c(-c2ccc(F)cc2)cc1N]

4,4"-Difluoro-[1,1':2',1"-terphenyl]-4',5'-diamine

A mixture of 2-amino-4,5-dibromoaniline (532 mg, 2 mmol), (4-fluorophenyl)boronic acid (784 mg, 5.6 mmol) and K$_2$CO$_3$ solution (2 M in water, 7.5 mL) in dioxane (15 mL) was degassed and Pd(dppf)$_2$Cl$_2$ (163 mg, 0.2 mmol) was added. The reaction mixture was stirred at 90° C. for 3 hours. It was extracted with EtOAc and washed with water and brine. After concentration it was purified by column chromatography on silica gel to afford the product (510 mg, 86% yield) as a brown solid. $^1$H NMR (300 MHz, CDCl$_3$) δ 7.01 (m, 4H), 6.92 (m, 4H), 6.74 (s, 2H), 3.51 (br, 4H).

Step 2

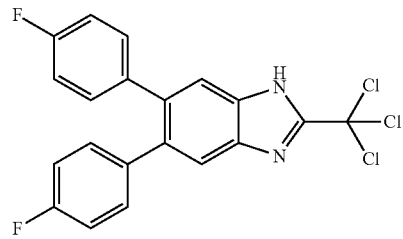 [SMILES: Fc1ccc(-c2cc3nc(C(Cl)(Cl)Cl)[nH]c3cc2-c2ccc(F)cc2)cc1]

5,6-Bis(4-Fluorophenyl)-2-(trichloromethyl)-1H-benzo[d]imidazole

To a solution of 4,4"-difluoro-[1,1':2',1"-terphenyl]-4',5'-diamine (500 mg, 1.7 mmol) in acetic acid (5 mL) was added methyl 2,2,2-trichloroacetimidate (0.27 mL, 2.2 mmol). It was stirred at room temperature for 5 hours. Then ice was added and the precipitate was filtered and washed with water. It was purified by column chromatography on silica gel using EtOAc/methylene chloridemethylene chloride as eluent to give the product (430 mg, 58% yield) as a pale brown powder. $^1$H NMR (300 MHz, CDCl$_3$) δ 9.87 (br, 1H), 7.88 (s, 1H), 7.50 (s, 1H), 7.08 (m, 4H), 6.94 (m, 4H).

Step 3

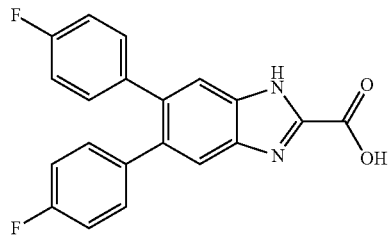 [SMILES: O=C(O)c1nc2cc(-c3ccc(F)cc3)c(-c3ccc(F)cc3)cc2[nH]1]

5,6-Bis(4-Fluorophenyl)-1H-benzo[d]imidazole-2-carboxylic Acid

To a solution of 5,6-bis(4-fluorophenyl)-2-(trichloromethyl)-1H-benzo[d]imidazole (130 mg, 0.3 mmol) in THF (4 mL) was added NaOH solution in water. It was stirred at room temperature for 3 hours and TLC showed no starting material left. Then the organic solvent was removed under reduced pressure. The mixture was acidified and the precipitate was filtered and washed with water to afford the product (50 mg, 48% yield) as a pale brown powder. It was dried on air and used for next step reaction without purification. ¹H NMR (300 MHz, DMSO-d₆) δ 8.15 (s, 1H), 7.58 (s, 1H), 7.08 (m, 4H), 6.98 (m, 4H).

Step 4

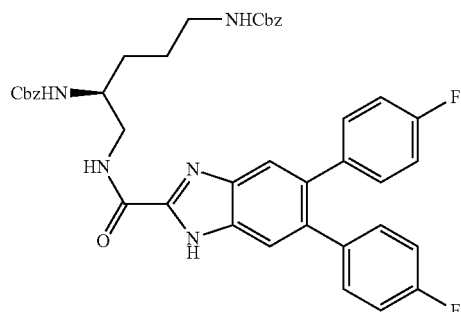

Dibenzyl (5-(5,6-bis(4-fluorophenyl)-1H-benzo[d]imidazole-2-carboxamido)pentane-1,4-diyl)(S)-dicarbamate To a solution of 5,6-bis(4-fluorophenyl)-1H-benzo[d]imidazole-2-carboxylic acid (50 mg, 0.14 mmol) in dry DMF (2 mL) was added DIPEA (0.05 mL, 0.28 mmol), HOBt (12 mg, 0.08 mmol) and EDC (33 mg, 0.17 mmol). The reaction mixture was stirred at room temperature and dibenzyl (5-aminopentane-1,4-diyl)-(S)-dicarbamate (intermediate A) (55 mg, 0.14 mmol) was added. It was stirred at room temperature overnight. The reaction mixture was diluted with EtOAc and washed with water and brine. The organic layer was dried over anhydrous sodium sulfate and filtered. The filtrate was concentrated and purified using column chromatography with silica gel to give the product (50 mg, 50% yield) as a white solid. ¹H NMR (300 MHz, CDCl₃) δ 7.65 (s, 2H), 7.31 (m, 10H), 7.07 (m, 4H), 6.89 (m, 4H), 5.05 (m, 4H), 3.86 (m, 1H), 3.59 (m, 1H), 3.21 (m, 2H), 1.60 (m, 4H).

Example 2. Preparation of (S)—N-(2,5-diaminopentyl)-5,7-bis(4-fluorophenyl)-1H-benzo[d]imidazole-2-carboxamide Dihydrochloride

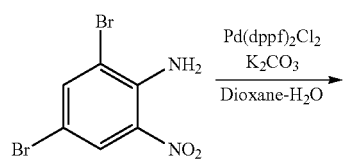

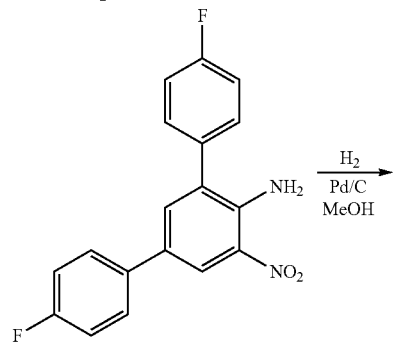

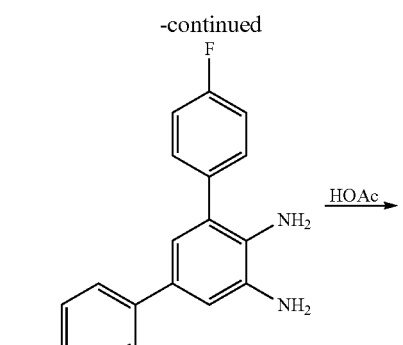

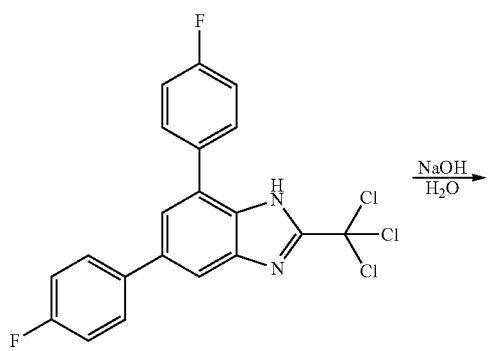

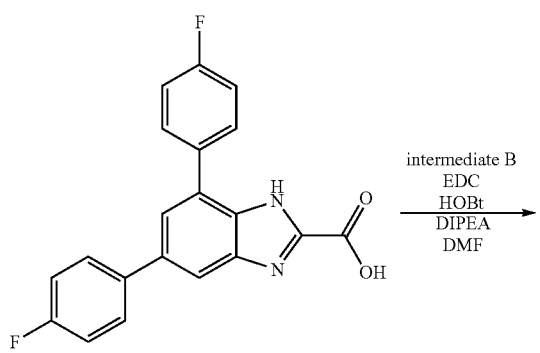

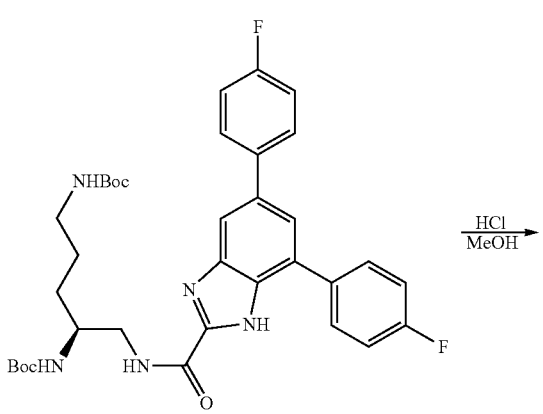

-continued

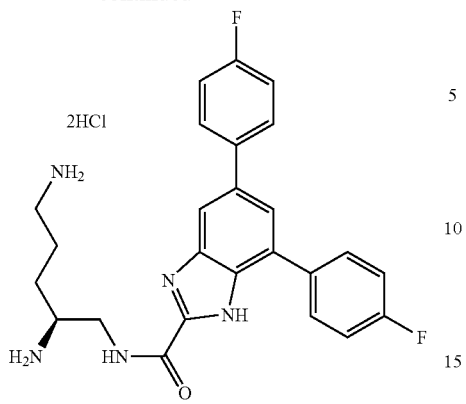

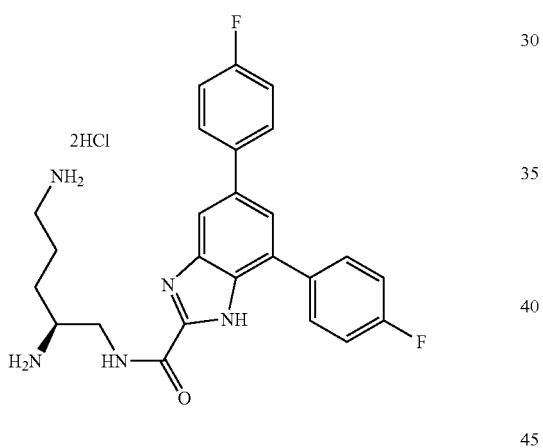

(S)—N-(2,5-Diaminopentyl)-5,7-bis(4-fluorophenyl)-1H-benzo[d]imidazole-2-carboxamide Dihydrochloride To a solution of di-tert-butyl (5-(5,7-bis(4-fluorophenyl)-1H-benzo[d]imidazole-2-carboxamido)pentane-1,4-diyl) (S)-dicarbamate (37 mg, 0.06 mmol) in MeOH (5 mL) was added HCl solution (4 M in dioxane, 0.15 mL, 0.6 mmol). It was stirred at room temperature overnight and solvent was removed under reduced pressure. The residue was triturated with EtOAc and the precipitate was collected as an off-white powder (27 mg, 70% yield). $^1$H NMR (300 MHz, D$_2$O) δ 7.93 (s, 1H), 7.84 (s, 1H), 7.71 (m, 4H), 7.22 (m, 4H), 3.74 (m, 1H), 3.61 (m, 1H), 3.45 (m, 1H), 2.93 (m, 2H), 1.78 (m, 4H).

The requisite intermediates were prepared as described in the following paragraphs.

Step 1

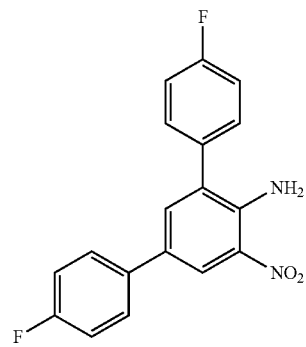 [SMILES: Nc1c(-c2ccc(F)cc2)cc(-c2ccc(F)cc2)cc1[N+](=O)[O-]]

4,4''-Difluoro-5'-nitro-[1,1': 3',1''-terphenyl]-4'-amine

A mixture of 2-nitro-46-dibromoaniline (592 mg, 2 mmol), (4-fluorophenyl)boronic acid (1.12 g, 8 mmol) and K$_2$CO$_3$ solution (2 M in water, 6 mL) in dioxane (15 mL) was degassed and Pd(dppf)$_2$Cl$_2$ (163 mg, 0.2 mmol) was added. The reaction mixture was stirred at 100° C. overnight. It was extracted with EtOAc and washed with water and brine. After concentration it was purified by column chromatography on silica gel to afford the product (401 mg, 61% yield) as a yellow solid. H NMR (300 MHz, CDCl$_3$) δ 8.36 (s, 1H), 7.53 (m, 2H), 7.51 (s, 1H), 7.44 (m, 2H), 7.24 (m, 2H), 7.12 (m, 2H), 6.26 (br, 2H).

Step 2

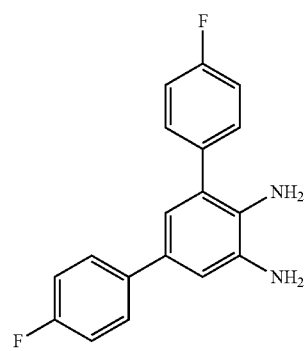

4,4''-Difluoro-[1,1':3',1''-terphenyl]-4',5'-diamine 4,4''-difluoro-5'-nitro-[1,1':3',1''-terphenyl]-4'-amine (400 mg, 1.2 mmol) was dissolved in methanol and EtOAc (10 mL/10 mL) then Pd/C (10%, 100 mg) was added and stirred under H$_2$ overnight. It was filtered through a pad of Celite and washed with MeOH. After concentration the product (330 mg, 91% yield) was collected as a brown solid. $^1$H NMR (300 MHz, CDCl$_3$) δ 7.47 (m, 4H), 7.13 (m, 2H), 7.04 (m, 2H), 6.93 (s, 1H), 6.88 (s, 1H), 3.54 (br, 4H).

Step 3

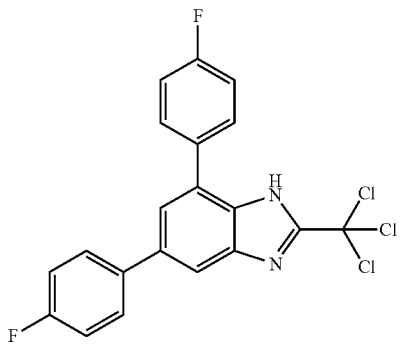 [SMILES: Fc1ccc(-c2cc(-c3ccc(F)cc3)c3[nH]c(C(Cl)(Cl)Cl)nc3c2)cc1]

5,7-Bis(4-fluorophenyl)-2-(trichloromethyl)-1H-benzo[d]imidazole

To a solution of 4,4''-difluoro-[1,1':3',1''-terphenyl]-4',5'-diamine (330 mg, 1.1 mmol) in acetic acid (10 mL) was added methyl 2,2,2-trichloroacetimidate (0.175 mL, 1.4 mmol). It was stirred at room temperature for 6 hours. Then ice was added and the precipitate was filtered and washed with water to provide the crude product which was used for next step reaction without purification.

Step 4

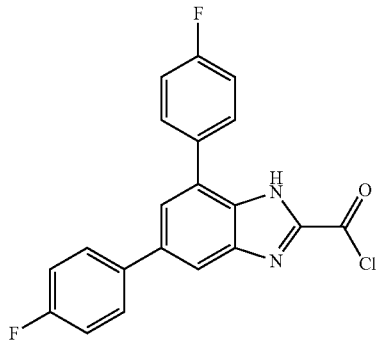 [SMILES: O=C(Cl)c1nc2cc(-c3ccc(F)cc3)cc(-c3ccc(F)cc3)c2[nH]1]

5,7-Bis(4-fluorophenyl)-1H-benzo[d]imidazole-2-carboxylic Acid

To the crude 5,7-bis(4-fluorophenyl)-2-(trichloromethyl)-1H-benzo[d]imidazole got from the previous step in THF (4 mL) was added NaOH solution in water (1.2 M, 4 mL). It was stirred at room temperature for 3 hours and TLC showed no starting material left. Then the organic solvent was removed under reduced pressure. The mixture was acidified and the precipitate was filtered and washed with water to afford the product (168 mg, 48% yield in two steps) as a brown powder. The crude product was dried on air and used for next step reaction without purification. $^1$H NMR (300 MHz, DMSO-$d_6$) δ 8.24 (s, 1H), 7.77 (m, 2H), 7.60 (s, 1H), 7.30 (m, 6H).

Step 5

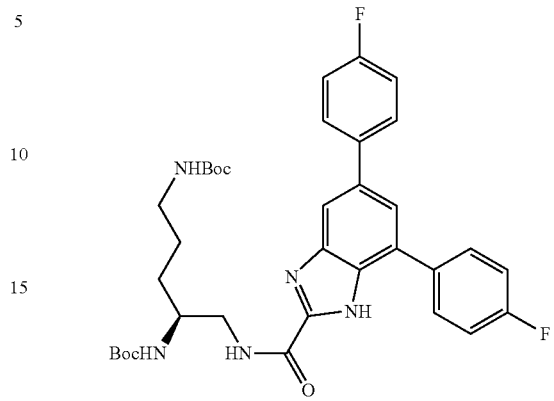

Di-tert-butyl (5-(5,7-bis(4-fluorophenyl)-1H-benzo[d]imidazole-2-carboxamido)pentane-1,4-diyl)(S)-dicarbamate To a solution of 5,7-bis(4-fluorophenyl)-1H-benzo[d]imidazole-2-carboxylic acid (70 mg, 0.2 mmol) in dry methylene chloridemethylene chloride (10 mL) was added DIPEA (0.1 mL, 0.6 mmol), HOBt (20 mg, 0.13 mmol) and EDC (52 mg, 0.26 mmol). The reaction mixture was stirred at room temperature and di-tert-butyl (5-aminopentane-1,4-diyl)(S)-dicarbamate (intermediate B) (64 mg, 0.2 mmol) was added. The reaction mixture was stirred at room temperature overnight. Then it was concentrated and purified by column chromatography on silica gel to give the product (49 mg, 38% yield) as a white solid. 1H NMR (300 MHz, CDCl$_3$) δ 7.90 (s, 1H), 7.56 (m, 4H), 7.49 (s, 1H), 7.14 (m, 4H), 4.89 (br, 1H), 4.72 (br, 1H), 3.89 (m, 1H), 3.60 (m, 1H), 3.54 (m, 1H), 3.13 (m, 2H), 1.73 (m, 2H), 1.62 (m, 2H), 1.41 (s, 9H), 1.35 (s, 9H).

Example 3. Preparation of (S)—N-(2,5-diaminopentyl)-5-(4-fluorophenyl)-7-(trifluoromethyl)-1H-benzo[d]imidazole-2-carboxamide Dihydrochloride

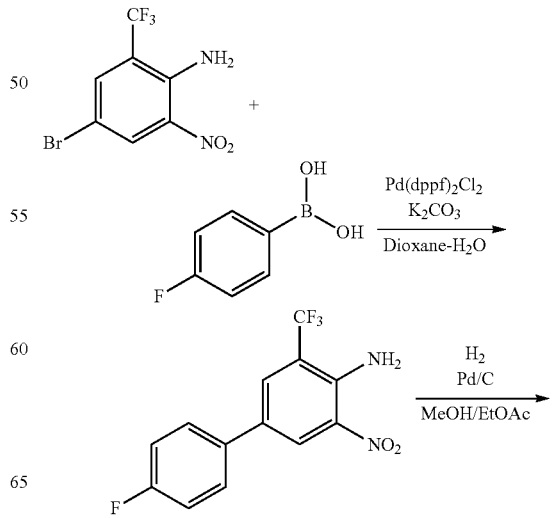

-continued

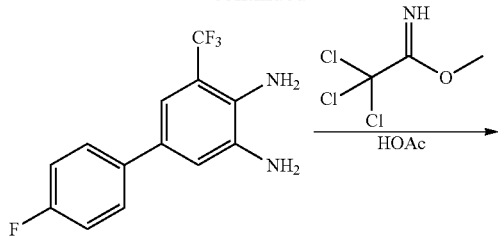

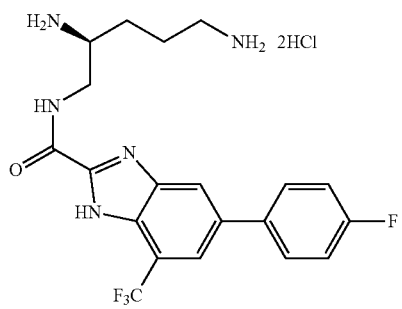 [SMILES: NCCC[C@H](N)CNC(=O)c1nc2cc(-c3ccc(F)cc3)cc(C(F)(F)F)c2[nH]1]

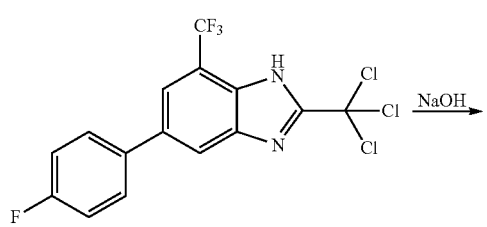

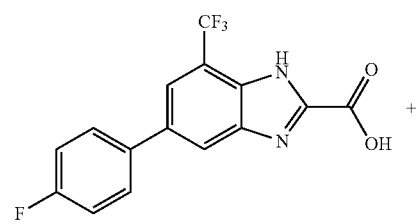

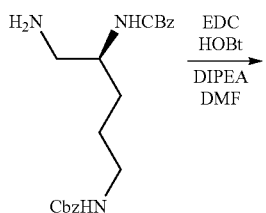

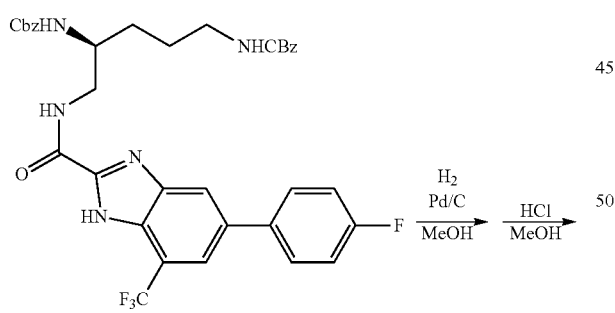

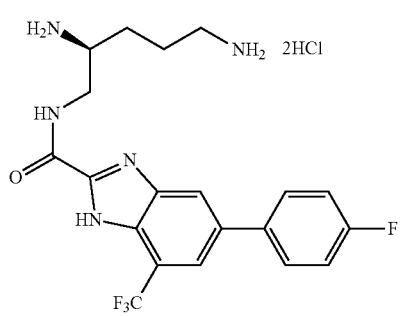

(S)—N-(2,5-Diaminopentyl)-5-(4-fluorophenyl)-7-(trifluoromethyl)-1H-benzo[d]imidazole-2-carboxamide Dihydrochloride To a solution of dibenzyl (5-(5-(4-fluorophenyl)-7-(trifluoromethyl)-1H-benzo[d]imidazole-2-carboxamido)pentane-1,4-diyl) (S)-dicarbamate (34 mg, 0.05 mmol) in methanol (5 mL) was added Pd/C (10%, 20 mg). It was stirred under $H_2$ overnight. The solid was filtered off through a pad of Celite and concentrated under reduced pressure. To the solution in MeOH (3 mL) was added HCl solution in dioxane (4 M, 0.04 mL) and it was stirred at room temperature for 1 hour then concentrated under reduced pressure. The residue was triturated with EtOAc and the precipitate was collected and dried under reduced pressure to provide the title compound (19 mg, 77% yield in two steps) as an off-white powder. $^1$H NMR (300 MHz, $D_2O$) δ 8.04 (s, 1H), 7.69 (s, 1H), 7.10 (m, 2H), 6.95 (m, 2H), 3.79 (m, 1H), 3.73 (m, 1H), 3.60 (m, 1H), 3.04 (m, 2H), 1.88 (m, 4H).

The requisite intermediates were prepared as described in the following paragraphs.

Step 1

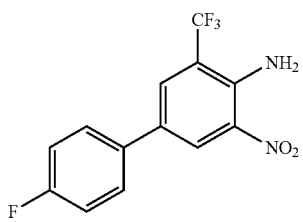

4'-Fluoro-3-nitro-5-(trifluoromethyl)-[1,1'-biphenyl]-4-amine

A mixture of 4-bromo-2-nitro-6-(trifluoromethyl)aniline (570 mg, 2 mmol), (4-fluorophenyl)boronic acid (420 mg, 3 mmol) and $K_2CO_3$ (2 M solution in water, 3 mL) in dioxane (5 mL) was degassed and Pd(dppf)$_2C_2$ (82 mg, 0.1 mmol) was added. The reaction mixture was stirred at 85° C. overnight. It was extracted with EtOAc and washed with water and brine. After concentration it was purified by column chromatography on silica gel to afford the product (480 mg, 80% yield) as a yellow solid.

Step 2

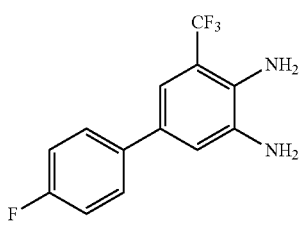 [SMILES: Nc1c([N+](=O)[O-])cc(-c2ccc(F)cc2)cc1C(F)(F)F]

4'-Fluoro-5-(trifluoromethyl)-[1,1'-biphenyl]-3,4-diamine

4'-fluoro-3-nitro-5-(trifluoromethyl)-[1,1'-biphenyl]-4-amine (470 mg, 1.57 mmol) was dissolved in methanol and EtOAc (10 mL/10 mL) and Pd/C (10%, 50 mg) was added and stirred under $H_2$ overnight. It was filtered through a pad of Celite and washed with MeOH. After concentration, the product (400 mg, 94% yield) was collected as a grey powder. $^1H$ NMR (300 MHz, $CDCl_3$) δ 7.47 (m, 2H), 7.19 (s, 1H), 7.12 (m, 2H), 7.06 (s, 1H), 3.99 (br, 2H), 3.53 (br, 2H).

Step 3

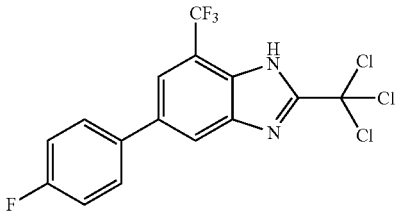 [SMILES: Fc1ccc(-c2cc(C(F)(F)F)c3[nH]c(C(Cl)(Cl)Cl)nc3c2)cc1]

5-(4-Fluorophenyl)-2-(trichloromethyl)-7-(trifluoromethyl)-1H-benzo[d]imidazole

To a solution of 4'-fluoro-5-(trifluoromethyl)-[1,1'-biphenyl]-3,4-diamine (0.39 g, 1.44 mmol) in acetic acid (3 mL) was added methyl 2,2,2-trichloroacetimidate (0.18 mL, 1.87 mmol). It was stirred at room temperature for 6 hours. Then ice was added and the precipitate was filtered and washed with water to provide the crude product as a pale brown powder. It was used for next step reaction without purification. $^1H$ NMR (300 MHz, $CDCl_3$) δ 8.18 (s, 1H), 7.76 (s, 1H), 7.52 (m, 2H), 7.15 (m, 2H).

Step 4

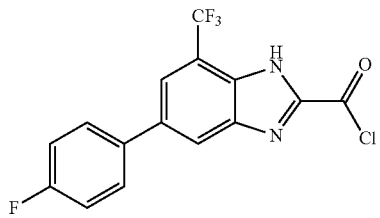 [SMILES: O=C(Cl)c1nc2cc(-c3ccc(F)cc3)cc(C(F)(F)F)c2[nH]1]

5-(4-Fluorophenyl)-7-(trifluoromethyl)-1H-benzo[d]imidazole-2-carboxylic Acid 5-(4-Fluorophenyl)-2-(trichloromethyl)-7-(trifluoromethyl)-1H-benzo[d]imidazole was dissolved in THF (10 mL) and NaOH solution (2 M, 8 mL) was added. It was stirred at room temperature for 3 hour and THF was removed under reduced pressure. It was acidified and the precipitate was filtered and washed with water. It was dried to provide a brown powder (260 mg, 56% yield in two steps). $^1H$ NMR (300 MHz, DMSO-$d_6$) δ 8.03 (s, 1H), 7.83 (s, 1H), 7.70 (m, 2H), 7.25 (m, 2H). MS (ESI+): 325.12 $[M+H]^+$ for $C_{15}H_8F_4N_2O_2$.

Step 5

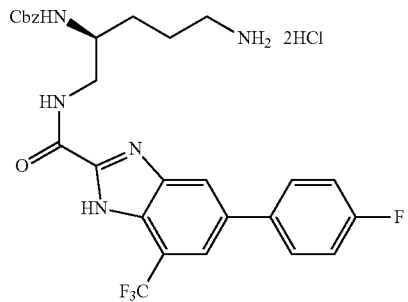 [SMILES: NCCC[C@@H](CNC(=O)c1nc2cc(-c3ccc(F)cc3)cc(C(F)(F)F)c2[nH]1)NC(=O)OCc1ccccc1]

Dibenzyl (5-(5-(4-fluorophenyl)-7-(trifluoromethyl)-1H-benzo[d]imidazole-2-carboxamido)pentane-1,4-diyl) (S)-dicarbamate To a solution of 5-(4-fluorophenyl)-7-(trifluoromethyl)-1H-benzo[d]imidazole-2-carboxylic acid (63 mg, 0.2 mmol) in dry DMF (2 mL) was added DIPEA (0.07 mL, 0.39 mmol), HOBt (36 mg, 0.23 mmol) and EDC (45 mg, 0.23 mmol). The reaction mixture was stirred at room temperature and dibenzyl (5-aminopentane-1,4-diyl)-(S)-dicarbamate (intermediate A) (50 mg, 0.13 mmol) was added. The reaction mixture was stirred at room temperature overnight. It was diluted with EtOAc and washed with water and brine. The organic layer was dried over anhydrous sodium sulfate and filtered. The filtrate was concentrated and purified by column chromatography on silica gel to give the product (35 mg, 39% yield) as an off-white solid. $^1H$ NMR (300 MHz, $CDCl_3$) δ 8.12 (s, 1H), 7.68 (s, 1H), 7.48 (m, 2H), 7.30 (m, 10H), 7.15 (m, 2H), 5.37 (br, 1H), 5.13 (br, 1H), 5.05 (m, 4H), 3.96 (m, 1H), 3.60 (m, 1H), 3.50 (m, 1H), 3.20 (m, 2H), 1.61 (m, 4H).

Example 4. Preparation of (S)—N-(2,5-diaminopentyl)-5-(4-fluorophenyl)-1-methyl-7-(trifluoromethyl)-1H-benzo[d]imidazole-2-carboxamide Dihydrochloride

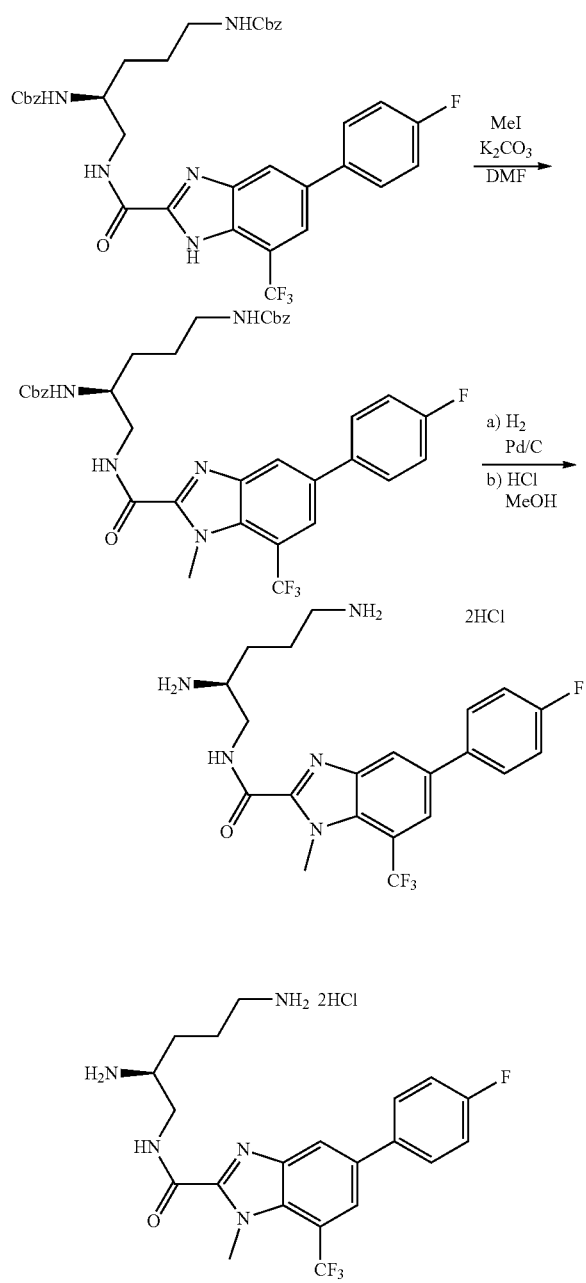

(S)—N-(2,5-Diaminopentyl)-5-(4-fluorophenyl)-1-methyl-7-(trifluoromethyl)-1H-benzo[d]imidazole-2-carboxamide Dihydrochloride To a solution of dibenzyl (5-(5-(4-fluorophenyl)-1-methyl-7-(trifluoromethyl)-1H-benzo[d]imidazole-2-carboxamido)pentane-1,4-diyl)(S)-dicarbamate (34 mg, 0.048 mmol) in MeOH (5 mL) was added Pd/C (10%, 15 mg). The reaction mixture was stirred under $H_2$ overnight. The solid was filtered through a Celite pad and concentrated. The intermediate was dissolved in MeOH (5 mL) and HCl solution in dioxane (4 M, 0.1 mL, 0.4 mmol) was added. It was stirred at room temperature for 1 hour and concentrated. The residue was triturated with EtOAc and the precipitate was collected and dried under reduced pressure to give the product (20 mg, 95% yield) as an off-white powder. $^1$H NMR (300 MHz, DMSO-$d_6$) δ 8.31 (s, 1H), 7.89 (m, 3H), 7.36 (t, J=8.7 Hz, 2H), 4.21 (s, 3H), 3.66-3.42 (m, 3H), 2.82 (m, 2H), 1.51 (m, 4H).

The requisite intermediates were prepared as described in the following paragraphs.

Step 1

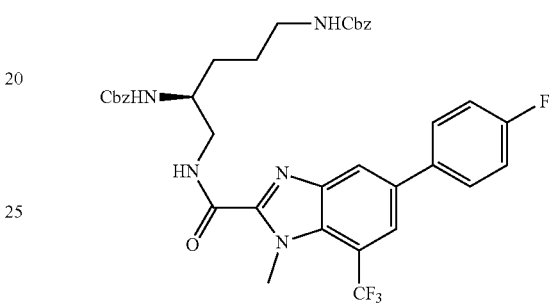

Dibenzyl (5-(5-(4-fluorophenyl)-1-methyl-7-(trifluoromethyl)-1H-benzo[d]imidazole-2-carboxamido)pentane-1,4-diyl)(S)-dicarbamate To a solution of dibenzyl (5-(5-(4-fluorophenyl)-7-(trifluoromethyl)-1H-benzo[d]imidazole-2-carboxamido)pentane-1,4-diyl) (S)-dicarbamate (35 mg, 0.05 mmol) in DMF (0.5 mL) was added $K_2CO_3$ (27 mg, 0.2 mmol) and MeI (46 mg, 0.3 mmol). It was stirred at room temperature overnight and then extracted with EtOAc and washed with water. The crude product was purified by column chromatography on silica gel using 30-50% EtOAc/Hexane to give the product (34 mg, 94% yield) as an off-white powder. $^1$H NMR (300 MHz, CDCl$_3$) δ 7.81 (s, 1H), 7.68 (s, 1H), 7.62 (m, 2H), 7.26 (m, 10H), 7.22 (m, 2H), 5.07 (m, 4H), 4.19 (s, 3H), 3.93 (m, 1H), 3.55 (m, 2H), 3.23 (m, 2H), 1.66 (m, 4H).

Example 5. Preparation of (S)—N-(2,5-diaminopentyl)-5-(4-fluorophenyl)-1-methyl-1H-benzo[d]imidazole-2-carboxamide Dihydrochloride

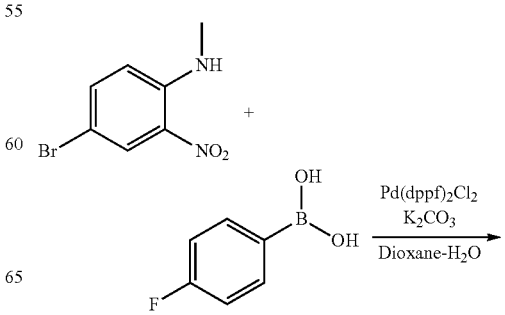

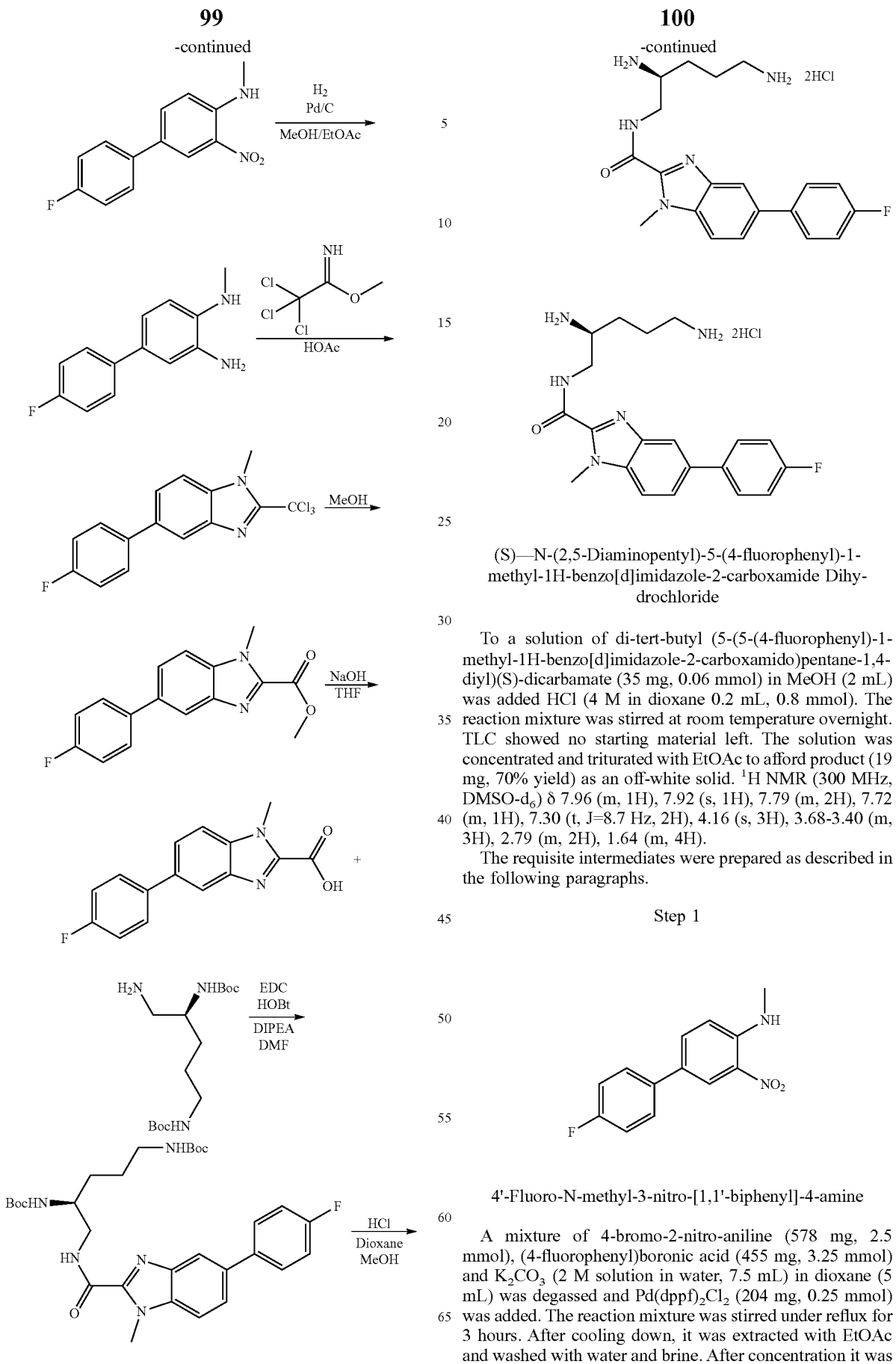

(S)—N-(2,5-Diaminopentyl)-5-(4-fluorophenyl)-1-methyl-1H-benzo[d]imidazole-2-carboxamide Dihydrochloride To a solution of di-tert-butyl (5-(5-(4-fluorophenyl)-1-methyl-1H-benzo[d]imidazole-2-carboxamido)pentane-1,4-diyl)(S)-dicarbamate (35 mg, 0.06 mmol) in MeOH (2 mL) was added HCl (4 M in dioxane 0.2 mL, 0.8 mmol). The reaction mixture was stirred at room temperature overnight. TLC showed no starting material left. The solution was concentrated and triturated with EtOAc to afford product (19 mg, 70% yield) as an off-white solid. $^1$H NMR (300 MHz, DMSO-$d_6$) δ 7.96 (m, 1H), 7.92 (s, 1H), 7.79 (m, 2H), 7.72 (m, 1H), 7.30 (t, J=8.7 Hz, 2H), 4.16 (s, 3H), 3.68-3.40 (m, 3H), 2.79 (m, 2H), 1.64 (m, 4H).

The requisite intermediates were prepared as described in the following paragraphs.

Step 1

4'-Fluoro-N-methyl-3-nitro-[1,1'-biphenyl]-4-amine

A mixture of 4-bromo-2-nitro-aniline (578 mg, 2.5 mmol), (4-fluorophenyl)boronic acid (455 mg, 3.25 mmol) and $K_2CO_3$ (2 M solution in water, 7.5 mL) in dioxane (5 mL) was degassed and Pd(dppf)$_2$Cl$_2$ (204 mg, 0.25 mmol) was added. The reaction mixture was stirred under reflux for 3 hours. After cooling down, it was extracted with EtOAc and washed with water and brine. After concentration it was purified by column chromatography on silica gel using 0-20% EtOAc in hexane to afford product (510 mg, 83% yield) as a red powder.

Step 2

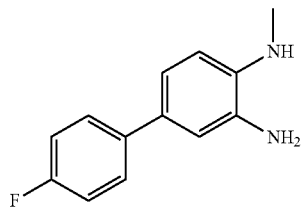 [SMILES: CNc1ccc(-c2ccc(F)cc2)cc1[N+](=O)[O-]]

4'-Fluoro-N4-methyl-[1,1'-biphenyl]-3,4-diamine

4'-fluoro-N-methyl-3-nitro-[1,1'-biphenyl]-4-amine (500 mg, 2 mmol) was dissolved in methanol and EtOAc (10 mL/10 mL) and Pd/C (10%, 50 mg) was added and stirred under $H_2$ overnight. The reaction mixture was filtered through a pad of Celite and washed with MeOH. After concentration, the product (430 mg, 98% yield) was collected as a grey solid. $^1$H NMR (300 MHz, CDCl$_3$) δ 7.47 (m, 2H), 7.06 (m, 3H), 6.92 (d, J=2.1 Hz, 1H), 6.71 (d, J=8.1 Hz, 1H), 3.39 (br, 3H), 2.91 (s, 3H).

Step 3

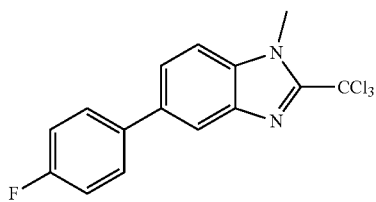

5-(4-Fluorophenyl)-1-methyl-2-(trichloromethyl)-1H-benzo[d]imidazole

To a solution of 4'-fluoro-N4-methyl-[1,1'-biphenyl]-3,4-diamine (0.34 g, 1.57 mmol) in acetic acid (5 mL) was added methyl 2,2,2-trichloroacetimidate (0.24 mL, 1.94 mmol). It was stirred at room temperature overnight. TLC showed no starting material left. Then ice was added and the precipitate was filtered and washed with water to provide the crude product (0.45 g, 83% yield). It was used for next step reaction without purification. $^1$H NMR (300 MHz, CDCl$_3$) δ 8.04 (s, 1H), 7.59 (m, 3H), 7.45 (d, J=8.7 Hz, 1H), 7.15 (d, J=8.1 Hz, 2H), 4.13 (s, 3H).

Step 4

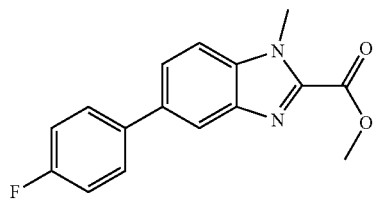 [SMILES: COC(=O)c1nc2cc(-c3ccc(F)cc3)ccc2n1C]

Methyl 5-(4-fluorophenyl)-1-methyl-1H-benzo[d]imidazole-2-carboxylate 5-(4-Fluorophenyl)-1-methyl-2-(trichloromethyl)-1H-benzo[d]imidazole (450 mg, 1.3 mmol) was dissolved in methanol (50 mL). It was heated at 65° C. until no starting material left monitored by TLC. It was concentrated and diluted with EtOAc then washed with NaHCO$_3$ solution. After concentration the product was collected as a brown powder (350 mg, 94% yield). $^1$H NMR (300 MHz, CDCl$_3$) δ 7.99 (s, 1H), 7.58 (d, J=8.1 Hz, 1H), 7.48 (t, J=8.7 Hz, 2H), 7.45 (d, J=8.1 Hz, 1H), 7.01 (t, J=8.7 Hz, 2H), 4.13 (s, 3H), 3.96 (s, 3H).

Step 5

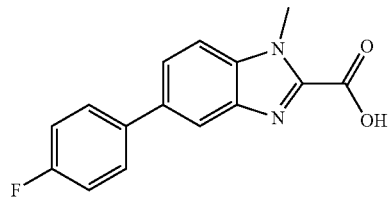 [SMILES: Cn1c(C(=O)O)nc2cc(-c3ccc(F)cc3)ccc21]

5-(4-Fluorophenyl)-1-methyl-1H-benzo[d]imidazole-2-carboxylic Acid

To a solution of methyl 5-(4-fluorophenyl)-1-methyl-1H-benzo[d]imidazole-2-carboxylate (115 mg, 0.4 mmol) in THF (2 mL) was added NaOH solution (2 M, 2 mL). The reaction mixture was stirred at room temperature for 3 hour. TLC showed no SM left. Then it was adjusted into acidic and solvent was removed then it was extracted with MeOH. The organic layers were dried and concentrated to give product (72 mg, 66% yield) as an off-white solid. $^1$H NMR (300 MHz, DMSO-d$_6$) δ 7.79 (s, 1H), 7.55 (m, 4H), 7.42 (m, 1H), 7.05 (t, J=8.7 Hz, 2H), 3.82 (s, 3H).

Step 6

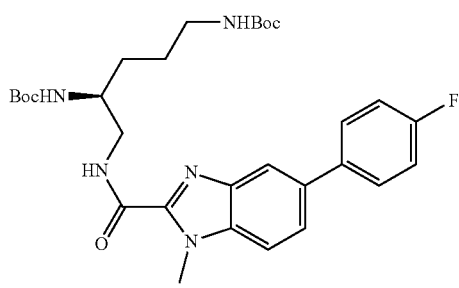 [SMILES: Cn1c(C(=O)NC[C@H](CCCNC(=O)OC(C)(C)C)NC(=O)OC(C)(C)C)nc2cc(-c3ccc(F)cc3)ccc21]

Di-tert-butyl (5-(5-(4-fluorophenyl)-1-methyl-1H-benzo[d]imidazole-2-carboxamido)pentane-1,4-diyl) (S)-dicarbamate To a solution of 5-(4-fluorophenyl)-1-methyl-1H-benzo[d]imidazole-2-carboxylic acid (27 mg, 0.1 mmol) in dry DMF (1.5 mL) was added DIPEA (0.045 mL, 0.25 mmol), HOBt (14 mg, 0.09 mmol) and EDC (21 mg, 0.11 mmol). The reaction mixture was stirred at room temperature and di-tert-butyl (5-aminopentane-1,4-diyl)(S)-dicarbamate (intermediate B) (32 mg, 0.1 mmol) was added. The reaction mixture was stirred at room temperature overnight. Then it was concentrated and purified by column chromatography on silica gel to give the product (39 mg, 68% yield) as a white solid. ¹H NMR (300 MHz, CD₃COCD₃) δ 7.90 (s, 1H), 7.76 (m, 1H), 7.73 (m, 1H), 7.70 (s, 1H), 7.39 (m, 1H), 7.24 (t, J=8.7 Hz, 2H), 4.26 (s, 3H), 3.87 (m, 1H), 3.63 (m, 1H), 3.58 (m, 1H), 3.10 (m, 2H), 1.64 (m, 2H), 1.58 (m, 2H), 1.38 (s, 9H), 1.37 (s, 9H).

Example 6. Preparation of (S)—N-(2,5-diaminopentyl)-5-(4-(trifluoromethyl)phenyl)-1H-benzo[d]imidazole-2-carboxamide Dihydrochloride

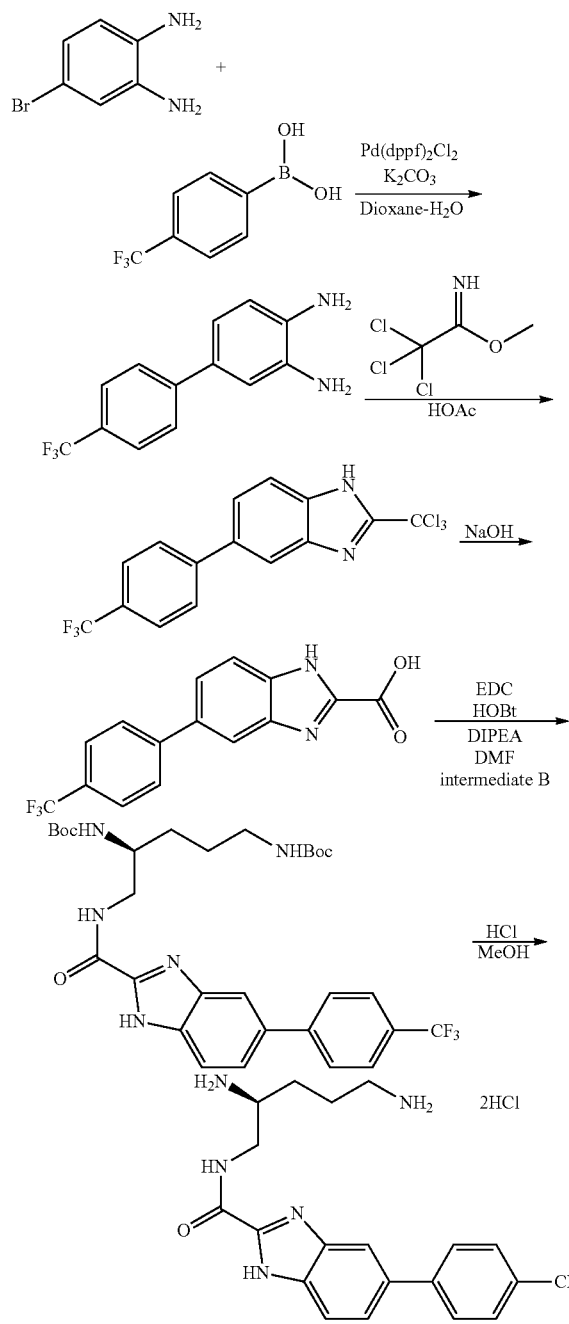

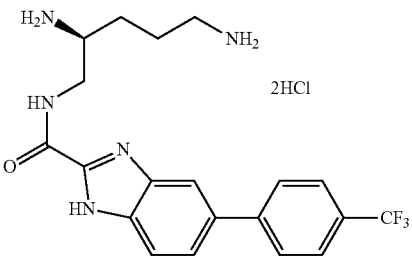 [SMILES: NCCC[C@H](N)CNC(=O)c1nc2cc(-c3ccc(C(F)(F)F)cc3)ccc2[nH]1]

(S)—N-(2,5-Diaminopentyl)-5-(4-(trifluoromethyl)phenyl)-1H-benzo[d]imidazole-2-carboxamide Dihydrochloride To a solution of di-tert-butyl (5-(5-(4-(trifluoromethyl)phenyl)-1H-benzo[d]imidazole-2-carboxamido)pentane-1,4-diyl)(S)-dicarbamate (35 mg, 0.06 mmol) in MeOH (2 mL) was added HCl (0.15 mL, 4M in dioxane). The reaction mixture was stirred at room temperature overnight. TLC showed no starting material left. The solution was concentrated and triturated with EtOAc to afford product (17 mg, 71% yield) as a white solid. ¹H NMR (400 MHz, D₂O) δ 7.81 (s, 1H), 7.76 (m, 6H), 3.76 (m, 1H), 3.69 (m, 1H), 3.65 (m, 1H), 3.11 (m, 2H), 1.89 (m, 4H).

The requisite intermediates were prepared as described in the following paragraphs.

Step 1

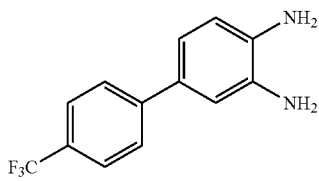 [SMILES: Nc1ccc(-c2ccc(C(F)(F)F)cc2)cc1N]

4'-(Trifluoromethyl)-[1,1'-biphenyl]-3,4-diamine

A mixture of 2-amino-4-bromoaniline (748 mg, 4 mmol), (4-trifluorophenyl)boronic acid (950 mg, 5 mmol) and K₂CO₃ (2 M in water, 6 mL) in dioxane (18 mL) was degassed and Pd(dppf)₂Cl₂ (70 mg, 0.08 mmol) was added. The reaction mixture was stirred at 85° C. overnight. It was extracted with EtOAc and washed with water and brine. After concentration it was purified by column chromatography on silica gel using 40-50% EtOAc in hexane to afford the product as a brown powder (625 mg, 62% yield). ¹H NMR (300 MHz, CDCl₃) δ 7.62 (s, 4H), 6.98 (dd, J=1.5, 7.5 Hz, 1H), 6.97 (s, 1H), 6.79 (dd, J=0.6, 7.5 Hz, 1H), 3.51 (br, 4H).

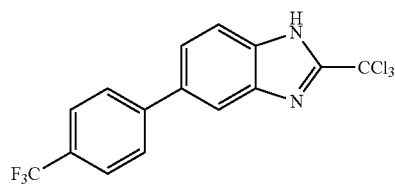

2-(Trichloromethyl)-5-(4-(trifluoromethyl)phenyl)-1H-benzo[d]imidazole

To a solution of 4'-(trifluoromethyl)-[1,1'-biphenyl]-3,4-diamine (0.25 g, 1 mmol) in acetic acid (5 mL) was added methyl 2,2,2-trichloroacetimidate (0.15 mL, 1.2 mmol). It was stirred at room temperature overnight. TLC showed no starting material left. Then ice was added and the precipitate was filtered and washed with water to provide the crude product which was used for next step reaction without purification.

Step 3

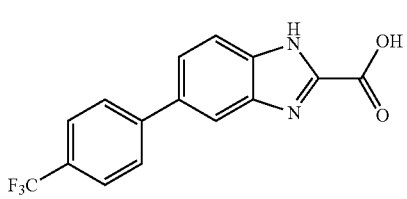 [SMILES: O=C(O)c1nc2cc(-c3ccc(C(F)(F)F)cc3)ccc2[nH]1]

5-(4-(Trifluoromethyl)phenyl)-1H-benzo[d]imidazole-2-carboxylic Acid

To a solution of 2-(trichloromethyl)-5-(4-(trifluoromethyl)phenyl)-1H-benzo[d]imidazole in THF (4 mL) was added NaOH solution (2 M, 2 mL). The reaction mixture was stirred at room temperature overnight. TLC showed no SM left. Then it was adjusted into acidic and solvent was removed then it was extracted with MeOH. The organic layers were dried and concentrated to give product (183 mg, 60% yield for two steps) as a pale brown solid. $^1$H NMR (300 MHz, DMSO-$d_6$) δ 8.33 (s, 1H), 7.98 (m, 4H), 7.80 (m, 2H), 7.72 (m, 1H), 7.58 (m, 1H).

Step 4

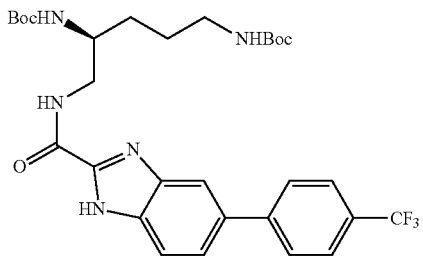 [SMILES: CC(C)(C)OC(=O)NCCC[C@@H](CNC(=O)c1nc2cc(-c3ccc(C(F)(F)F)cc3)ccc2[nH]1)NC(=O)OC(C)(C)C]

Di-tert-butyl (5-(5-(4-(trifluoromethyl)phenyl)-1H-benzo[d]imidazole-2-carboxamido)pentane-1,4-diyl) (S)-dicarbamate To a solution of 5-(4-(trifluoromethyl)phenyl)-1H-benzo[d]imidazole-2-carboxylic acid (62 mg, 0.2 mmol) in dry DMF (2 mL) was added DIPEA (0.07 mL, 0.4 mmol), HOBt (19 mg, 0.12 mmol) and EDC (38 mg, 0.21 mmol). The reaction mixture was stirred at room temperature and di-tert-butyl (5-aminopentane-1,4-diyl)(S)-dicarbamate (intermediate B) (64 mg, 0.2 mmol) was added. The reaction mixture was stirred at room temperature overnight. Then it was concentrated and purified by column chromatography on silica gel to give the product (35 mg, 57% yield) as a white solid.

Example 7. Preparation of (S)-5-(3-cyanophenyl)-N-(2,5-diaminopentyl)-1H-benzo[d]imidazole-2-carboxamide Dihydrochloride

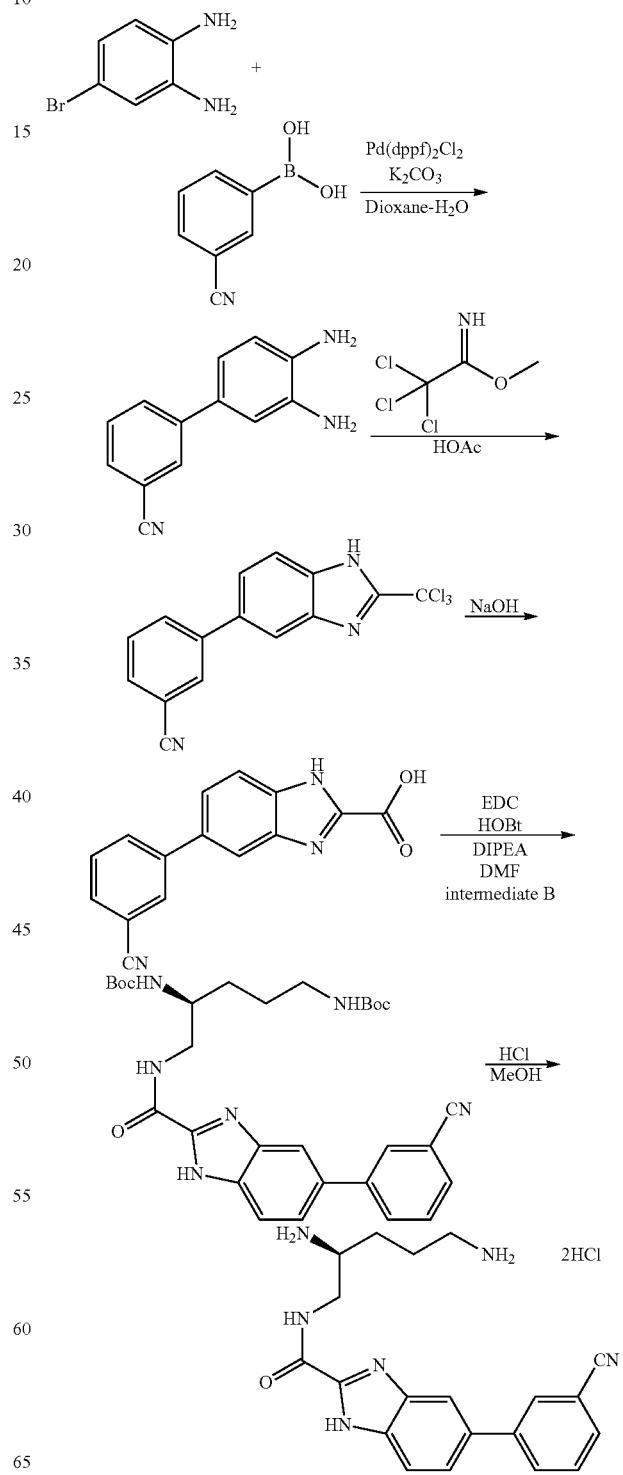

107

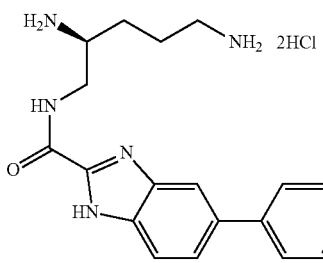

(S)-5-(3-Cyanophenyl)-N-(2,5-diaminopentyl)-1H-benzo[d]imidazole-2-carboxamide Dihydrochloride To a solution of di-tert-butyl (5-(5-(3-cyanophenyl)-1H-benzo[d]imidazole-2-carboxamido)pentane-1,4-diyl)(S)-dicarbamate (42 mg, 0.07 mmol) in MeOH (2 mL) was added HCl (0.08 mL, 4M in dioxane). The reaction mixture was stirred at room temperature overnight. TLC showed no starting material left. The solution was concentrated and triturated with methylene chloridemethylene chloride to afford product (30 mg, 95% yield) as a brown solid. $^1$H NMR (300 MHz, D$_2$O) δ 7.82 (m, 2H), 7.75 (s, 1H), 7.67 (m, 1H), 7.64 (m, 1H), 7.57 (m, 2H), 3.78 (m, 1H), 3.68 (m, 1H), 3.62 (m, 1H), 3.05 (m, 2H), 1.84 (m, 4H).

The requisite intermediates were prepared as described in the following paragraphs.

Step 1

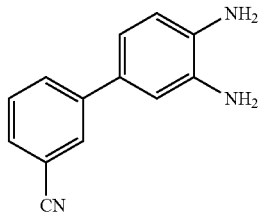 [SMILES: N#Cc1cccc(-c2ccc(N)c(N)c2)c1]

3',4'-Diamino-[1,1'-biphenyl]-3-carbonitrile

A mixture of 2-amino-4-bromoaniline (526 mg, 3 mmol), (3-cyanophenyl)boronic acid (529 mg, 3.6 mmol) and K$_2$CO$_3$ (2 M in water, 4.5 mL) in dioxane (14 mL) was degassed and Pd(dppf)$_2$Cl$_2$ (70 mg, 0.08 mmol) was added. The reaction mixture was stirred at 85° C. overnight. It was extracted with EtOAc and washed with water and brine. After concentration it was purified by column chromatography on silica gel using 50-70% EtOAc in hexane to afford the product (435 mg, 69% yield) as a brown powder. $^1$H NMR (300 MHz, CDCl$_3$) δ 7.79 (t, J=1.2 Hz, 1H), 7.75 (m, 1H), 7.52 (m, 1H), 7.46 (m, 1H), 6.93 (m, 1H), 6.92 (s, 1H), 6.78 (m, 1H), 3.51 (br, 4H).

Step 2

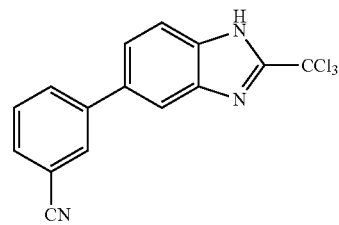

3-(2-(Trichloromethyl)-1H-benzo[d]imidazol-5-yl)benzonitrile

To a solution of 3',4'-diamino-[1,1'-biphenyl]-3-carbonitrile (0.21 g, 1 mmol) in acetic acid (5 mL) was added methyl 2,2,2-trichloroacetimidate (0.15 mL, 1.2 mmol). It was stirred at room temperature overnight. TLC showed no starting material left. Then ice was added and the precipitate was filtered and washed with water to provide the crude product which was used for next step reaction without purification.

Step 3

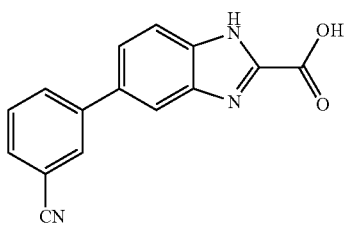 [SMILES: N#Cc1cccc(-c2ccc3[nH]c(C(=O)O)nc3c2)c1]

5-(3-Cyanophenyl)-1H-benzo[d]imidazole-2-carboxylic Acid

To a solution of 3-(2-(trichloromethyl)-1H-benzo[d]imidazol-5-yl)benzonitrile in THF (4 mL) was added NaOH solution (2 M, 3 mL). The reaction mixture was stirred at room temperature overnight. TLC showed no starting material left. Then it was adjusted into acidic and solvent was removed then it was extracted with MeOH. The organic layers were dried and concentrated to give product (145 mg, 55% yield for two steps) as a pale brown solid.

Step 4

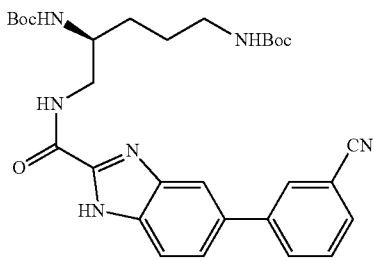 [SMILES: CC(C)(C)OC(=O)NCCC[C@@H](CNC(=O)c1nc2cc(-c3cccc(C#N)c3)ccc2[nH]1)NC(=O)OC(C)(C)C]

Di-tert-butyl (5-(5-(3-cyanophenyl)-1H-benzo[d]imidazole-2-carboxamido)pentane-1,4-diyl)(S)-dicarbamate To a solution of 5-(3-cyanophenyl)-1H-benzo[d]imidazole-2-carboxylic acid (55 mg, 0.2 mmol) in dry DMF (1 mL) was added DIPEA (0.07 mL, 0.4 mmol), HOBt (18 mg, 0.11 mmol) and EDC (36 mg, 0.2 mmol). The reaction mixture was stirred at room temperature and di-tert-butyl (5-aminopentane-1,4-diyl)(S)-dicarbamate (intermediate B) (42 mg, 0.13 mmol) was added. It was stirred at room temperature overnight then concentrated and purified by column chromatography on silica gel using 40-60% EtOAc in hexanes to give the product (46 mg, 63% yield) as an off-white solid. $^1$H NMR (300 MHz, CDCl$_3$) δ 8.26 (br, 1H), 7.80 (m, 3H), 7.59 (m, 2H), 7.50 (m, 2H), 5.08 (br, 1H), 4.81 (br, 1H), 3.95 (m, 1H), 3.65 (m, 2H), 3.14 (m, 2H), 1.60 (m, 2H), 1.51 (m, 2H), 1.41 (s, 9H), 1.36 (s, 9H).

Example 8. Preparation of (S)—N-(2,5-diaminopentyl)-5-(4-methoxyphenyl)-1H-benzo[d]imidazole-2-carboxamide Dihydrochloride

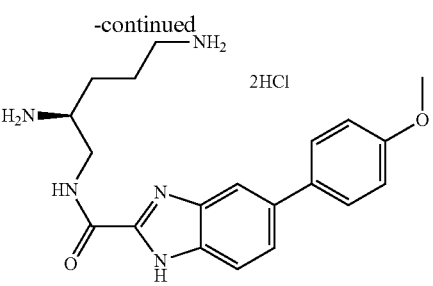

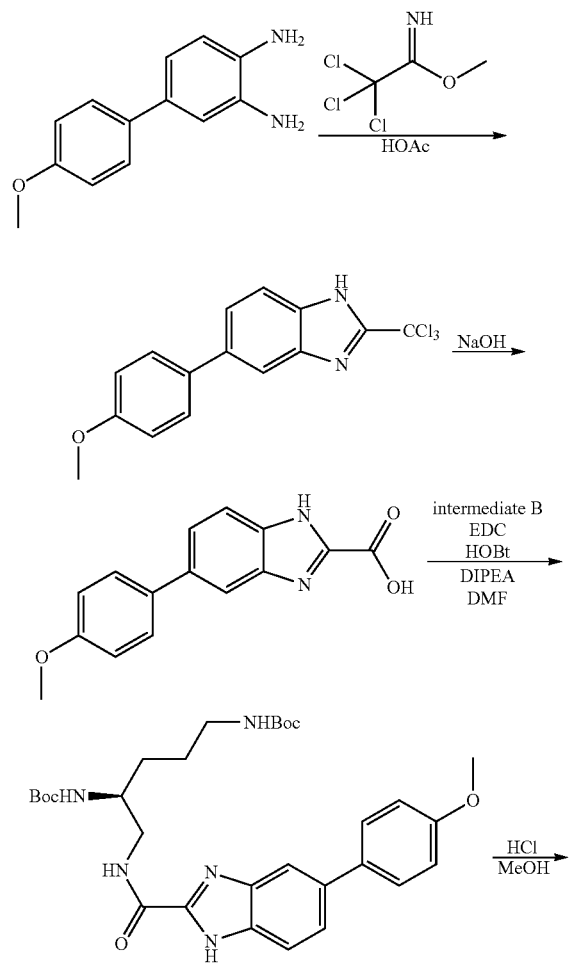

(S)—N-(2,5-Diaminopentyl)-5-(4-methoxyphenyl)-1H-benzo[d]imidazole-2-carboxamide Dihydrochloride To a solution of di-tert-butyl (5-(5-(4-methoxyphenyl)-1H-benzo[d]imidazole-2-carboxamido)pentane-1,4-diyl) (S)-dicarbamate (15 mg, 0.026 mmol) in MeOH (5 mL) was added HCl solution (4 M in dioxane, 0.1 mL). The reaction mixture was stirred at room temperature overnight and solvent was removed. The residue was triturated with EtOAc and the precipitate was collected as a pale brown powder (8 mg, 70% yield). $^1$H NMR (300 MHz, D$_2$O) δ 8.20 (br, 1H), 7.88 (s, 1H), 7.77 (m, 1H), 7.70 (m, 1H), 7.68 (m, 2H), 7.11 (m, 2H), 3.86 (s, 3H), 3.76 (m, 1H), 3.70 (m, 1H), 3.62 (m, 1H), 3.05 (m, 2H), 1.83 (m, 4H).

The requisite intermediates were prepared as described in the following paragraphs.

Step 1

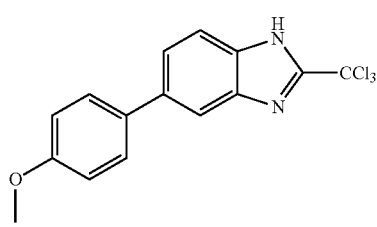

5-(4-Methoxyphenyl)-2-(trichloromethyl)-1H-benzo[d]imidazole

To a solution of 4'-methoxy-[1,1'-biphenyl]-3,4-diamine (0.214 g, 1 mmol) in acetic acid (5 mL) was added methyl 2,2,2-trichloroacetimidate (0.15 mL, 1.2 mmol). The reaction mixture was stirred at room temperature for 5 hours. Then ice was added and the precipitate was filtered and washed with water. After drying the crude product was collected and used for next step reaction without purification.

Step 2

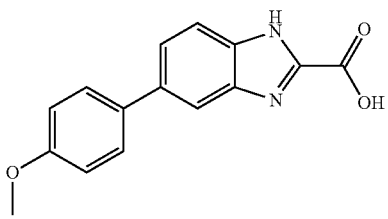 [SMILES: COc1ccc(-c2ccc3[nH]c(C(=O)O)nc3c2)cc1]

5-(4-Methoxyphenyl)-1H-benzo[d]imidazole-2-carboxylic Acid

To the solution of 5-(4-methoxyphenyl)-2-(trichloromethyl)-1H-benzo[d]imidazole in THF (10 mL) was added NaOH (1.2 M, 5 mL). It was stirred at room temperature for 3 hrs. THF was removed under reduced pressure and it was acidified. The precipitate was filtered and washed with water. It was dried to provide the product as a pale brown powder (120 mg, 45% in 2 steps). It was used for reaction without further purification. $^1$H NMR (300 MHz, DMSO-$d_6$) δ 7.66 (s, 1H), 7.58 (m, 1H), 7.55 (m, 2H), 7.42 (m, 1H), 7.00 (m, 2H), 3.77 (s, 3H).

Step 3

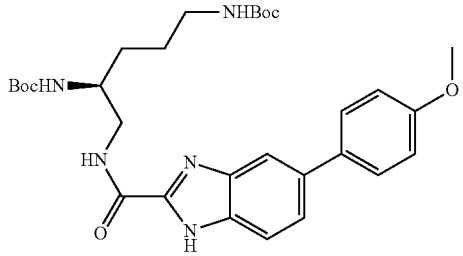 [SMILES: COc1ccc(-c2ccc3[nH]c(C(=O)NC[C@H](CCCNC(=O)OC(C)(C)C)NC(=O)OC(C)(C)C)nc3c2)cc1]

Di-tert-butyl (5-(5-(4-methoxyphenyl)-1H-benzo[d]imidazole-2-carboxamido)pentane-1,4-diyl)(S)-dicarbamate To a solution of 5-(4-methoxyphenyl)-1H-benzo[d]imidazole-2-carboxylic acid (53 mg, 0.2 mmol) in dry methylene chloridemethylene chloride (10 mL) was added DIPEA (0.11 mL, 0.6 mmol), HOBt (63 mg, 0.2 mmol) and EDC (38 mg, 0.2 mmol). The reaction mixture was stirred at room temperature and di-tert-butyl (5-aminopentane-1,4-diyl)(S)-dicarbamate (intermediate B) (63 mg, 0.2 mmol) was added. It was stirred at room temperature overnight then concentrated and purified by column chromatography on silica gel (40-70% ethyl acetate/hexanes) to give the product (26 mg, 23% yield) as a white solid. $^1$H NMR (300 MHz, CDCl$_3$) δ 8.06 (br, 1H), 7.75 (m, 1H), 7.62 (s, 1H), 7.55 (m, 1H), 7.53 (m, 2H), 6.98 (m, 2H), 4.96 (br, 1H), 4.72 (br, 1H), 3.85 (s, 3H), 3.62 (m, 1H), 3.27 (m, 2H), 1.79 (m, 2H), 1.45 (m, 2H), 1.41 (s, 9H), 1.26 (s, 9H).

Example 9. Preparation of (S)-1-(5-(4-fluorophenyl)-1H-benzo[d]imidazol-2-yl)butane-1,4-diamine Dihydrochloride

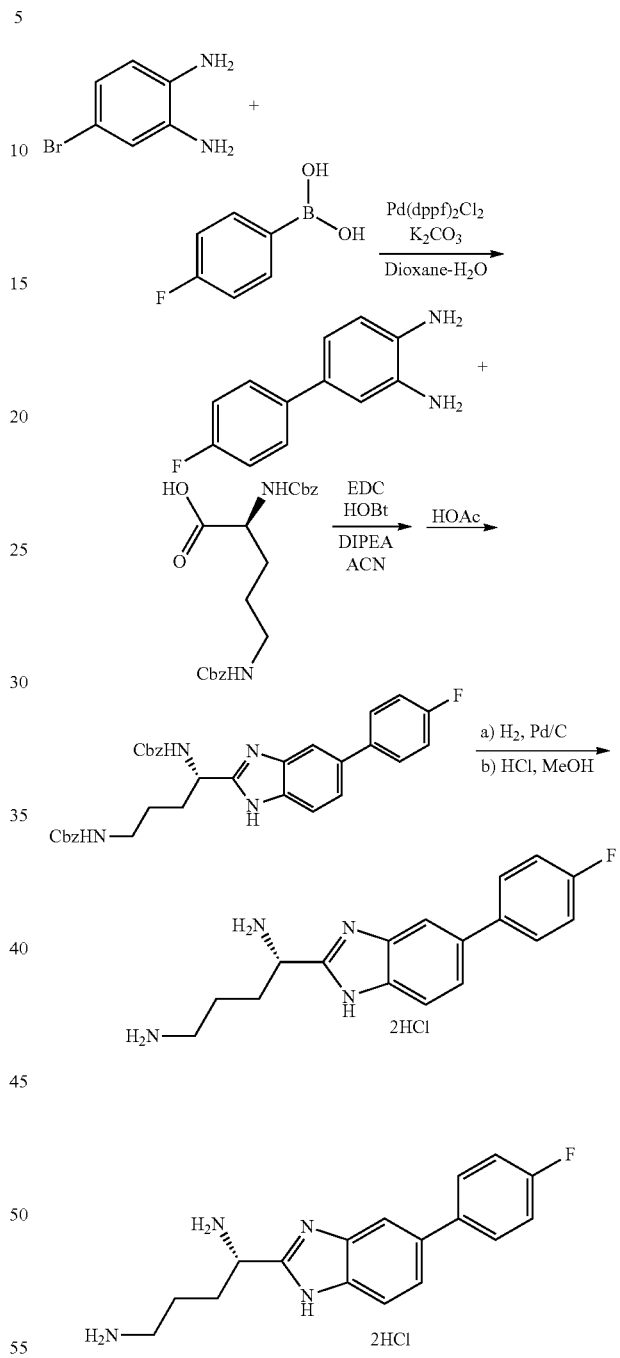

(S)-1-(5-(4-Fluorophenyl)-1H-benzo[d]imidazol-2-yl)butane-1,4-diamine Dihydrochloride To a solution of dibenzyl (1-(5-(4-fluorophenyl)-1H-benzo[d]imidazol-2-yl)butane-1,4-diyl)(S)-dicarbamate (40 mg, 0.07 mmol) in MeOH (10 mL) was added Pd/C (10%, 80 mg). The reaction mixture was stirred under H$_2$ overnight. It was filtered through a pad of Celite and concentrated under reduced pressure. It was dissolved in MeOH (2 mL) and HCl solution (4 M in dioxane, 0.1 mL) was added.

It was stirred at room temperature and solvent was removed under reduced pressure. The residue was triturated with EtOAc and the precipitate was collected as a white powder (14 mg, 66% yield). $^1$H NMR (300 MHz, D$_2$O) 7.89 (m, 1H), 7.76 (s, 1H), 7.73 (m, 1H), 7.71 (m, 2H), 7.17 (t, J=8.1 Hz, 2H), 4.80 (m, 1H), 3.00 (m, 2H), 2.35 (m, 2H), 1.80 (m, 2H).

The requisite intermediates were prepared as described in the following paragraphs.

Step 1

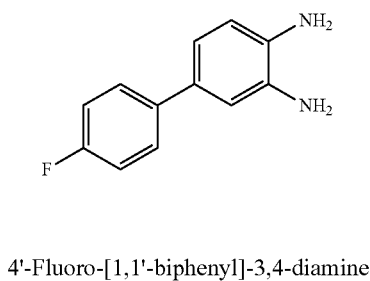

4'-Fluoro-[1,1'-biphenyl]-3,4-diamine

A mixture of 2-amino-4-bromoaniline (1.87 g, 10 mmol), (4-fluorophenyl)boronic acid (1.82 g, 13 mmol) and K$_2$CO$_3$ (2 M in water, 15 mL) in dioxane (30 mL) was degassed and Pd(dppf)$_2$Cl$_2$ (210 mg, 0.25 mmol) was added. The reaction mixture was stirred at 80° C. for 3 hours. It was extracted with EtOAc and washed with water and brine. After concentration it was purified by column chromatography on silica gel to afford the product (1.21 g, 59% yield) as a brown solid. $^1$H NMR (300 MHz, CDCl$_3$) δ 7.39 (m, 2H), 7.09 (m, 1H), 7.00 (m, 2H), 6.84 (s, 1H), 6.68 (m, 1H), 3.41 (br, 4H).

Step 2

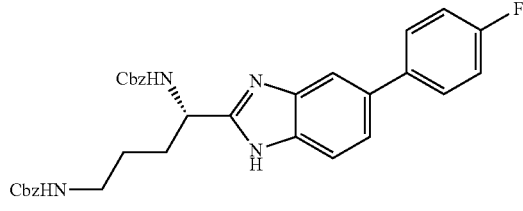 [SMILES: O=C(NCCC[C@H](NC(=O)OCc1ccccc1)c1nc2cc(-c3ccc(F)cc3)ccc2[nH]1)OCc1ccccc1]

Dibenzyl (1-(5-(4-fluorophenyl)-1H-benzo[d]imidazol-2-yl)butane-1,4-diyl)(S)-dicarbamate To a mixture of Z-Orn(Z)—OH (240 mg, 0.6 mmol), DIPEA (0.1 mL, 0.05 mmol), HOBt (100 mg, 0.65 mmol) and EDC (123 mg, 0.65 mmol) in dry acetonitrile (8 mL) was added 4'-fluoro-[1,1'-biphenyl]-3,4-diamine (101 mg, 0.5 mmol). The reaction mixture was stirred at room temperature overnight. Then it was extracted with EtOAc and concentrated. The crude intermediate was dissolved in acetic acid (5 mL) and heated at 65° C. overnight. Acetic acid was removed under reduced pressure and the residue was purified by column chromatography on silica gel to provide a white powder (126 mg, 37% yield). $^1$H NMR (300 MHz, CDCl$_3$) δ 7.49 (m, 2H), 7.37 (m, 2H), 7.28 (m, 10H), 7.24 (m, 1H), 7.08 (t, J=8.7 Hz, 2H), 6.40 (br, 1H), 5.09 (m, 4H), 5.06 (m, 1H), 3.26 (m, 1H), 3.15 (m, 1H), 2.11 (m, 1H), 2.01 (m, 1H), 1.60 (m, 2H).

Example 10. Preparation of (S)—N-(2,5-diaminopentyl)-2-(6-(4-fluorophenyl)-1H-benzo[d]imidazol-2-yl)acetamide Dihydrochloride

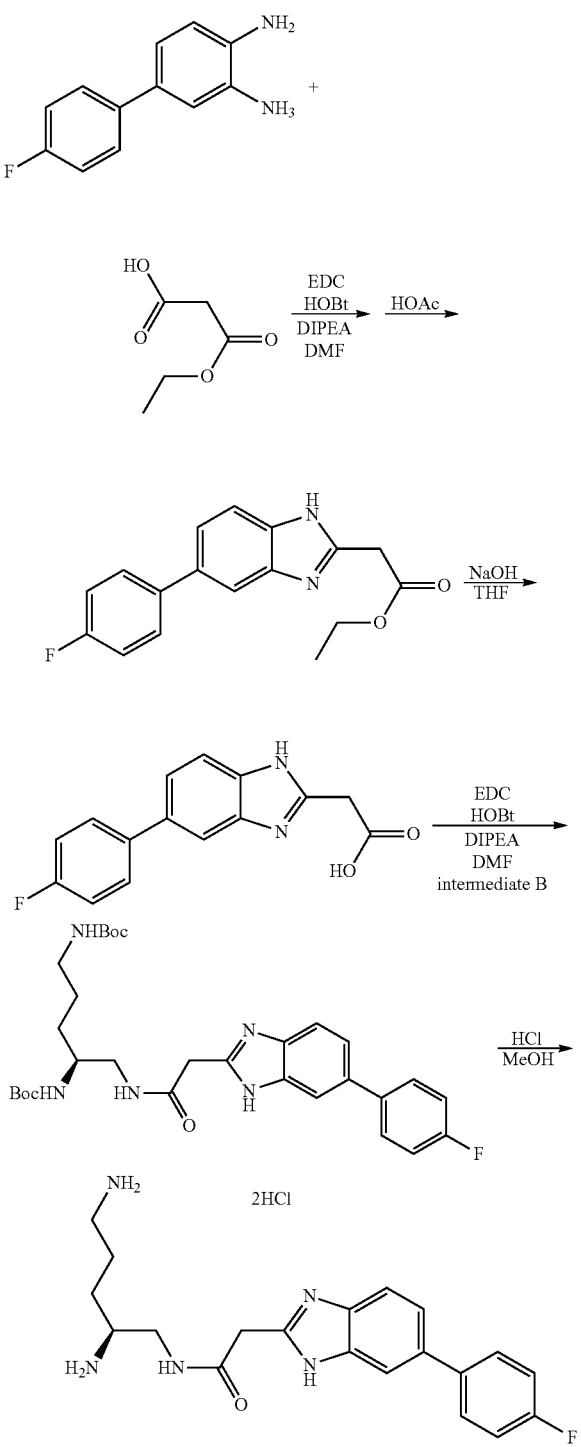

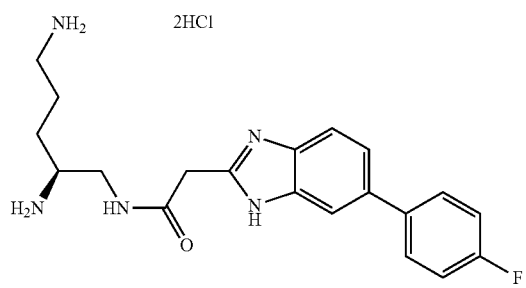 [SMILES: NCCC[C@H](N)CNC(=O)Cc1nc2ccc(-c3ccc(F)cc3)cc2[nH]1]

(S)—N-(2,5-Diaminopentyl)-2-(6-(4-fluorophenyl)-1H-benzo[d]imidazol-2-yl)acetamide Dihydrochloride To a solution of di-tert-butyl (5-(2-(6-(4-fluorophenyl)-1H-benzo[d]imidazol-2-yl)acetamido)pentane-1,4-diyl)(S)-dicarbamate (40 mg, 0.07 mmol) in MeOH (5 mL) was added HCl solution (4 M in dioxane, 0.15 mL). It was stirred at room temperature overnight and solvent was removed under reduced pressure. The residue was triturated with EtOAc and precipitate was collected as an off-white powder (20 mg, 65% yield). $^1$H NMR (300 MHz, D$_2$O) δ 7.76 (s, 1H), 7.68 (m, 2H), 7.59 (m, 2H), 7.19 (t, J=8.4 Hz, 2H), 3.50 (m, 1H), 3.34 (m, 2H), 2.94 (m, 2H), 2.76 (s, 2H), 1.72 (m, 4H).

The requisite intermediates were prepared as described in the following paragraphs.

Step 1

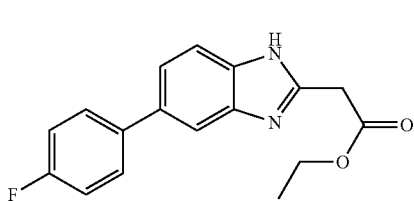 [SMILES: CCOC(=O)Cc1nc2cc(-c3ccc(F)cc3)ccc2[nH]1]

Ethyl 2-(5-(4-fluorophenyl)-1H-benzo[d]imidazol-2-yl)acetate

To a solution of 4'-fluoro-[1,1'-biphenyl]-3,4-diamine (202 mg, 1 mmol) in methylene chloride (10 mL) was added 3-ethoxy-3-oxopropanoic acid (132 mg, 1 mmol), HOBt (92 mg, 0.6 mmol), EDC (192 mg, 1 mmol) and DIPEA (0.22 mL, 3 mmol). After stirred at room temperature overnight, it was extracted with EtOAc and washed with water and brine. After concentration the crude intermediate was dissolved in acetic acid (2 mL) and heated at 75° C. for 6 hours. Acetic acid was removed under reduced pressure and the residue was purified by column chromatography on silica gel to provide a white powder (121 mg, 41% yield). $^1$H NMR (300 MHz, CDCl$_3$) δ 7.71 (s, 1H), 7.62 (m, 1H), 7.55 (m, 2H), 7.42 (m, 1H), 7.11 (m, 2H), 4.24 (q, J=9 Hz, 2H), 4.08 (s, 2H), 1.28 (t, J=9 Hz, 2H).

Step 2

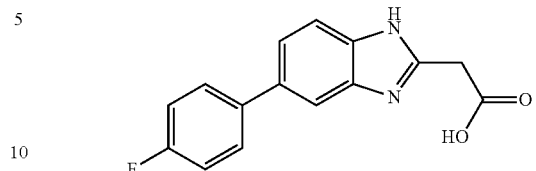

2-(5-(4-Fluorophenyl)-1H-benzo[d]imidazol-2-yl)acetic Acid

To a solution of ethyl 2-(5-(4-fluorophenyl)-1H-benzo[d]imidazol-2-yl)acetate (100 mg, 0.33 mmol) in THF (5 mL) was added NaOH solution in water (1.2 M, 2 mL). It was stirred at room temperature for 2 hour and THF was removed under reduced pressure and washed with EtOAc. The aqueous phase was acidified with HCl solution and extracted with EtOAc. It was concentrated to provide the product as a white powder (52 mg, 58% yield). The crude product was used for reaction without further purification. $^1$H NMR (300 MHz, CDCl$_3$) δ 11.56 (br, 2H), 7.66 (s, 1H), 7.55 (m, 1H), 7.39 (m, 3H), 7.05 (m, 2H), 2.66 (s, 2H).

Step 3

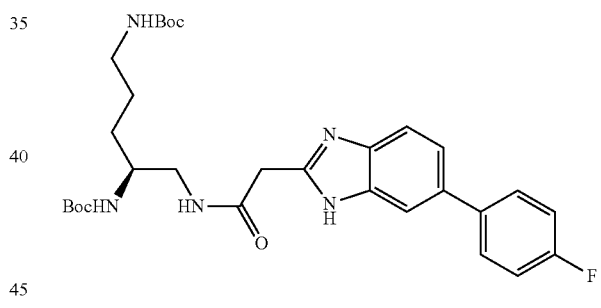

Di-tert-butyl (5-(2-(6-(4-fluorophenyl)-1H-benzo[d]imidazol-2-yl)acetamido)pentane-1,4-diyl)(S)-dicarbamate To a solution of 2-(5-(4-fluorophenyl)-1H-benzo[d]imidazol-2-yl)acetic acid (27 mg, 0.1 mmol) in dry methylene chloride (5 mL) was added DIPEA (0.05 mL, 0.3 mmol), HOBt (15 mg, 0.1 mmol) and EDC (38 mg, 0.2 mmol). The reaction mixture was stirred at room temperature for 5 minutes and di-tert-butyl (5-aminopentane-1,4-diyl)(S)-dicarbamate (intermediate B) (63 mg, 0.2 mmol) was added. The reaction mixture was stirred at room temperature overnight. Then it was concentrated and purified by column chromatography on silica gel (50-80% ethyl acetate/hexanes) to give the product (40 mg, 70% yield) as a white solid. $^1$H NMR (300 MHz, CDCl$_3$) δ 7.71 (s, 1H), 7.56 (m, 2H), 7.55 (m, 1H), 7.40 (m, 1H), 7.14 (m, 2H), 6.29 (br, 1H), 4.72 (br, 1H), 4.62 (br, 1H), 3.67 (m, 1H), 3.27 (m, 2H), 3.12 (m, 2H), 2.66 (s, 2H), 1.55 (m, 4H).

Example 11. Preparation of N-(((2S)-4-(2-aminopropan-2-yl)pyrrolidin-2-yl)methyl)-6-(4-fluorophenyl)-1H-benzo[d]imidazole-2-carboxamide Dihydrochloride

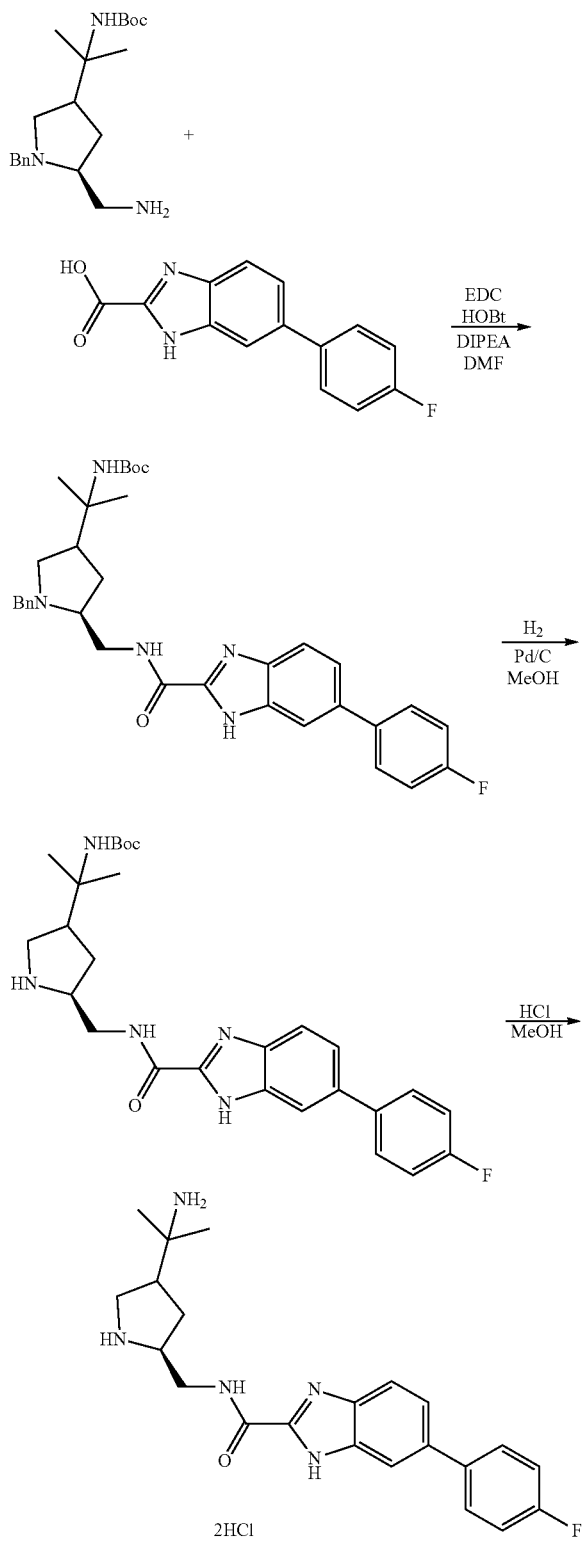

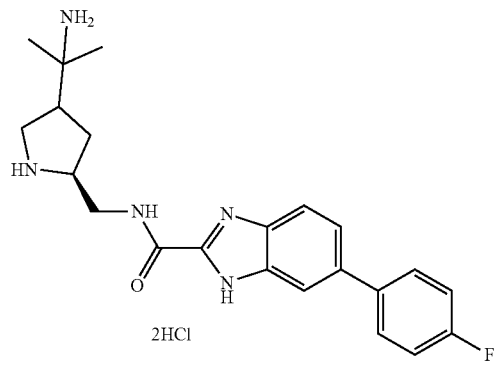 [SMILES: CC(C)(N)C1CN[C@H](CNC(=O)c2nc3ccc(-c4ccc(F)cc4)cc3[nH]2)C1]

N-(((2S)-4-(2-Aminopropan-2-yl)pyrrolidin-2-yl)methyl)-6-(4-fluorophenyl)-1H-benzo[d]imidazole-2-carboxamide Dihydrochloride To a solution of tert-butyl (2-((3S)-5-((6-(4-fluorophenyl)-1H-benzo[d]imidazole-2-carboxamido)methyl)pyrrolidin-3-yl)propan-2-yl)carbamate (11 mg, 0.07 mmol) in MeOH (2 mL) was added HCl solution (4 M in dioxane, 0.1 mL). It was stirred at room temperature overnight and solvent was removed under reduced pressure. The residue was triturated with EtOAc and the product was collected as a white powder (9 mg, 87% yield). $^{1}$H NMR (300 MHz, CD$_3$OD) δ 7.97 (s, 1H), 7.85 (m, 2H), 7.72 (m, 2H), 7.23 (t, J=8.4 Hz, 2H), 4.08 (m, 1H), 3.94 (m, 1H), 3.72 (m, 1H), 3.56 (m, 1H), 3.21 (m, 1H), 2.84 (m, 1H), 2.38 (m, 1H), 1.85 (m, 1H), 1.42 (s, 6H). MS (ESI+): 396.25 [M+H]$^{+}$ for C$_{22}$H$_{26}$FN$_5$O.

The requisite intermediates were prepared as described in the following paragraphs.

Step 1

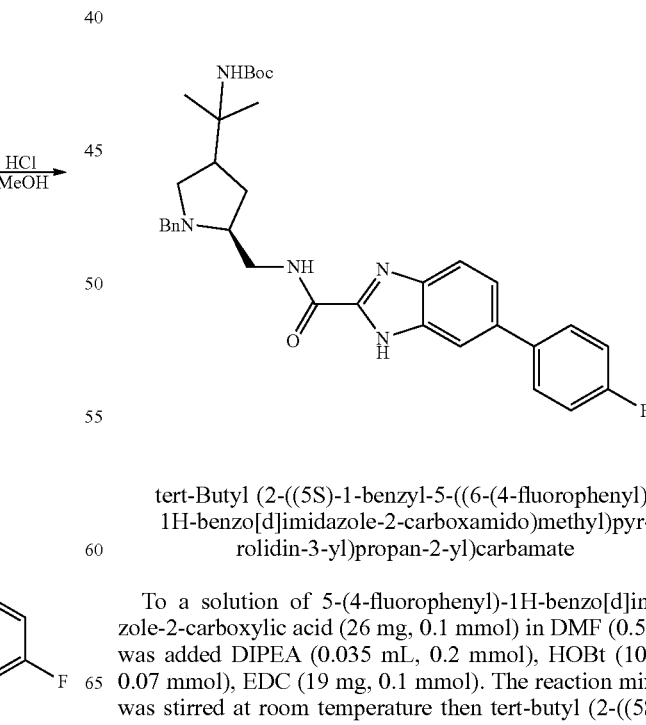

tert-Butyl (2-((5S)-1-benzyl-5-((6-(4-fluorophenyl)-1H-benzo[d]imidazole-2-carboxamido)methyl)pyrrolidin-3-yl)propan-2-yl)carbamate To a solution of 5-(4-fluorophenyl)-1H-benzo[d]imidazole-2-carboxylic acid (26 mg, 0.1 mmol) in DMF (0.5 mL) was added DIPEA (0.035 mL, 0.2 mmol), HOBt (10 mg, 0.07 mmol), EDC (19 mg, 0.1 mmol). The reaction mixture was stirred at room temperature then tert-butyl (2-((5S)-5-(aminomethyl)-1-benzylpyrrolidin-3-yl)propan-2-yl)carbamate (intermediate J) (24 mg, 0.07 mmol) was added and the reaction was continued to stir at room temperature overnight. The reaction mixture was diluted with EtOAc. The combined organic layer was washed with water and brine then dried over anhydrous sodium sulfate and filtered. The filtrate was then concentrated and purified by column chromatography on silica gel using 20-30% ethyl acetate in hexanes to give the product (14 mg, 34% yield) as a white solid. $^1$H NMR (300 MHz, CDCl$_3$) δ 7.95 (m, 2H), 7.85 (d, J=9 Hz, 1H), 7.59 (m, 4H), 7.41 (m, 1H), 7.34 (m, 1H), 7.27 (m, 1H), 7.13 (m, 2H), 5.35 (br, 1H), 4.13 (m, 1H), 3.93 (m, 1H), 3.52 (m, 1H), 3.24 (d, J=13.5 Hz, 1H), 2.93 (m, 1H), 2.80 (m, 1H), 2.46 (m, 1H), 2.86 (m, 1H), 2.09 (m, 1H), 1.65 (m, 1H), 1.36 (s, 9H), 1.25 (s, 3H), 1.21 (s, 3H).

Step 2

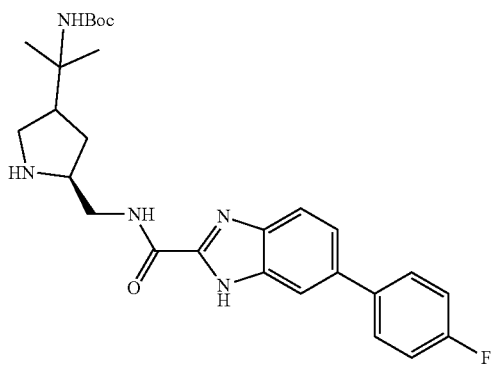 [SMILES: CC(C)(C)OC(=O)NC(C)(C)C1CN[C@H](CNC(=O)c2nc3ccc(-c4ccc(F)cc4)cc3[nH]2)C1]

tert-Butyl (2-(5S)-5-((6-(4-fluorophenyl)-1H-benzo[d]imidazole-2-carboxamido)methyl)pyrrolidin-3-yl)propan-2-yl)carbamate To a solution of tert-butyl (2-((5S)-1-benzyl-5-((6-(4-fluorophenyl)-1H-benzo[d]imidazole-2-carboxamido)methyl)pyrrolidin-3-yl)propan-2-yl)carbamate (14 mg, 0.024 mmol) in methanol (5 mL) was added Pd/C (10%, 20 mg). The reaction mixture was stirred under H$_2$ overnight. The solid was filtered off through a pad of Celite and concentrated under reduced pressure to provide the product (11 mg, 92% yield) as a white powder. $^1$HNMR (300 MHz, CDCl$_3$) δ 8.81 (br, 1H), 7.46 (m, 2H), 7.31 (m, 2H), 7.20 (m, 1H), 7.01 (m, 2H), 4.83 (br, 1H), 4.28 (m, 1H), 4.08 (m, 1H), 3.72 (m, 1H), 3.49 (m, 1H), 3.21 (m, 1H), 2.09 (m, 1H), 1.88 (m, 2H), 1.36 (s, 9H), 1.25 (s, 3H), 1.20 (s, 3H).

Example 12. Preparation of (S)-4-(5-(4-fluorophenyl)-1H-benzo[d]imidazole-2-carboxamido) butane-1,3-diaminium Chloride

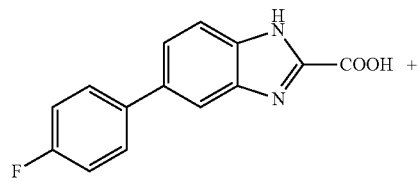

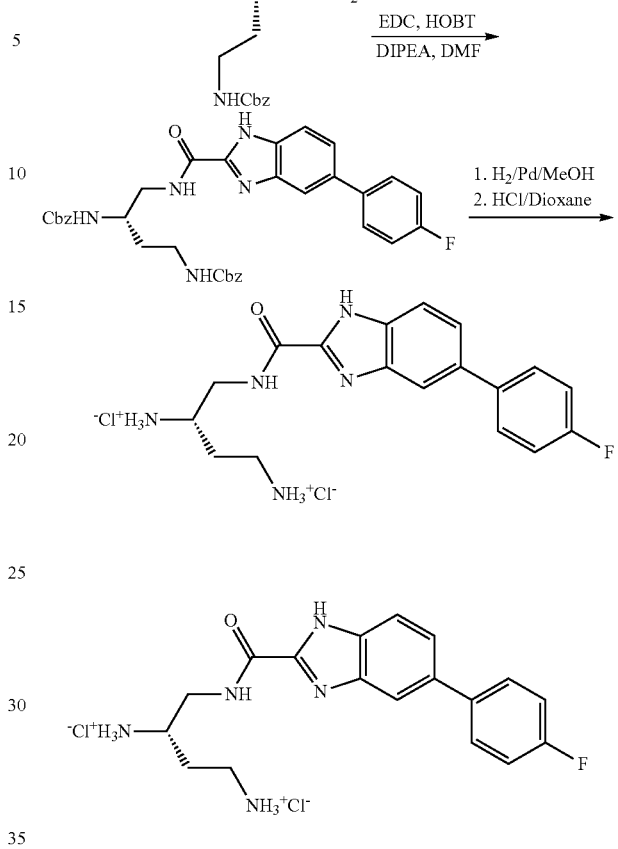

(S)-4-(5-(4-Fluorophenyl)-1H-benzo[d]imidazole-2-carboxamido) butane-1,3-diaminium Chloride To a solution of dibenzyl (4-(5-(4-fluorophenyl)-1H-benzo[d]imidazole-2-carboxamido) butane-1,3-diyl)(S)-dicarbamate (50 mg, 0.082 mmol) in MeOH (1 mL) was added 5 mg 10% palladium on carbon. The reaction was hydrogenated under hydrogen gas balloon at room temperature overnight. The reaction was filtered through Celite, washed with MeOH and concentrated. The residue was triturated with EtOAc to afford product (28 mg, 82% yield) as a yellow solid. $^1$H NMR (300 MHz, DMSO-d$_6$) δ 9.21 (s, 1H), 8.25 (s, 3H), 8.05 (s, 3H), 7.82-7.70 (m, 3H) 7.60-7.57 (m, 2H), 7.33-7.27 (m, 2H), 3.59-3.70 (m, 2H), 3.00 (m, 2H), 1.92 (m, 1H), 1.33-1.15 (m, 2H).

The requisite intermediates were prepared as described in the following paragraphs.

Step 1

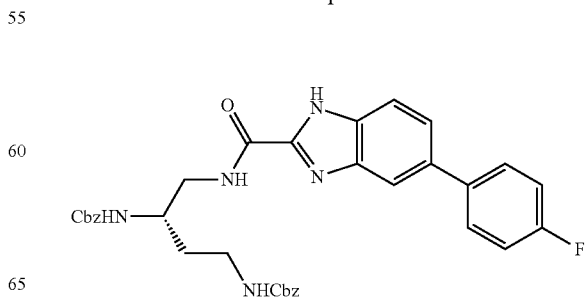

Dibenzyl (4-(5-(4-fluorophenyl)-1H-benzo[d]imidazole-2-carboxamido)butane-1,3-diyl)(S)-dicarbamate To 5-(4-fluorophenyl)-1H-benzo[d]imidazole-2-carboxylic acid (50 mg, 0.20 mmol) in DMF (3 mL) was added DIPEA (0.069 mL, 0.40 mmol), HOBt (16 mg, 0.12 mmol), EDC (46 mg, 0.24 mmol). The reaction mixture was stirred at room temperature for 5 minutes. Dibenzyl (4-aminobutane-1,3-diyl)(S)-dicarbamate (intermediate C) (73 mg, 0.20 mmol) was added and the reaction was stirred at room temperature overnight. The reaction mixture was then diluted with EtOAc and washed with 15% LiCl and brine. The organic layer was dried over sodium sulfate and filtered. The filtrate was then concentrated and purified on an ISCO column chromatography with silica gel (0-100% ethyl acetate/hexanes) to give the product (100 mg, 82% yield) as a yellow solid. $^1$H NMR (300 MHz, CDCl$_3$) δ 11.04 (s, 1H), 8.06 (s, 1H), 7.88 (s, 1H), 7.78-7.79 (m, 1H), 7.59-7.53 (m, 3H), 7.33-7.32 (m, 4H), 7.32-7.23 (m, 6H), 7.14-7.10 (m, 2H), 5.03-5.11 (m, 4H), 3.99 (m, 1H), 3.60-3.36 (m, 3H), 3.09 (m, 1H), 1.81 (m, 2H).

Example 13. Preparation of (S)-3-(5-(4-fluorophenyl)-1H-benzo[d]imidazole-2-carboxamido) propane-1,2-diaminium Dihydrochloride

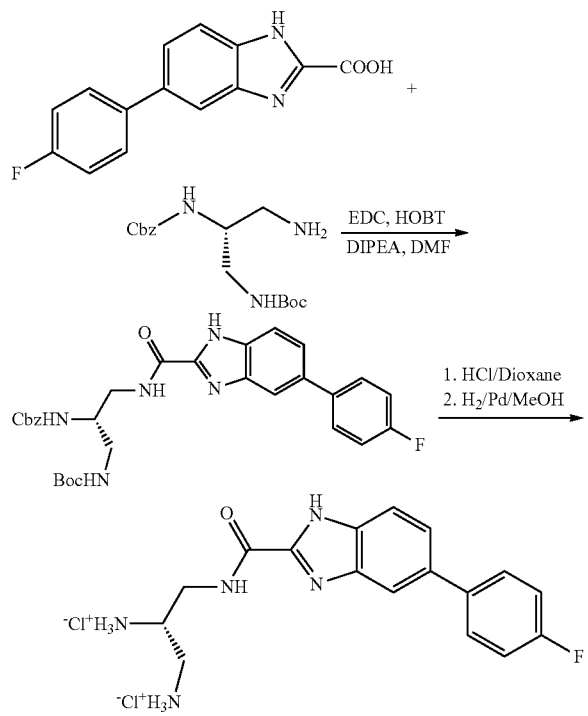

(S)-3-(5-(4-Fluorophenyl)-1H-benzo[d]imidazole-2-carboxamido) propane-1,2-diaminium Dihydrochloride To a solution of benzyl tert-butyl (3-(5-(4-fluorophenyl)-1H-benzo[d]imidazole-2-carboxamido) propane-1,2-diyl)(R)-dicarbamate (68 mg, 0.14 mmol) in MeOH (1 mL) was added 0.3 mL 4N HCl in dioxane. The reaction mixture was stirred at room temperature overnight. The resulting residue was then added 5 mg 10% palladium on carbon. The reaction mixture was hydrogenated under hydrogen gas balloon at room temperature overnight. The reaction was filtered through Celite pad, washed with MeOH and concentrated. The residue was added 0.3 mL 4N HCl in dioxane and stirred for 10 min. The mixture was concentrated under reduced pressure and triturated with EtOAc to afford product (42 mg, 87% yield) as a yellow solid. $^1$H NMR (300 MHz, DMSO-d$_6$) δ 9.34 (s, 1H), 9.01-8.60 (s, 6H), 7.79-7.59 (m, 5H), 7.29 (m, 2H), 3.67 (m, 3H), 3.15 (m, 2H).

The requisite intermediate was prepared as described in the following paragraph.

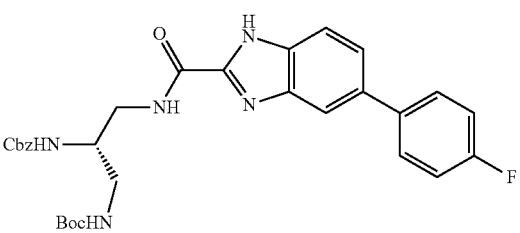 [SMILES: CC(C)(C)OC(=O)NC[C@@H](CNC(=O)c1nc2cc(-c3ccc(F)cc3)ccc2[nH]1)NC(=O)OCc1ccccc1]

Benzyl tert-butyl (3-(5-(4-fluorophenyl)-1H-benzo[d]imidazole-2-carboxamido)propane-1,2-diyl)(R)-dicarbamate To 5-(4-fluorophenyl)-1H-benzo[d]imidazole-2-carboxylic acid (50 mg, 0.20 mmol) in DMF (1 mL) was added DIPEA (0.069 mL, 0.40 mmol), HOBt (16 mg, 0.12 mmol), EDC (46 mg, 0.24 mmol). The reaction mixture was stirred at room temperature for 5 minutes. Benzyl tert-butyl (3-aminopropane-1,2-diyl)(R)-dicarbamate (intermediate D) (72 mg, 0.20 mmol) was added and the reaction was stirred at room temperature overnight. The reaction mixture was then diluted with EtOAc and washed with 15% LiCl and brine. The organic layer was dried over sodium sulfate and filtered. The filtrate was then concentrated under reduced pressure and purified on an ISCO chromatograph using silica gel (0-100% ethyl acetate/hexanes) to give the product (68 mg, 57% yield) as a yellow oil. $^1$H NMR (300 MHz, CDCl$_3$) δ 12.88 (s, 1H), 8.92-8.87 (m, 1H), 8.02 (s, 1H), 7.83-7.73 (m, 1H), 7.52-7.45 (m, 4H), 7.40-7.19 (m, 5H), 7.04-7.01 (m, 3H), 5.03-4.89 (m, 2H), 4.12-4.07 (m, 1H), 3.72-3.69 (m, 2H), 3.37 (m, 2H), 1.45-1.38 (m, 9H).

Example 14. Preparation of (S)-5-((amino(iminio)methyl)amino)-1-(5-(4-fluorophenyl)-1H-benzo[d]imidazole-2-carboxamido) pentan-2-aminium Chloride

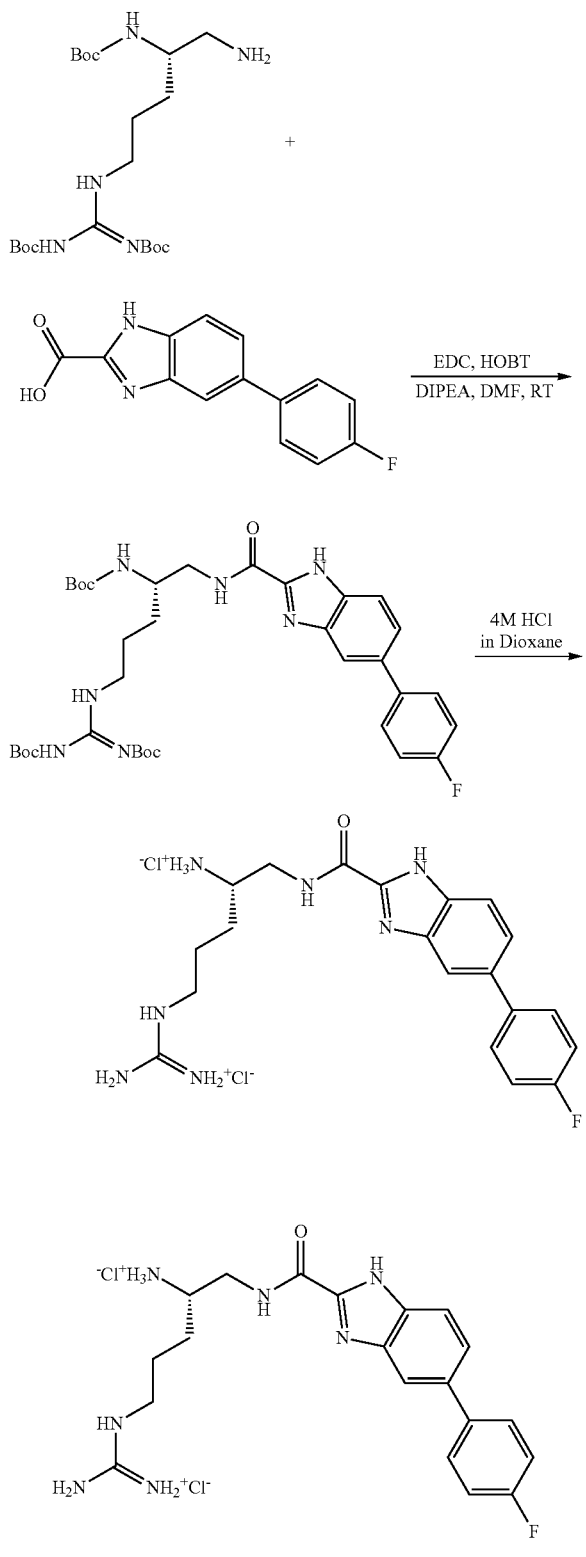

(S)-5-((Amino(iminio)methyl)amino)-1-(5-(4-fluorophenyl)-1H-benzo[d]imidazole-2-carboxamido) pentan-2-aminium Chloride To a solution of (S)—N-(2-N-Boc-amino-5-2',3'-di-Boc-guanidinopentyl)-5-(4-fluorophenyl)-1H-benzo[d]imidazole-2-carboxamide (99 mg, 0.14 mmol) in MeOH (1 mL) was added 0.3 mL 4 M HCl in dioxane. The reaction was stirred at room temperature overnight. The residue was concentrated and triturated with EtOAc to afford product (47 mg, 70% yield) as a brown solid. $^1$H NMR (300 MHz, DMSO-d6) δ 9.17 (s, 2H), 8.21-8.09 (m, 6H), 7.68-7.56 (m, 6H), 7.25 (m, 2H), 3.51 (m, 2H), 3.29 (m, 1H), 2.75 (m, 2H), 1.65 (m, 4H).

The requisite intermediate was prepared as described in the following paragraph.

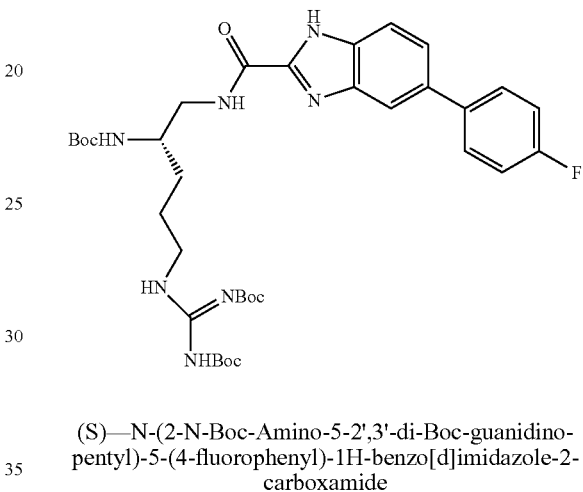

(S)—N-(2-N-Boc-Amino-5-2',3'-di-Boc-guanidinopentyl)-5-(4-fluorophenyl)-1H-benzo[d]imidazole-2-carboxamide To 5-(4-fluorophenyl)-1H-benzo[d]imidazole-2-carboxylic acid (50 mg, 0.20 mmol) in DMF (1 mL) was added DIPEA (0.069 mL, 0.40 mmol), HOBt (16 mg, 0.12 mmol), EDC (46 mg, 0.24 mmol). The reaction mixture was stirred at room temperature for 5 minutes. (S)-1-(4-N-Boc-amino-5-aminopentyl)-2,3-di-Boc-guanidine (intermediate H) (92 mg, 0.20 mmol) was added and the reaction was continued to stir at room temperature overnight. The reaction mixture was then diluted with EtOAc and washed with 15% LiCl and brine. The organic layer was dried over sodium sulfate and filtered. Filtrate was then concentrated and purified on an ISCO chromatograph using silica gel (0-100% ethyl acetate/hexanes) to give the product (99 mg, 71% yield) as a yellow oil. $^1$H NMR (300 MHz, CDCl$_3$) δ 12.28 (s, 1H), 8.37-8.33 (m, 1H), 7.86-7.75 (m, 2H), 7.59-7.45 (m, 4H), 7.12-7.07 (m, 2H), 3.95 (m, 1H), 3.63-3.55 (m, 2H), 3.14-3.12 (m, 2H), 2.08-2.05 (m, 1H), 1.62 (m, 4H), 1.49-1.23 (m, 27H).

Example 15. Preparation of (S)-4-(5-(4-methoxyphenyl)-1H-benzo[d]imidazole-2-carboxamido)butane-1,3-diaminium Dihydrochloride

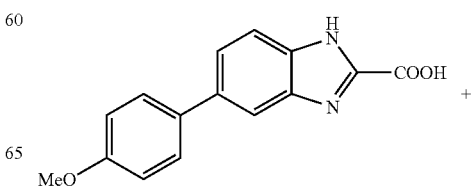

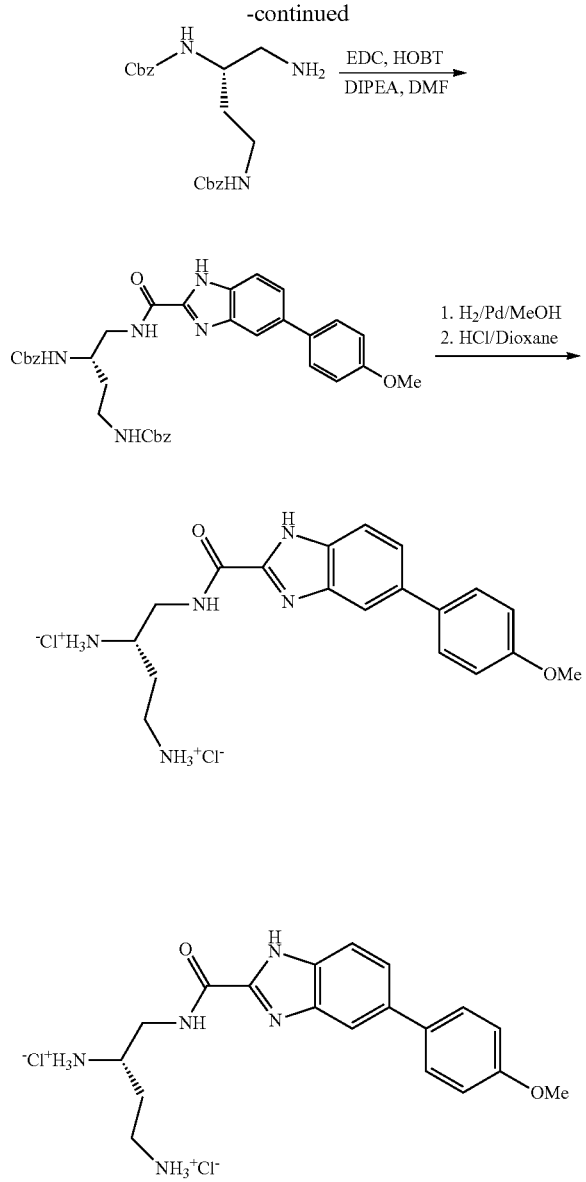

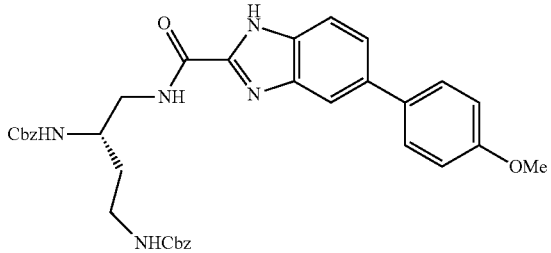 [SMILES: COc1ccc(-c2ccc3[nH]c(C(=O)NC[C@H](CCNC(=O)OCc4ccccc4)NC(=O)OCc4ccccc4)nc3c2)cc1]

Dibenzyl (4-(5-(4-methoxyphenyl)-1H-benzo[d]imidazole-2-carboxamido)butane-1,3-diyl)(S)-dicarbamate To 5-(4-methoxyphenyl)-1H-benzo[d]imidazole-2-carboxylic acid (55 mg, 0.21 mmol) in DMF (1 mL) was added DIPEA (0.073 mL, 0.42 mmol), HOBt (17 mg, 0.13 mmol), EDC (49 mg, 0.25 mmol). The reaction mixture was stirred at room temperature for 5 minutes. Dibenzyl (4-aminobutane-1,3-diyl)(S)-dicarbamate (intermediate C) (77 mg, 0.21 mmol) was added and the reaction was continued to stir at room temperature overnight. The reaction mixture was then diluted with EtOAc and washed with 15% LiCl and brine. The organic layer was dried over sodium sulfate and filtered. Filtrate was then concentrated and purified on an ISCO chromatograph using silica gel (0-100% ethyl acetate/hexanes) to give the product (88 mg, 68% yield) as a yellow oil. $^1$H NMR (300 MHz, CDCl$_3$) δ 8.52 (m, 1H), 8.02 (s, 1H), 7.85-7.72 (m, 2H), 7.53-7.44 (m, 4H), 7.29-7.17 (m, 9H), 6.93-6.91 (m, 2H), 5.10-4.91 (m, 4H), 4.05 (m, 1H), 3.82 (s, 3H), 3.59 (m, 2H), 3.44-3.42 (m, 1H), 3.05-3.03 (m, 1H), 1.78-1.63 (m, 2H).

Example 16. Preparation of N-((2S)-2,5-diamino-6-methylheptyl)-5-(4-fluorophenyl)-1H-benzo[d]imidazole-2-carboxamide Dihydrochloride

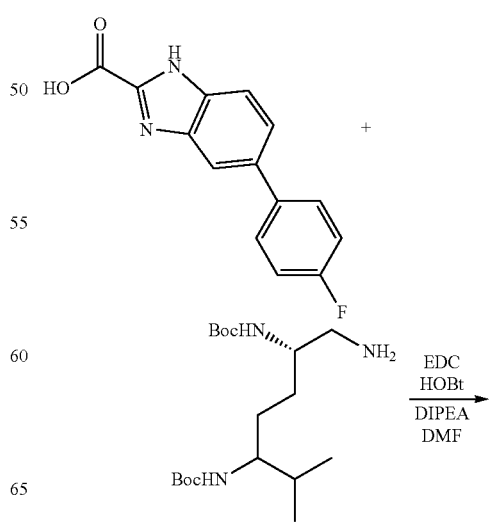

(S)-4-(5-(4-Methoxyphenyl)-1H-benzo[d]imidazole-2-carboxamido)butane-1,3-diaminium Dihydrochloride To a solution of dibenzyl (4-(5-(4-methoxyphenyl)-1H-benzo[d]imidazole-2-carboxamido)butane-1,3-diyl)(S)-dicarbamate (88 mg, 0.093 mmol) in MeOH (3 mL) was added 7 mg 10% palladium on carbon. The reaction was hydrogenated under hydrogen gas balloon at room temperature overnight. The reaction was filtered through Celite, washed with MeOH and concentrated. The residue was triturated with EtOAc to afford product (43 mg, 71% yield) as a yellow solid. $^1$H NMR (300 MHz, DMSO-d6) δ 9.29-9.38 (m, 1H), 8.45 (s, 3H), 8.24-8.19 (m, 3H), 7.78-7.70 (m, 2H), 7.64-7.54 (m, 3H), 7.20-7.02 (d, 2H), 3.79 (s, 3H), 3.68-3.37 (m, 4H), 3.06-2.95 (m, 1H), 3.05, 2.04-1.79 (m, 2H).

The requisite intermediate was prepared as described in the following paragraph.

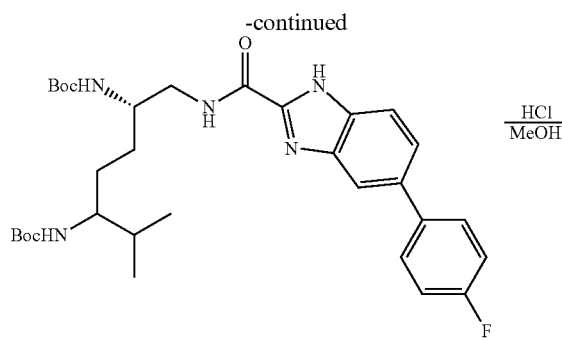

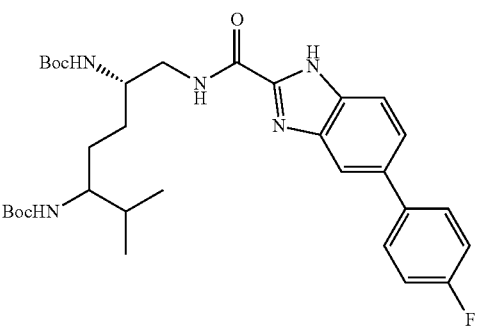

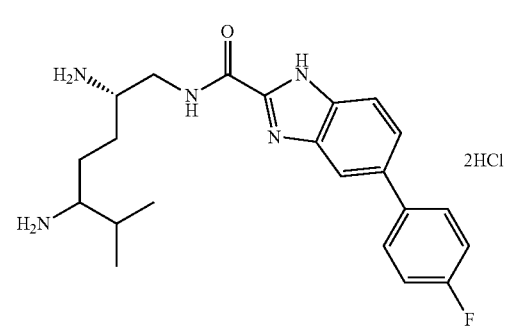

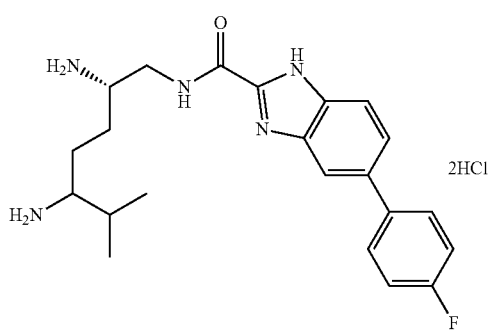 [SMILES: CC(C)C(N)CC[C@H](N)CNC(=O)c1nc2cc(-c3ccc(F)cc3)ccc2[nH]1]

N-((2S)-2,5-Diamino-6-methylheptyl)-5-(4-fluorophenyl)-1H-benzo[d]imidazole-2-carboxamide Dihydrochloride To the solution of di-tert-butyl ((2S)-1-(5-(4-fluorophenyl)-1H-benzo[d]imidazole-2-carboxamido)-6-methylheptane-2,5-diyl)dicarbamate (50 mg, 0.08 mmol) in MeOH (3 mL) was added HCl solution in dioxane (4 M, 0.2 mL) and it was stirred at room temperature overnight then condensed under reduced pressure. The residue was triturated with EtOAc and the beige solid was collected by filtration to provide the title compound (30 mg, 76% yield). $^1$H NMR (300 MHz, DMSO-$d_6$) δ 9.15 (br. s, 1H), 8.13 (br. s, 3H), 8.00 (br. s, 3H), 7.80 (s, 1H), 7.74-7.70 (m, 3H), 7.59 (d, J=8.4 Hz, 1H), 7.33-7.27 (m, 2H), 3.60-3.40 (m, 2H), 2.96 (m, 2H), 1.88 (m, 1H), 1.70 (m, 4H), 0.92 (m, 6H).

The requisite intermediate was prepared as described in the following paragraph.

Di-tert-butyl ((2S)-1-(5-(4-fluorophenyl)-1H-benzo[d]imidazole-2-carboxamido)-6-methylheptane-2,5-diyl)dicarbamate To a solution of 5-(4-fluorophenyl)-1H-benzo[d]imidazole-2-carboxylic acid (51 mg, 0.2 mmol) in dry DMF (2 mL) was added DIPEA (0.07 mL, 0.40 mmol), HOBt (16 mg, 0.12 mmol) and EDC (46 mg, 0.24 mmol). The reaction mixture was stirred at room temperature for 5 minutes and di-tert-butyl ((2S)-1-amino-6-methylheptane-2,5-diyl)dicarbamate (intermediate I) (72 mg, 0.20 mmol) was added. The reaction was continued to stir at room temperature overnight. It was then diluted with EtOAc and washed with water and brine. The organic layer was dried over anhydrous sodium sulfate and filtered. The filtrate was concentrated under reduced pressure and purified on silica gel to give the product (50 mg, 43% yield) as a light yellow solid. $^1$H NMR (300 MHz, CDCl$_3$) δ 7.98-7.79 (m, 2H), 7.63-7.49 (m, 4H), 7.16-7.10 (m, 2H), 3.87 (m, 1H), 3.60 (m, 2H), 3.42 (m, 1H), 1.30-1.74 (m, 23H), 0.85 (m, 6H).

Example 17. Preparation of (S)—N-(2,5-diaminopentyl)-5-(4-fluorophenyl)-1H-benzo[d]imidazole-2-carboxamide Dihydrochloride

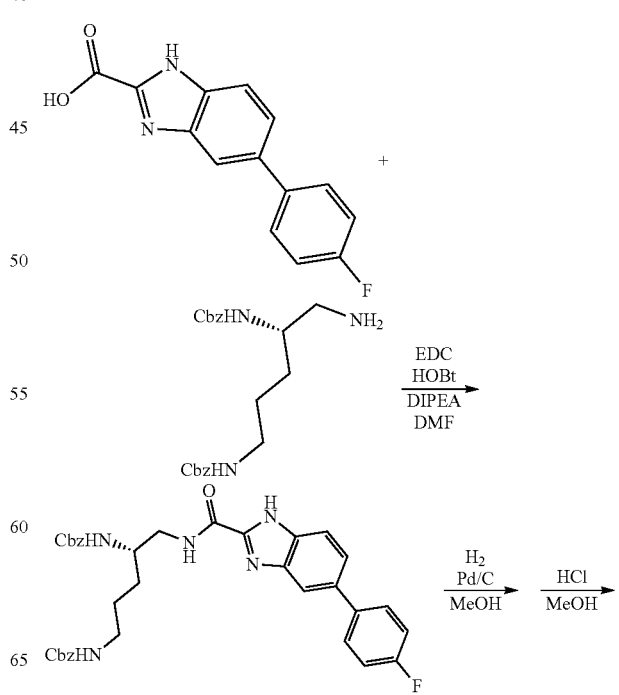

-continued

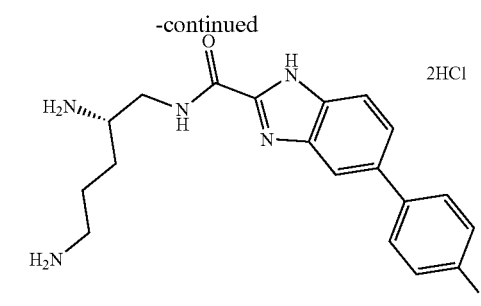

2HCl

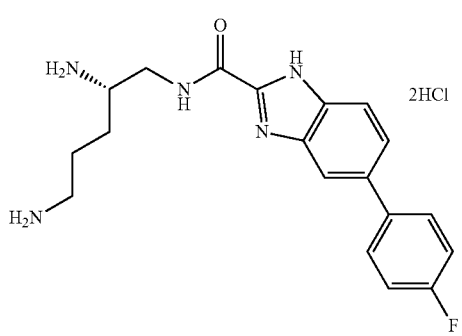 [SMILES: NCCC[C@H](N)CNC(=O)c1nc2cc(-c3ccc(F)cc3)ccc2[nH]1]

2HCl (S)—N-(2,5-Diaminopentyl)-5-(4-fluorophenyl)-1H-benzo[d]imidazole-2-carboxamide Dihydrochloride To a solution of (S)-dibenzyl (5-(5-(4-fluorophenyl)-1H-benzo[d]imidazole-2-carboxamido)pentane-1,4-diyl)dicarbamate (300 mg, 0.48 mmol) in methanol (15 mL) was added Pd/C (10%, 60 mg). The reaction mixture was stirred under H$_2$ overnight. The solid was filtered off through a Celite pad and the filtrate was condensed under reduced pressure to give a residue. The residue was dissolved in MeOH (5 mL) was added HCl solution in dioxane (4 M, 0.3 mL) and the mixture was stirred at room temperature overnight then concentrated under reduced pressure. The crude product was triturated with EtOAc and the beige solid was collected by filtration to provide the title compound (175 mg, 85% yield in two steps). $^1$H NMR (300 MHz, DMSO-d$_6$) δ 9.17 (br. s, 1H), 8.16 (br. s, 3H), 8.02 (br. s, 3H), 7.80 (s, 1H), 7.74-7.70 (m, 3H), 7.59 (d, J 8.4 Hz, 1H), 7.33-7.27 (m, 2H), 3.60-3.40 (m, 2H), 2.79 (m, 3H), 1.67 (m, 4H).

The requisite intermediate was prepared as described in the following paragraph.

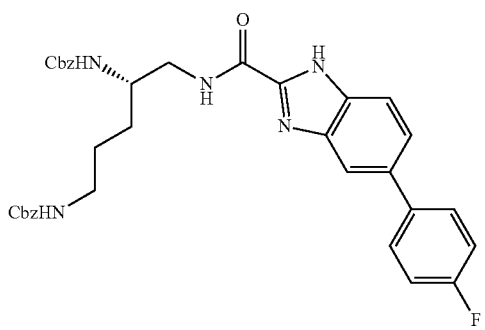 [SMILES: O=C(NCCC[C@@H](CNC(=O)c1nc2cc(-c3ccc(F)cc3)ccc2[nH]1)NC(=O)OCc1ccccc1)OCc1ccccc1]

(S)-Dibenzyl (5-(5-(4-fluorophenyl)-1H-benzo[d]imidazole-2-carboxamido)pentane-1,4-diyl)dicarbamate To a solution of 5-(4-fluorophenyl)-1H-benzo[d]imidazole-2-carboxylic acid (256 mg, 1.0 mmol) in dry DMF (5 mL) was added DIPEA (0.34 mL, 2.0 mmol), HOBt (81 mg, 0.60 mmol) and EDC (230 mg, 1.20 mmol). The reaction mixture was stirred at room temperature for 5 minutes and (S)-dibenzyl (5-aminopentane-1,4-diyl)dicarbamate (intermediate A) (385 mg, 1.0 mmol) was added. The reaction was stirred at room temperature overnight. It was then diluted with EtOAc and washed with water and brine. The organic layer was dried over anhydrous sodium sulfate and filtered. The filtrate was concentrated and purified on silica gel to give the product (300 mg, 48% yield) as a yellow solid. $^1$H NMR (300 MHz, DMSO-d$_6$) δ 8.88 (br. s, 1H), 7.53-7.80 (m, 2H), 7.21-7.36 (m, 15H), 4.97 (m, 4H), 3.75 (m, 1H), 3.20-3.40 (m, 2H), 2.96 (m, 2H), 1.45 (m, 4H).

Example 18. Preparation of (R)—N-(2,5-diaminopentyl)-5-(4-fluorophenyl)-1H-benzo[d]imidazole-2-carboxamide Dihydrochloride

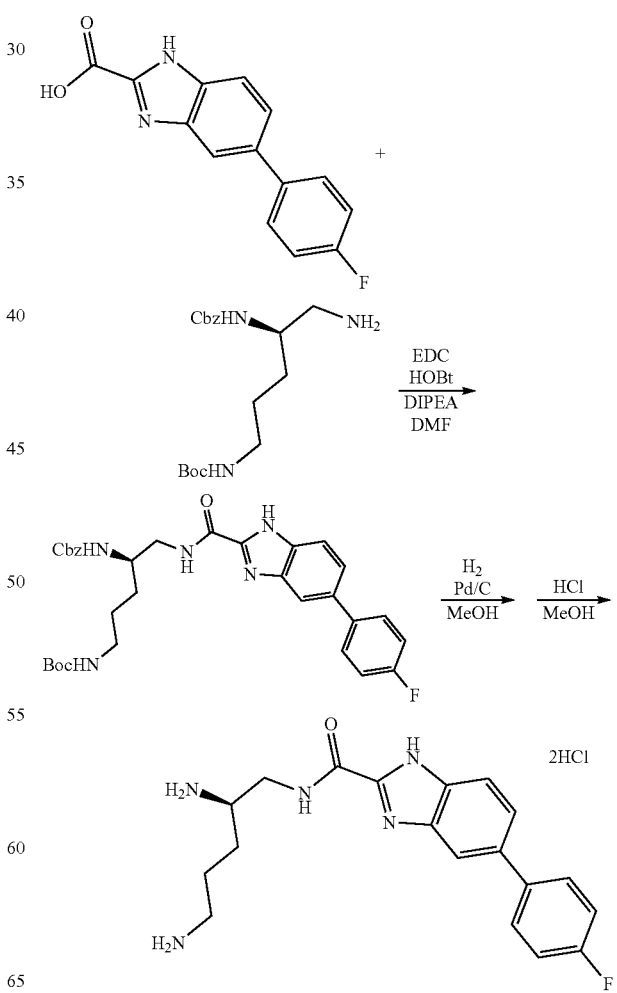

131

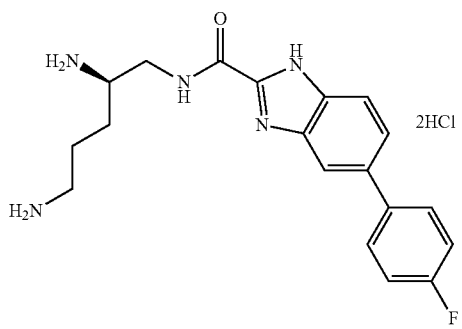 [SMILES: NCCC[C@@H](N)CNC(=O)c1nc2cc(-c3ccc(F)cc3)ccc2[nH]1]

(R)—N-(2,5-Diaminopentyl)-5-(4-fluorophenyl)-1H-benzo[d]imidazole-2-carboxamide Dihydrochloride To a solution of (R)-benzyl tert-butyl (5-(5-(4-fluorophenyl)-1H-benzo[d]imidazole-2-carboxamido)pentane-1,4-diyl)dicarbamate (80 mg, 0.14 mmol) in methanol (10 mL) was added Pd/C (10%, 20 mg). It was stirred under $H_2$ overnight. The solid was filtered off through a Celite pad and the filtrate was concentrated under reduced pressure to give a residue. The residue was dissolved in MeOH (3 mL) and HCl solution in dioxane (4 M, 0.2 mL) was added and it was stirred at room temperature overnight then concentrated under reduced pressure. The crude product was triturated with EtOAc and the beige solid was collected by filtration to provide the title compound (175 mg, 85% yield in two steps). $^1$H NMR (300 MHz, DMSO-$d_6$) δ 9.16 (br. s, 1H), 8.15 (br. s, 3H), 8.00 (br. s, 3H), 7.80 (s, 1H), 7.70-7.74 (m, 3H), 7.59 (d, J 8.4 Hz, 1H), 7.27-7.33 (m, 2H), 3.40-3.60 (m, 2H), 2.80 (m, 3H), 1.67 (m, 4H).

The requisite intermediate was prepared as described in the following paragraph.

132

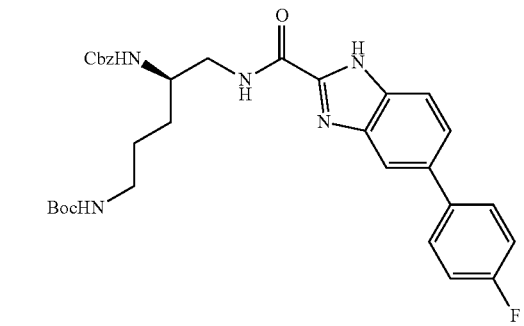 [SMILES: CC(C)(C)OC(=O)NCCC[C@H](CNC(=O)c1nc2cc(-c3ccc(F)cc3)ccc2[nH]1)NC(=O)OCc1ccccc1]

(R)-Benzyl tert-butyl (5-(5-(4-fluorophenyl)-1H-benzo[d]imidazole-2-carboxamido)pentane-1,4-diyl) dicarbamate To a solution of 5-(4-fluorophenyl)-1H-benzo[d]imidazole-2-carboxylic acid (130 mg, 0.5 mmol) in dry DMF (2 mL) was added DIPEA (0.18 mL, 1.0 mmol), HOBt (40 mg, 0.30 mmol) and EDC (115 mg, 0.6 mmol). The reaction mixture was stirred at room temperature for 5 minutes and (R)-benzyl tert-butyl (5-aminopentane-1,4-diyl)dicarbamate (intermediate F) (175 mg, 0.5 mmol) was added. The reaction was continued to stir at room temperature overnight. It was then diluted with EtOAc and washed with water and brine. The organic layer was dried over anhydrous sodium sulfate and filtered. The filtrate was concentrated and purified on silica gel to give the product (161 mg, 54% yield) as a yellow solid. $^1$H NMR (300 MHz, CDCl$_3$) δ 8.20 (br. s, 1H), 7.82 (m, 1H), 7.44-7.59 (m, 4H), 7.08-7.32 (m, 7H), 5.00 (m, 2H), 3.96 (m, 1H), 3.59 (m, 2H), 3.15 (m, 2H), 1.45-1.80 (m, 4H), 1.41 (s, 9H).

Example 19. Preparation of (S)-1-benzyl-N-(2,5-diaminopentyl)-6-(4-fluorophenyl)-1H-benzo[d]imidazole-2-carboxamide and (S)-1-benzyl-N-(2,5-diaminopentyl)-5-(4-fluorophenyl)-1H-benzo[d]imidazole-2-carboxamide Dihydrochloride

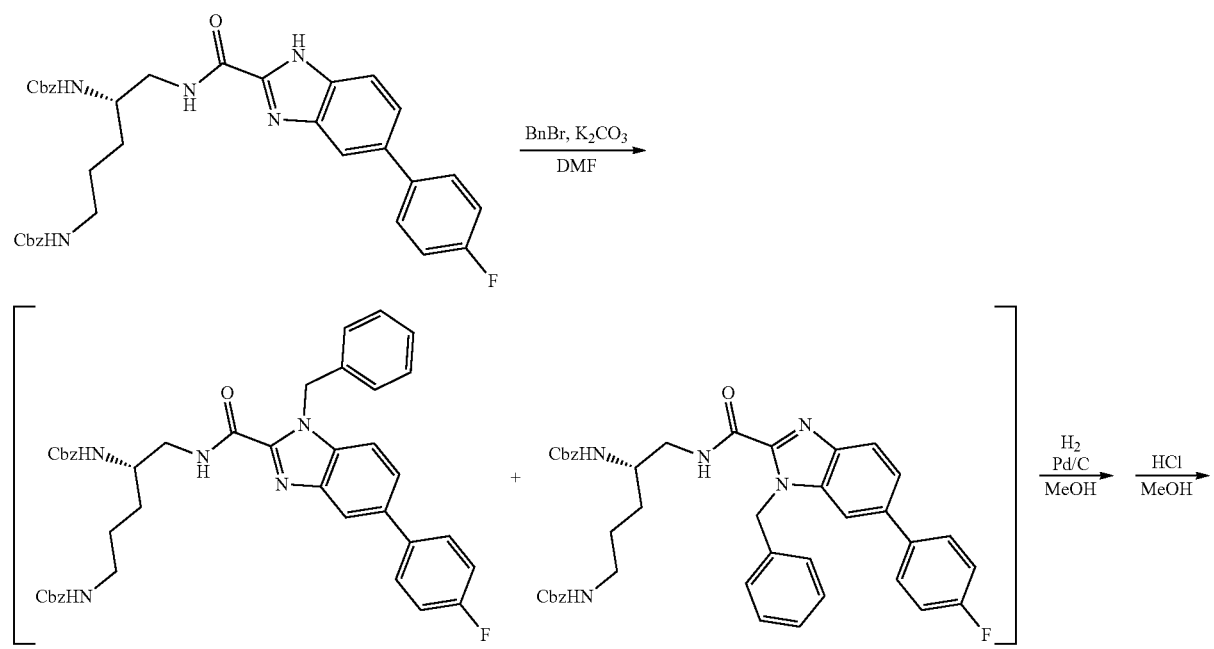

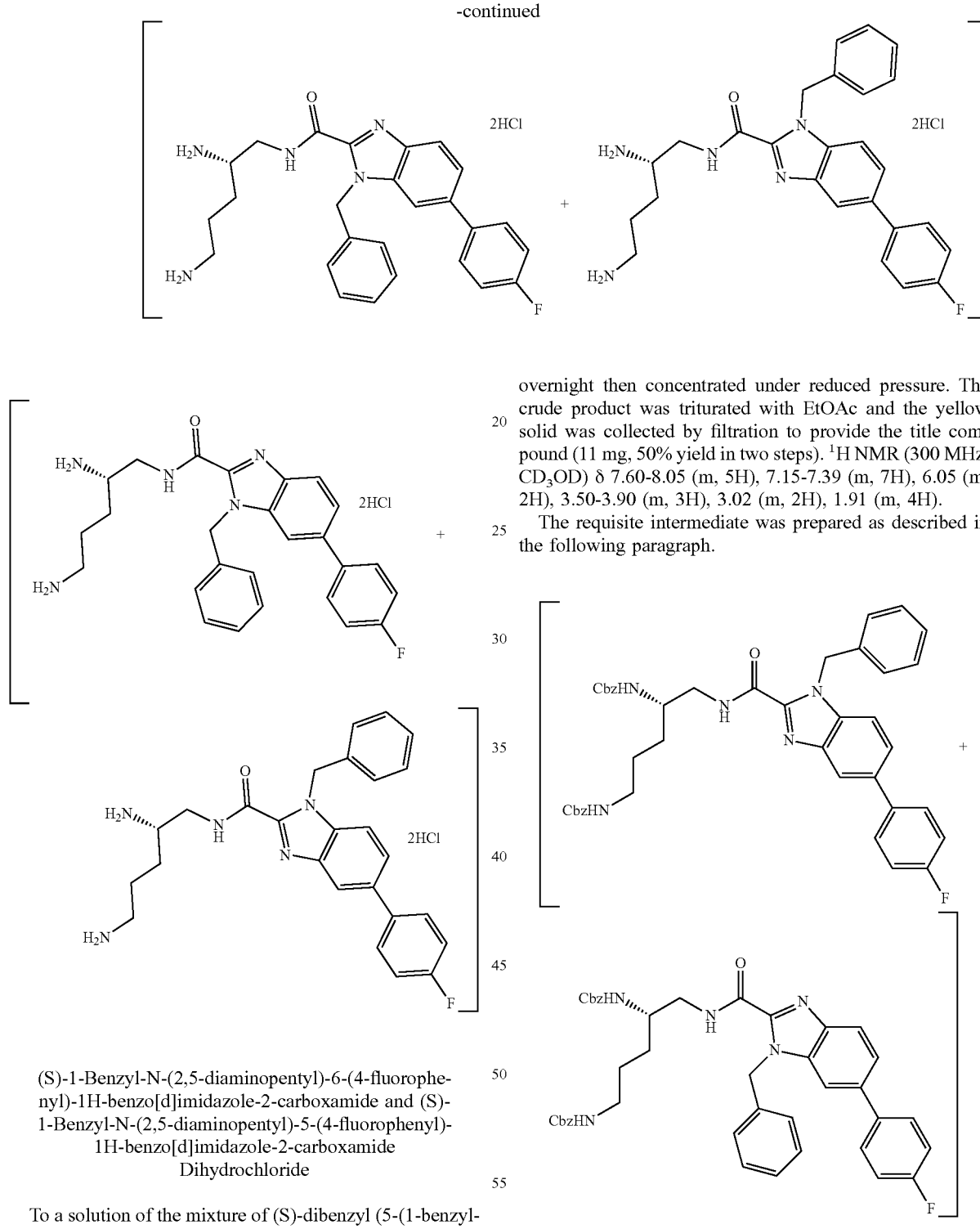

overnight then concentrated under reduced pressure. The crude product was triturated with EtOAc and the yellow solid was collected by filtration to provide the title compound (11 mg, 50% yield in two steps). $^1$H NMR (300 MHz, CD$_3$OD) δ 7.60-8.05 (m, 5H), 7.15-7.39 (m, 7H), 6.05 (m, 2H), 3.50-3.90 (m, 3H), 3.02 (m, 2H), 1.91 (m, 4H).

The requisite intermediate was prepared as described in the following paragraph.

(S)-1-Benzyl-N-(2,5-diaminopentyl)-6-(4-fluorophenyl)-1H-benzo[d]imidazole-2-carboxamide and (S)-1-Benzyl-N-(2,5-diaminopentyl)-5-(4-fluorophenyl)-1H-benzo[d]imidazole-2-carboxamide Dihydrochloride To a solution of the mixture of (S)-dibenzyl (5-(1-benzyl-5-(4-fluorophenyl)-1H-benzo[d]imidazole-2-carboxamido)pentane-1,4-diyl)dicarbamate and (S)-dibenzyl (5-(1-benzyl-6-(4-fluorophenyl)-1H-benzo[d]imidazole-2-carboxamido)pentane-1,4-diyl)dicarbamate (30 mg, 0.04 mmol) in methanol (10 mL) was added Pd/C (10%, 20 mg). It was stirred under H$_2$ overnight. The solid was filtered off through a Celite pad and the filtrate was concentrated under reduced pressure to give a residue. The residue was dissolved in MeOH (2 mL) was added HCl solution in dioxane (4 M, 0.2 mL) and it was stirred at room temperature (S)-Dibenzyl (5-(1-benzyl-5-(4-fluorophenyl)-1H-benzo[d]imidazole-2-carboxamido)pentane-1,4-diyl)dicarbamate and (S)-Dibenzyl (5-(1-benzyl-6-(4-fluorophenyl)-1H-benzo[d]imidazole-2-carboxamido)pentane-1,4-diyl)dicarbamate To a solution of (S)-dibenzyl (5-(5-(4-fluorophenyl)-1H-benzo[d]imidazole-2-carboxamido)pentane-1,4-diyl)dicarbamate (25 mg, 0.04 mmol) in dry DMF (1 mL) was added BnBr (0.07 mL, 0.06 mmol), and K$_2$CO$_3$ (18 mg, 0.13 mmol). The reaction mixture was stirred at room temperature overnight. It was then diluted with EtOAc and washed with water and brine. The organic layer was dried over anhydrous sodium sulfate and filtered. The filtrate was concentrated and purified on silica gel to give the product (23 mg, 79% yield) as a yellow solid. $^1$H NMR (300 MHz, DMSO-d$_6$) δ 8.08 (br. s, 1H), 7.80-7.90 (m, 1H), 7.10-7.56 (m, 21H), 5.92 (m, 2H), 5.06 (m, 4H), 3.88 (m, 1H), 3.54 (m, 2H), 3.19 (m, 2H), 1.60 (m, 4H).

Example 20. Preparation of (R)—N-(2,5-diaminopentyl)-6-(4-fluorophenyl)-1-methyl-1H-benzo[d]imidazole-2-carboxamide and (R)—N-(2,5-diaminopentyl)-5-(4-fluorophenyl)-1-methyl-1H-benzo[d]imidazole-2-carboxamidedihydrochloride

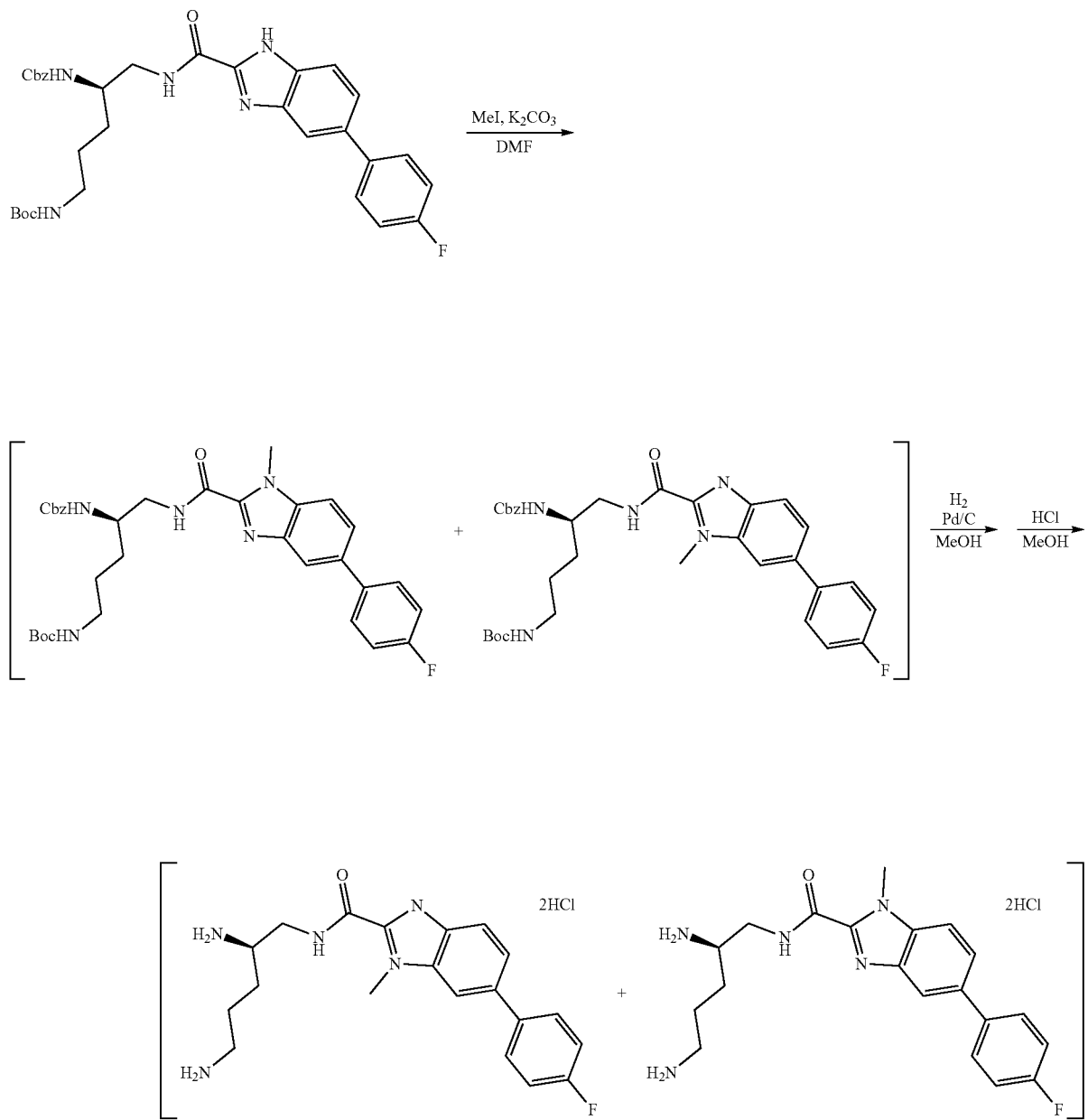

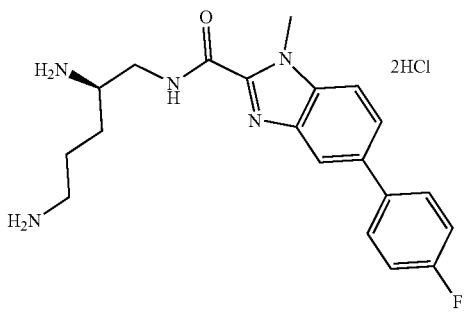

(R)—N-(2,5-Diaminopentyl)-6-(4-fluorophenyl)-1-methyl-1H-benzo[d]imidazole-2-carboxamide and
(R)—N-(2,5-Diaminopentyl)-5-(4-fluorophenyl)-1-methyl-1H-benzo[d]imidazole-2-carboxamide Dihydrochloride To a solution of the mixture of (R)-benzyl tert-butyl (5-(5-(4-fluorophenyl)-1-methyl-1H-benzo[d]imidazole-2-carboxamido)pentane-1,4-diyl)dicarbamate and (R)-benzyl tert-butyl (5-(6-(4-fluorophenyl)-1-methyl-1H-benzo[d]imidazole-2-carboxamido)pentane-1,4-diyl)dicarbamate (64 mg, 0.11 mmol) in methanol (10 mL) was added Pd/C (10%, 25 mg). It was stirred under H₂ overnight. The solid was filtered off through a Celite pad and the filtrate was concentrated under reduced pressure to give a residue. The residue was dissolved in MeOH (2 mL) was added HCl solution in dioxane (4 M, 0.3 mL) and it was stirred at room temperature overnight then concentrated under reduced pressure. The crude product was triturated with EtOAc and the yellow solid was collected by filtration to provide the title compound (22 mg, 46% yield in two steps). $^1$H NMR (300 MHz, DMSO-$d_6$) δ 9.18 (br. s, 1H), 8.16 (br. s, 3H), 8.02 (br. s, 3H), 7.62-7.99 (m, 7H), 7.31 (m, 2H), 4.19 (s, 1.5H), 4.15 (s, 1.5H), 3.38-3.70 (m, 3H), 2.80 (m, 2H), 1.68 (m, 4H).

The requisite intermediate was prepared as described in the following paragraph.

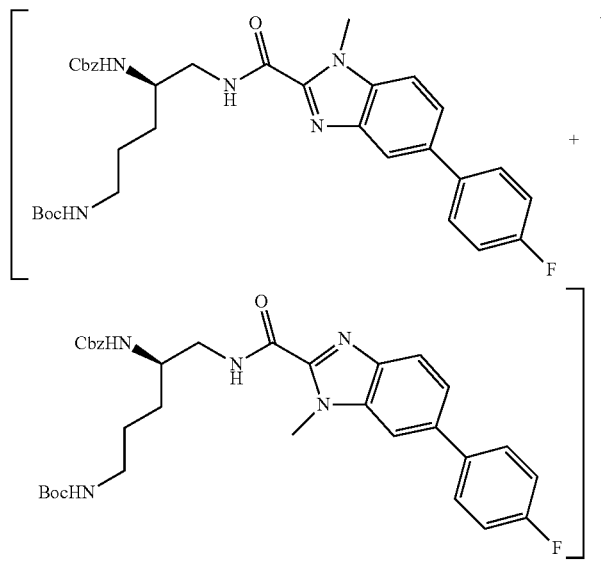

(R)-Benzyl tert-butyl (5-(5-(4-fluorophenyl)-1-methyl-1H-benzo[d]imidazole-2-carboxamido)pentane-1,4-diyl)dicarbamate and (R)-Benzyl tert-butyl (5-(6-(4-fluorophenyl)-1-methyl-1H-benzo[d]imidazole-2-carboxamido)pentane-1,4-diyl)dicarbamate To a solution of (R)-benzyl tert-butyl (5-(5-(4-fluorophenyl)-1H-benzo[d]imidazole-2-carboxamido)pentane-1,4-diyl)dicarbamate (80 mg, 0.14 mmol) in dry DMF (1.5 mL) was added MeI (0.03 mL, 0.21 mmol), and K₂CO₃ (58 mg, 0.42 mmol). The reaction mixture was stirred at room temperature overnight. It was then diluted with EtOAc and washed with water and brine. The organic layer was dried over anhydrous sodium sulfate and filtered. The filtrate was concentrated under reduced pressure and purified on silica gel to give the product (64 mg, 78% yield) as a yellow solid. $^1$H NMR (300 MHz, CDCl₃) δ 8.00 (br. s, 1H), 7.85 (m, 1H), 7.46-7.64 (m, 4H), 7.13-7.33 (m, 7H), 5.07 (m, 2H), 4.21 (s, 1.5H), 4.20 (s, 1.5H), 3.89 (m, 1H), 3.57 (m, 2H), 3.14 (m, 2H), 1.45-1.70 (m, 4H), 1.42 (s, 9H).

Example 21. Preparation of N-(((2S,4R)-4-(aminomethyl)pyrrolidin-2-yl)methyl)-5-(4-fluorophenyl)-1H-benzo[d]imidazole-2-carboxamide Dihydrochloride

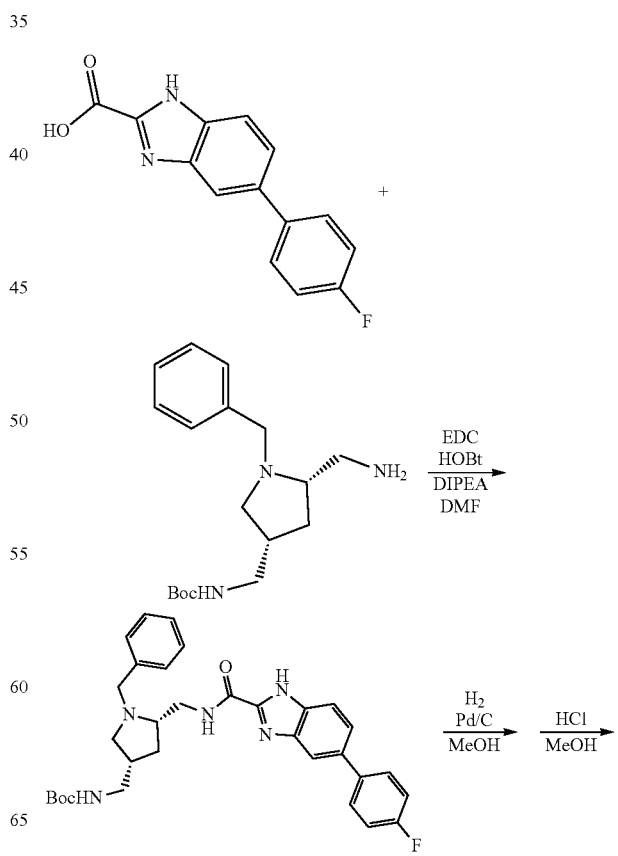

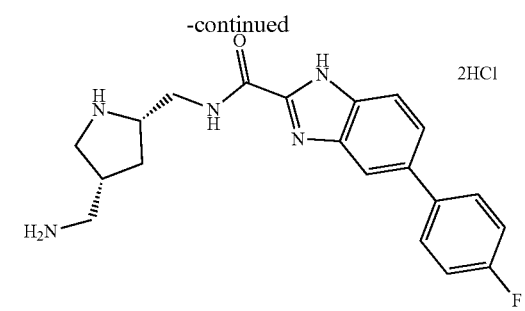

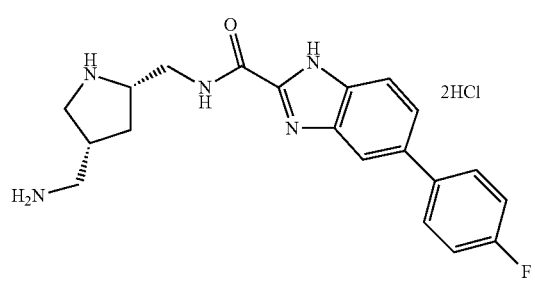 [SMILES: NC[C@@H]1CN[C@H](CNC(=O)c2nc3cc(-c4ccc(F)cc4)ccc3[nH]2)C1]

N-(((2S,4R)-4-(Aminomethyl)pyrrolidin-2-yl)
methyl)-5-(4-fluorophenyl)-1H-benzo[d]imidazole-
2-carboxamide Dihydrochloride To a solution of tert-butyl (((3R,5S)-1-benzyl-5-((5-(4-fluorophenyl)-1H-benzo[d]imidazole-2-carboxamido)methyl)pyrrolidin-3-yl)methyl)carbamate (40 mg, 0.07 mmol) in methanol (10 mL) was added Pd/C (10%, 20 mg). It was stirred under H₂ overnight. The solid was filtered off through a Celite pad and the filtrate was concentrated under reduced pressure to give a residue. The residue was dissolved in MeOH (3 mL) was added HCl solution in dioxane (4 M, 0.4 mL) and it was stirred at room temperature overnight then concentrated under reduced pressure. The crude product was triturated with EtOAc and the beige solid was collected by filtration to provide the title compound (16 mg, 51% yield in two steps) as beige solid. ¹H NMR (300 MHz, DMSO-d₆) δ 9.51 (m, 1H), 9.25 (m, 2H), 8.11 (br. s, 3H), 7.80 (s, 1H), 7.75-7.60 (m, 3H), 7.61-7.57 (m, 1H), 7.32-7.25 (m, 2H), 4.32 (m, 1H), 3.60-3.40 (m, 2H), 3.39-2.70 (m, 4H), 2.40-2.05 (m, 2H), 1.41 (m, 1H).

The requisite intermediate was prepared as described in the following paragraph.

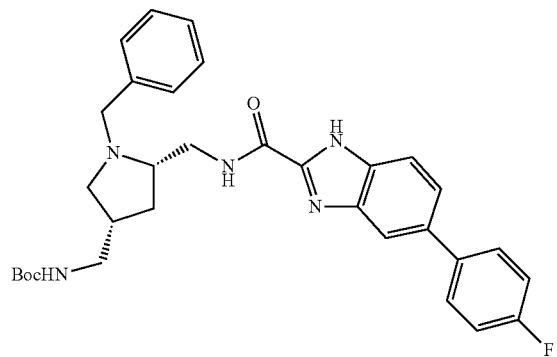 [SMILES: CC(C)(C)OC(=O)NC[C@H]1C[C@@H](CNC(=O)c2nc3cc(-c4ccc(F)cc4)ccc3[nH]2)N(Cc2ccccc2)C1]

tert-Butyl (((3R,5S)-1-benzyl-5-((5-(4-fluorophenyl)-1H-benzo[d]imidazole-2-carboxamido)methyl)pyrrolidin-3-yl)methyl)carbamate To a solution of 5-(4-fluorophenyl)-1H-benzo[d]imidazole-2-carboxylic acid (51 mg, 0.2 mmol) in dry DMF (1.5 mL) was added DIPEA (0.07 mL, 0.4 mmol), HOBt (16 mg, 0.12 mmol) and EDC (46 mg, 0.24 mmol). The reaction mixture was stirred at room temperature for 5 minutes and tert-butyl (((3R,5S)-5-(aminomethyl)-1-benzylpyrrolidin-3-yl)methyl)carbamate (intermediate J) (64 mg, 0.2 mmol) was added. The reaction was continued to stir at room temperature overnight. It was then diluted with EtOAc and washed with water and brine. The organic layer was dried over anhydrous sodium sulfate and filtered. The filtrate was concentrated and purified on silica gel to give the product (40 mg, 36% yield) as a yellow solid. ¹H NMR (300 MHz, CDCl₃) δ 7.89-0.76 (m, 1H), 7.55 (m, 5H), 7.29 (M, 5H), 7.12 (m, 2H), 4.61 (m, 1H), 4.30 (m, 1H), 3.59 (s, 2H), 3.19-2.90 (m, 4H), 2.20-1.75 (m, 4H), 1.40 (s, 9H).

Example 22. Preparation of N-(((2S,4S)-4-(aminomethyl)pyrrolidin-2-yl)methyl)-5-(4-fluorophenyl)-1H-benzo[d]imidazole-2-carboxamidedihydrochloride

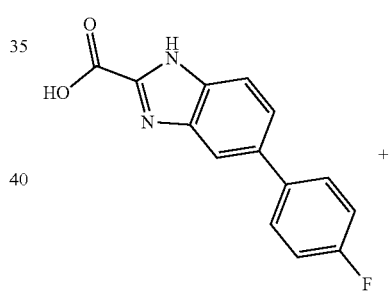

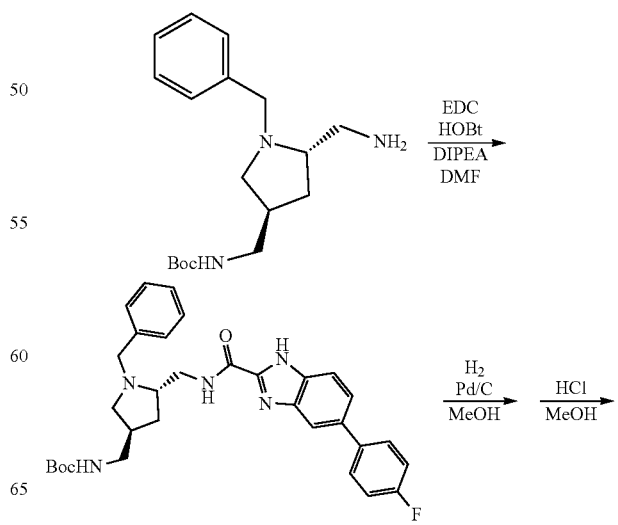

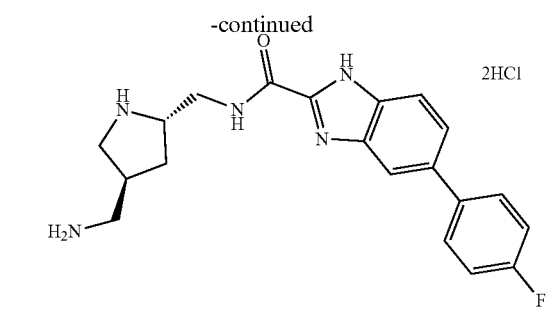

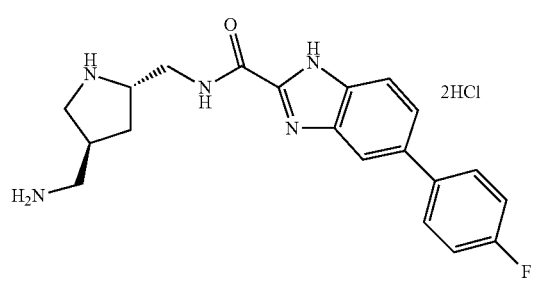 [SMILES: NC[C@H]1CN[C@H](CNC(=O)c2nc3cc(-c4ccc(F)cc4)ccc3[nH]2)C1]

N-(((2S,4S)-4-(Aminomethyl)pyrrolidin-2-yl)methyl)-5-(4-fluorophenyl)-1H-benzo[d]imidazole-2-carboxamidedihydrochloride To a solution of tert-butyl (((3S,5S)-1-benzyl-5-((5-(4-fluorophenyl)-1H-benzo[d]imidazole-2-carboxamido)methyl)pyrrolidin-3-yl)methyl)carbamate (80 mg, 0.07 mmol) in methanol (15 mL) was added Pd/C (10%, 40 mg). It was stirred under $H_2$ overnight. The solid was filtered off through a Celite pad and the filtrate was concentrated under reduced pressure to give a residue. The residue was dissolved in MeOH (3 mL) was added HCl solution in dioxane (4 M, 0.4 mL) and it was stirred at room temperature overnight then concentrated under reduced pressure. The crude product was triturated with EtOAc and the beige solid was collected by filtration to provide the title compound (33 mg, 52% yield in two steps) as an off white solid. $^1$H NMR (300 MHz, DMSO-$d_6$) δ 9.70 (m, 1H), 9.29 (m, 2H), 8.23 (br. s, 3H), 7.81 (s, 1H), 7.75-7.70 (m, 3H), 7.61-7.57 (m, 1H), 7.32-7.25 (m, 2H), 3.78 (m, 1H), 3.68 (m, 2H), 3.35 (m, 1H), 3.11 (m, 1H), 2.93 (m, 2H), 2.61 (m, 1H), 2.30 (m, 1H), 1.54-1.43 (m, 1H).

The requisite intermediate was prepared as described in the following paragraph.

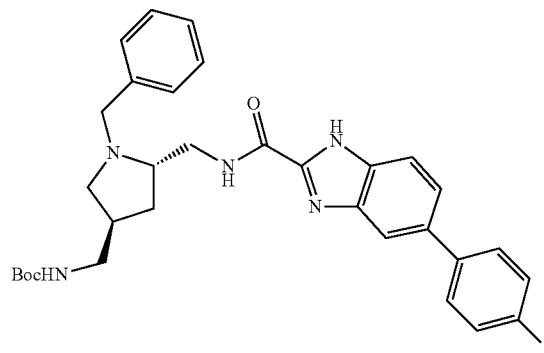

tert-Butyl (((3S,5S)-1-benzyl-5-((5-(4-fluorophenyl)-1H-benzo[d]imidazole-2-carboxamido)methyl)pyrrolidin-3-yl)methyl)carbamate To a solution of 5-(4-fluorophenyl)-1H-benzo[d]imidazole-2-carboxylic acid (140 mg, 0.55 mmol) in dry DMF (4 mL) was added DIPEA (0.20 mL, 1.1 mmol), HOBt (45 mg, 0.33 mmol) and EDC (127 mg, 0.66 mmol). The reaction mixture was stirred at room temperature for 5 minutes and tert-butyl (((3S,5S)-5-(aminomethyl)-1-benzylpyrrolidin-3-yl)methyl)carbamate (intermediate K) (175 mg, 0.55 mmol) was added. The reaction was stirred at room temperature overnight. It was then diluted with EtOAc and washed with water and brine. The organic layer was dried over anhydrous sodium sulfate and filtered. The filtrate was concentrated and purified on silica gel to give the product (173 mg, 57% yield) as an off white solid. $^1$H NMR (300 MHz, CDCl$_3$) δ 7.96-7.84 (m, 1H), 7.58 (m, 5H), 7.29 (M, 5H), 7.12 (m, 2H), 5.10 (m, 1H), 4.08 (m, 1H), 3.84 (m, 1H), 3.49 (m, 1H), 3.31 (d, J=11.1 Hz, 1H), 3.08 (m, 2H), 2.77 (m, 2H), 2.42-2.15 (m, 3H), 1.36 (s, 9H).

Example 23. Preparation of (S)-5-bromo-N-(2,5-diaminopentyl)-1H-benzo[d]imidazole-2-carboxamide Hydrogen Chloride Salt

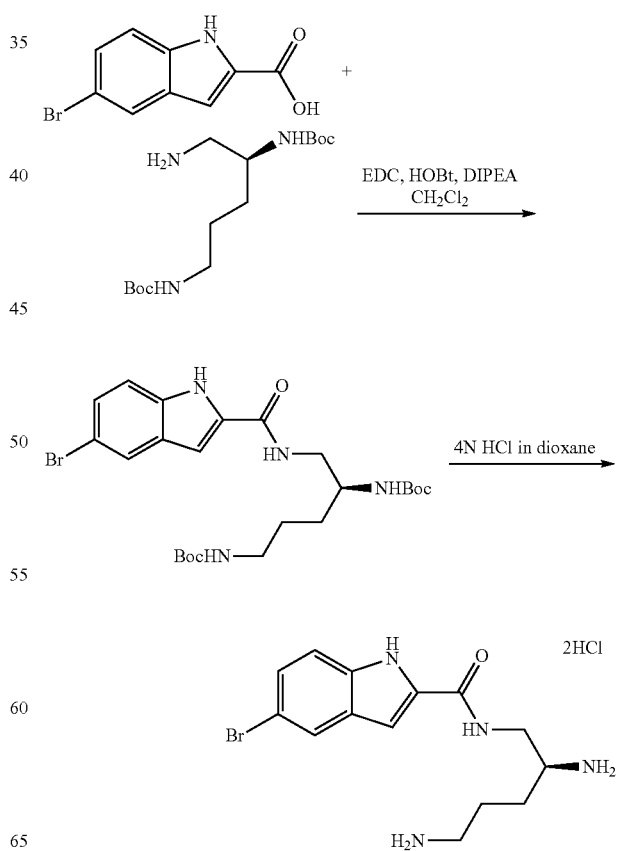

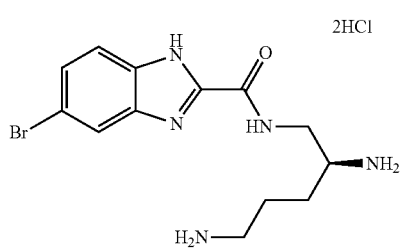 [SMILES: NCCC[C@H](N)CNC(=O)c1nc2cc(Br)ccc2[nH]1]

(S)-5-Bromo-N-(2,5-diaminopentyl)-1H-benzo[d]imidazole-2-carboxamide Hydrogen Chloride Salt To a solution of di-tert-butyl (5-(5-bromo-1H-benzo[d]imidazole-2-carboxamido)-pentane-1,4-diyl)(S)-dicarbamate (22 mg, 0.05 mmol) in MeOH (1 mL) was added HCl (0.30 mL, 4 M in dioxane). The reaction mixture was stirred at room temperature overnight. TLC showed no starting material left. The solution was concentrated and triturated with EtOAc to afford product (17 mg, 100% yield) as a white solid. $^1$H NMR (300 MHz, DMSO-$d_6$) 9.17 (br., 1H), 8.14 (br., 3H), 8.01 (br., 3H), 7.81 (s, 1H), 7.59 (d, J=8.4 Hz, 1H), 7.44 (d, J=8.4 Hz, 1H), 3.53 (m, 2H), 3.35 (m, 1H), 2.80-2.77 (m, 2H), 1.66 (m, 4H).

The requisite intermediate was prepared as follows:

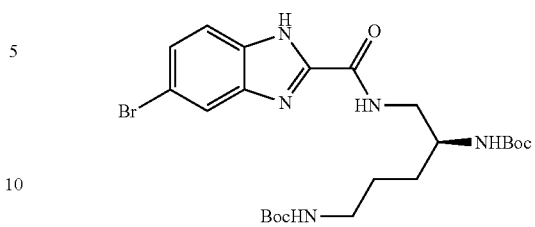

Di-tert-butyl (5-(5-bromo-1H-benzo[d]imidazole-2-carboxamido)pentane-1,4-diyl)(S)-dicarbamate To a solution of 5-bromo-1H-benzo[d]imidazole-2-carboxylic acid (120 mg, 0.5 mmol) in dry dichloromethane (6 mL) was added DIPEA (0.17 mL, 1.0 mmol), HOBt (37 mg, 0.27 mmol) and EDC (104 mg, 0.55 mmol). The reaction mixture was stirred at room temperature and a solution of di-tert-butyl (5-aminopentane-1,4-diyl)(S)-dicarbamate (intermediate B) (143 mg, 0.45 mmol) in dichloromethane (2 mL) was added. The reaction mixture was stirred at room temperature overnight. The reaction mixture was concentrated under reduced pressure and purified by column chromatography on silica gel to give the product (123 mg, 50% yield) as a white solid. 1H NMR (300 MHz, CDCl$_3$) 7.91 (s, 1H), 7.68-7.60 (m, 1H), 7.41-7.32 (m, 1H), 4.81 (br, 1H), 4.69 (br, 1H), 3.86 (m, 1H), 3.58 (m, 2H), 3.15 (m, 2H), 1.58-1.48 (m, 4H), 1.41 (s, 9H), 1.37 (s, 9H).

Example 24. Preparation of (S)—N-(2,5-diaminopentyl)-1-(4-fluorobenzyl)-6-(4-fluorophenyl)-1H-benzo[d]imidazole-2-carboxamide and (S)—N-(2,5-diaminopentyl)-1-(4-fluorobenzyl)-5-(4-fluorophenyl)-1H-benzo[d]imidazole-2-carboxamide Hydrogen Chloride Salt

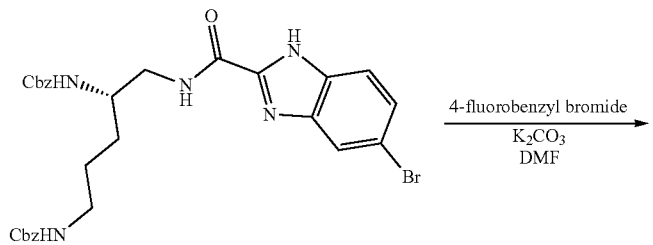

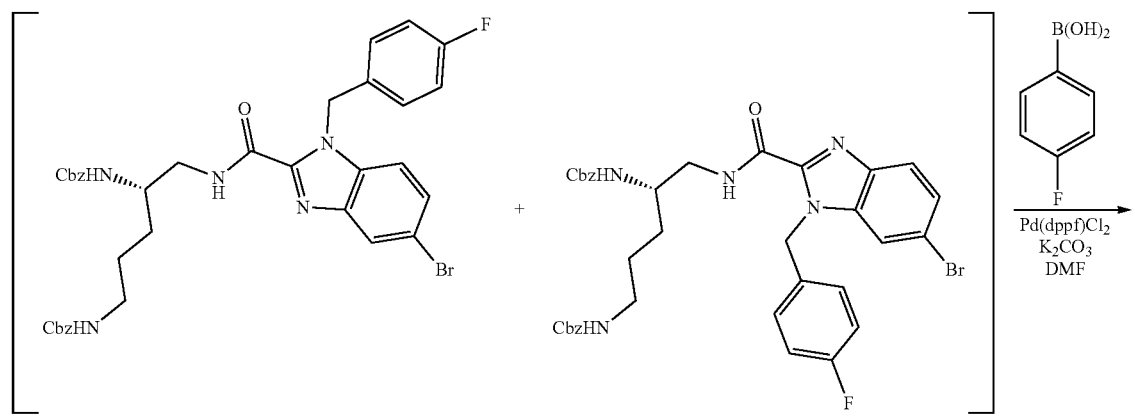

-continued

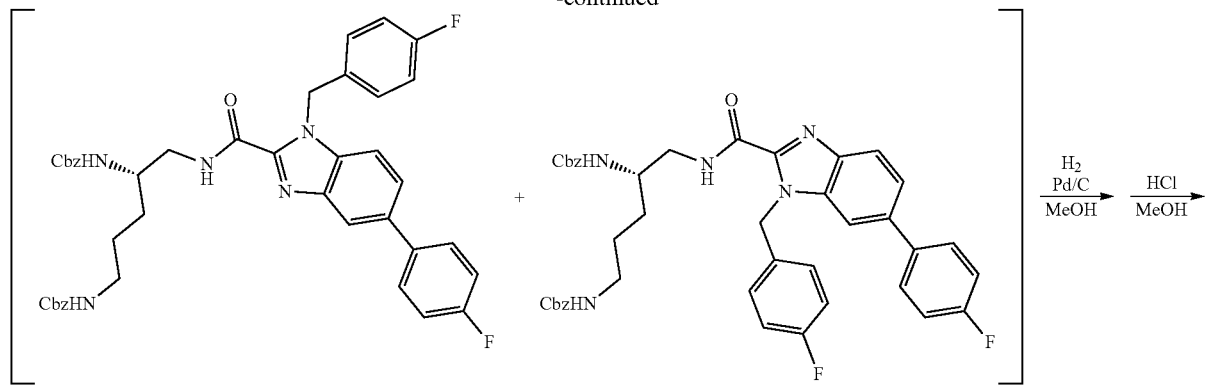

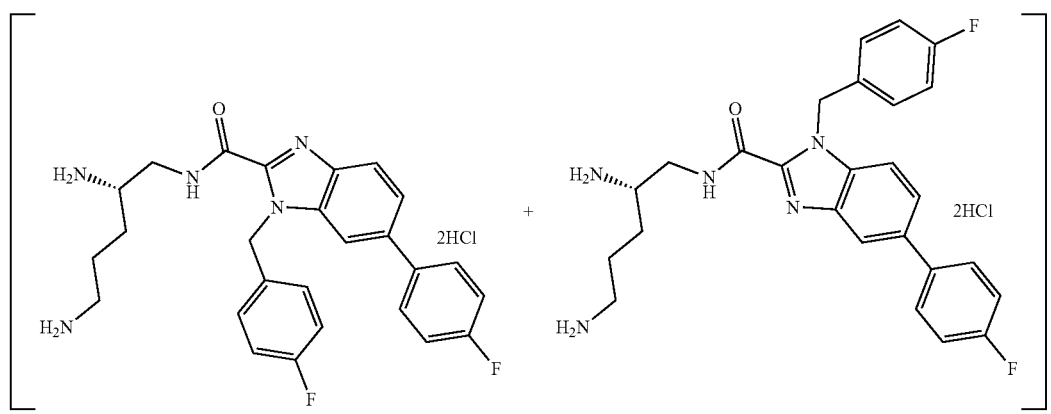

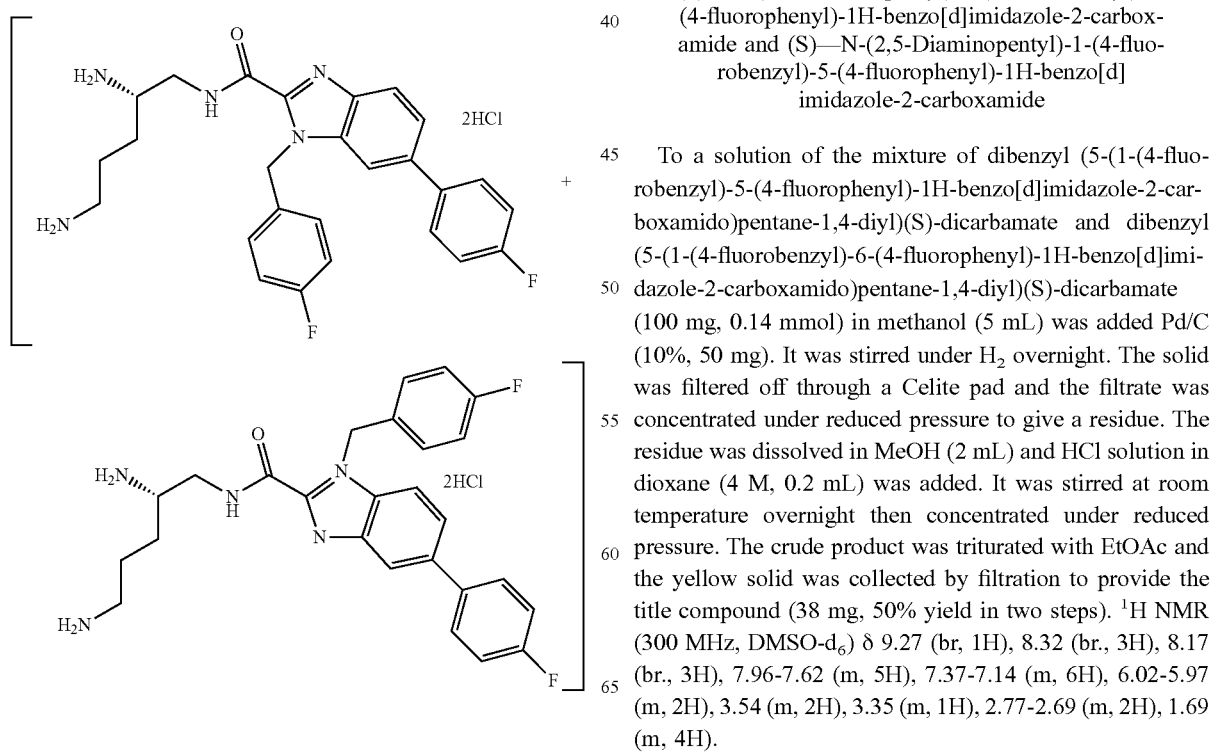

(S)—N-(2,5-Diaminopentyl)-1-(4-fluorobenzyl)-6-(4-fluorophenyl)-1H-benzo[d]imidazole-2-carboxamide and (S)—N-(2,5-Diaminopentyl)-1-(4-fluorobenzyl)-5-(4-fluorophenyl)-1H-benzo[d]imidazole-2-carboxamide To a solution of the mixture of dibenzyl (5-(1-(4-fluorobenzyl)-5-(4-fluorophenyl)-1H-benzo[d]imidazole-2-carboxamido)pentane-1,4-diyl)(S)-dicarbamate and dibenzyl (5-(1-(4-fluorobenzyl)-6-(4-fluorophenyl)-1H-benzo[d]imidazole-2-carboxamido)pentane-1,4-diyl)(S)-dicarbamate (100 mg, 0.14 mmol) in methanol (5 mL) was added Pd/C (10%, 50 mg). It was stirred under $H_2$ overnight. The solid was filtered off through a Celite pad and the filtrate was concentrated under reduced pressure to give a residue. The residue was dissolved in MeOH (2 mL) and HCl solution in dioxane (4 M, 0.2 mL) was added. It was stirred at room temperature overnight then concentrated under reduced pressure. The crude product was triturated with EtOAc and the yellow solid was collected by filtration to provide the title compound (38 mg, 50% yield in two steps). $^1$H NMR (300 MHz, DMSO-$d_6$) δ 9.27 (br, 1H), 8.32 (br., 3H), 8.17 (br., 3H), 7.96-7.62 (m, 5H), 7.37-7.14 (m, 6H), 6.02-5.97 (m, 2H), 3.54 (m, 2H), 3.35 (m, 1H), 2.77-2.69 (m, 2H), 1.69 (m, 4H).

The requisite intermediates were prepared as follows:

Step 1

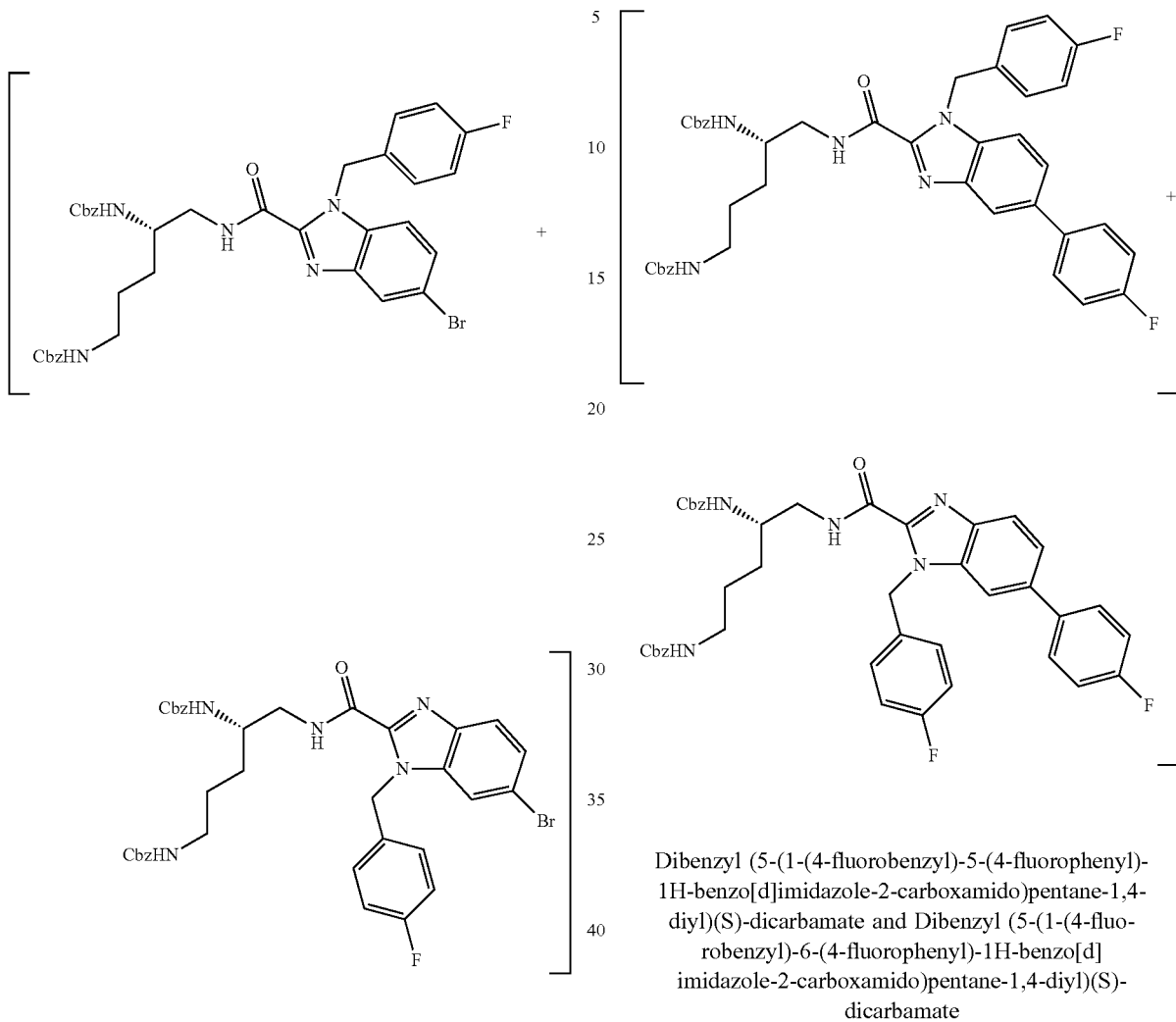

Step 2

Dibenzyl (5-(1-(4-fluorobenzyl)-5-(4-fluorophenyl)-1H-benzo[d]imidazole-2-carboxamido)pentane-1,4-diyl)(S)-dicarbamate and Dibenzyl (5-(1-(4-fluorobenzyl)-6-(4-fluorophenyl)-1H-benzo[d]imidazole-2-carboxamido)pentane-1,4-diyl)(S)-dicarbamate Dibenzyl (5-(5-bromo-1-(4-fluorobenzyl)-1H-benzo[d]imidazole-2-carboxamido)pentane-1,4-diyl)(S)-dicarbamate and Dibenzyl (5-(6-bromo-1-(4-fluorobenzyl)-1H-benzo[d]imidazole-2-carboxamido)pentane-1,4-diyl)(S)-dicarbamate To a solution of dibenzyl (5-(5-bromo-1H-benzo[d]imidazole-2-carboxamido)pentane-1,4-diyl)(S)-dicarbamate (150 mg, 0.25 mmol) in dry DMF (4 mL) was added 4-fluorobenzyl bromide (0.07 mL, 0.53 mmol), and $K_2CO_3$ (106 mg, 0.77 mmol). The reaction mixture was stirred at room temperature overnight. It was then diluted with EtOAc and washed with water and brine. The organic layer was dried over anhydrous sodium sulfate and filtered. The filtrate was concentrated and purified on silica gel to give the product (140 mg, 78% yield) as a yellow solid. $^1$H NMR (300 MHz, CDCl$_3$) δ 8.11 (br., 1H), 7.88 (m, 1H), 7.62-6.89 (m, 16H), 5.84-5.72 (m, 2H), 5.05 (m, 4H), 3.88 (m, 1H), 3.52-3.50 (m, 2H), 3.20-3.19 (m, 2H), 1.59 (m, 4H).

Dibenzyl (5-(5-bromo-1-(4-fluorobenzyl)-1H-benzo[d]imidazole-2-carboxamido)-pentane-1,4-diyl)(S)-dicarbamate and dibenzyl (5-(6-bromo-1-(4-fluorobenzyl)-1H-benzo[d]imidazole-2-carboxamido)pentane-1,4-diyl)(S)-dicarbamate (140 mg, 0.20 mmol), 4-fluorophenyl boronic acid (70 mg, 0.50 mmol), Pd(dppf)Cl$_2$ (15 mg, 0.02 mmol) and potassium carbonate (30 mg, 0.22 mmol) were dissolved in a mixture of dioxane (8 mL) and water (2 mL). The mixture was purged with nitrogen, and it was refluxed overnight. The reaction mixture was then diluted with EtOAc and washed with water and brine. The organic layer was dried over anhydrous sodium sulfate and filtered. The filtrate was concentrated and purified on silica gel to give the product (100 mg, 68% yield) as a yellow solid. $^1$H NMR (300 MHz, CDCl$_3$) δ 8.16 (br., 1H), 7.90-7.80 (m, 1H), 7.59-7.12 (m, 18H), 6.99-6.93 (m, 2H), 5.89-5.83 (m, 2H), 5.09 (m, 4H), 3.89 (m, 1H), 3.54 (m, 2H), 3.21-3.20 (m, 2H), 1.59 (m, 4H).

149

Example 25. Preparation of (S)-6-(4-aminophenyl)-N-(2,5-diaminopentyl)-1H-benzo[d]imidazole-2-carboxamide Hydrogen Chloride Salt

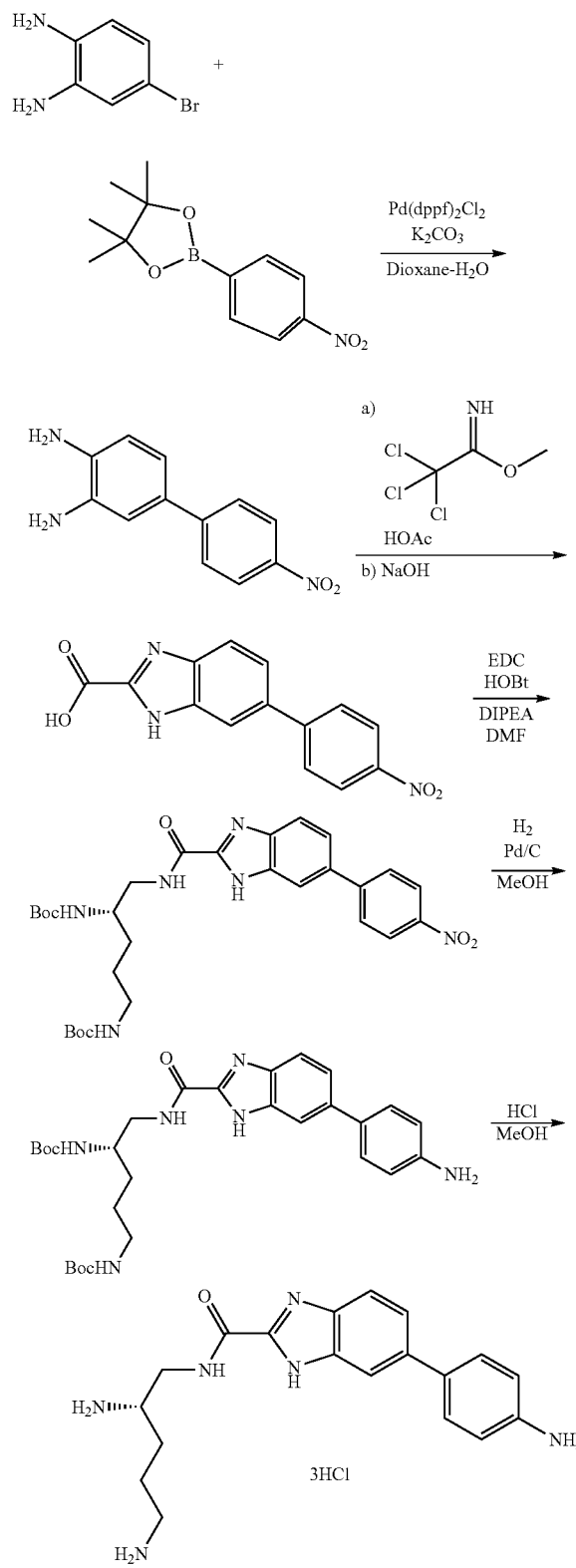

150

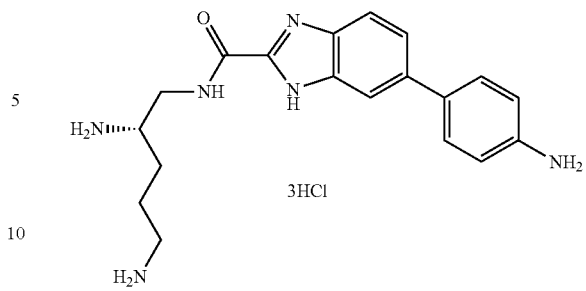

(S)-6-(4-Aminophenyl)-N-(2,5-diaminopentyl)-1H-benzo[d]imidazole-2-carboxamide Hydrogen Chloride Salt To a solution of (S)-di-tert-butyl (5-(6-(4-aminophenyl)-1H-benzo[d]imidazole-2-carboxamido)pentane-1,4-diyl)dicarbamate (15 mg, 0.029 mmol) in MeOH (1 mL) was added HCl (0.10 mL, 4M in dioxane). The reaction mixture was stirred at room temperature overnight. TLC showed no starting material left. The solution was concentrated and triturated with EtOAc to afford product (10 mg, 75% yield) as an off-white solid. $^1$H NMR (300 MHz, D$_2$O) δ 7.80 (s, 1H), 7.67 (m, 2H), 7.60 (m, 2H), 7.33 (m, 2H), 3.65 (m, 1H), 3.53 (m, 1H), 3.48 (m, 1H), 2.88 (m, 2H), 1.68 (m, 4H). The requisite intermediates were prepared as follows:

Step 1

4'-Nitro-[1,1'-biphenyl]-3,4-diamine

A mixture of 2-amino-4-bromoaniline (0.50 g, 3 mmol), (4-nitrophenyl)boronic acid (0.57 g, 3 mmol) and K$_2$CO$_3$ (2 M in water, 4.5 mL) in dioxane (9 mL) was degassed and Pd(dppf)Cl$_2$ (120 mg, 0.15 mmol) was added. The reaction mixture was stirred at 100° C. for 3 hours. It was extracted with EtOAc and washed with water and brine. After concentration under reduced pressure, the residue was purified by column chromatography on silica gel to afford the product as a brown powder (0.335 g, 49% yield).

Step 2

5-(4-Nitrophenyl)-1H-benzo[d]imidazole-2-carboxylic Acid

To a solution of 4'-nitro-[1,1'-biphenyl]-3,4-diamine (0.095 g, 0.41 mmol) in acetic acid (1 mL) was added methyl 2,2,2-trichloroacetimidate (0.062 mL, 0.5 mmol). It was stirred at room temperature overnight. TLC showed no starting material left. Ice was added and the precipitate was filtered and washed with water to provide the crude product. To the crude ester in THF (2 mL) was added NaOH solution (1.2 M, 1 mL). The reaction mixture was stirred at room temperature overnight. TLC showed no starting material left. The reaction mixture was then concentrated under reduced pressure and made acidic. The resulting precipitate was filtered and washed with water to give product (105 mg, 90% yield for two steps) as a pale brown solid after dried under reduced pressure. It was used for next step reaction without purification.

Step 3

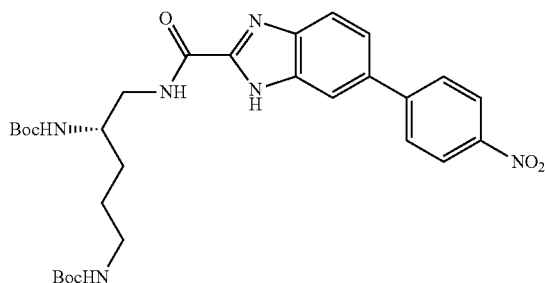 [SMILES: CC(C)(C)OC(=O)NCCC[C@@H](CNC(=O)c1nc2ccc(-c3ccc([N+](=O)[O-])cc3)cc2[nH]1)NC(=O)OC(C)(C)C]

(S)-Di-tert-butyl (5-(6-(4-nitrophenyl)-1H-benzo[d]imidazole-2-carboxamido)pentane-1,4-diyl)dicarbamate To a solution of 5-(4-nitrophenyl)-1H-benzo[d]imidazole-2-carboxylic acid (155 mg, 0.55 mmol) in dry DMF (3 mL) was added DIPEA (0.193 mL, 1.1 mmol), HOBt (105 mg, 0.67 mmol) and EDC (250 mg, 1.3 mmol). The reaction mixture was stirred at room temperature and di-tert-butyl (5-aminopentane-1,4-diyl)(S)-dicarbamate (intermediate B) (174 mg, 0.55 mmol) was added. The reaction mixture was stirred at room temperature overnight. The reaction mixture was concentrated under reduced pressure and the residue purified by column chromatography on silica gel to give the product (170 mg, 53% yield) as a yellow solid. $^1$H NMR (300 MHz, CDCl$_3$) δ 8.31 (d, J=8.1 Hz, 2H), 8.01 (m, 2H), 7.77 (d, J=8.1 Hz, 2H), 7.64 (s, 1H), 6.28 (br, 1H), 4.82 (br, 1H), 4.70 (br, 1H), 3.87 (m, 1H), 3.67 (m, 2H), 3.15 (m, 2H), 1.65 (m, 4H), 1.27 (s, 9H), 1.25 (s, 9H).

Step 4

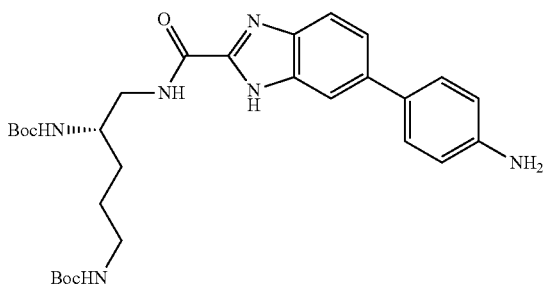

(S)-Di-tert-butyl (5-(6-(4-aminophenyl)-1H-benzo[d]imidazole-2-carboxamido)pentane-1,4-diyl)dicarbamate (S)-Di-tert-butyl (5-(6-(4-nitrophenyl)-1H-benzo[d]imidazole-2-carboxamido)pentane-1,4-diyl)dicarbamate (55 mg, 0.094 mmol) was dissolved in methanol and EtOAc (5 mL/5 mL) then Pd/C (10%, 30 mg) was added and stirred under H$_2$ overnight. The reaction mixture was filtered through a pad of Celite and washed with EtOAc. After concentration under reduced pressure, the residue was purified by column chromatography on silica gel to give the product (35 mg, 67% yield) as a white powder. $^1$H NMR (300 MHz, CDCl$_3$) δ 8.59 (br, 1H), 7.68 (m, 2H), 7.56 (s, 1H), 7.46 (d, J=8.1 Hz, 2H), 6.78 (d, J=8.1 Hz, 2H), 5.04 (br, 1H), 4.75 (br, 1H), 3.87 (m, 1H), 3.61 (m, 2H), 3.15 (m, 2H), 1.62 (m, 4H), 1.42 (s, 9H), 1.38 (s, 9H).

Example 26. Preparation of (S)—N-(2,5-diaminopentyl)-1-(2-fluoro-5-nitrobenzyl)-5-(4-nitrophenyl)-1H-benzo[d]imidazole-2-carboxamide and (S)—N-(2,5-diaminopentyl)-1-(2-fluoro-5-nitrobenzyl)-6-(4-nitrophenyl)-1H-benzo[d]imidazole-2-carboxamide Trifluoroacetic Acid Salt

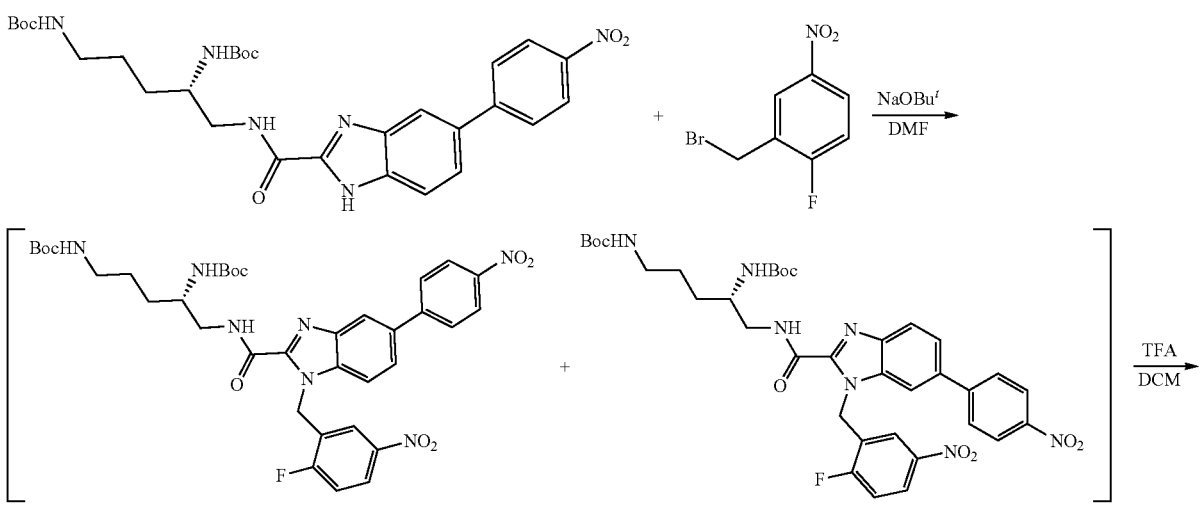

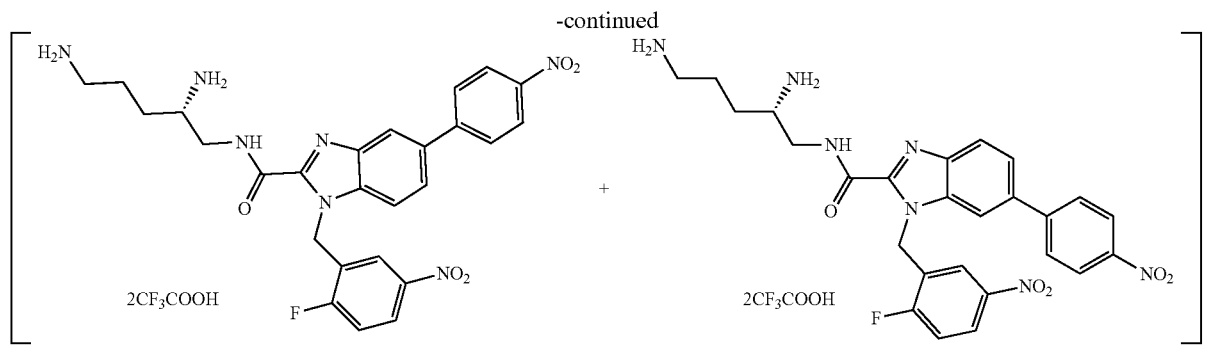

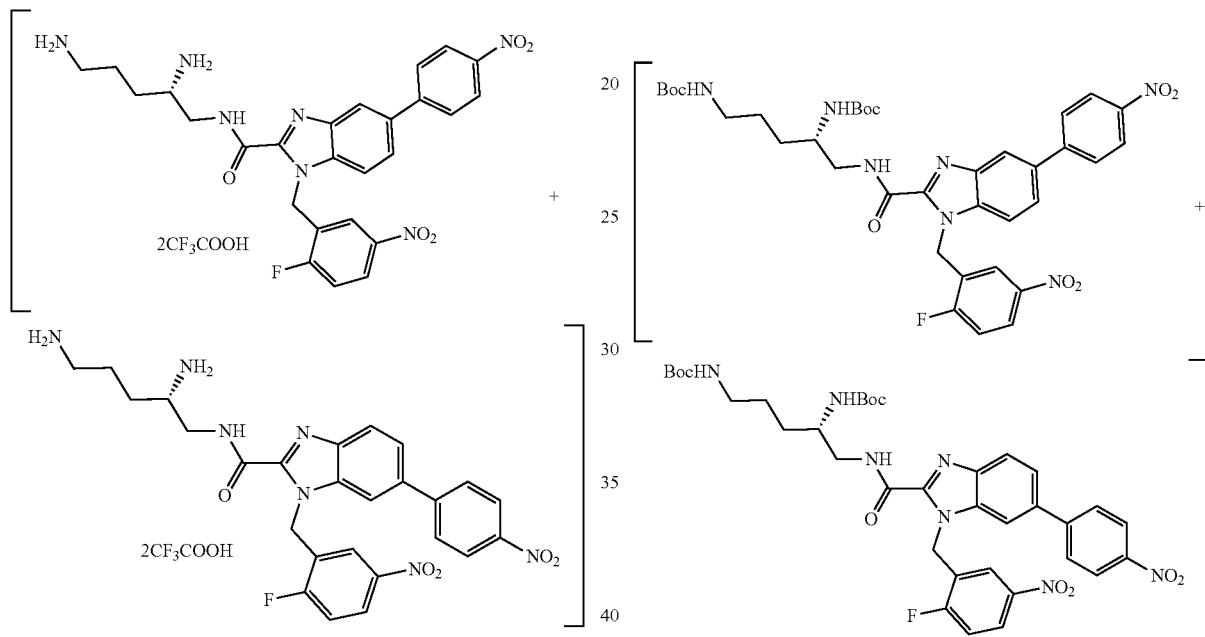

(S)—N-(2,5-Diaminopentyl)-1-(2-fluoro-5-nitrobenzyl)-5-(4-nitrophenyl)-1H-benzo[d]imidazole-2-carboxamide and (S)—N-(2,5-Diaminopentyl)-1-(2-fluoro-5-nitrobenzyl)-6-(4-nitrophenyl)-1H-benzo[d]imidazole-2-carboxamide Trifluoroacetic Acid Salt To a solution of the mixture of (S)-di-tert-butyl (5-(1-(2-fluoro-5-nitrobenzyl)-5-(4-nitrophenyl)-1H-benzo[d]imidazole-2-carboxamido)pentane-1,4-diyl)dicarbamate and (S)-di-tert-butyl (5-(1-(2-fluoro-5-nitrobenzyl)-6-(4-nitrophenyl)-1H-benzo[d]imidazole-2-carboxamido)pentane-1,4-diyl)dicarbamate (9 mg, 0.012 mmol) in methylene chloride (1 mL) was added TFA (0.5 mL) and it was stirred at room temperature then concentrated under reduced pressure. The crude product was triturated with EtOAc and the yellow solid was collected to provide the title compound (6 mg, 64% yield). $^1$H NMR (300 MHz, D$_2$O) δ 8.25 (m, 1H), 8.02 (m, 2H), 7.87 (m, 2H), 7.59 (m, 3H), 7.40 (m, 2H), 5.88 (m, 2H), 3.73 (m, 1H), 3.64 (m, 2H), 3.07 (m, 2H), 1.85 (m, 4H).

The requisite intermediates were prepared as follows:

(S)-Di-tert-butyl (5-(1-(2-fluoro-5-nitrobenzyl)-5-(4-nitrophenyl)-1H-benzo[d]imidazole-2-carboxamido)pentane-1,4-diyl)dicarbamate and (S)-Di-tert-butyl (5-(1-(2-fluoro-5-nitrobenzyl)-6-(4-nitrophenyl)-1H-benzo[d]imidazole-2-carboxamido)pentane-1,4-diyl) dicarbamate To a solution of (S)-di-tert-butyl (5-(5-(4-nitrophenyl)-1H-benzo[d]imidazole-2-carboxamido)pentane-1,4-diyl)dicarbamate (13 mg, 0.023 mmol) in dry DMF (0.2 mL) was added 2-(bromomethyl)-1-fluoro-4-nitrobenzene (7.5 mg, 0.032 mmol), and NaOBu$^t$ (4 mg, 0.042 mmol). The reaction mixture was stirred at room temperature overnight. It was then diluted with EtOAc and washed with water and brine. The organic layer was dried over anhydrous sodium sulfate and filtered. The filtrate was concentrated and purified on silica gel to give the product (9 mg, 78% yield) as a yellow solid. $^1$H NMR (300 MHz, CDCl$_3$) δ 8.38 (m, 2H), 8.24 (m, 2H), 8.02 (m, 1H), 7.84 (m, 3H), 7.69 (m, 1H), 7.16 (m, 1H), 6.19 (m, 2H), 4.71 (br, 2H), 3.91 (m, 1H), 3.65 (m, 1H), 3.55 (m, 1H), 3.21 (m, 2H), 1.65 (m, 4H), 1.47 (s, 9H), 1.42 (s, 9H).

Example 27. Preparation of (S)—N-(2,5-diaminopentyl)-1-(2-fluoro-5-nitrobenzyl)-5-(4-fluorophenyl)-1H-benzo[d]imidazole-2-carboxamide and (S)—N-(2,5-diaminopentyl)-1-(2-fluoro-5-nitrobenzyl)-6-(4-fluorophenyl)-1H-benzo[d]imidazole-2-carboxamide Trifluoroacetic Acid Salt

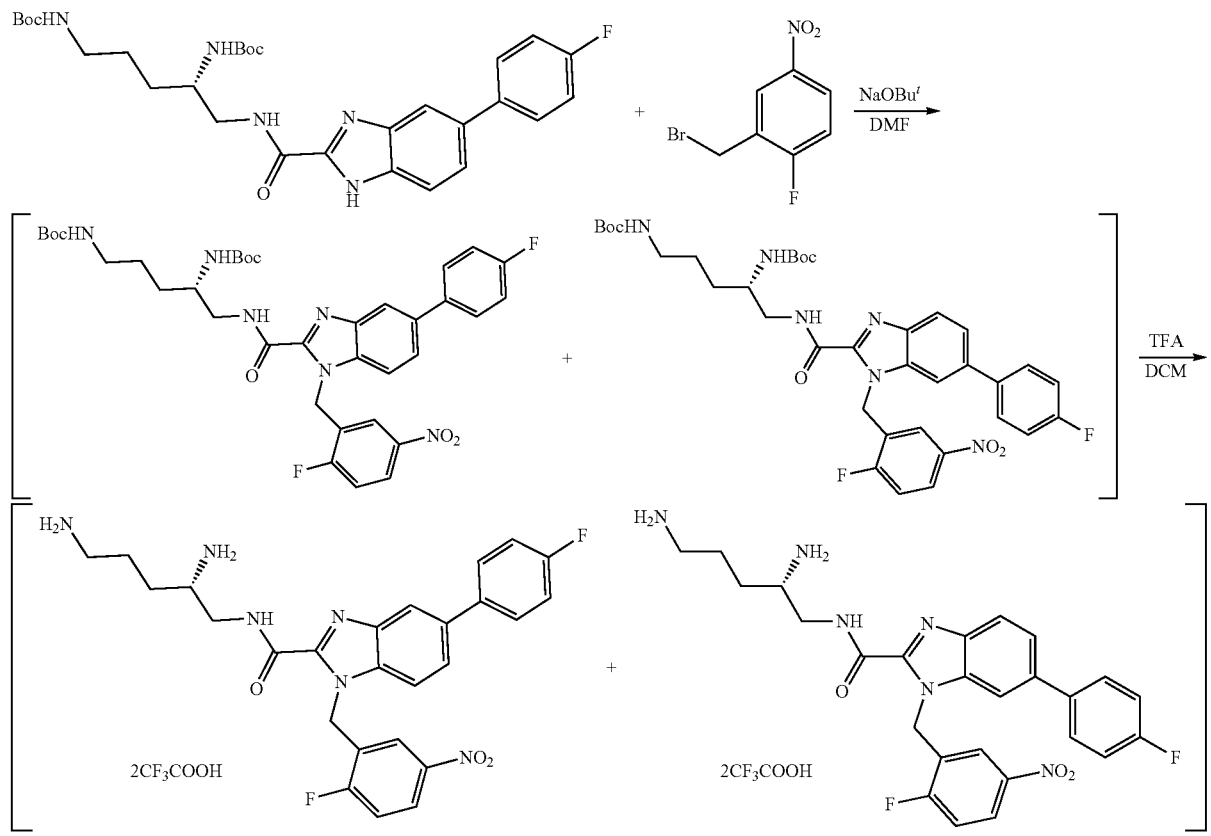

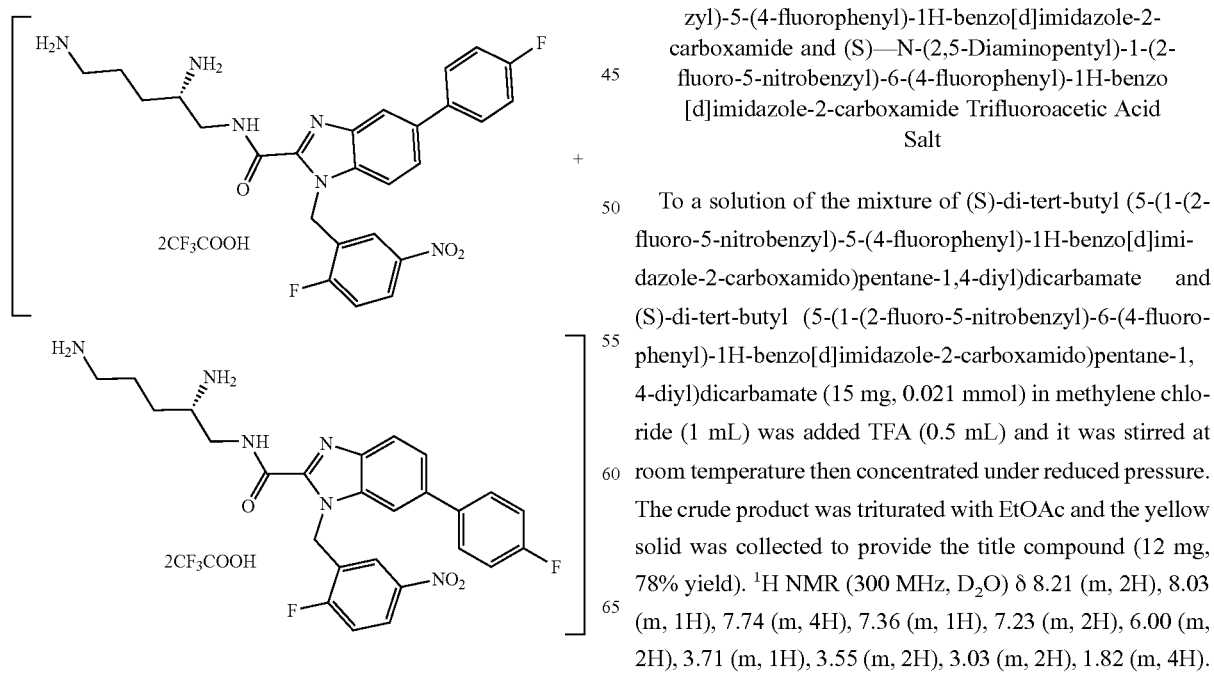

(S)—N-(2,5-Diaminopentyl)-1-(2-fluoro-5-nitrobenzyl)-5-(4-fluorophenyl)-1H-benzo[d]imidazole-2-carboxamide and (S)—N-(2,5-Diaminopentyl)-1-(2-fluoro-5-nitrobenzyl)-6-(4-fluorophenyl)-1H-benzo[d]imidazole-2-carboxamide Trifluoroacetic Acid Salt To a solution of the mixture of (S)-di-tert-butyl (5-(1-(2-fluoro-5-nitrobenzyl)-5-(4-fluorophenyl)-1H-benzo[d]imidazole-2-carboxamido)pentane-1,4-diyl)dicarbamate and (S)-di-tert-butyl (5-(1-(2-fluoro-5-nitrobenzyl)-6-(4-fluorophenyl)-1H-benzo[d]imidazole-2-carboxamido)pentane-1,4-diyl)dicarbamate (15 mg, 0.021 mmol) in methylene chloride (1 mL) was added TFA (0.5 mL) and it was stirred at room temperature then concentrated under reduced pressure. The crude product was triturated with EtOAc and the yellow solid was collected to provide the title compound (12 mg, 78% yield). $^1$H NMR (300 MHz, D$_2$O) δ 8.21 (m, 2H), 8.03 (m, 1H), 7.74 (m, 4H), 7.36 (m, 1H), 7.23 (m, 2H), 6.00 (m, 2H), 3.71 (m, 1H), 3.55 (m, 2H), 3.03 (m, 2H), 1.82 (m, 4H).

The requisite intermediates were prepared as follows:

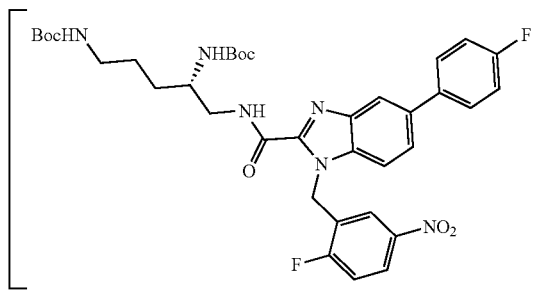

+

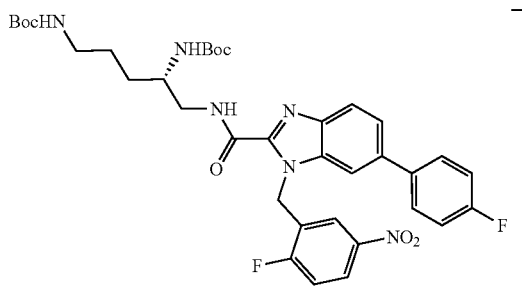

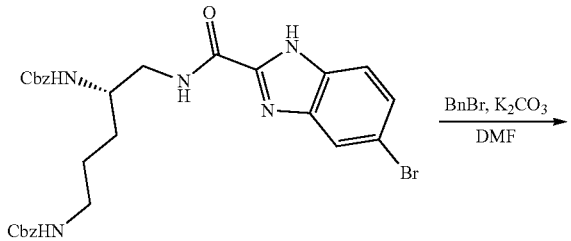

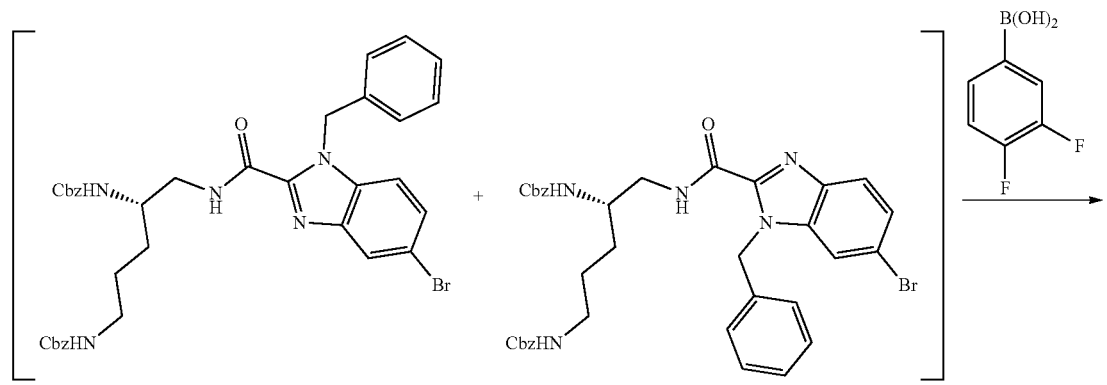

(S)-Di-tert-butyl (5-(1-(2-fluoro-5-nitrobenzyl)-5-(4-fluorophenyl)-1H-benzo[d]imidazole-2-carboxamido)pentane-1,4-diyl)dicarbamate and (S)-Di-tert-butyl (5-(1-(2-fluoro-5-nitrobenzyl)-6-(4-fluorophenyl)-1H-benzo[d]imidazole-2-carboxamido)pentane-1,4-diyl)dicarbamate To a solution of (S)-di-tert-butyl (5-(5-(4-fluorophenyl)-1H-benzo[d]imidazole-2-carboxamido)pentane-1,4-diyl)dicarbamate (25 mg, 0.045 mmol) in dry DMF (0.5 mL) was added 2-(bromomethyl)-1-fluoro-4-nitrobenzene (21 mg, 0.090 mmol), and NaOBu$^t$ (6.5 mg, 0.067 mmol). The reaction mixture was stirred at room temperature. It was then diluted with EtOAc and washed with water and brine. The organic layer was dried over anhydrous sodium sulfate and filtered. The filtrate was concentrated and purified on silica gel to give the product (15 mg, 47% yield) as a yellow solid. $^1$H NMR (300 MHz, CDCl$_3$) δ 8.20 (m, 2H), 7.97 (m, 1H), 7.84 (m, 1H), 7.57 (m, 2H), 7.47 (m, 1H), 7.26 (m, 1H), 7.16 (m, 2H), 6.12 (s, 2H), 4.68 (br, 1H), 4.64 (br, 1H), 3.86 (m, 1H), 3.56 (m, 1H), 3.51 (m, 1H), 3.13 (m, 2H), 1.65 (m, 4H), 1.46 (s, 9H), 1.43 (s, 9H).

Example 28. Preparation of (S)-1-benzyl-N-(2,5-diaminopentyl)-6-(3,4-difluorophenyl)-1H-benzo[d]imidazole-2-carboxamide and (S)-1-benzyl-N-(2,5-diaminopentyl)-5-(3,4-difluorophenyl)-1H-benzo[d]imidazole-2-carboxamide Hydrogen Chloride Salts

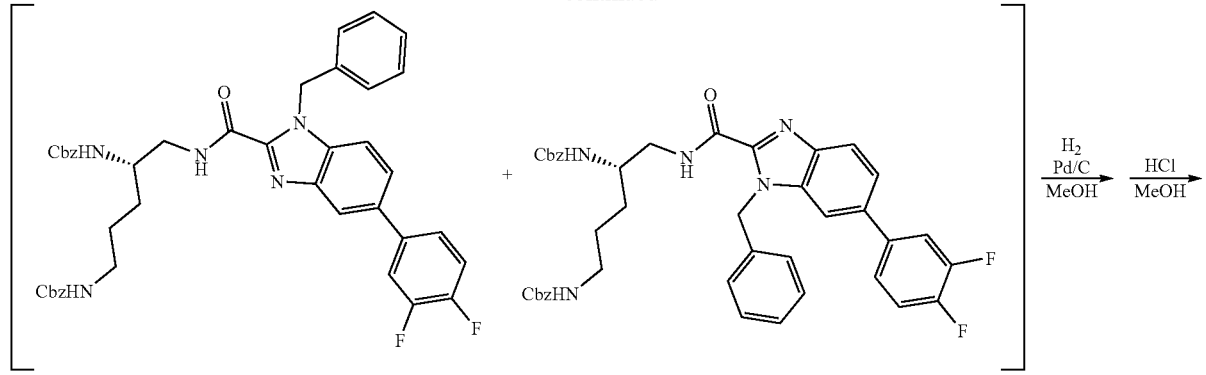

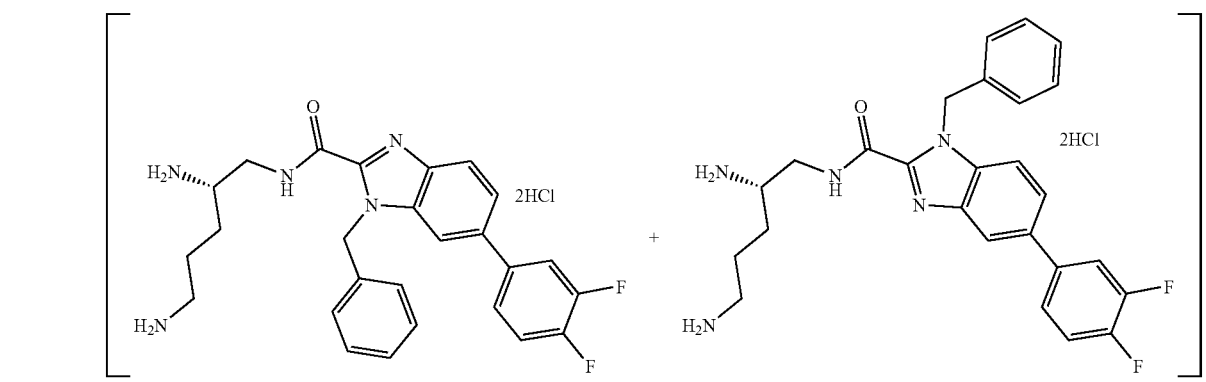

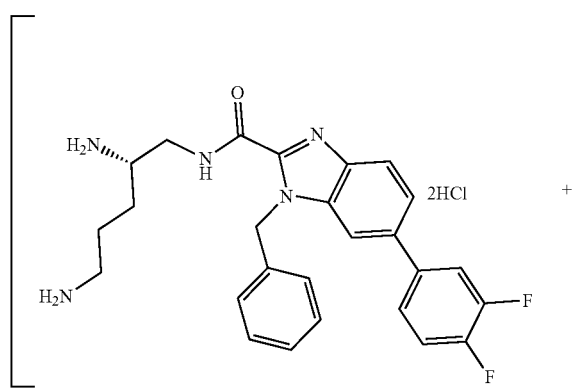

(S)-1-Benzyl-N-(2,5-diaminopentyl)-6-(3,4-difluorophenyl)-1H-benzo[d]imidazole-2-carboxamide and (S)-1-Benzyl-N-(2,5-diaminopentyl)-5-(3,4-difluorophenyl)-1H-benzo[d]imidazole-2-carboxamide Hydrogen Chloride Salts To a solution of the mixture of dibenzyl (5-(1-benzyl-5-(3,4-difluorophenyl)-1H-benzo[d]imidazole-2-carboxamido)pentane-1,4-diyl)(S)-dicarbamate and dibenzyl (5-(1-benzyl-6-(3,4-difluorophenyl)-1H-benzo[d]imidazole-2-carboxamido)pentane-1,4-diyl)(S)-dicarbamate (64 mg, 0.09 mmol) in methanol (20 mL) was added Pd/C (10%, 40 mg). The reaction mixture was stirred under H₂. The solid was filtered off through a Celite pad and the filtrate was concentrated under reduced pressure to give a residue. The residue was dissolved in MeOH (2 mL) and HCl solution in dioxane (4 M, 0.2 mL) was added. The mixture was stirred at room temperature for 30 min then concentrated under reduced pressure. The crude product was triturated with EtOAc and the yellow solid was collected by filtration to provide the title compound (28 mg, 60% yield in two steps).

The requisite intermediates were prepared as follows:

Step 1

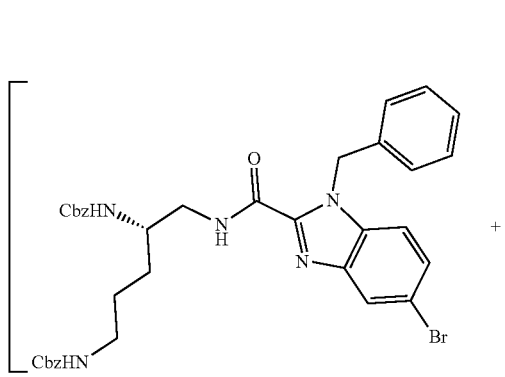

+

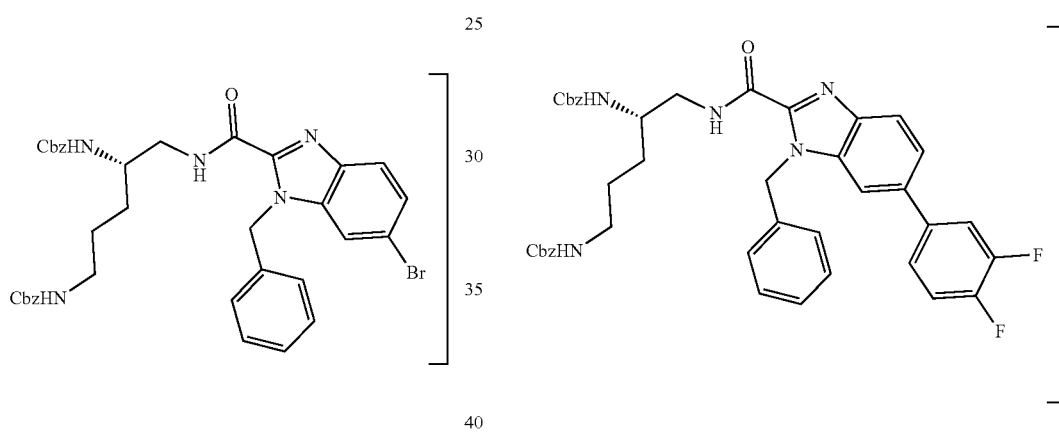

Dibenzyl (5-(1-benzyl-5-bromo-1H-benzo[d]imidazole-2-carboxamido)pentane-1,4-diyl)(S)-dicarbamate and Dibenzyl (5-(1-benzyl-6-bromo-1H-benzo[d]imidazole-2-carboxamido)pentane-1,4-diyl)(S)-dicarbamate To a solution of dibenzyl (5-(5-bromo-1H-benzo[d]imidazole-2-carboxamido)pentane-1,4-diyl)(S)-dicarbamate (196 mg, 0.34 mmol) in dry DMF (2 mL) was added BnBr (88 mg, 0.51 mmol), $K_2CO_3$ (93 mg, 0.64 mmol). The reaction mixture was stirred at room temperature overnight. The reaction mixture was diluted with EtOAc and washed with water and brine. The organic layer was dried over anhydrous sodium sulfate and filtered. The filtrate was concentrated and purified using column chromatography with silica gel to give the product (220 mg, 92% yield) as a white solid. $^1$H NMR (300 MHz, $CDCl_3$) δ 8.03 (br, 1H), 7.63-7.40 (m, 2H), 7.36-7.20 (m, 15H), 7.11 (m, 1H), 5.84 (m, 2H), 5.08 (m, 2H), 5.06 (s, 2H), 3.87 (m, 1H), 3.53 (m, 1H), 3.20 (m, 2H), 1.58 (m, 4H).

Step 2

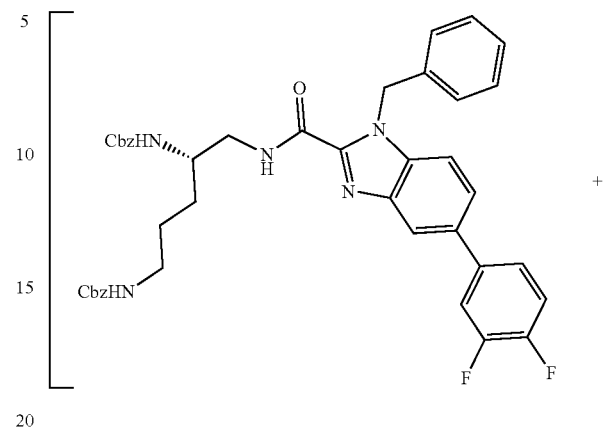

Dibenzyl (5-(1-benzyl-5-(3,4-difluorophenyl)-1H-benzo[d]imidazole-2-carboxamido)pentane-1,4-diyl) (S)-dicarbamate and Dibenzyl (5-(1-benzyl-6-(3,4-difluorophenyl)-1H-benzo[d]imidazole-2-carboxamido)pentane-1,4-diyl)(S)-dicarbamate A mixture of dibenzyl (5-(1-benzyl-5-bromo-1H-benzo[d]imidazole-2-carboxamido)pentane-1,4-diyl)(S)-dicarbamate and dibenzyl (5-(1-benzyl-6-bromo-1H-benzo[d]imidazole-2-carboxamido)pentane-1,4-diyl)(S)-dicarbamate (70 mg, 0.1 mmol), (3,4-difluorophenyl) boronic acid (32 mg, 0.2 mmol) and $K_2CO_3$ (52 mg, 0.3 mmol) in dioxane (15 mL) and water (5 mL) was degassed and Pd(dppf)$Cl_2$ (15 mg, 0.02 mmol) was added. The reaction mixture was stirred at 90° C. for 3 hours. It was extracted with EtOAc and washed with water and brine. After concentration under reduced pressure, it was purified by column chromatography on silica gel to afford the product (64 mg, 88% yield) as a yellow solid.

Example 29. Preparation of (S)-1-benzyl-N-(2,5-di aminopentyl)-6-(4-methoxyphenyl)-1H-benzo[d] imidazole-2-carboxamide and (S)-1-benzyl-N-(2,5-diaminopentyl)-5-(4-methoxyphenyl)-1H-benzo[d] imidazole-2-carboxamide Hydrogen Chloride Salts
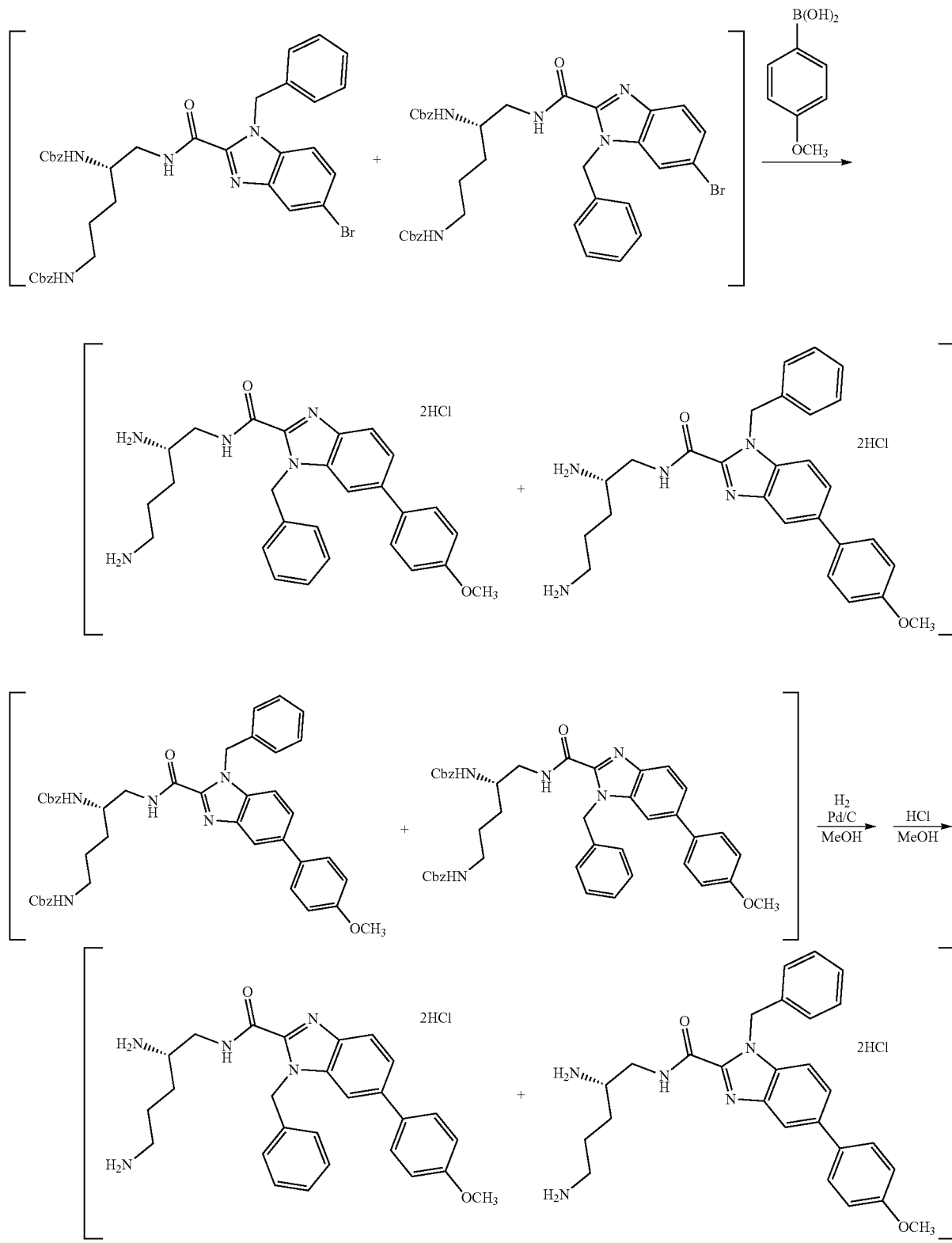

(S)-1-Benzyl-N-(2,5-diaminopentyl)-6-(4-methoxyphenyl)-1H-benzo[d]imidazole-2-carboxamide and (S)-1-Benzyl-N-(2,5-diaminopentyl)-5-(4-methoxyphenyl)-1H-benzo[d]imidazole-2-carboxamide Hydrogen Chloride Salts To a solution of the mixture of dibenzyl (5-(1-benzyl-5-(4-methoxyphenyl)-1H-benzo[d]imidazole-2-carboxamido)pentane-1,4-diyl)(S)-dicarbamate and dibenzyl (5-(1-benzyl-6-(4-methoxyphenyl)-1H-benzo[d]imidazole-2-diyl)(S)-dicarbamate (70 mg, 0.1 mmol) in methanol (20 mL) was added Pd/C (10%, 40 mg). It was stirred under H$_2$. The solid was filtered off through a Celite pad and the filtrate was concentrated under reduced pressure to give a residue. The residue was dissolved in MeOH (2 mL) and HCl solution in dioxane (4 M, 0.2 mL) was added. The reaction mixture was stirred at room temperature for 30 minutes then concentrated under reduced pressure. The crude product was triturated with EtOAc and the solid was collected by filtration to provide the title compound (22 mg, 43% yield in two steps). $^1$H NMR (300 MHz, DMSO-d$_6$) δ 8.26 (br, 2H), 8.11 (br, 2H), 7.89 (s, 1H), 7.63 (m, 1H), 7.60 (m, 3H), 7.29 (m, 5H), 7.01 (d, J=8.1 Hz, 2H), 5.99 (s, 2H), 3.78 (s, 3H), 3.54 (s, 1H), 3.39 (s, 2H), 2.78 (s, 2H), 1.67 (m, 4H).

The requisite intermediates were prepared as follows:

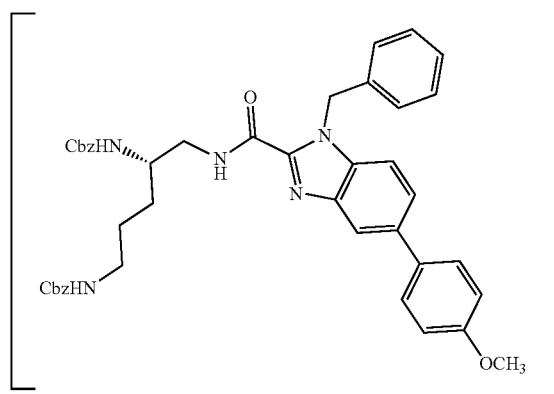

+

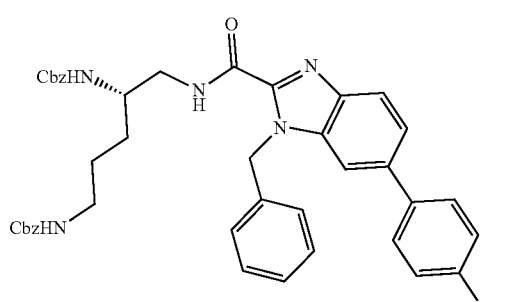

Dibenzyl (5-(1-benzyl-5-(4-methoxyphenyl)-1H-benzo[d]imidazole-2-carboxamido)pentane-1,4-diyl)(S)-dicarbamate and Dibenzyl (5-(1-benzyl-6-(4-methoxyphenyl)-1H-benzo[d]imidazole-2-carboxamido)pentane-1,4-diyl)(S)-dicarbamate A mixture of dibenzyl (5-(1-benzyl-5-bromo-1H-benzo[d]imidazole-2-carboxamido)pentane-1,4-diyl)(S)-dicarbamate and dibenzyl (5-(1-benzyl-6-bromo-1H-benzo[d]imidazole-2-carboxamido)pentane-1,4-diyl)(S)-dicarbamate (66 mg, 0.09 mmol), (4-methoxyphenyl)boronic acid (30 mg, 0.2 mmol) and K$_2$CO$_3$ (52 mg, 0.3 mmol) in dioxane (15 mL) and water (5 mL) was degassed and Pd(dppf)$_2$Cl$_2$ (15 mg, 0.02 mmol) was added. The reaction mixture was stirred at 90° C. for 3 hours. The cooled reaction mixture was extracted with EtOAc and washed with water and then brine. After concentration under reduced pressure, it was purified by column chromatography on silica gel to afford the product (57 mg, 84% yield) as a solid. $^1$H NMR (300 MHz, CDCl$_3$) δ 8.03 (br, 1H), 7.78 (m, 1H), 7.55 (m, 2H), 7.50 (m, 1H), 7.25 (m, 16H), 6.98 (m, 2H), 5.92 (m, 2H), 5.08 (m, 2H), 5.06 (s, 2H), 3.86 (s, 3H), 3.55 (m, 1H), 3.55 (m, 2H), 3.20 (m, 2H), 1.63 (m, 4H).

Example 30. Preparation of (S)—N-(2,5-diaminopentyl)-5,6-bis(4-fluorophenyl)-1-methyl-1H-benzo[d]imidazole-2-carboxamidehydrogen Chloride Salt

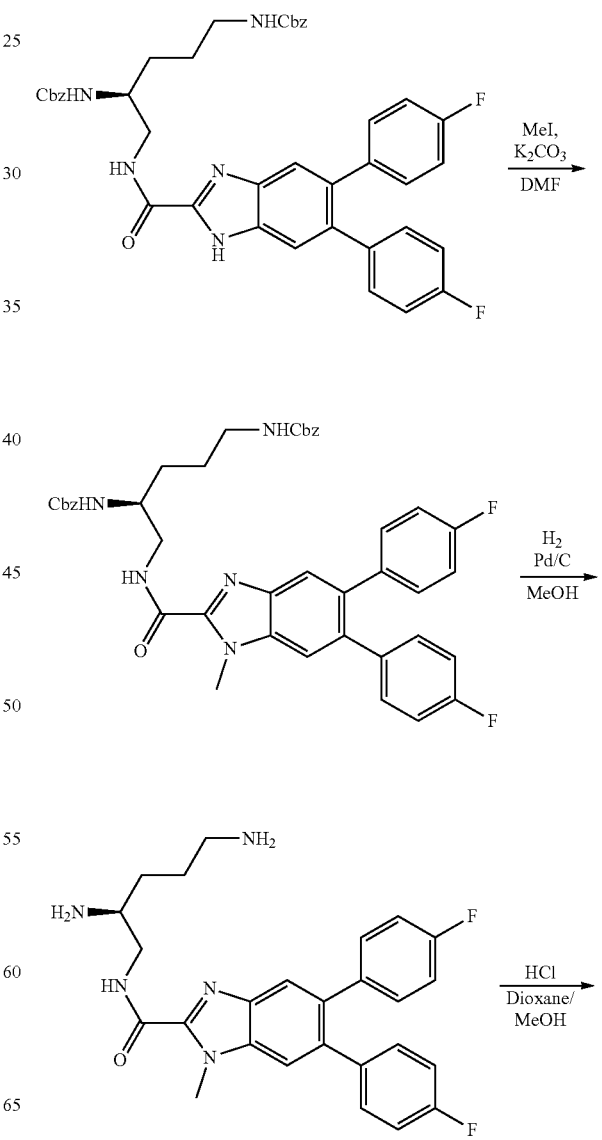

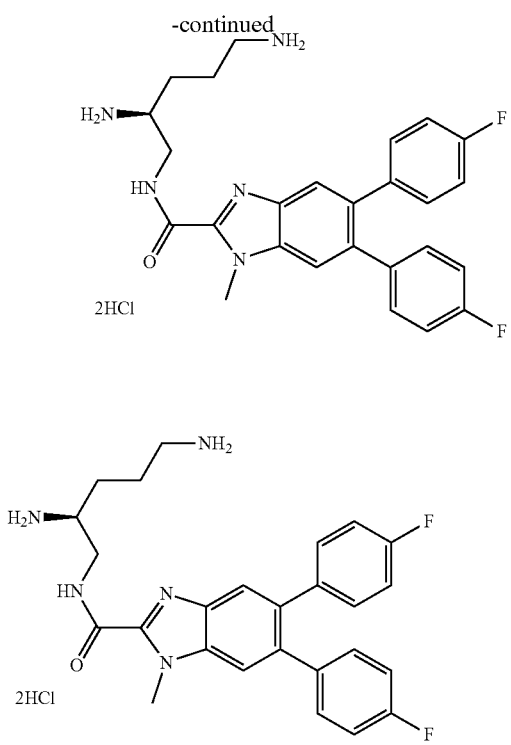

(S)—N-(2,5-Diaminopentyl)-5,6-bis(4-fluorophenyl)-1-methyl-1H-benzo[d]imidazole-2-carboxamide hydrogen Chloride Salt To a solution of dibenzyl (5-(5,6-bis(4-fluorophenyl)-1-methyl-1H-benzo[d]imidazole-2-carboxamido)pentane-1,4-diyl)(S)-dicarbamate (25 mg, 0.031 mmol) in MeOH (10 mL) was added Pd/C (10%, 25 mg). The reaction mixture was hydrogenated under hydrogen gas balloon at room temperature overnight. The solid was filtered off through a Celite pad, washed with methanol and concentrated under reduced pressure. The residue was dissolved in MeOH (5 mL) and HCl in dioxane (4 M, 0.2 mL) was added. The mixture was stirred at room temperature then solvent was removed under reduced pressure. The residue was triturated with EtOAc and the precipitate was collected and dried under reduced pressure to provide the title compound (12 mg, 63% yield in two steps) as an off-white powder. $^1$H NMR (300 MHz, CDCl$_3$) δ 8.12 (br, 1H), 7.77 (s, 1H), 7.41 (s, 1H), 7.09 (m, 4H), 6.93 (m, 4H), 4.26 (s, 3H), 3.58 (m, 1H), 3.27 (m, 1H), 3.02 (m, 1H), 2.75 (m, 2H), 1.62-1.37 (m, 4H).

The requisite intermediate was prepared as follows:

Dibenzyl (5-(1-benzyl-5,6-bis(4-fluorophenyl)-1H-benzo[d]imidazole-2-carboxamido)pentane-1,4-diyl) (S)-dicarbamate To a solution of dibenzyl (5-(5,6-bis(4-fluorophenyl)-1H-benzo[d]imidazole-2-carboxamido)pentane-1,4-diyl)(S)-dicarbamate (30 mg, 0.04 mmol) in dry DMF (2 mL) was added BnBr (8.5 mg, 0.05 mmol), K$_2$CO$_3$ (11 mg, 0.08 mmol). The reaction mixture was stirred at room temperature overnight. The reaction mixture was diluted with EtOAc and washed with water and brine. The organic layer was dried over anhydrous sodium sulfate and filtered. The filtrate was concentrated and purified using column chromatography with silica gel to give the product (25 mg, 74% yield) as a white solid. $^1$H NMR (300 MHz, CDCl$_3$) δ 8.01 (br, 1H), 7.74 (s, 1H), 7.39 (s, 1H), 7.31 (m, 10H), 7.09 (m, 4H), 6.93 (m, 4H), 5.07 (m, 4H), 4.15 (s, 3H), 3.89 (m, 1H), 3.56 (m, 2H), 3.21 (m, 2H), 1.60 (m, 4H).

Example 31. Preparation of (S)-1-benzyl-N-(2,5-diaminopentyl)-5,6-bis(4-fluorophenyl)-1H-benzo[d]imidazole-2-carboxamide Hydrogen Chloride Salt

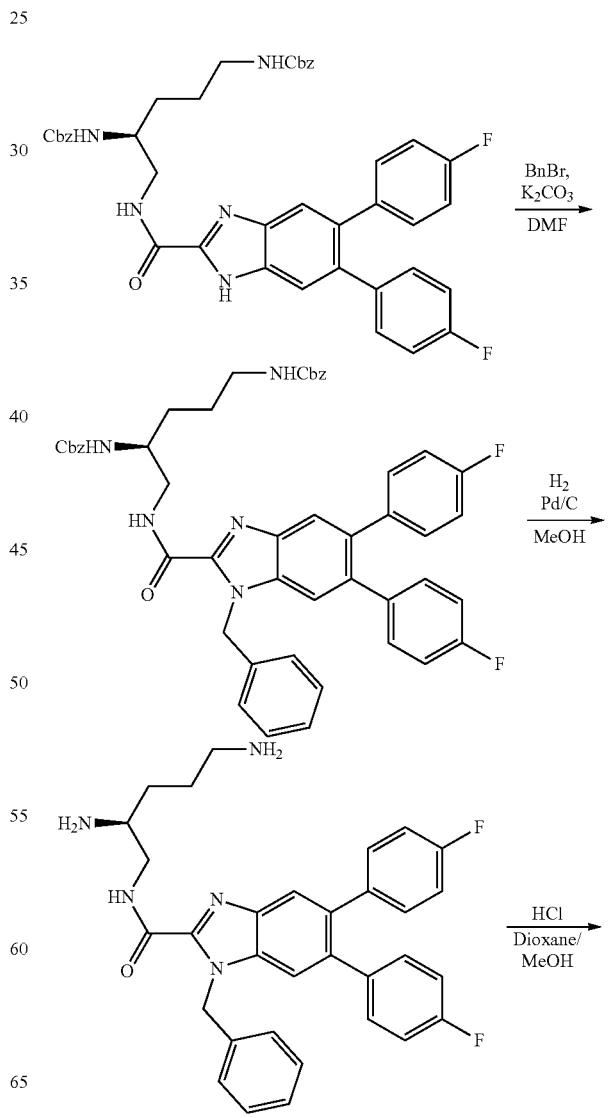

-continued

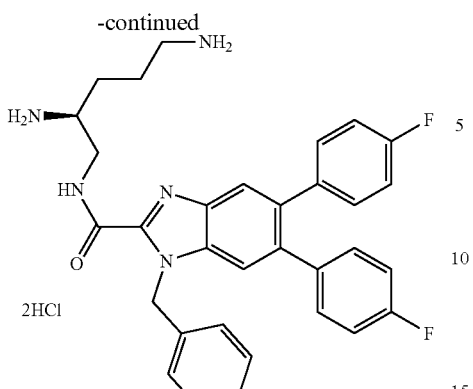

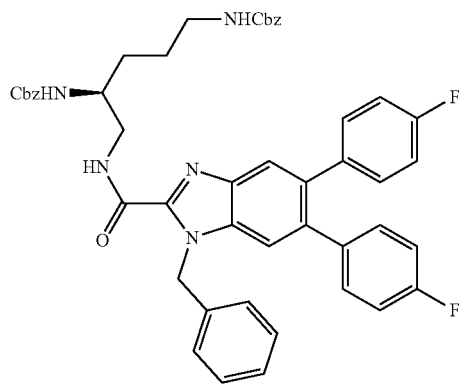

Dibenzyl (5-(1-benzyl-5,6-bis(4-fluorophenyl)-1H-benzo[d]imidazole-2-carboxamido)pentane-1,4-diyl) (S)-dicarbamate To a solution of dibenzyl (5-(5,6-bis(4-fluorophenyl)-1H-benzo[d]imidazole-2-carboxamido)pentane-1,4-diyl)(S)-dicarbamate (30 mg, 0.04 mmol) in dry DMF (2 mL) was added BnBr (8.5 mg, 0.05 mmol), $K_2CO_3$ (11 mg, 0.08 mmol). The reaction mixture was stirred at room temperature overnight. The reaction mixture was diluted with EtOAc and washed with water and brine. The organic layer was dried over anhydrous sodium sulfate and filtered. The filtrate was concentrated and the residue purified using column chromatography with silica gel to give the product (25 mg, 74% yield) as a white solid. $^1$H NMR (300 MHz, $CDCl_3$) δ 8.05 (br, 1H), 7.76 (s, 1H), 7.31 (m, 16H), 7.03 (m, 4H), 6.90 (m, 4H), 5.92 (m, 2H), 5.12 (m, 2H), 5.07 (s, 2H), 3.89 (m, 1H), 3.56 (m, 2H), 3.21 (m, 2H), 1.57 (m, 4H).

Example 32. Description of General Test Methods

Intrinsic MIC Assays

MIC assays were conducted in accordance with Clinical and Laboratory Standards Institute (CLSI) guidelines for broth microdilution. A 96-well plate containing cation-adjusted Mueller-Hinton (CAMH broth with 2-fold serial dilution of compounds was inoculated with log-phase bacterial at $5 \times 10^5$ CFU/mL. The final volume in each well was 100 µL. Each compound was tested in duplicate. The microtiter plates were incubated in an aerobic environment for 18 hours at 37° C. Then the bacterial growth was tested by reading the plate with a VersaMax plate reader (Molecular Devices, Inc.) at 600 nm. The MIC was defined as the lowest compound concentration that inhibited 90% of bacteria growth.

The intrinsic MIC of the experimental EPIs was tested with the method described. The 2-fold serial dilution begins with 100 µg/mL of tested compound in the first column of the 96-well plates.

The following Gram-negative bacterial strains were included in these assays:
Escherichia coli ATCC 25922
Klebsiella pneumoniae ATCC 13883 and ATCC 10031
Pseudomonas aeruginosa ATCC 27853.
Acinetobacter baumannii ATCC 19606

Bacterial EPI Assays

Tier 1 Testing

The EPI assay for the purposes of these studies represents a MIC assay in which the MIC of the antibiotic against the

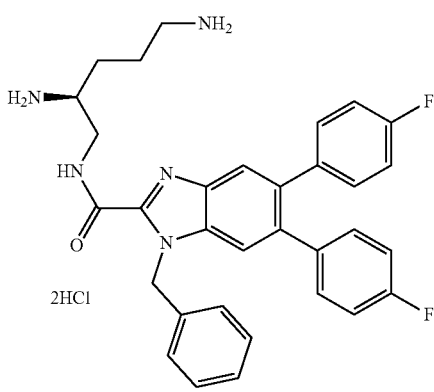 [SMILES: NCCC[C@H](N)CNC(=O)c1nc2cc(-c3ccc(F)cc3)c(-c3ccc(F)cc3)cc2n1Cc1ccccc1]

(S)-1-Benzyl-N-(2,5-diaminopentyl)-5,6-bis(4-fluorophenyl)-1H-benzo[d]imidazole-2-carboxamide Hydrogen Chloride Salt To a solution of dibenzyl (5-(5,6-bis(4-fluorophenyl)-1H-benzo[d]imidazole-2-carboxamido)pentane-1,4-diyl)(S)-dicarbamate (25 mg, 0.031 mmol) in MeOH (10 mL) was added Pd/C (10%, 25 mg). The reaction mixture was hydrogenated under hydrogen gas balloon at room temperature. The solid was filtered off through a Celite pad, washed with methanol and concentrated under reduced pressure. The residue was dissolved in MeOH (5 mL) and HCl in dioxane (4 M, 0.2 mL) was added. The mixture was stirred at room temperature then solvent was removed under reduced pressure. The residue was triturated with EtOAc and the precipitate was collected and dried under reduced pressure to provide the title compound (12 mg, 63% yield in two steps) as an off-white powder. $^1$H NMR (300 MHz, $CDCl_3$) δ 8.17 (br, 1H), 7.78 (s, 1H), 7.37 (s, 1H), 7.28 (m, 5H), 7.05 (m, 4H), 6.91 (m, 4H), 6.02 (s, 2H), 3.60 (m, 1H), 3.26 (m, 1H), 3.02 (m, 1H), 2.75 (m, 2H), 1.62-1.42 (m, 4H).

bacteria is tested in the presence of an experimental efflux pump inhibitor (EPI). The highest concentration of the EPI present in the assay typically is ½ of the intrinsic MIC of the compound. If the intrinsic MIC of the EPI is greater than 100 µg/mL, the EPI assay was tested with 50 µg/mL. Using serial dilutions of the EPI, its enhancement of antibiotic activity was then evaluated. The relative EPI activity was decided by comparing the MIC of the antibiotic in the presence of the EPI compound with the intrinsic MIC of the antibiotic alone. For the evaluation of the efficacy of an EPI against bacteria that were pre-exposed to an antibiotic, the inoculum of bacteria that used was developed from a bacterial culture isolated as a single colony following exposure at ½ the MIIC of the antibiotic (so as to induce efflux pump expression), was to be used in combination with the EPI.

Example 33. Standard EPI Assays

The impact of Example 3 on the MIC values of two test antibiotics (levofloxacin and cefepime) against *P. aeruginosa* ATCC 27853 were evaluated using our standard EPI assay. Both levofloxacin and cefepime are known substrates of efflux pumps in *P. aeruginosa*, and are thus well-suited to be test antibiotics to assay for EPI activity.

In our standard EPI assay, the MIC of the test antibiotic is determined in the absence and presence of sub-inhibitory concentrations of the EPI. Initially, the sub-inhibitory concentration used was ½×MIC of the EPI. As the intrinsic MIC of Example 3 against *P. aeruginosa* ATCC 27853 is 25 µg/mL, we used 12.5 g/mL (½×MIC) of the Example 3 in the standard EPI assay. The MIC of levofloxacin against *P. aeruginosa* ATCC 27853 in the absence of EPI is 1 µg/mL. In the presence of 6.25 µg/mL of the Example 3, the MIC of levofloxacin was markedly reduced to 0.016 µg/mL, a 64-fold reduction relative to the MIC of levofloxacin in the absence of EPI (1 µg/mL). Similar methodology was employed to examine the synergy with *Escherichia coli* ATCC 25922 in the presence of varied concentrations of these EPIs using clarithromycin as the antibiotic.

Tier 2 Testing

A second tier of in vitro evaluation was performed for those compounds that exhibited EPI activity wherein bacteria were pre-exposed to the antibiotic at ½ of its MIC. This novel method of assessment provided a better prediction of those compounds that did demonstrate synergy with an antibiotic in vitro to demonstrate similar efficacy in vivo in mouse models of infection. These "Pre-exposure Bacterial EPI Assays" proved to be very effective method for prioritizing the selection of compounds for further assessment in vivo.

Example 34. Pre-Exposure Bacterial EPI Assays

For the Pre-exposure EPI assay, *P. aeruginosa* ATCC 27853 bacteria used in the assay were first grown in CAMH at 37° C. overnight in the presence of ½×MIC of the test antibiotic (cefepime or levofloxacin). The principle underlying this pre-exposure is that exposure of the bacteria to sub-inhibitory concentrations of the test antibiotic will induce expression of efflux pumps, if any, and may represent the scenario in vivo more accurately.

The MIC of cefepime against *P. aeruginosa* bacteria that have been pre-exposed to cefepime was determined to be 16 µg/mL, 8-fold higher than the MIC of cefepime against unexposed *P. aeruginosa* (2 µg/mL). The impact on the MIC of cefepime against pre-exposed bacteria was then assayed in a manner similar to the standard EPI assay described above, with the exception that pre-exposed bacteria were used to inoculate the 96-well plates.

Thus by using the Pre-exposure EPI assay, information regarding the ability of an EPI to inhibit efflux pumps induced upon exposure to different antibiotics can be gleaned. This information is valuable in directing in vivo experiments and predicting the efficacy of a particular EPI-antibiotic pair.

Example 35. Fluorescent-Based Cellular Assay for Efflux Inhibition

The impact of potential EPI compounds on the activity of efflux pumps was also evaluated with a fluorescence-based cellular assay that measures the efflux of Hoechst 33342, a known substrate of Gram-negative bacterial efflux pumps. When bound to intracellular bacterial DNA, Hoechst 33342 fluoresces brightly, while the unbound fluorophore outside the bacterial cell exhibits little or no fluorescence. Thus, the efflux of Hoechst 33342 from inside to outside the bacterial cell is associated with a substantive decrease in fluorescence.

Bacterial cells were harvested from overnight cultures by centrifugation, and the cell pellet was washed with phosphate-buffered containing 1 mM $MgCl_2$ (PBSM). After washing the cells, the cell pellets were resuspended in PBSM to achieve a final OD at 600 nm of 0.6 to 0.9. The ATP required for efflux pump function was then depleted by addition of carbonyl cyanide 3-chlorophenylhydrazone (CCCP) to a final concentration in the range of 3 to 10 M. Hoechst 33342 was then added to a final concentration of 10 µM, and the cells were incubated aerobically at 37° C. for 0.5 to 18 hours. The bacterial suspension (200 µL) was added to wells of a black, flat-bottom 96-well plate containing test EPI compounds at concentrations of ranging from 1.6 to 25 µg/mL or an equivalent volume of the vehicle (DMSO) alone. A plate vortexer was used to mix the bacterial cells with the test EPI compounds, and the plates are pre-incubated at 37° C. for 5 minutes. After the pre-incubation, Hoechst 33342 efflux was initiated by addition of glucose to a final concentration of 10 to 50 mM. A SpectraMax® 2 fluorescent plate reader (Molecular Devices, Inc., Sunnyvale, Calif.) was used to monitor the fluorescence of each well at 37° C. once per minute for 20 to 60 minutes. The excitation and emission wavelengths were set at 355 and 460 nm, respectively. *E. coli* ATCC 25922, *K. pneumoniae* ATCC 13883, *P. aeruginosa* ATCC 27853, and *Acinetobacter baumannii* ATCC 19606 were used as model Gram-negative bacterial strains in this assay.

A general method for the in vivo assessment of bacterial EPIs is complicated by the fact that that both the antibiotic and the EPI need to be present for synergy to be achieved. A general method was discovered that has proven to be effective in establishing the relative efficacy of bacterial EPIs in a mouse septicemia model. The bacterial EPI is administered initially intravenously to mice with septicemia, followed 5 minutes later by the intravenous administration or oral administration of the antibiotic. A second administration of the EPI is then administered subcutaneously after an additional 5 minutes to act as a booster, followed by the final administration of the antibiotic either intravenously or orally after the second administration of the EPI. In many instances, this regiment has proved effective in demonstrating synergy and allowing survival of the infected mice. In a few instances, a second regiment of both EPI and antibiotic as administered on day 1 was required after 24 hours to affect cures.

Example 36. Methods of Assessment of In Vivo Efficacy of Efflux Pump Inhibitors

Determination of the in vivo efficacy of bacterial efflux pump inhibitors (EPIs) can be efficiently determined using a mouse septicemia model of infection. The systemic infection is initiated by a 500 ul intraperitoneal injection of an inoculum containing bacteria (such as *P. aeruginosa* [ATCC 27853]) at a concentration of approximately $5 \times 10^5$ cells in 5% mucin in Swiss Webster female mice. The experimental groups (4-6 infected mice each) consist of both positive and negative controls, as well as infected mice treated with antibiotic alone or EPI alone, as well as the EPI administered in combination with the antibiotic. Five mutes post-infection an EPI is administered iv with an antibiotic such as cefepime (250 ul of a 10 mg/ml solution) being administered 10 minutes post-infection. A second dose of the EPI is then administered sc 20 minutes post-infection, with cefepime again being administered (250 ul of a 10 mg/ml solution) 25 minutes post-infection. Mice treated with cefepime alone were injected with an iv dose (250 ul of a 10 mg/ml solution) b.i.d. at 10 and 25 minutes post-infection. Mice treated with EPI alone were treated iv 5 minutes post infection and sc 20 minutes post-infection. Additional experimental groups consisting of 4-6 infected mice were untreated or treated with vehicle alone at the appropriate time points. If required, this regiment would be repeated 24 hours post-infection on day 2 of the assay.

| Experiment | EPI | % Survival (24 hr) Vehicle Controls | % Survival* (72 hr) Antibiotic Only | % Survival (72 hr) Antibiotic + EPI |
|---|---|---|---|---|
| #521 | Example 22 | 0% | 25%***** | 75% |

*cefepime, 10 mg/ml b.i.d.; 250 ul;
Example 22; 2.0 mg/ml b.i.d.

Example 37

The following can illustrate representative pharmaceutical dosage forms, containing a compound of formula I ('Compound X') or a pharmaceutically acceptable salt thereof, for therapeutic or prophylactic use in humans. The tablets can optionally comprise an enteric coating.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| Compound X = (free acid form) | 10.0 |
| Monobasic sodium phosphate | 0.3 |
| Dibasic sodium phosphate | 1.1 |

-continued

| (v) Injection 2 (10 mg/mL) | mg/mL |
|---|---|
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:
1. A compound of formula I:

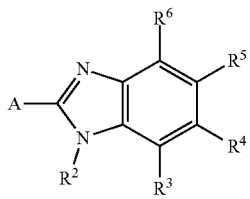

wherein:
A is —C(=O)N(R$^{a1}$)—R$^1$, —(C$_1$-C$_3$)alkyl-C(=O)N(R$^{a1}$)R$^1$, —(C$_1$-C$_3$)alkyl-O—R$^1$, —O—R$^1$, —(C$_1$-C$_3$)alkyl-N(R$^{a1}$)—R$^1$, —N(R$^{a1}$)—R$^1$, or R$^1$;
R$^2$ is hydrogen, (C$_1$-C$_6$)alkyl or phenyl(C$_1$-C$_6$)alkyl-, wherein the phenyl is optionally substituted with one or more (C$_1$-C$_6$)alkyl, —O(C$_1$-C$_6$)alkyl, halo or —NO$_2$;
R$^1$ is:

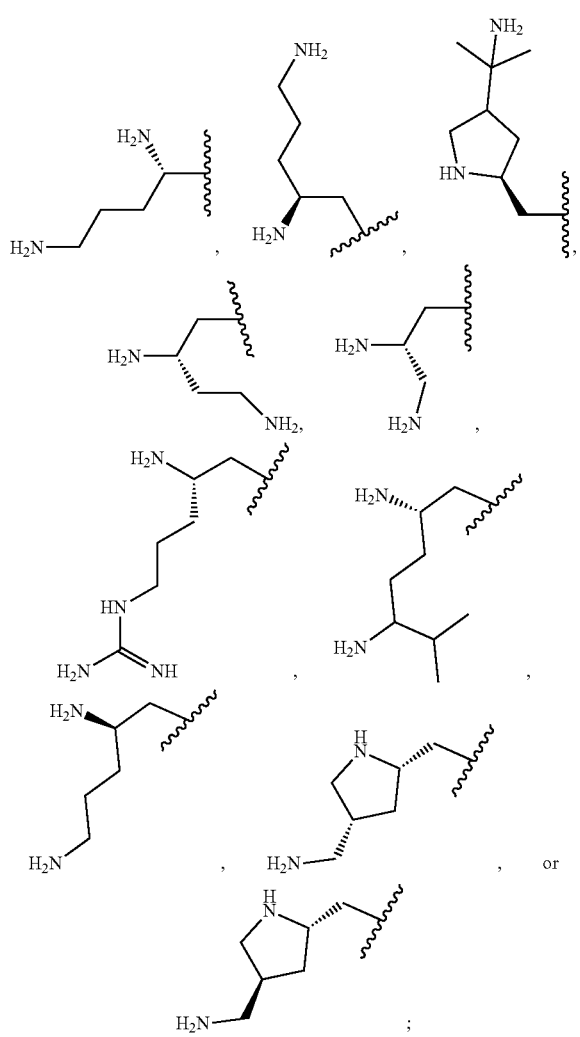

R$^3$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

R$^4$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

R$^5$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

R$^6$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

each R$^{a1}$ is independently hydrogen, (C$_1$-C$_4$)alkyl or (C$_3$-C$_7$)carbocyclyl;
and
each R$^{a3}$ and R$^{b3}$ is independently hydrogen, (C$_1$-C$_4$)alkyl or (C$_3$-C$_7$)carbocyclyl;
or a salt thereof.

2. The compound of claim 1, wherein A is —C(=O)N(R$^{a1}$)—R$^1$, —(C$_1$-C$_3$)alkyl-C(=O)N(R$^{a1}$)R$^1$, or R$^1$.

3. The compound of claim 1, wherein A is —C(=O)N(R$^{a1}$)—R$^1$.

4. The compound of claim 1, wherein R$^2$ is hydrogen, (C$_1$-C$_6$)alkyl, or phenyl(C$_1$-C$_6$)alkyl-, wherein the phenyl is optionally substituted with one or more (C$_1$-C$_6$)alkyl, —O(C$_1$-C$_6$)alkyl, halogen or —NO$_2$.

5. The compound of claim 1, wherein R$^3$ is hydrogen, (C$_1$-C$_4$)haloalkyl, or aryl wherein the aryl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy.

6. The compound of claim 1, wherein R$^3$ is hydrogen, trifluoromethyl or 4-fluorophenyl.

7. The compound of claim 1, wherein R$^4$ is hydrogen or phenyl wherein the phenyl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy.

8. The compound of claim 1, wherein R$^4$ is hydrogen, 4-fluorophenyl, 4-aminophenyl, 4-nitrophenyl, 3,4-difluorophenyl, or 4-methoxyphenyl.

9. The compound of claim 1 wherein R$^5$ is hydrogen or phenyl wherein the phenyl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy.

10. The compound of claim 1, wherein R$^5$ is hydrogen, 4-fluorophenyl, 4-trifluormethylphenyl, 4-methoxyphenyl, 3-cyanophenyl, bromo, 4-nitrophenyl, or 3,4-difluorophenyl.

11. The compound of claim 1, wherein R$^6$ is hydrogen, halo, (C$_1$-C$_4$)alkyl, (C$_1$-C$_4$)haloalkyl, or (C$_1$-C$_4$)alkoxy.

12. The compound of claim 1, wherein $R^6$ is hydrogen.
13. The compound of claim 1, wherein A is:
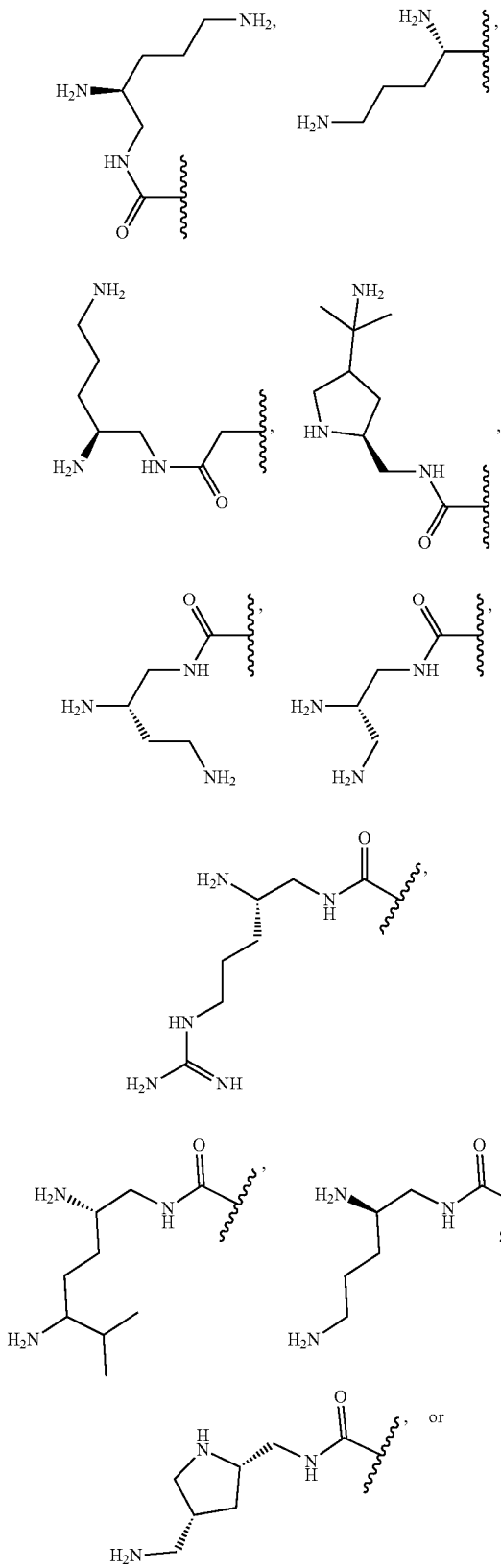
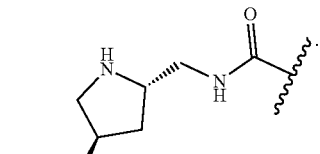
14. The compound of claim 1 that is:
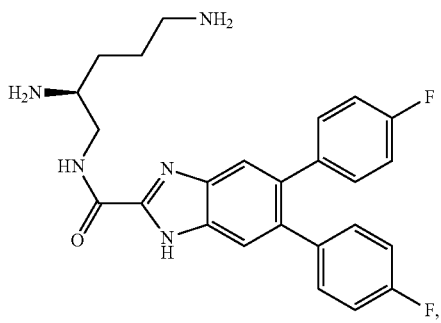
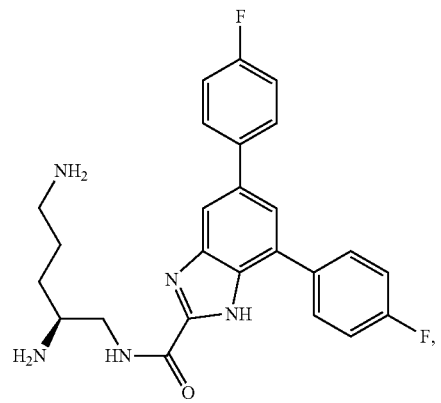
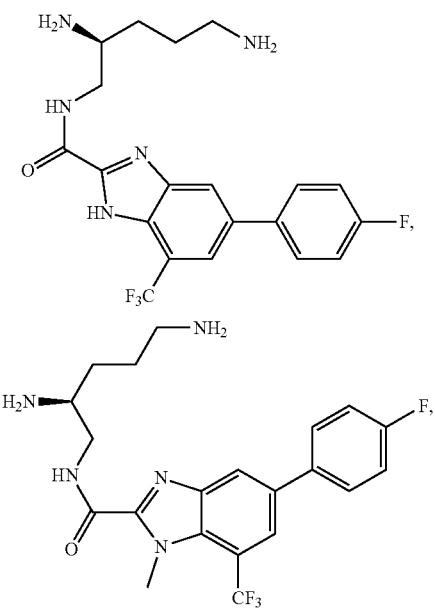

179
-continued
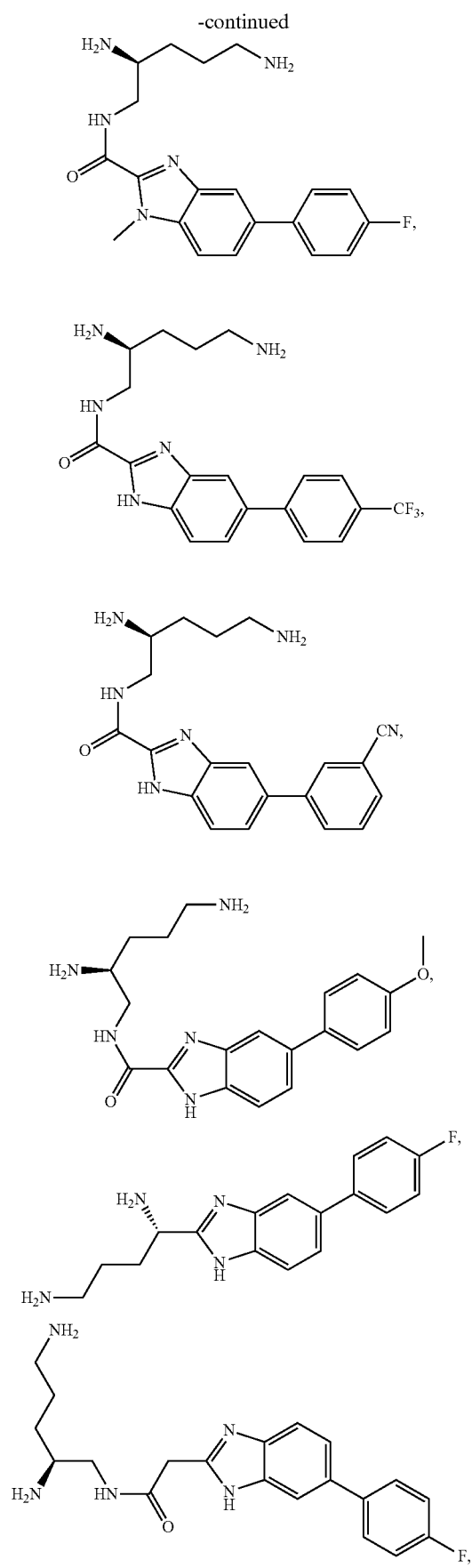
180
-continued
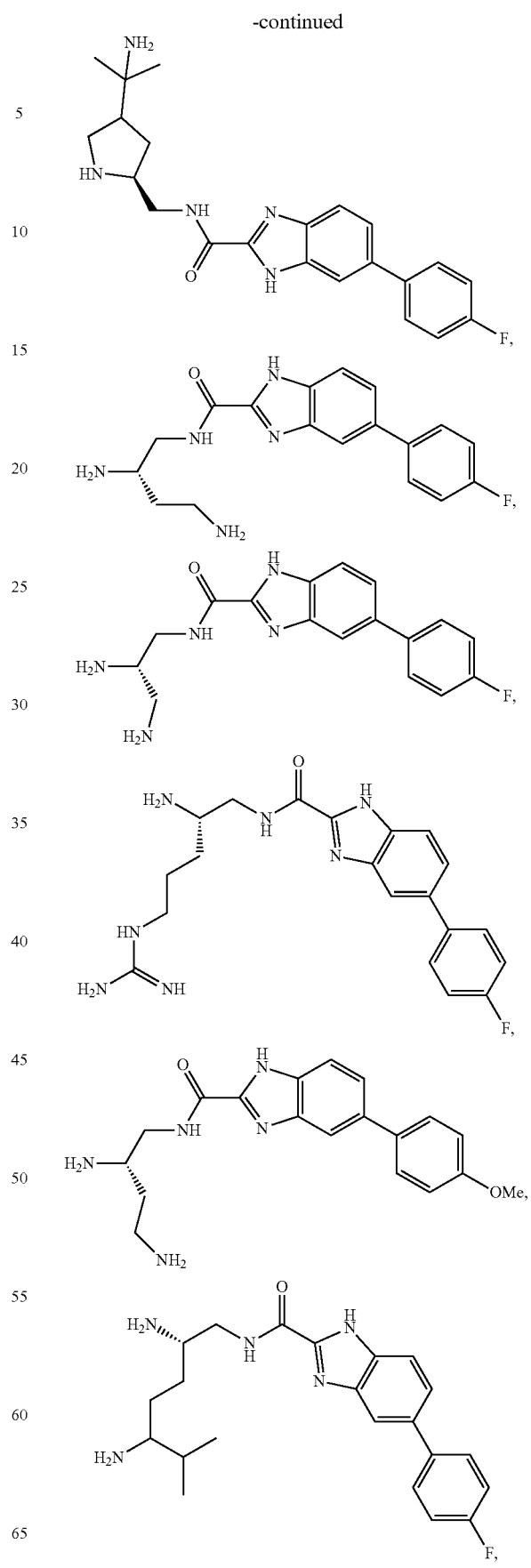

181
-continued
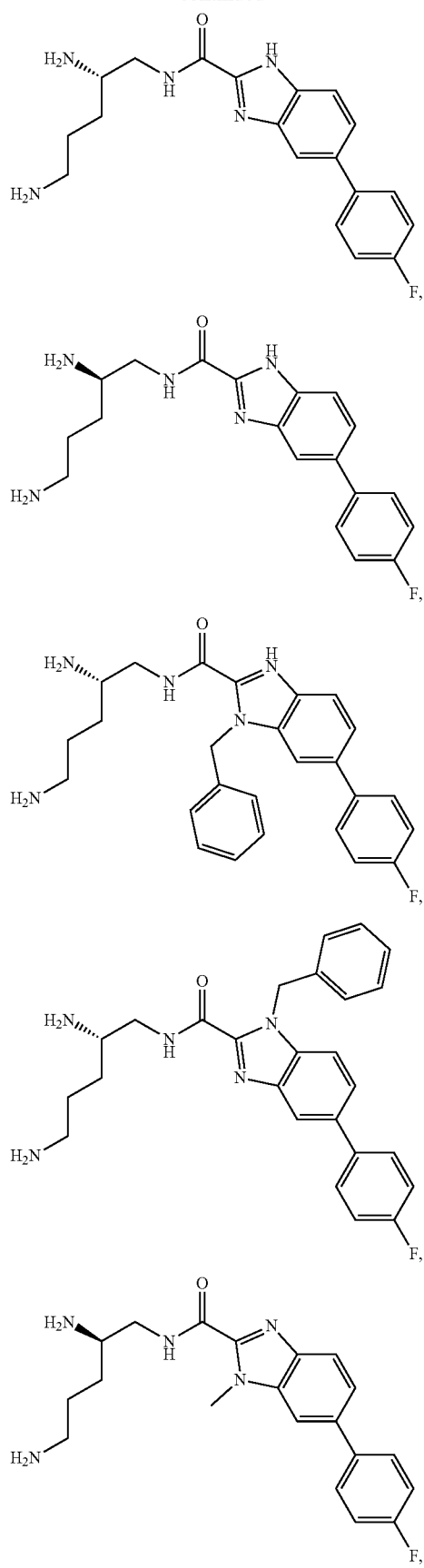
182
-continued
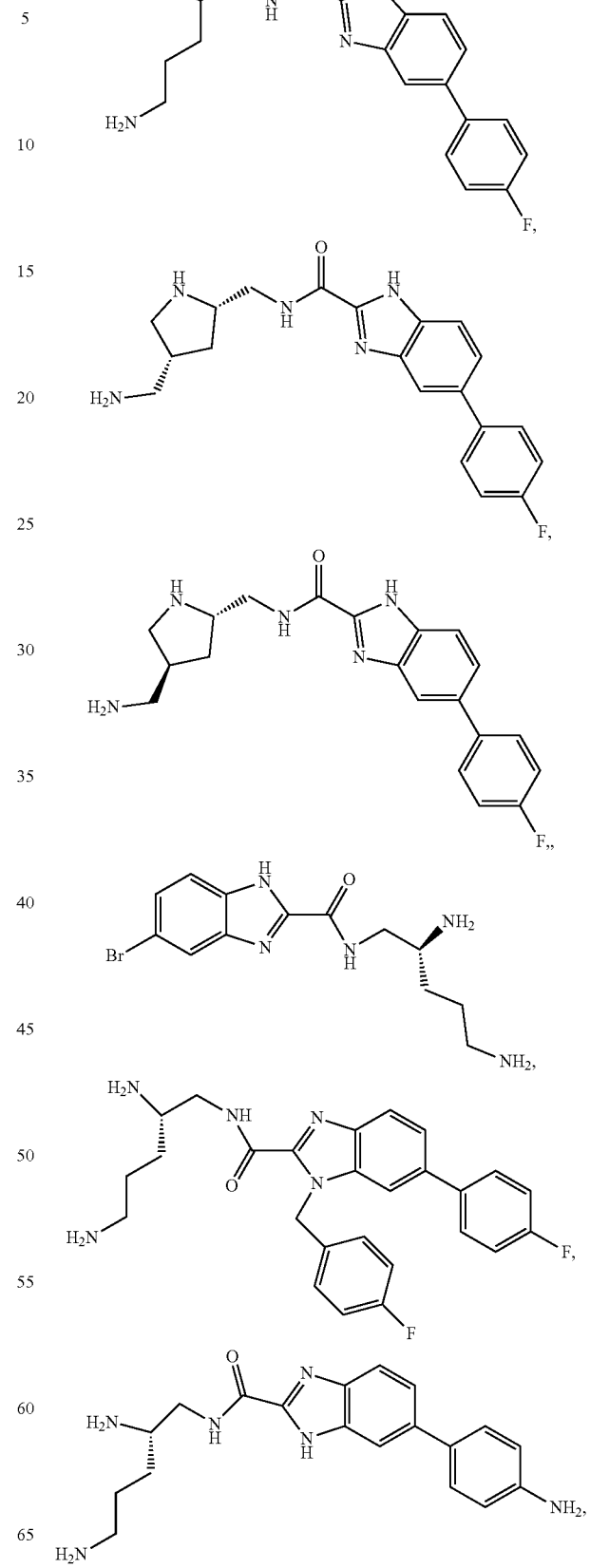

-continued

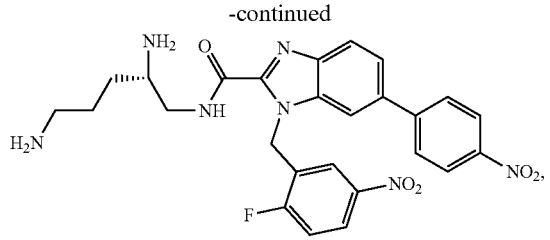
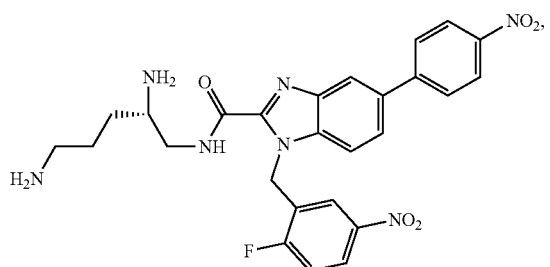
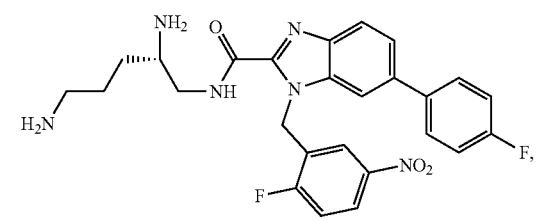
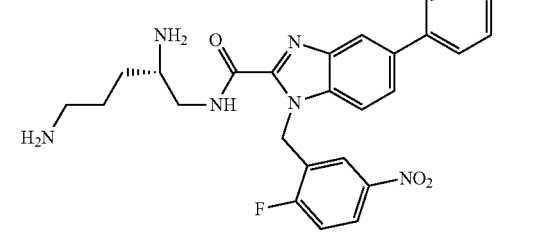
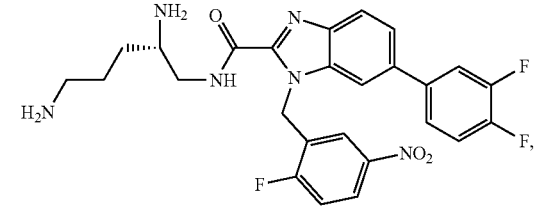
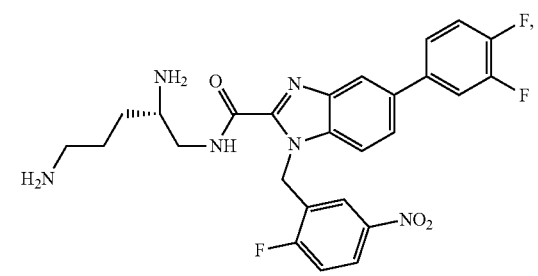
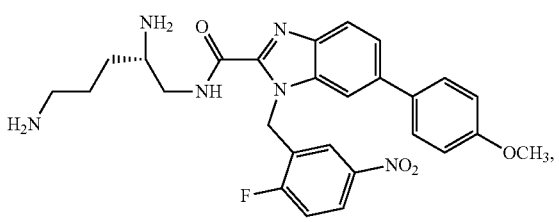

-continued

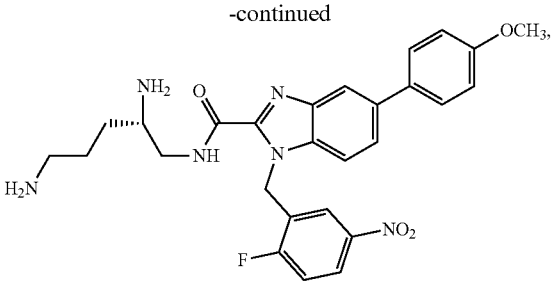
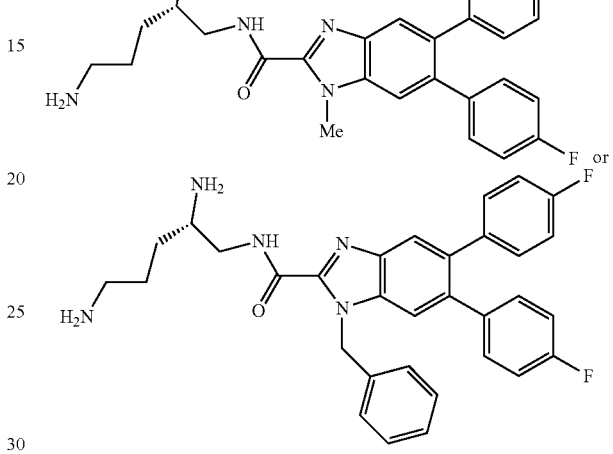

or a salt thereof.

15. A pharmaceutical composition comprising a compound or a pharmaceutically acceptable salt thereof as described in claim 1, and a pharmaceutically acceptable vehicle.

16. A pharmaceutical composition comprising a compound of formula I:

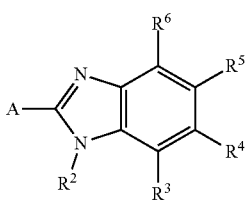

wherein:
A is —C(=O)N(R$^{a1}$)—R$^1$, —(C$_1$-C$_3$)alkyl-C(=O)N(R$^{a1}$)R$^1$, —(C$_1$-C$_3$)alkyl-O—R$^1$, —O—R$^1$, —(C$_1$-C$_3$)alkyl-N(R$^{a1}$)—R$^1$, —N(R$^{a1}$)—R$^1$, or R$^1$;

R$^2$ is hydrogen, (C$_1$-C$_6$)alkyl or phenyl(C$_1$-C$_6$)alkyl-, wherein the phenyl is optionally substituted with one or more (C$_1$-C$_6$)alkyl, —O(C$_1$-C$_6$)alkyl, halo or —NO$_2$;

R$^1$ is:
(a) (C$_1$-C$_{16}$)alkyl substituted with one or more groups selected from the group consisting of —NR$^{b2}$R$^{c2}$, —NHNH$_2$, —C(=NR$^{a2}$)(NR$^{b2}$R$^{c2}$), —NR$^{a2}$C(=NR$^{a2}$)(R$^{d2}$), and —NR$^{a2}$C(=NR$^{a2}$)(NR$^{b2}$R$^{c2}$); or
(b) (C$_3$-C$_7$)carbocyclyl, (C$_3$-C$_7$)carbocyclyl-(C$_1$-C$_4$)alkyl-, 4-7 membered monocyclic heterocyclyl, or 4-7 membered monocyclic heterocyclyl-(C$_1$-C$_4$)alkyl-, wherein each (C$_3$-C$_7$)carbocyclyl or (C$_3$-C$_7$)carbocyclyl-(C$_1$-C$_4$)alkyl- is substituted with one or more groups selected from the group consisting of Z and —(C$_1$-C$_6$)alkyl substituted with one or more Z, and wherein each 4-7 membered monocyclic heterocyclyl or 4-7 membered monocyclic heterocyclyl-(C$_1$-C$_4$)alkyl- is optionally substituted with one or more groups selected from the group consisting of Z and —(C$_1$-C$_6$) alkyl substituted with one or more Z, wherein each Z is independently selected from the group consisting of NR$^{b2}$R$^{c2}$, —NHNH$_2$, —C(=NR$^{a2}$)(NR$^{b2}$R$^{c2}$), —NR$^{a2}$C(=NR$^{a2}$)(R$^{d2}$), and —NR$^{a2}$C(=NR$^{a2}$) (NR$^{b2}$R$^{c2}$) and wherein each (C$_3$-C$_7$)carbocyclyl, (C$_3$-C$_7$)carbocyclyl-(C$_1$-C$_4$)alkyl-, 4-7 membered monocyclic heterocyclyl, or 4-7 membered monocyclic heterocyclyl-(C$_1$-C$_4$)alkyl-, is independently optionally substituted independently with one or more (C$_1$-C$_4$) alkyl;

R$^3$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

R$^4$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

R$^5$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

R$^6$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

each R$^{a1}$ is independently hydrogen, (C$_1$-C$_4$)alkyl or (C$_3$-C$_7$)carbocyclyl;

each R$^{a2}$ is independently hydrogen, (C$_1$-C$_4$)alkyl or (C$_3$-C$_7$)carbocyclyl;

each R$^{b2}$ and R$^{c2}$ is independently hydrogen, (C$_1$-C$_4$)alkyl or (C$_3$-C$_7$)carbocyclyl;

R$^{d2}$ is (C$_1$-C$_6$)alkyl or (C$_3$-C$_7$)carbocyclyl; and each R$^{a3}$ and R$^{b3}$ is independently hydrogen, (C$_1$-C$_4$)alkyl or (C$_3$-C$_7$)carbocyclyl;

or a pharmaceutically acceptable salt thereof, one or more antibacterial agents and a pharmaceutically acceptable vehicle provided that when R$^4$ is halo, R$^5$ is halo and A is —C(=O)N(R$^{a1}$)—R$^1$, then R$^1$ does not represent morpholinyl.

17. A method of inhibiting a bacterial efflux pump in an animal comprising administering to the animal a compound or a pharmaceutically acceptable salt thereof as described in claim 1.

18. A method of treating a bacterial infection in an animal comprising co-administering to the animal a compound or a pharmaceutically acceptable salt thereof as described in claim 1 and one or more antibacterial agents.

19. A method of treating a bacterial infection in an animal comprising co-administering to the animal a compound of formula I:

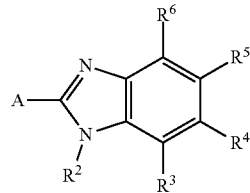

wherein:

A is —C(=O)N(R$^{a1}$)—R$^1$, —(C$_1$-C$_3$)alkyl-C(=O)N (R$^{a1}$)R$^1$, —(C$_1$-C$_3$)alkyl-O—R$^1$, —O—R$^1$, —(C$_1$-C$_3$) alkyl-N(R$^{a1}$)—R$^1$, —N(R$^{a1}$)—R$^1$, or R$^1$;

R$^2$ is hydrogen, (C$_1$-C$_6$)alkyl or phenyl(C$_1$-C$_6$)alkyl-, wherein the phenyl is optionally substituted with one or more (C$_1$-C$_6$)alkyl, —O(C$_1$-C$_6$)alkyl, halo or —NO$_2$;

R$^1$ is:

(a) (C$_1$-C$_6$)alkyl substituted with one or more groups selected from the group consisting of —NR$^{b2}$R$^{c2}$, —NHNH$_2$, —C(=NR$^{a2}$)(NR$^{b2}$R$^{c2}$), —NR$^{a2}$C (=NR$^{a2}$)(R$^{d2}$), and —NR$^{a2}$C(=NR$^{a2}$)(NR$^{b2}$R$^{c2}$); or (b) (C$_3$-C$_7$)carbocyclyl, (C$_3$-C$_7$)carbocyclyl-(C$_1$-C$_4$)alkyl-, 4-7 membered monocyclic heterocyclyl, or 4-7 membered monocyclic heterocyclyl-(C$_1$-C$_4$)alkyl-, wherein each (C$_3$-C$_7$)carbocyclyl or (C$_3$-C$_7$)carbocyclyl-(C$_1$-C$_4$)alkyl- is substituted with one or more groups selected from the group consisting of Z and —(C$_1$-C$_6$)alkyl substituted with one or more Z, and wherein each 4-7 membered monocyclic heterocyclyl or 4-7 membered monocyclic heterocyclyl-(C$_1$-C$_4$)alkyl- is substituted with one or more groups selected from the group consisting of Z and —(C$_1$-C$_6$)alkyl substituted with one or more Z, wherein each Z is independently selected from the group consisting of NR$^{b2}$R$^{c2}$, —NHNH$_2$, —C(=NR$^{a2}$)(NR$^{b2}$R$^{c2}$), —NR$^{a2}$C(=NR$^{a2}$)(R$^{d2}$), and —NR$^{a2}$C(=NR$^{a2}$) (NR$^{b2}$R$^{c2}$) and wherein each (C$_3$-C$_7$)carbocyclyl, (C$_3$-C$_7$)carbocyclyl-(C$_1$-C$_4$)alkyl-, 4-7 membered monocyclic heterocyclyl, or 4-7 membered monocyclic heterocyclyl-(C$_1$-C$_4$)alkyl-, is independently optionally substituted independently with one or more (C$_1$-C$_4$) alkyl;

R$^3$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

R$^4$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of NR$^{a3}$R$^{b3}$, halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

R$^5$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of $NR^{a3}R^{b3}$, halo, —OH, —NO$_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^6$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of $NR^{a3}R^{b3}$, halo, —OH, —NO$_2$, —CN, ($C_1$-$C_4$)alkyl, ($C_1$-$C_4$)haloalkyl, ($C_1$-$C_4$)alkoxy, and ($C_1$-$C_4$)haloalkoxy;

each $R^{a1}$ is independently hydrogen, ($C_1$-$C_4$)alkyl or ($C_3$-$C_7$)carbocyclyl;

each $R^{a2}$ is independently hydrogen, ($C_1$-$C_4$)alkyl or ($C_3$-$C_7$)carbocyclyl;

each $R^{b2}$ and $R^{c2}$ is independently hydrogen, ($C_1$-$C_4$)alkyl or ($C_3$-$C_7$)carbocyclyl;

$R^{d2}$ is ($C_1$-$C_6$)alkyl or ($C_3$-$C_7$)carbocyclyl; and each $R^{a3}$ and $R^{b3}$ is independently hydrogen, ($C_1$-$C_4$)alkyl or ($C_3$-$C_7$)carbocyclyl;

or a pharmaceutically acceptable salt thereof and one or more antibacterial agents provided that when $R^4$ is halo, $R^5$ is halo and A is —C(=O)N($R^{a1}$)—$R^1$, then $R^1$ does not represent morpholinyl.

* * * * *

UNITED STATES PATENT AND TRADEMARK OFFICE
CERTIFICATE OF CORRECTION

PATENT NO. : 11,180,459 B2
APPLICATION NO. : 16/492907
DATED : November 23, 2021
INVENTOR(S) : LaVoie et al.

Page 1 of 1

It is certified that error appears in the above-identified patent and that said Letters Patent is hereby corrected as shown below:

In the Claims

Column 186, Line 23, Claim 19, please delete "$(C_1-C_6)$alkyl" and insert -- $(C_1-C_{16})$alkyl -- therefor.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*